US010087240B2

(12) United States Patent
Weiner et al.

(10) Patent No.: US 10,087,240 B2
(45) Date of Patent: Oct. 2, 2018

(54) DNA ANTIBODY CONSTRUCTS AND METHOD OF USING SAME

(71) Applicants: David Weiner, Merion, PA (US); Karuppiah Muthumani, Cherry Hill, NJ (US); Seleeke Flingai, Minneapolis, MN (US); Niranjan Sardesai, Blue Bell, PA (US)

(72) Inventors: David Weiner, Merion, PA (US); Karuppiah Muthumani, Cherry Hill, NJ (US); Seleeke Flingai, Minneapolis, MN (US); Niranjan Sardesai, Blue Bell, PA (US)

(73) Assignee: INOVIO PHARMACEUTICALS, INC., Plymouth Meeting, PA (US)

( * ) Notice: Subject to any disclaimer, the term of this patent is extended or adjusted under 35 U.S.C. 154(b) by 0 days.

(21) Appl. No.: 15/103,970

(22) PCT Filed: Dec. 13, 2014

(86) PCT No.: PCT/US2014/070188

§ 371 (c)(1),
(2) Date: Jun. 13, 2016

(87) PCT Pub. No.: WO2015/089492

PCT Pub. Date: Jun. 18, 2015

(65) Prior Publication Data

US 2016/0311891 A1 Oct. 27, 2016

Related U.S. Application Data

(63) Continuation of application No. PCT/US2013/075137, filed on Dec. 13, 2013.

(51) Int. Cl.

| | |
|---|---|
| ***C07K 16/10*** | (2006.01) |
| ***A61K 48/00*** | (2006.01) |
| ***C07K 16/32*** | (2006.01) |
| ***A61K 39/00*** | (2006.01) |
| ***C12N 7/00*** | (2006.01) |
| ***C07K 14/005*** | (2006.01) |
| ***A61K 39/12*** | (2006.01) |
| ***A61K 39/42*** | (2006.01) |
| *A61M 37/00* | (2006.01) |

(52) U.S. Cl.

CPC .......... *C07K 16/1081* (2013.01); *C07K 16/10* (2013.01); *C07K 16/1063* (2013.01); *C07K 16/32* (2013.01); *A61K 48/005* (2013.01); *A61K 2039/505* (2013.01); *A61K 2039/53* (2013.01); *A61M 2037/0007* (2013.01); *C07K 2317/10* (2013.01); *C07K 2317/55* (2013.01); *C07K 2317/60* (2013.01); *C07K 2317/76* (2013.01); *C12N 2740/16111* (2013.01); *C12N 2770/24111* (2013.01); *C12N 2770/36111* (2013.01)

(58) Field of Classification Search

CPC .. A61K 2039/505; A61K 39/12; A61K 39/00; A61K 39/42; A61K 2039/525; C12N 7/00; C12N 2770/24134; C12N 15/1131; C07K 14/005; C07K 2317/55; C07K 14/70503

See application file for complete search history.

(56) References Cited

U.S. PATENT DOCUMENTS

| | | | |
|---|---|---|---|
| 2012/0014945 | A1 | 1/2012 | Wu et al. |
| 2012/0107356 | A1 | 5/2012 | Vadrevu et al. |
| 2012/0232133 | A1 | 9/2012 | Balaz et al. |
| 2012/0269723 | A1 | 10/2012 | Brinkmann et al. |
| 2012/0282264 | A1 | 11/2012 | Mascola et al. |
| 2013/0177573 | A1 | 7/2013 | Williamson et al. |
| 2013/0243789 | A1 | 9/2013 | Carson et al. |

FOREIGN PATENT DOCUMENTS

| | | | |
|---|---|---|---|
| CN | 102470170 | 5/2012 | |
| CN | 102344493 | 9/2014 | |
| WO | 2005/118864 | 12/2005 | |
| WO | 2007/014162 | 2/2007 | |
| WO | WO-2009031045 A2 * | 3/2009 | ......... C07K 16/1081 |
| WO | 2011/038290 | 3/2011 | |

OTHER PUBLICATIONS

Kim et al. "Two-promoter vector is highly efficient for overproduction of protein complexes." Protein Sci 13(6):1698-703. May 7, 2004.

Ellison et al. "The nucleotide sequence of a human immunoglobulin C gamma1 gene." Nucleic Acid Res 10(13):4071-9. Jul. 10, 1982.

NCHU Administrator, "Antibody Structure Ag-Ab interactions." 2007. Oline (http://www.as.nchu.edu.tw/lab/5c/course/antibody/week%203%20Antibody%20structure%20Ag-Ab%20interactions.pdf).

Fang et al. "An antibody delivery system for regulated expression of therapeutic levels of monoclonal antibodies in vivo." Mol Ther 15(6):1153-9. Mar. 20, 2007.

Lund et al. "Expression and characterization of truncated forms of humanized L243 lgG1. Architectural features can influence synthesis of its oligosaccharide chains and affect superoxide production triggered through human Fcgamma receptor I." Eur J Biochem 267(24):7246-57. Dec. 25, 2001.

(Continued)

*Primary Examiner* — Rachel B Gill

(74) *Attorney, Agent, or Firm* — Riverside Law LLP

(57) ABSTRACT

The present invention relates to a composition including a recombinant nucleic acid sequence that encodes an antibody and a method of generating a synthetic antibody in a subject by administering the composition to the subject. The invention also provides a method of preventing and/or treating disease in a subject using the composition and method of generation.

31 Claims, 74 Drawing Sheets

Specification includes a Sequence Listing.

(56) References Cited

OTHER PUBLICATIONS

Cao et al. "Oligomerization is required for the activity of recombinant soluble LOX-1" FEBS J 276(17):4909-20. Jul. 31, 2009.

* cited by examiner

Optimized Nucleic Acid Sequence Encoding IgG Heavy Chain

GGATCCGCCACCATGGAAACCGACACTCTGCTGCTGTGGGTGCTGCTGCTGTGGGTGCCCGGCTCAACAGGCGACGGC
GCTCAGGTCCAGCTGGTCCAGTCTGGAGCTGTGATCAAGACCCCTGGCAGCTCCGTCAAAATTTCTTGCAGAGCAAGTG
GCTACAACTTCCGGGACTATAGCATCCACTGGGTGCGGCTGATTCCTGATAAGGGATTTGAGTGGATCGGCTGGATCAA
GCCACTGTGGGGCGCTGTGTCCTACGCAAGGCAGCTGCAGGGGCGCGTCTCCATGACACGACAGCTGTCTCAGGACCC
AGACGATCCCGATTGGGGGGTGGCCTACATGGAGTTCAGTGGACTGACTCCCGCAGACACCGCCGAATATTTTTGCGTG
CGGAGAGGCTCCTGCGACTACTGTGGGGATTTCCCATGGCAGTATTGGTGTCAGGGAACTGTGGTCGTGGTCTCTAGTG
CATCAACCAAGGGCCCCAGCGTGTTTCCTCTGGCCCCATCAAGCAAAAGTACATCAGGAGGAACTGCAGCTCTGGGAT
GTCTGGTGAAGGATTACTTCCCCGAGCCTGTGACCGTCAGCTGGAACTCCGGAGCACTGACCTCCGGAGTGCACACATT
TCCCGCTGTCCTGCAGTCCTCTGGGCTGTACTCTCTGAGTTCAGTGGTCACAGTGCCTAGCTCCTCTCTGGGCACCCAGA
CATATATCTGCAACGTCAATCATAAGCCAAGTAATACTAAAGTGGACAAGAAAGTCGAACCCAAATCATGTTACCCCT
ATGACGTGCCTGATTATGCTTGATAACTCGAG (SEQ ID NO:6)

FIG. 1

Optimized Nucleic Acid Sequence Encoding IgG Light Chain

GGATCCGCCACCATGGAGACTGATACACTGCTGCTGTGGGTGCTGCTGCTGTGGGTGCCTGGCTCAACCGGCGACGGG
GCTCAGGTCCAGATTGTGCTGACCCAGAGCCCTGGCATCCTGTCACTGAGCCCAGGAGAGACCGCAACACTGTTCTGCA
AGGCCTCCCAGGGCGGGAACGCTATGACATGGTACCAGAAACGGAGAGGACAGGTGCCCCGACTGCTGATCTATGACA
CTTCAAGGCGAGCAAGCGGAGTGCCTGATCGATTTGTCGGCAGCGGCTCTGGGACAGACTTCTTTCTGACTATTAATAA
GCTGGACAGAGAGGATTTCGCTGTGTACTATTGCCAGCAGTTTGAATTCTTTGGACTGGGCAGCGAGCTGGAAGTGCAC
AGGACCGTCGCCGCTCCAAGTGTGTTCATTTTTCCCCCTAGCGATGAGCAGCTGAAATCCGGGACAGCCTCTGTGGTCT
GTCTGCTGAACAATTTCTACCCCCGCGAAGCAAAGGTGCAGTGGAAAGTCGACAACGCCCTGCAGAGTGGCAATTCAC
AGGAGAGCGTGACCGAACAGGACTCCAAGGATTCTACATATAGTCTGAGCTCCACTCTGACCCTGTCTAAAGCTGATTA
CGAGAAGCACAAAGTGTATGCATGCGAAGTCACTCATCAGGGCCTGTCTAGTCCTGTGACCAAGAGCTTTAACCGAGG
GGAGTGTTACCCATATGACGTCCCCGATTACGCCTGATAACTCGAG (SEQ ID NO:7)

Nucleic Acid Sequence Encoding the Heavy Chain (VH-CH1) of HIV-1 Env Fab

AAGCTTGCCGCCACCATGGAGACTGATACACTGCTGCTGTGGGTGCTGCTGCTGTGG
GTGCCAGGGTCAACCGGAGATGGGGCTCAGGTCCAGCTGGTCCAGAGCGGCGGACA
GATGAAGAAACCCGGCGAGAGCATGAGGATCTCCTGCAGAGCATCTGGATACGAGT
TCATCGACTGTACCCTGAACTGGATTAGGCTGGCTCCTGGAAAGAGACCAGAGTGG
ATGGGGTGGCTGAAACCACGAGGGGGAGCAGTGAATTACGCCCGGCCCCTGCAGGG
ACGAGTGACCATGACCAGGGACGTGTACAGCGATACCGCCTTCCTGGAGCTGCGGT
CCCTGACAGTGGACGATACTGCTGTCTACTTCTGCACACGCGGAAAGAACTGTGACT
ATAATTGGGATTTTGAACACTGGGGCCGGGGAACACCCGTGATCGTCAGCTCCCCCA
GTACTAAGGGACCTTCAGTGTTTCCACTGGCCCCCTCTAGTAAATCCACCTCTGGAG
GGACAGCCGCTCTGGGATGCCTGGTGAAAGATTATTTCCCCGAACCTGTGACCGTCA
GTTGGAACTCAGGGGCTCTGACTTCTGGCGTGCACACCTTTCCTGCAGTCCTGCAGT
CAAGCGGGCTGTACAGTCTGTCCTCTGTGGTCACTGTGCCTAGTTCAAGCCTGGGCA
CTCAGACCTATATTTGTAACGTGAATCATAAGCCATCCAATACAAAAGTGGACAAA
AAAGCCGAACCCAAATCCTGTTACCCTTATGATGTGCCCGACTACGCCTGACTCGAG
(SEQ ID NO:3)

FIG. 9

Light Chain (VL-CL) of HIV-1 Env Fab

AAGCTTGCCGCCACCATGGAAACCGATACACTGCTGCTGTGGGTGCTGCTGCTGTGG
GTGCCAGGAAGTACCGGGGATGGGGCTCAGGTCCAGATTGTGCTGACTCAGTCCCCT
GGGACCCTGTCTCTGAGTCCAGGCGAGACAGCTATCATTTCATGCCGAACTAGCCAG
TACGGCAGCCTGGCTTGGTATCAGCAGCGACCAGGACAGGCACCACGACTGGTCAT
CTACTCAGGCAGCACAAGGGCCGCTGGCATCCCCGACAGGTTCTCCGGCAGCAGGT
GGGGGCCTGATTACAACCTGACTATCTCTAATCTGGAGAGTGGGGACTTTGGCGTGT
ACTATTGCCAGCAGTATGAGTTCTTCGGCCAGGGAACTAAGGTGCAGGTGGACATC
AAAAGAACCGTGGCAGCCCCATCCGTCTTCATTTTTCCCCCTTCTGATGAGCAGCTG
AAGTCAGGCACCGCCAGCGTGGTCTGTCTGCTGAACAATTTCTACCCCCGGGAAGCC
AAGGTGCAGTGGAAAGTGGACAACGCTCTGCAGAGTGGAAATTCACAGGAGAGCGT
GACCGAACAGGACTCCAAGGATTCTACATATAGTCTGAGCAGCACCCTGACCCTGA
GTAAAGCAGATTACGAGAAGCACAAAGTGTATGCCTGTGAAGTCACACATCAGGGC
CTGAGGAGCCCCGTGACTAAAAGTTTCAACCGAGGAGAGTGCTACCCTTATGATGTG
CCCGACTACGCCTAACTCGAG (SEQ ID NO:4)

FIG. 10

VRC01 IgG

MDWTWILFLVAAATRVHSQVQLVQSGGQMKKPGESMRISCRASGYEFIDCTLNWIRLA
PGKRPEWMGWLKPRGGAVNYARPLQGRVTMTRDVYSDTAFLELRSLTVDDTAVYFCT
RGKNCDYNWDFEHWGRGTPVIVSSPSTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVD
KKAEPKSCEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSL
SLSPGKRGRKRRSGSGATNFSLLKQAGDVEENPGPMDWTWILFLVAAATRVHSEIVLTQ
SPGTLSLSPGETAIISCRTSQYGSLAWYQQRPGQAPRLVIYSGSTRAAGIPDRFSGSRWGP
DYNLTISNLESGDFGVYYCQQYEFFGQGTKVQVDIKRTVAAPSVFIFPPSDEQLKSGTAS
VVCLLNNFYPREAKVQWKVDNALQSGNSQESVTEQDSKDSTYSLSSTLTLSKADYEKH
KVYACEVTHQGLRSPVTKSFNRGEC (SEQ ID NO:5)

FIG. 15

FIG. 17A
Xho I
VL-CL
Ig-E Leader
Furin-GSG-P2A
Ch2
Ch3
Hinge
VH-Ch1
Ig-E Leader
Kozak
BamH1

Amino Acid Sequence of HIV-1 Env-PG9 Ig (before protease cleavage)
MDWTWRILFLVAAATGTHAEFGLSWVFLVAFLRGVQCQRLVESGGGVVQPGSSLRLSC
AASGFDFSRQGMHWVRQAPGQGLEWVAFIKYDGSEKYHADSVWGRLSISRDNSKDTL
YLQMNSLRVEDTATYFCVREAGGPDYRNGYNYYDFYDGYYNYHYMDVWGKGTTVT
VSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTHTCPPCPAPEL
LGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGKRGRKRRSGSGATNFSLLKQAGD
VEENPGPMAWTPLFLFLLTCCPGGSNSQSALTQPASVSGSPGQSITISCNGTSNDVGGYE
SVSWYQQHPGKAPKVVIYDVSKRPSGVSNRFSGSKSGNTASLTISGLQAEDEGDYYCKS
LTSTRRRVFGTGTKLTVLGQPKAAPSVTLFPPSSEELQANKATLVCLISDFYPGAVTVAW
KADSSPVKAGVETTTPSKQSNNKYAASSYLSLTPEQWKSHKSYSCQVTHEGSTVEKTV
APTECS (SEQ ID NO:2)

FIG. 18

Amino Acid Sequence of HIV-1 Env-4E10 Ig (before protease cleavage)
MDWTWRILFLVAAATGTHAQVQLVQSGAEVKRPGSSVTVSCKASGGSFSTYALSWVR
QAPGRGLEWMGGVIPLLTITNYAPRFQGRITITADRSTSTAYLELNSLRPEDTAVYYCAR
EGTTGWGWLGKPIGAFAHWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKS
LSLSPGKRGRKRRSGSGATNFSLLKQAGDVEENPGPMVLQTQVFISLLLWISGAYGEIVL
TQSPGTQSLSPGERATLSCRASQSVGNNKLAWYQQRPGQAPRLLIYGASSRPSGVADRF
SGSGSGTDFTLTISRLEPEDFAVYYCQQYGQSLSTFGQGTKVEKRTVAAPSVFIFPPSDEQ
LKSGTASVVCLLNNFYPREAKVQWKVDNALQSGNSQESVTEQDSKDSTYSLSSTLTLSK
ADYEKHKVYACEVTHQGLSSPVTKSFNRGE (SEQ ID NO:1)

FIG. 19

Nucleic Acid Sequence Encoding the VH-CH1 of anti-Her-2 Fab

GGATCCGCCACCATGGACTGGACATGGATTCTGTTTCTGGTCGCCGCCGCTACAAGAGTGCATTCCGAAGTGCAGCTGG
TCGAGAGTGGAGGGGGACTGGTGCAGCCCGGCGGATCTCTGCGACTGAGTTGCGCCGCTTCAGGCTTCACCTTTACAGA
CTACACCATGGATTGGGTGAGACAGGCACCTGGCAAGGGACTGGAGTGGGTGGCTGATGTCAACCCAAATAGTGGGGG
CTCAATCTACAACCAGAGGTTCAAGGGCAGGTTCACCCTGAGCGTGGACAGGTCCAAAAACACTCTGTATCTGCAGAT
GAATTCTCTGCGGGCTGAAGATACCGCAGTCTACTATTGCGCCCGCAATCTGGGCCCAAGCTTCTACTTTGACTATTGG
GGGCAGGGCACACTGGTGACTGTCAGCTCCGCTTCTACAAAGGGACCAAGCGTGTTCCCACTGGCACCCTCTAGTAAAT
CCACCTCTGGAGGGACAGCAGCCCTGGGCTGTCTGGTGAAAGACTATTTCCCCGAGCCTGTGACTGTCAGCTGGAACTC
CGGAGCACTGACTAGCGGAGTGCACACCTTTCCAGCCGTCCTGCAGTCAAGCGGCCTGTACTCCCTGTCCTCTGTGGTC
ACAGTGCCTAGTTCAAGCCTGGGAACTCAGACCTATATTTGTAATGTGAACCATAAACCAAGCAATACAAAGGTGGAC
AAGAAGGTGGAACCAAAATCCTGCTGATAACTCGAG (SEQ ID NO:40)

FIG. 32

Amino Acid Sequence of the VH-CH1 of anti-Her-2 Fab

MDWTWILFLVAAATRVHSEVQLVESGGGLVQPGGSLRLSCAASGFTFTDYTMDWVRQAPGKGLEWVADVNPNSGGSIYN
QRFKGRFTLSVDRSKNTLYLQMNSLRAEDTAVYYCARNLGPSFYFDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKKVEPKSC
(SEQ ID NO:41)

FIG. 33

Nucleic Acid Sequence Encoding the VL-CL of anti-Her-2 Fab

GGATCCGCCACCATGGATTGGACTTGGATTCTGTTCCTGGTCGCCGCCGCTACCCGCGTGCATTCCGATATTCAGATGA
CTCAGAGCCCCTCCTCACTGTCAGCCAGCGTGGGCGACCGAGTCACCATCACATGCAAAGCTTCTCAGGATGTGAGTAT
TGGGGTCGCATGGTACCAGCAGAAGCCAGGCAAAGCACCCAAGCTGCTGATCTATTCCGCCTCTTACAGGTATACAGG
AGTGCCCAGCAGATTCAGTGGCTCAGGAAGCGGGACTGACTTTACTCTGACCATCAGCTCCCTGCAGCCTGAGGATTTC
GCTACCTACTATTGCCAGCAGTACTATATCTACCCATATACCTTTGGCCAGGGAACAAAAGTGGAGATCAAGCGGACCG
TGGCCGCTCCCTCCGTCTTCATTTTTCCCCCTTCTGACGAACAGCTGAAGAGCGGAACAGCAAGCGTGGTCTGTCTGCT
GAACAATTTCTACCCTCGCGAGGCCAAAGTGCAGTGGAAGGTCGATAACGCTCTGCAGTCCGGGAATTCTCAGGAGAG
TGTGACTGAACAGGACTCAAAAGATAGCACCTATTCCCTGTCTAGTACACTGACTCTGAGCAAGGCAGACTACGAAAA
GCACAAAGTGTATGCCTGTGAGGTCACCCACCAGGGGCTGTCAAGTCCCGTCACCAAGTCCTTCAATAGAGGCGAATG
CTGATAACTCGAG (SEQ ID NO:42)

FIG. 34

Amino Acid Sequence of the VL-CL of anti-Her-2 Fab

MDWTWILFLVAAATRVHSDIQMTQSPSSLSASVGDRVTITCKASQDVSIGVAWYQQKPGKAPKLLIYSASYRYTGVPSRFSG
SGSGTDFTLTISSLQPEDFATYYCQQYYIYPYTFGQGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC (SEQ ID NO:43)

FIG. 35

Nucleic Acid Sequence Encoding anti-DENV Human IgG

GGATCCGCCACCATGGACTGGACTTGGAGGATTCTGTTTCTGGTCGCCGCCGCTACTGGGACTCACGCTCAGGCACATC
TGGTCGAATCTGGAGGAGGAGTGGTCCAGCCTGGCCGATCCCTGCGACTGTCTTGCGCAGCTAGCGCCTTCAACTTCAG
CACAAACGCAATGCACTGGGTGCGACAGGCACCAGGCAAGGGACTGGAGTGGGTCGCTGTGATCTCATACGACGGAA
GCCATAAGTACTATGCAGATTCTGTGAAAGGCCGGTTCACCATTTCCAGGGACAATTCTAAGAACACCCTGTATCTGCA
GATGAATAGCCTGCGCGCAGCCGATACCGCAGTGTACTATTGCGCAACTGTCGGCGTGCTGACCTGGCCAGTGAACGC
CGAATACTTTCACCATTGGGGACAGGGCAGTCTGGTCTCAGTGAGCTCCGCAAGTACTAAGGGACCATCAGTGTTCCCA
CTGGCACCCTCTAGTAAATCTACTAGTGGCGGGACCGCTGCACTGGGATGTCTGGTGAAGGACTATTTCCCCGAGCCTG
TCACCGTGAGCTGGAATTCCGGAGCCCTGACAAGCGGCGTCCACACTTTTCCCGCTGTGCTGCAGTCAAGCGGACTGTA
CTCCCTGTCCTCTGTGGTCACTGTGCCTAGTTCAAGCCTGGGCACTCAGACCTATATCTGCAATGTGAACCACAAGCCCT
CTAACACCAAAGTCGACAAGAAAGTGGAACCTAAGAGCTGTGATAAAACACATACTTGCCCACCTTGTCCAGCACCAG
AGCTGCTGGGAGGACCAAGCGTGTTCCTGTTTCCACCCAAGCCTAAAGACACACTGATGATTAGCCGGACACCTGAAG
TCACTTGCGTGGTCGTGGACGTGTCCCACGAGGACCCCGAAGTCAAGTTTAATTGGTACGTGGATGGCGTCGAGGTGCA
TAACGCCAAGACCAAACCCCGGGAGGAACAGTACAATAGCACATATAGAGTCGTGTCCGTCCTGACTGTGCTGCATCA
GGATTGGCTGAATGGGAAGGAGTATAAGTGCAAAGTGTCTAACAAGGCTCTGCCTGCACCAATCGAGAAAACCATTAG
CAAGGCTAAAGGCCAGCCTAGGGAACCACAGGTGTACACACTGCCTCCAAGTCGCGACGAGCTGACCAAGAATCAGGT
CTCCCTGACATGTCTGGTGAAAGGCTTCTATCCATCAGATATCGCCGTGGAGTGGGAAAGCAACGGGCAGCCCGAAAA
CAATTACAAGACCACACCCCCTGTGCTGGACTCTGATGGCAGTTTCTTTCTGTATTCTAAGCTGACCGTGGACAAAAGT
AGATGGCAGCAGGGGAATGTCTTTTCATGTAGCGTGATGCACGAGGCCCTGCACAACCATTACACACAGAAGTCCCTG
TCTCTGAGTCCCGGAAAGAGGGGCCGCAAACGGAGATCAGGGAGCGGAGCTACTAATTTCAGCCTGCTGAAACAGGCA
GGGGATGTGGAGGAAAACCCCGGACCTATGGCTTGGACCCCACTGTTCCTGTTTCTGCTGACATGCTGTCCCGGGGGCA
GCAATTCTCAGAGTGTCCTGACACAGCCACCATCAGTGAGCGGAGCACCAGGACAGAGGGTGACCATCTCCTGCACAG
GCAGCAGCAGCAACATTGGCGCCGGGTACGACGTGCATTGGTATCAGCAGCTGCCCGGCACCGCTCCTAAGCTGCTGA
TCTGTGGCAACAATAACCGCCCATCTGGGGTGCCCGATCGATTCTCCGGCTCTAAAAGTGGGACTTCAGCCAGCCTGGC
TATTACCGGCCTGCAGGCCGAGGACGAAGCTGATTACTATTGCCAGAGCTACGACTCAAGCCTGACCGGAGTCGTGTTC
GGAGGAGGAACCAAGCTGACAGTCCTGGGACAGCCTAAAGCCGCTCCAAGCGTGACACTGTTTCCTCCATCCTCTGAG
GAACTGCAGGCAAACAAGGCCACCCTGGTGTGCCTGATTTCCGACTTCTACCCCGGGGCAGTCACTGTGGCTTGGAAG
GCAGATAGTTCACCTGTCAAAGCCGGAGTGGAGACTACCACACCATCAAAGCAGAGCAATAACAAATACGCAGCCAG
CTCCTATCTGTCCCTGACCCCTGAGCAGTGGAAGTCTCACAAATCCTATTCTTGCCAGGTCACTCACGAAGGAAGCACT
GTGGAGAAAACTGTCGCACCAACCGAATGTAGTTGATAACTCGAG (SEQ ID NO:44)

FIG. 38

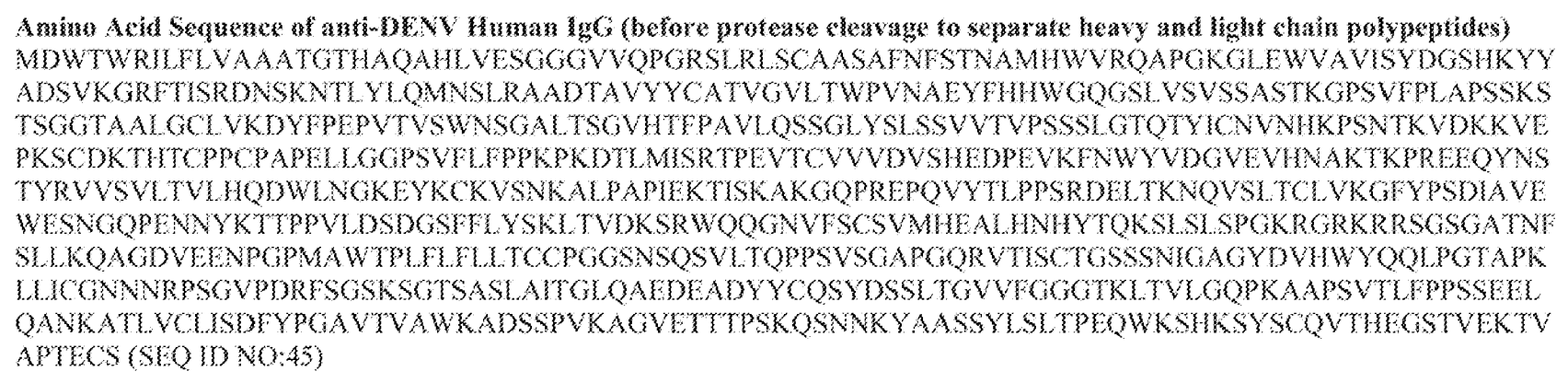

Amino Acid Sequence of anti-DENV Human IgG (before protease cleavage to separate heavy and light chain polypeptides)
MDWTWRILFLVAAATGTHAQAHLVESGGGVVQPGRSLRLSCAASAFNFSTNAMHWVRQAPGKGLEWVAVISYDGSHKYY
ADSVKGRFTISRDNSKNTLYLQMNSLRAADTAVYYCATVGVLTWPVNAEYFHHWGQGSLVSVSSASTKGPSVFPLAPSSKS
TSGGTAALGCLVKDYFPEPVTVSWNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSLSPGKRGRKRRSGSGATNF
SLLKQAGDVEENPGPMAWTPLFLFLLTCCPGGSNSQSVLTQPPSVSGAPGQRVTISCTGSSSNIGAGYDVHWYQQLPGTAPK
LLICGNNNRPSGVPDRFSGSKSGTSASLAITGLQAEDEADYYCQSYDSSLTGVVFGGGTKLTVLGQPKAAPSVTLFPPSSEEL
QANKATLVCLISDFYPGAVTVAWKADSSPVKAGVETTTPSKQSNNKYAASSYLSLTPEQWKSHKSYSCQVTHEGSTVEKTV
APTECS (SEQ ID NO:45)

FIG. 39

IgG Heavy Chain
METDTLLLWVLLLWVPGSTGDGAQVQLVQSGAVIKTPGSSVKISCRASGYNFRDYSIHWVRLIPDKGFEWIGWIKPLWGAV
SYARQLQGRVSMTRQLSQDPDDPDWGVAYMEFSGLTPADTAEYFCVRRGSCDYCGDFPWQYWCQGTVVVVSSASTKGPS
VFPLAPSSKSTSGGTAALGCLVKDYFPEPVTVSWNSGALTSGVHTFPAVLQSSGLYSLSSVVTVPSSSLGTQTYICNVNHKPS
NTKVDKKVEPKSCYPYDVPDYA (SEQ ID NO:46)

FIG. 42

IgG Light Chain
METDTLLLWVLLLWVPGSTGDGAQVQIVLTQSPGILSLSPGETATLFCKASQGGNAMTWYQKRRGQVPRLLIYDTSRRASG
VPDRFVGSGSGTDFFLTINKLDREDFAVYYCQQFEFFGLGSELEVHRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGECYPYDVPDYA
(SEQ ID NO:47)

FIG. 43

Amino Acid Sequence of the Heavy Chain (VH-CH1) of HIV-1 Env Fab
METDTLLLWVLLLWVPGSTGDGAQVQLVQSGGQMKKPGESMRISCRASGYEFIDCTLNWIRLAPGKRPEWMGWLKPRGG
AVNYARPLQGRVTMTRDVYSDTAFLELRSLTVDDTAVYFCTRGKNCDYNWDFEHWGRGTPVIVSSPSTKGPSVFPLAPSSK
STSGGTAALGCLVKDYFPEPVTVSWNSGALTSGVHTFPAVLQSSGLYSLSSVVTVPSSSLGTQTYICNVNHKPSNTKVDKKA
EPKSCYPYDVPDYA (SEQ ID NO:48)

FIG. 44

Amino Acid Sequence of the Light Chain (VL-CL) of HIV-1 Env Fab
METDTLLLWVLLLWVPGSTGDGAQVQIVLTQSPGTLSLSPGETAIISCRTSQYGSLAWYQQRPGQAPRLVIYSGSTRAAGIPD
RFSGSRWGPDYNLTISNLESGDFGVYYCQQYEFFGQGTKVQVDIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLRSPVTKSFNRGECYPYDVPDYA
(SEQ ID NO:49)

FIG. 45

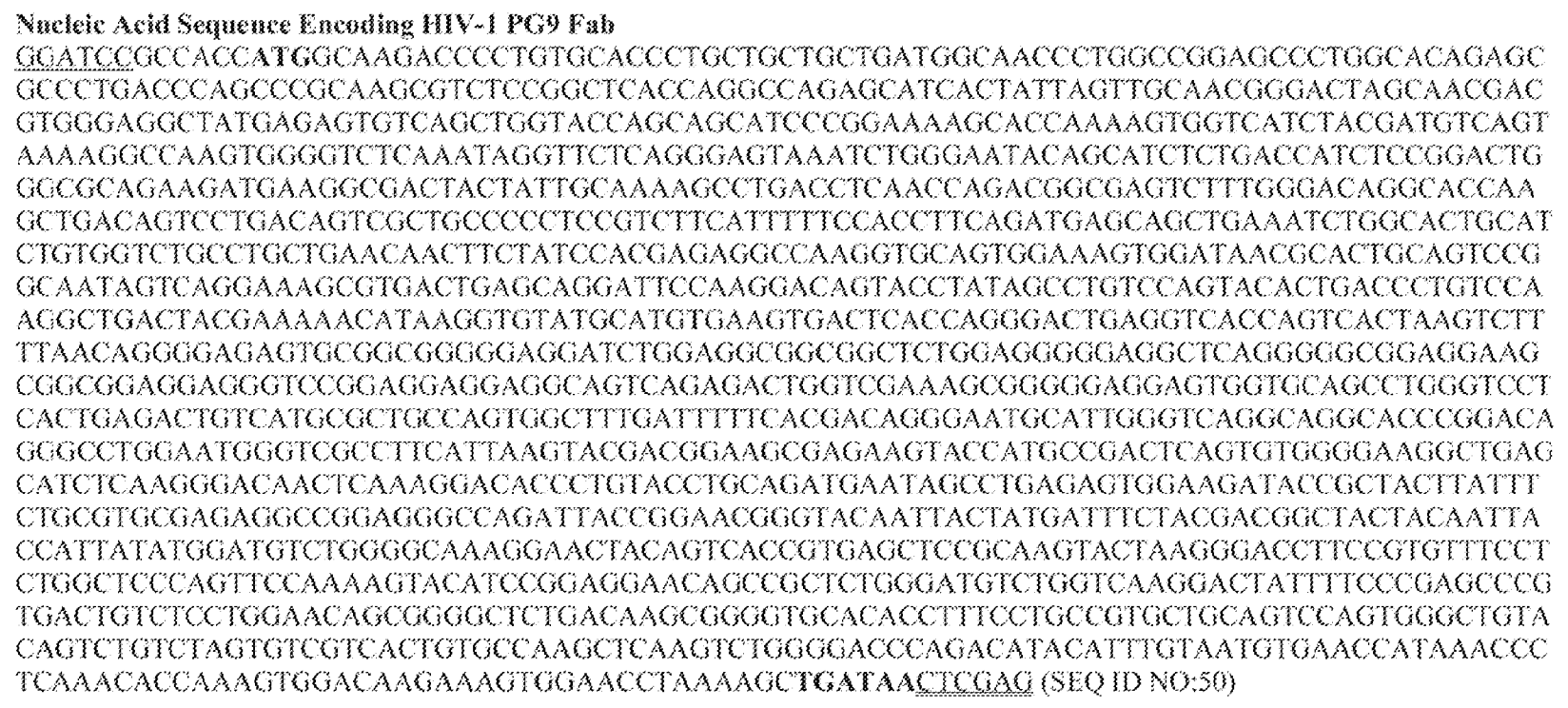

Nucleic Acid Sequence Encoding HIV-1 PG9 Fab

GGATCCGCCACCATGGCAAGACCCCTGTGCACCCTGCTGCTGCTGATGGCAACCCTGGCCGGAGCCCTGGCACAGAGC
GCCCTGACCCAGCCCGCAAGCGTCTCCGGCTCACCAGGCCAGAGCATCACTATTAGTTGCAACGGGACTAGCAACGAC
GTGGGAGGCTATGAGAGTGTCAGCTGGTACCAGCAGCATCCCGGAAAAGCACCAAAAGTGGTCATCTACGATGTCAGT
AAAAGGCCAAGTGGGGTCTCAAATAGGTTCTCAGGGAGTAAATCTGGGAATACAGCATCTCTGACCATCTCCGGACTG
GGCGCAGAAGATGAAGGCGACTACTATTGCAAAAGCCTGACCTCAACCAGACGGCGAGTCTTTGGGACAGGCACCAA
GCTGACAGTCCTGACAGTCGCTGCCCCCTCCGTCTTCATTTTTCCACCTTCAGATGAGCAGCTGAAATCTGGCACTGCAT
CTGTGGTCTGCCTGCTGAACAACTTCTATCCACGAGAGGCCAAGGTGCAGTGGAAAGTGGATAACGCACTGCAGTCCG
GCAATAGTCAGGAAAGCGTGACTGAGCAGGATTCCAAGGACAGTACCTATAGCCTGTCCAGTACACTGACCCTGTCCA
AGGCTGACTACGAAAAACATAAGGTGTATGCATGTGAAGTGACTCACCAGGGACTGAGGTCACCAGTCACTAAGTCTT
TTAACAGGGGAGAGTGCGGCGGGGGAGGATCTGGAGGCGGCGGCTCTGGAGGGGGAGGCTCAGGGGGCGGAGGAAG
CGGCGGAGGAGGGTCCGGAGGAGGAGGCAGTCAGAGACTGGTCGAAAGCGGGGGAGGAGTGGTGCAGCCTGGGTCCT
CACTGAGACTGTCATGCGCTGCCAGTGGCTTTGATTTTTCACGACAGGGAATGCATTGGGTCAGGCAGGCACCCGGACA
GGGCCTGGAATGGGTCGCCTTCATTAAGTACGACGGAAGCGAGAAGTACCATGCCGACTCAGTGTGGGGAAGGCTGAG
CATCTCAAGGGACAACTCAAAGGACACCCTGTACCTGCAGATGAATAGCCTGAGAGTGGAAGATACCGCTACTTATTT
CTGCGTGCGAGAGGCCGGAGGGCCAGATTACCGGAACGGGTACAATTACTATGATTTCTACGACGGCTACTACAATTA
CCATTATATGGATGTCTGGGGCAAAGGAACTACAGTCACCGTGAGCTCCGCAAGTACTAAGGGACCTTCCGTGTTTCCT
CTGGCTCCCAGTTCCAAAAGTACATCCGGAGGAACAGCCGCTCTGGGATGTCTGGTCAAGGACTATTTTCCCGAGCCCG
TGACTGTCTCCTGGAACAGCGGGGCTCTGACAAGCGGGGTGCACACCTTTCCTGCCGTGCTGCAGTCCAGTGGGCTGTA
CAGTCTGTCTAGTGTCGTCACTGTGCCAAGCTCAAGTCTGGGGACCCAGACATACATTTGTAATGTGAACCATAAACCC
TCAAACACCAAAGTGGACAAGAAAGTGGAACCTAAAAGCTGATAACTCGAG (SEQ ID NO:50)

FIG. 46

Amino Acid Sequence of HIV-1 PG9 Fab

MARPLCTLLLLMATLAGALAQSALTQPASVSGSPGQSITISCNGTSNDVGGYESVSWYQQHPGKAPKVVIYDVSKRPSGVSN
RFSGSKSGNTASLTISGLGAEDEGDYYCKSLTSTRRRVFGTGTKLTVLTVAAPSVFIFPPSDEQLKSGTASVVCLLNNFYPREA
KVQWKVDNALQSGNSQESVTEQDSKDSTYSLSSTLTLSKADYEKHKVYACEVTHQGLRSPVTKSFNRGECGGGGSGGGGS
GGGGSGGGGSGGGGSGGGGSQRLVESGGGVVQPGSSLRLSCAASGFDFSRQGMHWVRQAPGQGLEWVAFIKYDGSEKYH
ADSVWGRLSISRDNSKDTLYLQMNSLRVEDTATYFCVREAGGPDYRNGYNYYDFYDGYYNYHYMDVWGKGTTVTVSSAS
TKGPSVFPLAPSSKSTSGGTAALGCLVKDYFPEPVTVSWNSGALTSGVHTFPAVLQSSGLYSLSSVVTVPSSSLGTQTYICNV
NHKPSNTKVDKKVEPKS (SEQ ID NO:51)

FIG. 47

Nucleic Acid Sequence Encoding HIV-1 4E10 Fab

GGATCCGCCACCATGGCAAGACCTCTGTGCACTCTGCTGCTGCTGATGGCTACTCTGGCCGGGGCTCTGGCTGAGATTG
TCCTGACCCAGTCCCCTGGCACTCAGTCACTGTCCCCCGGCGAGCGCGCAACTCTGTCCTGCAGAGCAAGCCAGTCCGT
CGGGAACAACAAGCTGGCATGGTACCAGCAGCGCCCAGGACAGGCACCCAGGCTGCTGATCTACGGAGCAAGCTCCC
GGCCTAGCGGAGTCGCTGATAGATTCTCCGGAAGCGGCTCCGGGACCGATTTCACTCTGACCATCTCCAGGCTGGAACC
TGAGGATTTTGCCGTGTATTACTGTCAGCAGTACGGGCAGAGCCTGTCAACTTTCGGCCAGGGAACTAAAGTCGAAAA
GAGAACCGTGGCCGCACCAAGCGTCTTTATTTTTCCCCCTAGCGATGAACAGCTGAAATCCGGGACTGCTTCCGTGGTC
TGCCTGCTGAATAACTTCTATCCAAGAGAGGCAAAGGTGCAGTGGAAAGTGGACAACGCCCTGCAGAGCGGAAACTCA
CAGGAATCTGTGACAGAGCAGGACTCCAAGGATAGCACATACAGTCTGTCCTCAACTCTGACCCTGTCCAAAGCTGAC
TATGAGAAGCATAAAGTCTACGCATGTGAGGTGACCCACCAGGGACTGAGGTCCCCCGTCACTAAGTCCTTCAATAGA
GGCGAGTGCGGGGGCGGGGGCAGTGGCGGAGGGGGAAGTGGGGGCGGAGGGAGTGGCGGCGGCGGGAGTGGCGGCG
GCGGCTCAGGGGGCGGCGGCTCCCAGGTCCAGCTGGTCCAGAGCGGAGCCGAGGTCAAGAGACCAGGCTCTTCAGTCA
CCGTGAGCTGCAAAGCCAGCGGAGGCTCCTTTAGCACTTACGCCCTGTCATGGGTGCGGCAGGCCCCAGGCCGAGGCC
TGGAGTGGATGGGCGGCGTGATCCCCCTGCTGACCATTACTAACTATGCCCCTAGATTTGGAGGCCGGATCACCATCAC
AGCTGACAGATCCACATCCACAGCTTACCTGGAGCTGAACAGTCTGAGGCCCGAGGACACTGCAGTCTACTACTGTGC
ACGAGAAGGCACCACTGGATGGGGGTGGCTGGGGAAGCCCATCGGGGCTTTTGCACATTGGGGCGGAGGGACACTGGT
GACTGTGAGCTCTGCCAGCACTAAAGGGCCCAGTGTCTTCCCTCTGGCCCCAAGTTCCAAGAGTACATCAGGGGGCACC
GCCGCACTGGGGTGTCTGGTGAAGGATTACTTCCCAGAGCCCGTGACAGTCAGTTGGAACAGCGGCGCTCTGACCAGT
GGGGTGCACACTTTCCCAGCCGTGCTGCAGAGTTCAGGGCTGTACTCCCTGTCCTCAGTGGTGACTGTGCCCTCAAGCA
GTCTGGGGACTCAGACTTACATTTGTAATGTGAACCATAAACCCTCAAATACTAAAGTGGACAAAAAAGTGGAACCAA
AGAGCTGATAACTCGAG (SEQ ID NO:52)

FIG. 48

Amino Acid Sequence of HIV-1 4E10 Fab

MARPLCTLLLLMATLAGALAEIVLTQSPGTQSLSPGERATLSCRASQSVGNNKLAWYQQRPGQAPRLLIYGASSRPSGVADR
FSGSGSGTDFTLTISRLEPEDFAVYYCQQYGQSLSTFGQGTKVEKRTVAAPSVFIFPPSDEQLKSGTASVVCLLNNFYPREAKV
QWKVDNALQSGNSQESVTEQDSKDSTYSLSSTLTLSKADYEKHKVYACEVTHQGLRSPVTKSFNRGECGGGGSGGGGSGG
GGSGGGGSGGGGSGGGGSQVQLVQSGAEVKRPGSSVTVSCKASGGSFSTYALSWVRQAPGRGLEWMGGVIPLLTITNYAP
RFQGRITITADRSTSTAYLELNSLRPEDTAVYYCAREGTTGWGWLGKPIGAFAHWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHKPSNTKVDKKVEP
KS (SEQ ID NO:53)

FIG. 49

Nucleic Acid Sequence Encoding the HIV-1 VRC01 IgG1 Heavy Chain (VH/CH1/Hinge/CH2/CH3)
GGATCCGCCACCATGGATTGGACATGGATTCTGTTCCTGGTCGCCGCCGCAACTAGAGTGCATTCACAGGTGCAGCTGG
TGCAGTCAGGCGGGCAGATGAAGAAACCCGGCGAGAGTATGCGAATCTCATGCCGGGCTAGCGGGTACGAATTCATCG
ACTGTACCCTGAACTGGATTAGACTGGCACCTGGGAAGAGGCCAGAGTGGATGGGATGGCTGAAACCTAGAGGCGGG
GCAGTGAATTACGCCAGACCACTGCAGGGCAGGGTCACTATGACCCGCGACGTGTATTCTGATACCGCATTCCTGGAG
CTGCGAAGTCTGACAGTCGACGATACTGCCGTGTACTTCTGCACACGGGGCAAGAACTGTGACTATAATTGGGATTTTG
AACACTGGGGCAGGGGGACACCTGTCATTGTGAGCTCCCCAAGTACTAAGGGACCCTCAGTGTTTCCCCTGGCCCCTTC
TAGTAAAAGTACCTCAGGAGGCACAGCCGCTCTGGGATGCCTGGTGAAGGATTACTTCCCTGAGCCAGTCACCGTGAG
TTGGAACTCAGGCGCCCTGACAAGCGGGGTCCATACTTTTCCAGCTGTGCTGCAGTCAAGCGGGCTGTACTCCCTGTCC
TCTGTGGTCACAGTGCCCAGTTCAAGCCTGGGAACACAGACTTATATCTGTAACGTCAATCACAAGCCTAGCAATACTA
AAGTGGACAAGAAAGCCGAGCCTAAGAGCTGCGAACCAAAGTCCTGTGATAAAACCCATACATGCCCTCCCTGTCCAG
CTCCTGAACTGCTGGGCGGCCCATCCGTGTTCCTGTTTCCACCCAAGCCCAAAGACACCCTGATGATTAGCAGGACTCC
TGAGGTCACCTGCGTGGTCGTGGACGTGTCCCACGAGGACCCCGAAGTCAAGTTTAACTGGTACGTGGATGGCGTCGA
AGTGCATAATGCCAAGACAAAACCCCGGGAGGAACAGTACAACTCTACCTATAGAGTCGTGAGTGTCCTGACAGTGCT
GCACCAGGACTGGCTGAACGGGAAGGAGTATAAGTGCAAAGTGTCTAATAAGGCCCTGCCAGCTCCCATCGAGAAAAC
AATTTCCAAGGCAAAAGGCCAGCCAAGGGAACCCCAGGTGTACACTCTGCCTCCATCCCGCGACGAGCTGACTAAGAA
CCAGGTCTCTCTGACCTGTCTGGTGAAAGGATTCTATCCAAGCGATATCGCCGTGGAGTGGGAATCCAATGGCCAGCCC
GAGAACAATTACAAGACCACACCCCCTGTGCTGGACAGCGATGGCTCCTTCTTTCTGTATTCAAAGCTGACCGTGGATA
AAAGCCGCTGGCAGCAGGGGAACGTCTTTAGCTGCTCCGTGATGCACGAAGCTCTGCACAATCATTACACCCAGAAGT
CTCTGAGTCTGTCACCTGGCAAGTGATAACTCGAG (SEQ ID NO:54)

FIG. 52

Amino Acid Sequence of the HIV-1 VRC01 IgG1 Heavy Chain (VH/CH1/CH2/CH3)
MDWTWILFLVAAATRVHSQVQLVQSGGQMKKPGESMRISCRASGYEFIDCTLNWIRLAPGKRPEWMGWLKPRGGAVNYA
RPLQGRVTMTRDVYSDTAFLELRSLTVDDTAVYFCTRGKNCDYNWDFEHWGRGTPVIVSSPSTKGPSVFPLAPSSKSTSGGT
AALGCLVKDYFPEPVTVSWNSGALTSGVHTFPAVLQSSGLYSLSSVVTVPSSSLGTQTYICNVNHKPSNTKVDKKAEPKSCE
PKSCDKTHTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSLSPGK (SEQ ID NO:55)

FIG. 53

Nucleic Acid Sequence Encoding the HIV-1 VRC01 IgG Light Chain (VL/CL)

GGATCCGCCACCATGGATTGGACTTGGATTCTGTTCCTGGTGGCAGCCGCTACCAGAGTCCATTCCGAAATTGTGCTGA
CCCAGTCTCCCGGAACACTGTCTCTGAGTCCTGGCGAGACAGCCATCATTTCCTGTAGGACTTCTCAGTACGGGAGTCT
GGCATGGTATCAGCAGCGACCAGGACAGGCTCCTCGACTGGTCATCTACTCAGGAAGCACTCGGGCAGCCGGCATTCC
CGACCGATTCTCCGGGTCTCGGTGGGGACCTGATTACAACCTGACCATCTCAAATCTGGAAAGCGGAGACTTTGGCGTG
TACTATTGCCAGCAGTATGAGTTCTTTGGGCAGGGAACCAAGGTCCAGGTGGACATCAAACGCACAGTCGCTGCACCA
AGCGTGTTCATCTTTCCACCCTCAGATGAACAGCTGAAGTCCGGCACCGCCTCTGTGGTGTGCCTGCTGAACAATTTCTA
CCCCCGGGAGGCAAAGGTCCAGTGGAAAGTGGACAACGCCCTGCAGTCTGGCAATAGTCAGGAGTCAGTGACTGAAC
AGGACAGCAAGGATTCCACCTATTCTCTGTCCTCTACTCTGACCCTGAGCAAAGCTGATTACGAGAAGCACAAAGTGTA
TGCATGTGAGGTCACCCACCAGGGACTGCGGTCACCCGTCACCAAGAGCTTCAATCGCGGAGAGTGTTGATAACTCGA
G (SEQ ID NO:56)

FIG. 54

Amino Acid Sequence of the HIV-1 VRC01 IgG Light Chain (VL/CL)

MDWTWILFLVAAATRVHSEIVLTQSPGTLSLSPGETAIISCRTSQYGSLAWYQQRPGQAPRLVIYSGSTRAAGIPDRFSGSRW
GPDYNLTISNLESGDFGVYYCQQYEFFGQGTKVQVDIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLRSPVTKSFNRGEC (SEQ ID NO:57)

FIG. 55

Nucleic Acid Sequence Encoding the Heavy Chain (VH-CH1) of the CHIKV-Env-Fab

GGATCCGCCACCATGGATTGGACATGGAGGATTCTGTTTCTGGTCGCCGCCGCTACTGGAACTCACGCTCAGGTGCAGC
TGGTGCAGTCAGGGTCCGAACTGAAGAAACCAGGGGCATCTGTGAAGGTCAGTTGCAAAGCCTCAGGCTACACCCTGA
CACGGTATGCCATGACTTGGGTGCGCCAGGCTCCTGGACAGGGACTGGAGTGGATGGGCTGGATCAACACTTACACCG
GAAATCCAACTTATGTGCAGGGGTTCACCGGCCGATTCGTGTTTTCTCTGGACACTTCCGTCTCTACCGCCTTTCTGCAC
ATTACAAGTCTGAAGGCAGAGGACACTGCCGTGTACTTCTGCGCTAGGGAAGGCGGAGCAAGAGGCTTTGATTATTGG
GGCCAGGGAACCCTGGTGACAGTCAGCTCCGCCAGCACAAAGGGACCCTCCGTGTTCCCACTGGCTCCCTCTAGTAAA
AGTACATCAGGGGGCACTGCCGCTCTGGGATGTCTGGTCAAAGATTACTTCCCCGAACCTGTGACCGTCAGCTGGAACT
CCGGAGCTCTGACCAGCGGGGTGCATACATTTCCCGCAGTCCTGCAGTCAAGCGGACTGTACTCCCTGTCCTCTGTGGT
CACAGTGCCTAGTTCAAGCCTGGGGACACAGACTTATATCTGTAATGTGAACCATAAGCCAAGCAACACCAAAGTGGA
CAAAAAAGTGGAACCTAAGAGCTGCTGATAACTCGAG (SEQ ID NO:58)

FIG. 56

Amino Acid Sequence of the Heavy Chain (VH-CH1) of the CHIKV-Env-Fab

MDWTWRILFLVAAATGTHAQVQLVQSGSELKKPGASVKVSCKASGYTLTRYAMTWVRQAPGQGLEWMGWINTYTGNPT
YVQGFTGRFVFSLDTSVSTAFLHITSLKAEDTAVYFCAREGGARGFDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSNTKVDKKVEPKSC
(SEQ ID NO:59)

FIG. 57

Nucleic Acid Sequence Encoding the Light Chain (VL-CL) of the CHIKV-Env-Fab

GGATCCGCCACCATGGCATGGACCCCACTGTTCCTGTTCCTGCTGACTTGTTGTCCTGGCGGGAGCAATTCACAGAGCG
TCCTGACCCAGCCCCCTTCTGTGTCCGGAGCACCAGGACAGCGAGTCACAATCTCTTGCACTGGAAGCTCCTCTAACAT
TGGGGCCAGCCACGACGTGCATTGGTACCAGCAGCTGCCAGGGACCGCTCCCACACTGCTGATCTATGTGAACTCTAAT
AGGCCTAGTGGCGTCCCAGATAGATTTTCAGGGAGCAAGTCCGGCACCTCTGCTAGTCTGGCAATTACAGGACTGCAG
GCTGAGGACGAAGCAGATTACTATTGCCAGAGTTACGACTCAAACCTGTCAGGCAGCGCAGTGTTCGGAGGAGGAACT
AAGCTGACCGTCCTGGGACAGCCCAAAGCCGCTCCTTCTGTGACCCTGTTTCCCCCTAGTTCAGAGGAACTGCAGGCCA
ACAAGGCTACTCTGGTGTGTCTGATCTCCGACTTCTACCCTGGAGCAGTGACCGTCGCATGGAAGGCCGATAGCTCCCC
AGTGAAAGCTGGGGTCGAGACCACAACTCCCAGCAAGCAGTCCAACAACAAGTACGCAGCCTCTAGTTATCTGTCACT
GACACCTGAACAGTGGAAGAGCCACAAATCCTATTCTTGCCAAGTGACTCATGAGGGCAGTACCGTGGAAAAGACAGT
CGCCCCAACTGAGTGTTCCTGATAACTCGAG (SEQ ID NO:60)

FIG. 58

Amino Acid Sequence of the Light Chain (VL-CL) of the CHIKV-Env-Fab

MAWTPLFLFLLTCCPGGSNSQSVLTQPPSVSGAPGQRVTISCTGSSSNIGASHDVHWYQQLPGTAPTLLIYVNSNRPSGVPDR
FSGSKSGTSASLAITGLQAEDEADYYCQSYDSNLSGSAVFGGGTKLTVLGQPKAAPSVTLFPPSSEELQANKATLVCLISDFY
PGAVTVAWKADSSPVKAGVETTTPSKQSNNKYAASSYLSLTPEQWKSHKSYSCQVTHEGSTVEKTVAPTECS (SEQ ID
NO:61)

FIG. 59

Nucleic Acid Sequence Encoding HIV-1 Env-4E10 Ig

GGATCCGCCACCATGGATTGGACATGGAGGATTCTGTTTCTGGTCGCCGCCGCTACAGGAACTCACGCCCAGGTGCAG
CTGGTGCAGTCAGGAGCCGAAGTGAAGCGACCAGGCAGCTCCGTCACTGTGTCCTGCAAAGCATCTGGCGGATCATTC
AGCACCTACGCCCTGAGCTGGGTGAGACAGGCTCCTGGACGAGGACTGGAATGGATGGGAGGCGTCATCCCACTGCTG
ACAATTACTAACTACGCCCCCCGATTTCAGGGCAGGATCACCATTACAGCAGACCGCTCCACTTCTACCGCCTATCTGG
AGCTGAATAGCCTGAGACCAGAAGATACCGCAGTGTACTATTGCGCCCGGGAGGGAACCACAGGATGGGGATGGCTG
GGAAAGCCCATCGGGGCTTTCGCACACTGGGGCCAGGGAACCCTGGTCACAGTGTCTAGTGCCAGCACAAAGGGCCCC
TCCGTGTTTCCCCTGGCTCCTTCAAGCAAAAGTACTTCAGGAGGGACCGCCGCTCTGGGATGTCTGGTGAAGGACTACT
TCCCTGAGCCAGTCACCGTGTCCTGGAACTCTGGCGCTCTGACCTCCGGAGTGCATACATTTCCCGCAGTCCTGCAGTC
CTCTGGGCTGTACTCTCTGAGTTCAGTGGTCACTGTGCCTAGCTCCTCTCTGGGCACACAGACTTATATCTGCAACGTGA
ATCACAAGCCCTCCAATACCAAAGTCGACAAGAAAGTGGAACCTAAGTCTTGTGATAAAACCCATACATGCCCACCTT
GTCCAGCACCTGAGCTGCTGGGCGGACCTTCCGTGTTCCTGTTTCCACCCAAGCCAAAAGACACACTGATGATTAGCCG
GACACCTGAAGTGACTTGTGTGGTCGTGGACGTCAGCCACGAGGACCCCGAAGTGAAGTTCAACTGGTACGTGGATGG
CGTCGAGGTGCATAATGCCAAGACCAAACCCAGGGAGGAACAGTACAACTCTACTTATAGGGTCGTGAGTGTCCTGAC
CGTGCTGCACCAGGACTGGCTGAACGGAAGGAGTATAAGTGCAAAGTGTCCAATAAGGCCCTGCCAGCTCCCATCGA
GAAAACAATTTCTAAGGCTAAAGGCCAGCCACGCGAACCCCAGGTGTACACTCTGCCTCCCAGCAGGGACGAGCTGAC
CAAGAACCAGGTGAGTCTGACATGTCTGGTCAAAGGCTTCTATCCAAGCGATATCGCCGTGGAGTGGGAATCCAATGG
ACAGCCCGAAAACAATTACAAGACTACCCCCCCTGTGCTGGACAGTGATGGATCATTCTTTCTGTATTCCAAGCTGACC
GTGGACAAATCTCGCTGGCAGCAGGGGAACGTCTTTAGCTGCTCCGTGATGCACGAGGCCCTGCACAATCATTACACA
CAGAAGTCTCTGAGTCTGTCACCAGGCAAGCGGGGACGCAAAAGGAGAAGCGGGTCCGGCGCTACTAACTTCAGCCTG
CTGAAACAGGCAGGGGATGTGGAGGAAAATCCTGGCCCAATGGTCCTGCAGACCCAGGTGTTTATCTCACTGCTGCTGT
GGATTAGCGGGGCTTATGGCGAAATCGTGCTGACTCAGAGCCCCGGAACCCAGTCTCTGAGTCCTGGGGAGCGCGCTA
CACTGAGCTGTCGAGCATCACAGAGCGTGGGGAACAATAAGCTGGCATGGTACCAGCAGAGGCCTGGCCAGGCTCCAA
GACTGCTGATCTATGGCGCAAGTTCACGGCCTAGCGGAGTGGCAGACCGCTTCTCCGGATCTGGGAGTGGCACCGATTT
TACTCTGACCATTAGCAGGCTGGAGCCAGAAGACTTCGCTGTGTACTATTGCCAGCAGTACGGCCAGTCACTGAGCACA
TTTGGACAGGGGACTAAGGTCGAAAAAAGAACCGTGGCAGCCCCAAGTGTCTTCATTTTTCCACCCTCAGACGAGCAG
CTGAAGAGTGGAACAGCCTCAGTCGTGTGTCTGCTGAACAATTTCTACCCCAGGGAGGCCAAGGTCCAGTGGAAAGTG
GATAACGCTCTGCAGAGCGGCAATTCCCAGGAGTCTGTGACAGAACAGGACAGTAAGGATTCAACTTATAGCCTGAGC
TCCACACTGACTCTGTCCAAAGCAGATTACGAGAAGCACAAAGTGTATGCCTGCGAAGTCACCCATCAGGGACTGTCT
AGTCCTGTGACAAAGTCTTTTAACAGAGGGGAGTGATAACTCGAG (SEQ ID NO:62)

FIG. 60

Nucleic Acid Sequence Encoding HIV-1 Env-PG9 Ig

GGATCCGCCACCATGGACTGGACTTGGAGGATTCTGTTTCTGGTCGCCGCCGCAACTGGAACTCACGCTGAATTTGGAC
TGTCATGGGTCTTTCTGGTGGCCTTTCTGCGAGGGGTCCAGTGCCAGAGGCTGGTGGAGTCCGGAGGAGGAGTGGTCCA
GCCAGGCAGCTCCCTGCGACTGAGTTGTGCCGCTTCAGGGTTCGACTTTTCTAGACAGGGCATGCACTGGGTGCGGCAG
GCACCAGGACAGGGACTGGAGTGGGTGGCTTTCATCAAGTACGACGGAAGTGAAAAATATCATGCCGATTCAGTGTGG
GGGCGGCTGTCAATTAGCCGCGACAACTCCAAGGATACCCTGTACCTGCAGATGAATTCTCTGAGGGTCGAGGACACA
GCTACTTATTTCTGCGTGAGGGAAGCAGGCGGACCTGATTACAGAAACGGGTATAATTACTATGACTTTTACGATGGCT
ACTATAACTACCACTATATGGACGTGTGGGGCAAGGGAACCACAGTCACAGTGTCTAGTGCATCAACTAAAGGCCCAA
GCGTGTTTCCCCTGGCCCCTTCAAGCAAGTCCACTTCTGGAGGAACCGCAGCACTGGGATGTCTGGTGAAGGATTACTT
CCCTGAGCCAGTCACCGTGAGTTGGAACTCAGGCGCCCTGACTAGCGGAGTCCATACCTTTCCTGCTGTGCTGCAGTCC
TCTGGGCTGTACAGCCTGAGTTCAGTGGTCACAGTGCCAAGCTCCTCTCTGGGCACCCAGACATATATCTGCAACGTGA
ATCACAAGCCTAGCAATACTAAGGTCGACAAAAGAGTGGAACCAAAGAGCTGTGATAAAACTCATACCTGCCCACCTT
GTCCAGCACCTGAGCTGCTGGGAGGGCCTTCCGTGTTCCTGTTTCCACCCAAGCCAAAAGACACCCTGATGATTAGCCG
GACACCAGAAGTCACTTGCGTGGTCGTGGACGTGAGCCACGAGGACCCCGAAGTCAAGTTTAACTGGTACGTGGATGG
CGTCGAGGTGCATAATGCTAAGACAAAACCACGGGAGGAACAGTACAACTCCACATATCGCGTCGTGTCTGTCCTGAC
TGTGCTGCACCAGGACTGGCTGAACGGCAAGGAGTATAAGTGCAAAGTGTCCAATAAGGCACTGCCAGCCCCCATCGA
GAAAACCATTTCTAAGGCCAAAGGCCAGCCACGAGAACCCCAGGTGTACACACTGCCTCCAAGTAGGGACGAGCTGAC
TAAGAACCAGGTCTCTCTGACCTGTCTGGTGAAAGGCTTCTATCCCTCTGATATCGCTGTGGAGTGGGAAAGTAATGGA
CAGCCTGAAAACAATTACAAGACTACCCCCCCTGTGCTGGACAGCGATGGCAGCTTCTTCCTGTATAGCAAGCTGACCG
TGGACAAATCCAGATGGCAGCAGGGGAACGTCTTTAGTTGCTCAGTGATGCACGAGGCACTGCACAATCATTACACCC
AGAAAAGCCTGTCCCTGTCTCCTGGCAAGAGGGGAAGAAAAAGGAGAAGTGGGTCAGGCGCAACAAACTTCAGCCTG
CTGAAGCAGGCCGGAGATGTGGAGGAAAATCCTGGGCCAATGGCTTGGACCCCCCTGTTCCTGTTTCTGCTGACATGCT
GTCCTGGCGGAAGCAACTCCCAGTCTGCACTGACACAGCCAGCAAGTGTGTCAGGGAGCCCAGGACAGAGCATCACCA
TTTCCTGTAACGGCACAAGCAATGACGTCGGGGGCTACGAGTCCGTGTCTTGGTATCAGCAGCATCCTGGAAAGGCCCC
AAAAGTCGTGATCTACGATGTCAGCAAACGCCCCTCTGGGGTGAGTAACCGATTCAGTGGATCAAAGAGCGGGAATAC
CGCTTCTCTGACAATTAGTGGCCTGCAGGCAGAGGACGAAGGAGATTACTATTGCAAATCACTGACAAGCACTCGGCG
CCGAGTCTTCGGAACCGGGACAAAGCTGACTGTGCTGGGCCAGCCCAAAGCTGCACCTAGCGTGACCCTGTTTCCACCC
AGTTCAGAGGAACTGCAGGCTAATAAGGCAACACTGGTGTGTCTGATCTCCGACTTCTACCCTGGCGCTGTCACTGTGG
CCTGGAAGGCTGATAGCTCCCCAGTCAAAGCAGGAGTGGAAACAACTACCCCCTCCAAGCAGTCTAACAACAAGTACG
CCGCTTCTAGTTATCTGTCACTGACTCCCGAGCAGTGGAAGAGCCACAAATCCTATTCTTGCCAGGTGACCCATGAGGG
CTCCACTGTCGAAAAGACCGTGGCCCCTACAGAGTGTTCTTGATAACTCGAG (SEQ ID NO:63)

FIG. 61

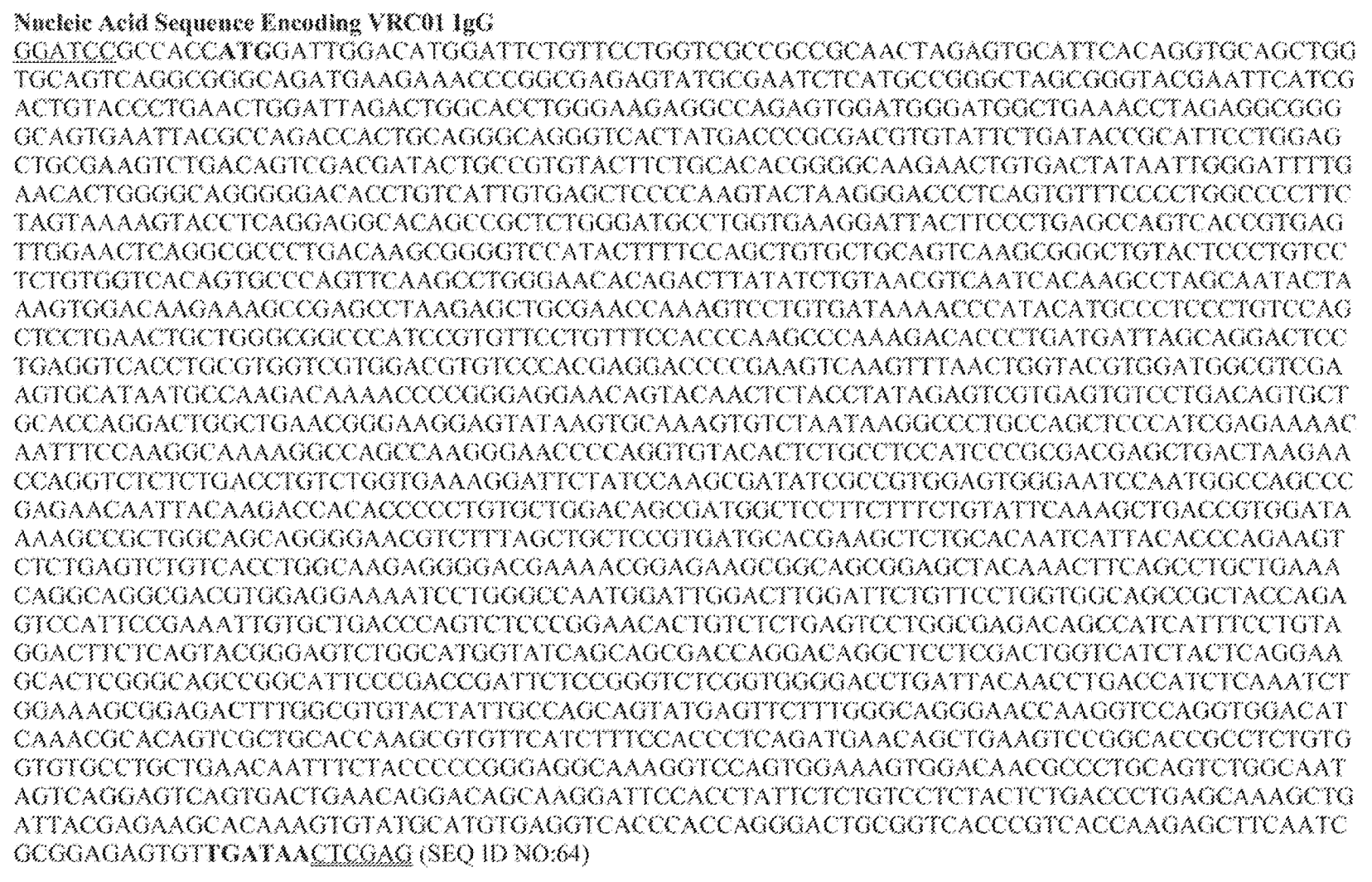

Nucleic Acid Sequence Encoding VRC01 IgG

GGATCCGCCACCATGGATTGGACATGGATTCTGTTCCTGGTCGCCGCCGCAACTAGAGTGCATTCACAGGTGCAGCTGG
TGCAGTCAGGCGGGCAGATGAAGAAACCCGGCGAGAGTATGCGAATCTCATGCCGGGCTAGCGGGTACGAATTCATCG
ACTGTACCCTGAACTGGATTAGACTGGCACCTGGGAAGAGGCCAGAGTGGATGGGATGGCTGAAACCTAGAGGCGGG
GCAGTGAATTACGCCAGACCACTGCAGGGCAGGGTCACTATGACCCGCGACGTGTATTCTGATACCGCATTCCTGGAG
CTGCGAAGTCTGACAGTCGACGATACTGCCGTGTACTTCTGCACACGGGGCAAGAACTGTGACTATAATTGGGATTTTG
AACACTGGGGCAGGGGGACACCTGTCATTGTGAGCTCCCCAAGTACTAAGGGACCCTCAGTGTTTCCCCTGGCCCCTTC
TAGTAAAAGTACCTCAGGAGGCACAGCCGCTCTGGGATGCCTGGTGAAGGATTACTTCCCTGAGCCAGTCACCGTGAG
TTGGAACTCAGGCGCCCTGACAAGCGGGGTCCATACTTTTCCAGCTGTGCTGCAGTCAAGCGGGCTGTACTCCCTGTCC
TCTGTGGTCACAGTGCCCAGTTCAAGCCTGGGAACACAGACTTATATCTGTAACGTCAATCACAAGCCTAGCAATACTA
AAGTGGACAAGAAAGCCGAGCCTAAGAGCTGCGAACCAAAGTCCTGTGATAAAACCCATACATGCCCTCCCTGTCCAG
CTCCTGAACTGCTGGGCGGCCCATCCGTGTTCCTGTTTCCACCCAAGCCCAAAGACACCCTGATGATTAGCAGGACTCC
TGAGGTCACCTGCGTGGTCGTGGACGTGTCCCACGAGGACCCCGAAGTCAAGTTTAACTGGTACGTGGATGGCGTCGA
AGTGCATAATGCCAAGACAAAACCCCGGGAGGAACAGTACAACTCTACCTATAGAGTCGTGAGTGTCCTGACAGTGCT
GCACCAGGACTGGCTGAACGGGAAGGAGTATAAGTGCAAAGTGTCTAATAAGGCCCTGCCAGCTCCCATCGAGAAAAC
AATTTCCAAGGCAAAAGGCCAGCCAAGGGAACCCCAGGTGTACACTCTGCCTCCATCCCGCGACGAGCTGACTAAGAA
CCAGGTCTCTCTGACCTGTCTGGTGAAAGGATTCTATCCAAGCGATATCGCCGTGGAGTGGGAATCCAATGGCCAGCCC
GAGAACAATTACAAGACCACACCCCCTGTGCTGGACAGCGATGGCTCCTTCTTTCTGTATTCAAAGCTGACCGTGGATA
AAAGCCGCTGGCAGCAGGGGAACGTCTTTAGCTGCTCCGTGATGCACGAAGCTCTGCACAATCATTACACCCAGAAGT
CTCTGAGTCTGTCACCTGGCAAGAGGGGACGAAAACGGAGAAGCGGCAGCGGAGCTACAAACTTCAGCCTGCTGAAA
CAGGCAGGCGACGTGGAGGAAAATCCTGGGCCAATGGATTGGACTTGGATTCTGTTCCTGGTGGCAGCCGCTACCAGA
GTCCATTCCGAAATTGTGCTGACCCAGTCTCCCGGAACACTGTCTCTGAGTCCTGGCGAGACAGCCATCATTTCCTGTA
GGACTTCTCAGTACGGGAGTCTGGCATGGTATCAGCAGCGACCAGGACAGGCTCCTCGACTGGTCATCTACTCAGGAA
GCACTCGGGCAGCCGGCATTCCCGACCGATTCTCCGGGTCTCGGTGGGGACCTGATTACAACCTGACCATCTCAAATCT
GGAAAGCGGAGACTTTGGCGTGTACTATTGCCAGCAGTATGAGTTCTTTGGGCAGGGAACCAAGGTCCAGGTGGACAT
CAAACGCACAGTCGCTGCACCAAGCGTGTTCATCTTTCCACCCTCAGATGAACAGCTGAAGTCCGGCACCGCCTCTGTG
GTGTGCCTGCTGAACAATTTCTACCCCCGGGAGGCAAAGGTCCAGTGGAAAGTGGACAACGCCCTGCAGTCTGGCAAT
AGTCAGGAGTCAGTGACTGAACAGGACAGCAAGGATTCCACCTATTCTCTGTCCTCTACTCTGACCCTGAGCAAAGCTG
ATTACGAGAAGCACAAAGTGTATGCATGTGAGGTCACCCACCAGGGACTGCGGTCACCCGTCACCAAGAGCTTCAATC
GCGGAGAGTGTTGATAACTCGAG (SEQ ID NO:64)

FIG. 62

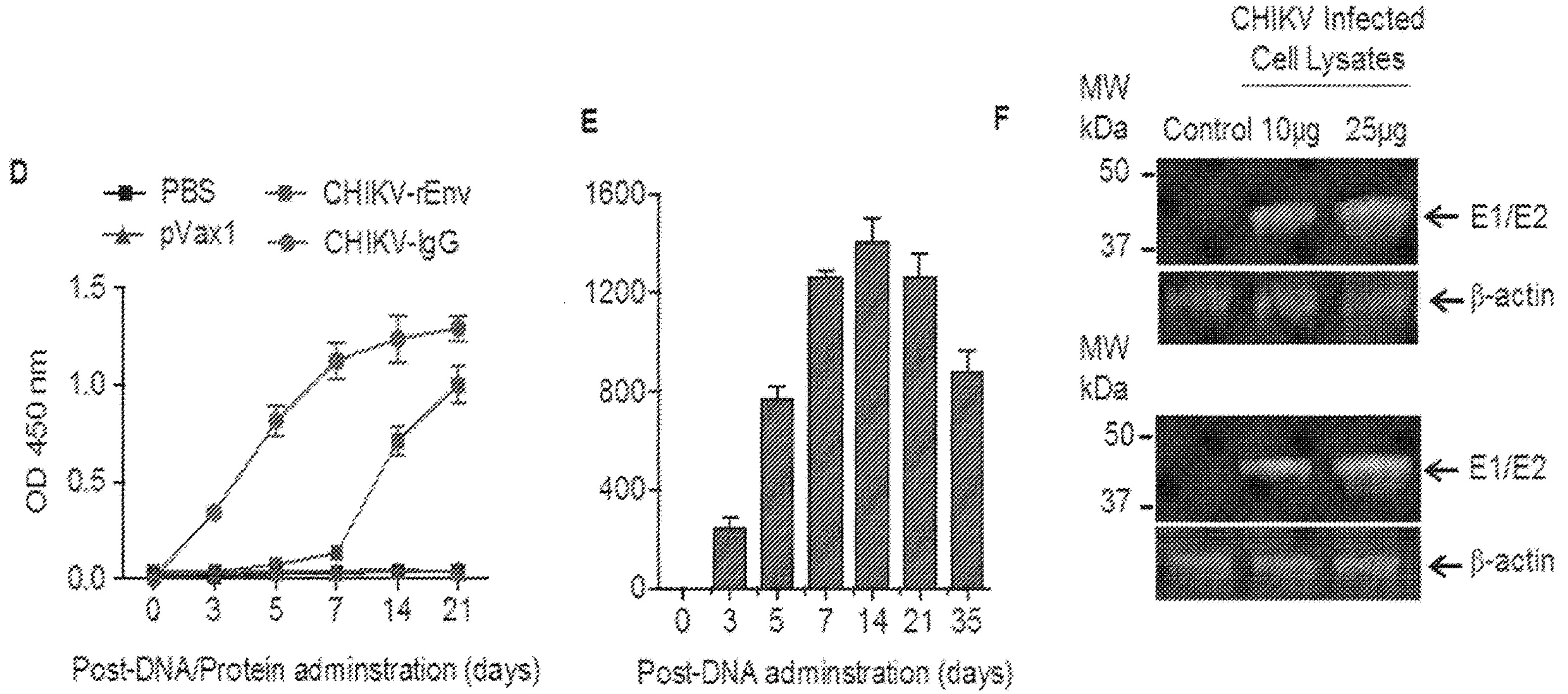
FIG. 63 (con't)

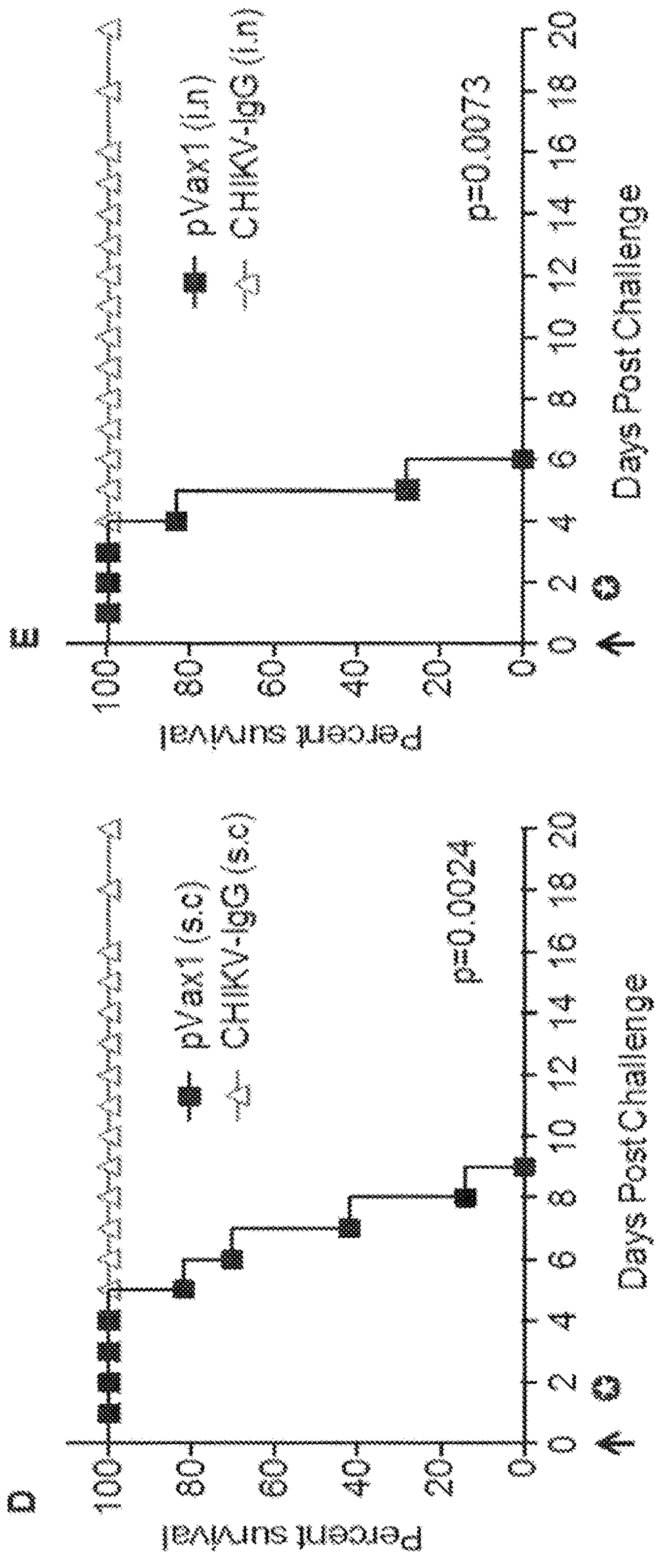
FIG. 66 (con't)

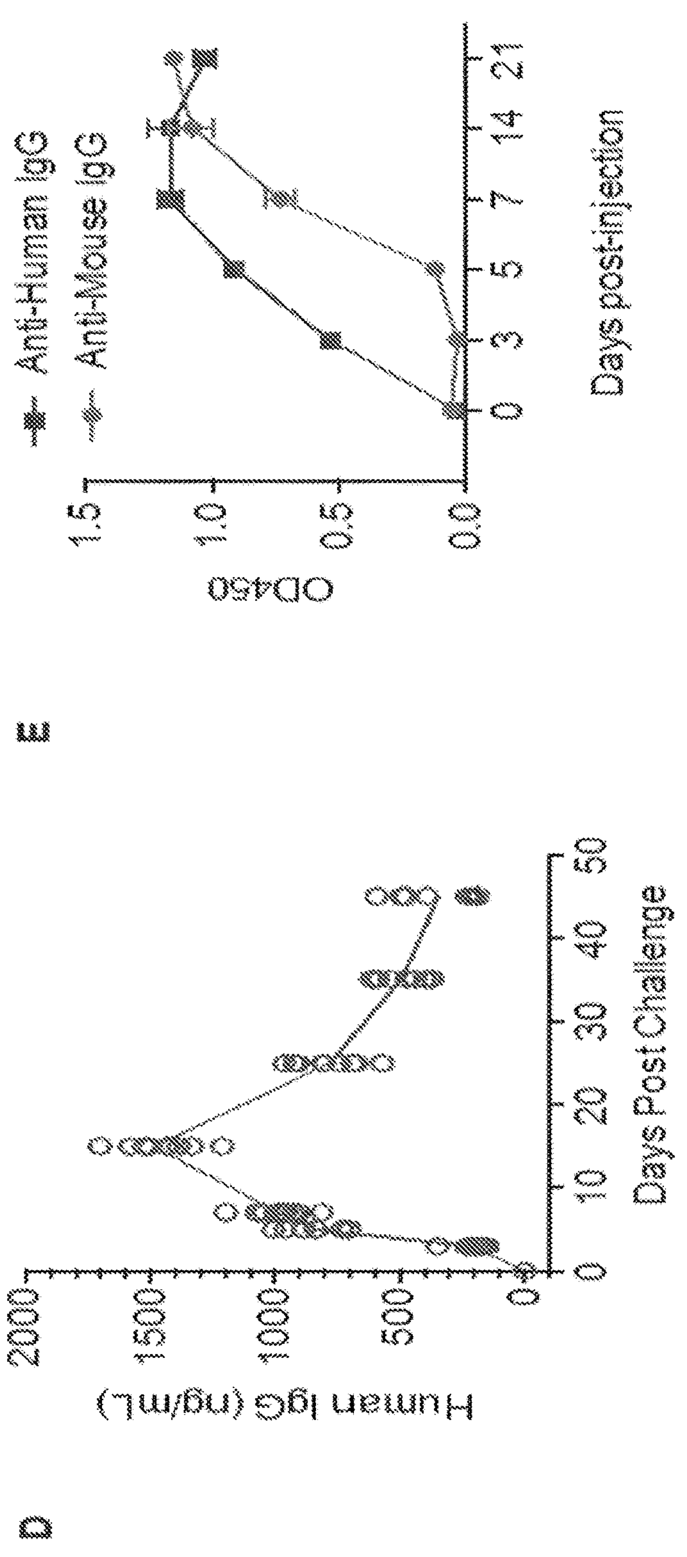
FIG. 67 (con't)

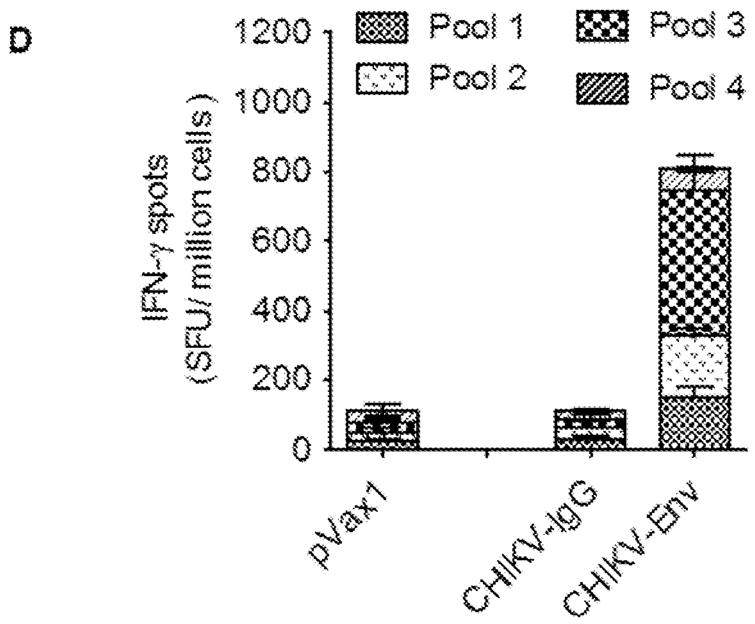
FIG. 68 (con't)

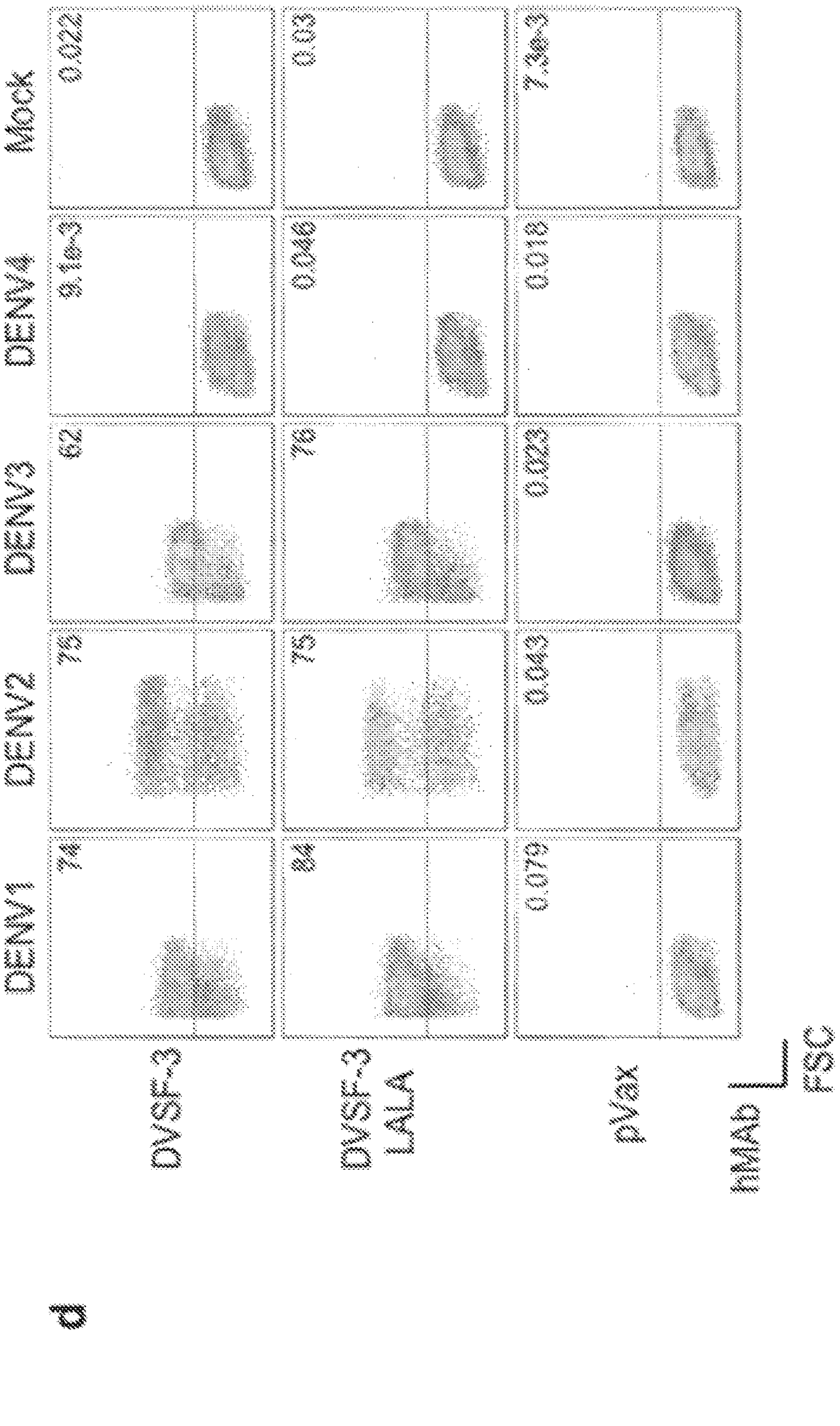
FIG. 69 (con't)

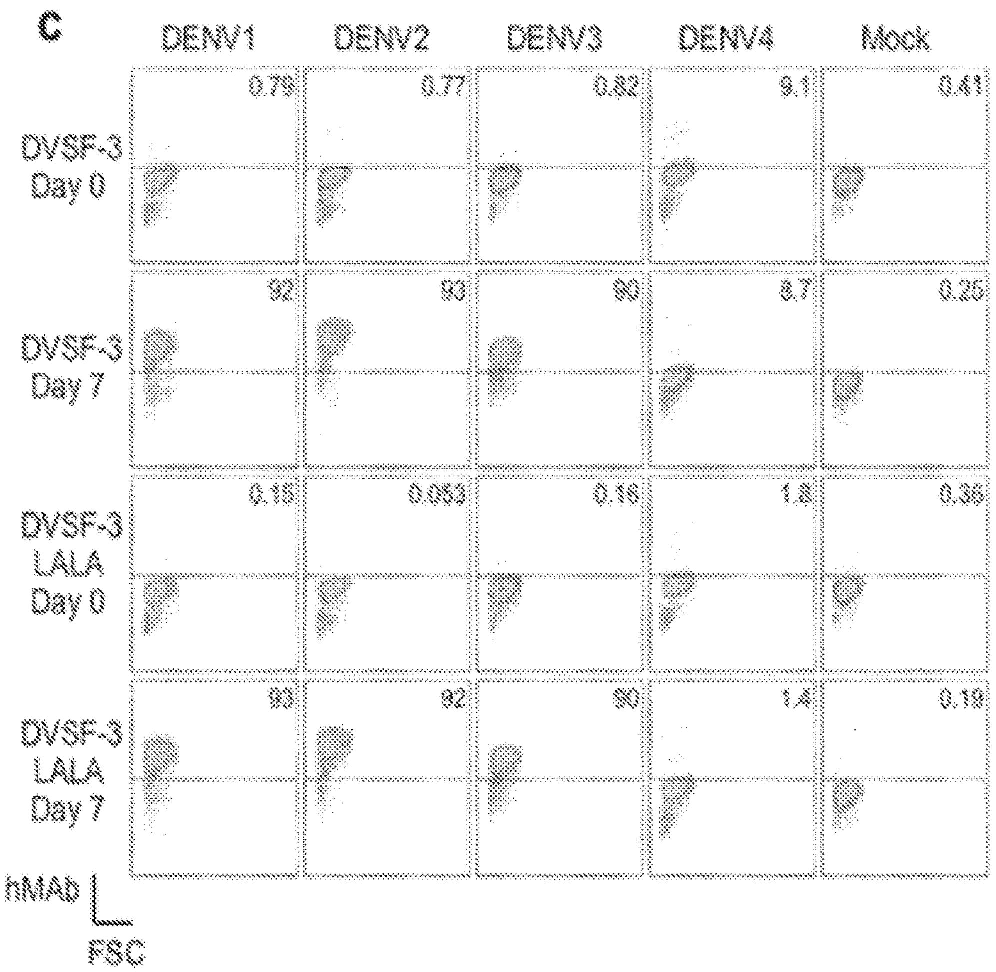
FIG. 70 (con't)

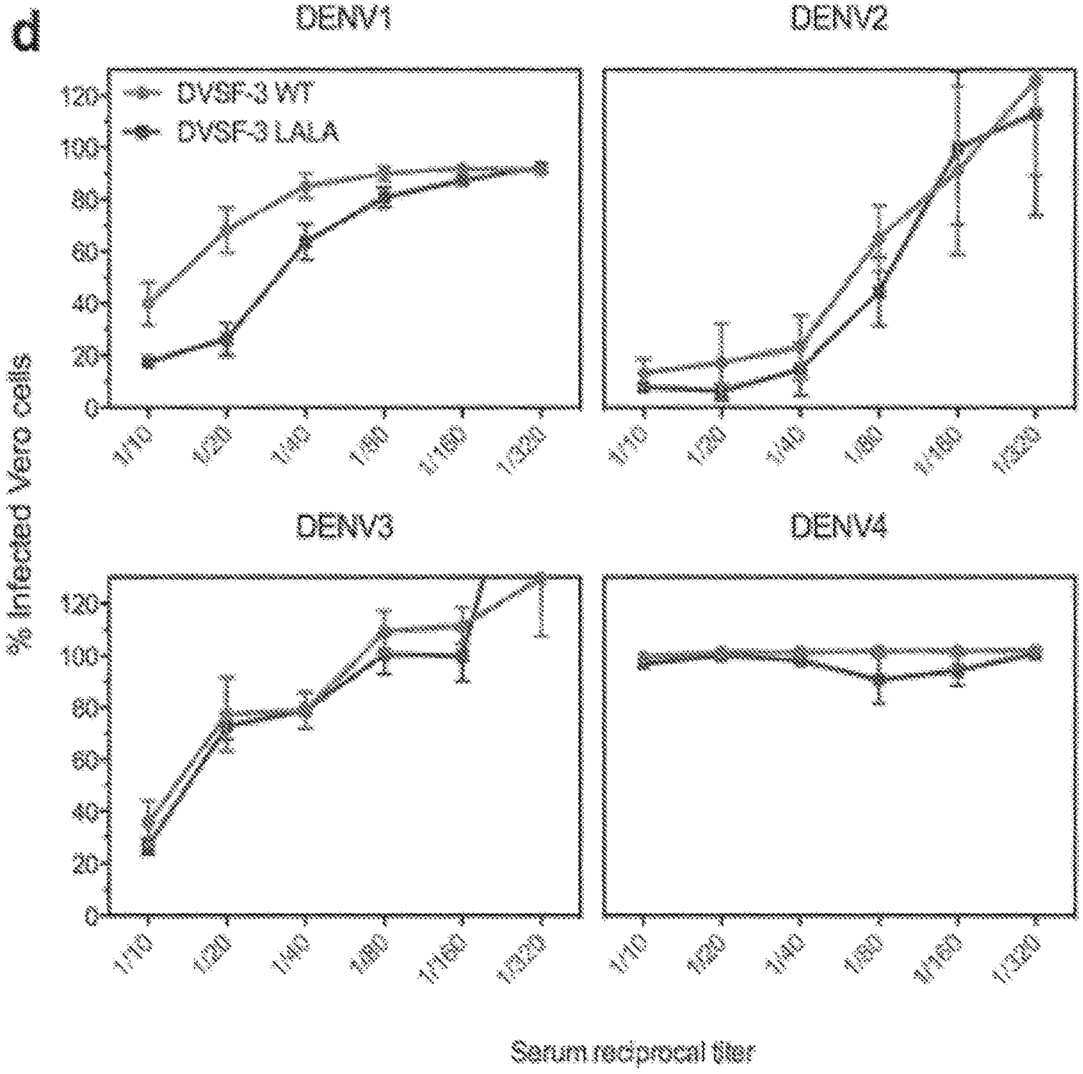
FIG. 70 (con't)

DNA ANTIBODY CONSTRUCTS AND METHOD OF USING SAME

CROSS-REFERENCE TO RELATED APPLICATIONS

This application is the U.S. national stage application filed under 35 U.S.C. § 371 claiming benefit to International Patent Application No. PCT/US14/070188, filed Dec. 13, 2014, which claims priority to PCT/US13/075137, filed Dec. 13, 2013, each of which is hereby incorporated by reference in their entirety.

TECHNICAL FIELD

The present invention relates to a composition comprising a recombinant nucleic acid sequence for generating a synthetic antibody, or fragments thereof, in vivo, and a method of preventing and/or treating disease in a subject by administering said composition.

BACKGROUND

The immunoglobulin molecule comprises two of each type of light (L) and heavy (H) chain, which are covalently linked by disulphide bonds (shown as S—S) between cysteine residues. The variable domains of the heavy chain (VH) and the light chain (VL) contribute to the binding site of the antibody molecule. The heavy-chain constant region is made up of three constant domains (CH1, CH2 and CH3) and the (flexible) hinge region. The light chain also has a constant domain (CL). The variable regions of the heavy and light chains comprise four framework regions (FRs; FR1, FR2, FR3 and FR4) and three complementarity-determining regions (CDRs; CDR1, CDR2 and CDR3). Accordingly, these are very complex genetic systems that have been difficult to assemble in vivo.

Targeted monoclonal antibodies (mAbs) represent one of the most important medical therapeutic advances of the last 25 years. This type of immune based therapy is now used routinely against a host of autoimmune diseases, treatment of cancer as well as infectious diseases. For malignancies, many of the immunoglobulin (Ig) based therapies currently used are in combination with cytotoxic chemotherapy regimens directed against tumors. This combination approach has significantly improved overall survival. Multiple mAb preparations are licensed for use against specific cancers, including Rituxan (Rituximab), a chimeric mAb targeting CD20 for the treatment of Non-Hodgkins lymphoma and Ipilimumab (Yervoy), a human mAb that blocks CTLA-4 and which has been used for the treatment of melanoma and other malignancies. Additionally, Bevacizumab (Avastin) is another prominent humanized mAb that targets VEGF and tumor neovascularization and has been used for the treatment of colorectal cancer. Perhaps the most high profile mAb for treatment of a malignancy is Trastuzumab (Herceptin), a humanized preparation targeting Her2/neu that has been demonstrated to have considerable efficacy against breast cancer in a subset of patients. Furthermore, a host of mAbs are in use for the treatment of autoimmune and specific blood disorders.

In addition to cancer treatments, passive transfer of polyclonal Igs mediate protective efficacy against a number of infectious diseases including diphtheria, hepatitis A and B, rabies, tetanus, chicken-pox and respiratory syncytial virus (RSV). In fact, several polyclonal Ig preparations provide temporary protection against specific infectious agents in individuals traveling to disease endemic areas in circumstances when there is insufficient time for protective Igs to be generated through active vaccination. Furthermore, in children with immune deficiency the Palivizumab (Synagis), a mAb, which targets RSV infection, has been demonstrated to clinically protect against RSV.

Antibody based treatments are not without risks. One such risk is antibody-dependent enhancement (ADE), which occurs when non-neutralising antiviral proteins facilitate virus entry into host cells, leading to increased infectivity in the cells. Some cells do not have the usual receptors on their surfaces that viruses use to gain entry. The antiviral proteins (i.e., the antibodies) bind to antibody Fc receptors that some of these cells have in the plasma membrane. The viruses bind to the antigen binding site at the other end of the antibody. This virus can use this mechanism to infect human macrophages, causing a normally mild viral infection to become life-threatening. The most widely known example of ADE occurs in the setting of infection with the dengue virus (DENV). It is observed when a person who has previously been infected with one serotype of DENV becomes infected many months or years later with a different serotype. In such cases, the clinical course of the disease is more severe, and these people have higher viremia compared with those in whom ADE has not occurred. This explains the observation that while primary (first) infections cause mostly minor disease (DF) in children, secondary infection (re-infection at a later date) is more likely to be associated with severe disease (DHF and/or DSS) in both children and adults. There are four antigenically different serotypes of DENV (DENV-1-DENV-4). Infection with DENV induces the production of neutralizing homotypic immunoglobulin G (IgG) antibodies which provide lifelong immunity against the infecting serotype. Infection with DENV also produces some degree of cross-protective immunity against the other three serotypes. In addition to inducing neutralizing heterotypic antibodies, infection with DENV can also induce heterotypic antibodies which neutralize the virus only partially or not at all. The production of such cross-reactive but non-neutralizing antibodies could be the reason for more severe secondary infections. Once inside the white blood cell, the virus replicates undetected, eventually generating very high virus titers which cause severe disease.

The clinical impact of mAb therapy is impressive. However, issues remain that limit the use and dissemination of this therapeutic approach. Some of these include the high cost of production of these complex biologics that can limit their use in the broader population, particularly in the developing world where they could have a great impact. Furthermore, the frequent requirement for repeat administrations of the mAbs to attain and maintain efficacy can be an impediment in terms of logistics and patient compliance. New antibodies that would reduce or eliminate the low in vivo efficacy of therapeutic antibodies due to competition with serum IgGs are needed. New antibodies that can eliminate antibody dependent enhancement in viruses like Dengue, HIV, RSV and others are needed. Bispecific antibodies, bifunctional antibodies, and antibody cocktails are needed to perform several functions that could prove therapeutic or prophylactic. Additionally, the long-term stability of these antibody formulations is frequently short and less than optimal. Thus, there remains a need in the art for a synthetic antibody molecule that can be delivered to a subject in a safe and cost effective manner.

SUMMARY

The present invention is directed to a nucleic acid molecule encoding a synthetic antibody comprising a nucleic acid sequence having at least about 95% identity over an entire length of the nucleic acid sequence selected from the group consisting of: (a) a nucleic acid sequence as set forth in SEQ ID NO:44; (b) a nucleic acid sequence as set forth in SEQ ID NO:67; (c) a nucleic acid sequence as set forth in SEQ ID NO:69; (d) a nucleic acid sequence as set forth in SEQ ID NO:71; (e) a nucleic acid sequence as set forth in SEQ ID NO:73; (f) a nucleic acid sequence as set forth in SEQ ID NO:75; (g) a nucleic acid sequence as set forth in SEQ ID NO:77; (h) a nucleic acid sequence as set forth in SEQ ID NO:58; (i) a nucleic acid sequence as set forth in SEQ ID NO:60; and (j) a nucleic acid sequence as set forth in SEQ ID NO:65. The present invention is further directed to a method of preventing a disease in a subject in need thereof, the method comprising administering the above nucleic molecule to the subject. The present invention is further directed to a method of treating a disease in a subject in need thereof, the method comprising administering the above nucleic molecule to the subject.

The present invention is also directed to a nucleic acid molecule encoding a synthetic antibody comprising a nucleic acid sequence encoding a protein having at least about 95% identity over an entire length of the amino acid sequence selected from the group consisting of: (a) an amino acid sequence as set forth in SEQ ID NO:45; (b) an amino acid sequence as set forth in SEQ ID NO:68; (c) an amino acid sequence as set forth in SEQ ID NO:70; (d) an amino acid sequence as set forth in SEQ ID NO:72; (e) an amino acid sequence as set forth in SEQ ID NO:74; (f) an amino acid sequence as set forth in SEQ ID NO:76; (g) an amino acid sequence as set forth in SEQ ID NO:78; (h) an amino acid sequence as set forth in SEQ ID NO:59; (i) an amino acid sequence as set forth in SEQ ID NO:61; and (j) an amino acid sequence as set forth in SEQ ID NO:66. The present invention is also directed to a composition comprising the above nucleic acid molecule. The present invention is further directed to a method of preventing a disease in a subject in need thereof, the method comprising administering the above nucleic molecule to the subject. The present invention is further directed to a method of treating a disease in a subject in need thereof, the method comprising administering the above nucleic molecule to the subject.

BRIEF DESCRIPTION OF THE DRAWINGS

FIG. 1 shows the nucleic acid sequence encoding an IgG heavy chain as described in Example 1.

FIG. 2 shows the nucleic acid sequence encoding an IgG light chain as described in Example 1.

FIG. 9 shows the nucleic acid sequence encoding the heavy chain (VH-CH1) of the HIV-1 Env Fab described in Examples 2-7.

FIG. 10 shows the nucleic acid sequence encoding the light chain (VL-CL) of the HIV-1 Env Fab described in Examples 2-7.

FIG. 15 shows the amino acid sequence of the VRC01 IgG.

FIG. 18 shows the amino acid sequence of HIV-1 Env-PG9 Ig before cleavage by furin.

FIG. 19 shows the amino acid sequence of HIV-1 Env-4E10 Ig before cleavage by furin.

FIG. 32 shows the nucleic acid sequence encoding the VH-CH1 of the anti-Her-2 Fab.

FIG. 33 shows the amino acid sequence encoded by the nucleic acid sequence of FIG. 32 (i.e., the amino acid sequence of the VH-CH1 of the anti-Her-2 Fab).

FIG. 34 shows the nucleic acid sequence encoding the VL-CL of the anti-Her-2 Fab.

FIG. 35 shows the amino acid sequence encoded by the nucleic acid sequence of FIG. 34 (i.e., the amino acid sequence of the VL-CL of the anti-Her-2 Fab).

FIG. 38 shows a nucleic acid sequence encoding the anti-Dengue virus (DENV) human IgG.

FIG. 39 shows the amino acid sequence encoded by the nucleic acid sequence of FIG. 39 (i.e., the amino acid sequence of the anti-DENV human IgG). In this amino acid sequence, protease cleavage has not yet occurred to separate the heavy and light chains into two separate polypeptides.

FIG. 42 shows the amino acid sequence encoded by the nucleic acid sequence of FIG. 1 (i.e., SEQ ID NO:6). This amino acid sequence is the amino acid sequence of the IgG heavy chain described in Example 1 below.

FIG. 43 shows the amino acid sequence encoded by the nucleic acid sequence of FIG. 2 (i.e., SEQ ID NO:7). This amino acid sequence is the amino acid sequence of the IgG light chain described in Example 1 below.

FIG. 44 shows the amino acid sequence encoded by the nucleic acid sequence of FIG. 9 (i.e., SEQ ID NO:3). This amino acid sequence is the amino acid sequence of the heavy chain (VH-CH1) of HIV-1 Env-Fab described in Examples 2-7.

FIG. 45 shows the amino acid sequence encoded by the nucleic acid sequence of FIG. 10 (i.e., SEQ ID NO:4). This amino acid sequence is the amino acid sequence of the light chain (VL-CL) of HIV-1 Env-Fab described in Examples 2-7.

FIG. 46 shows the nucleic acid sequence encoding the HIV-1 PG9 single chain Fab (scFab) described in Example 11 below.

FIG. 47 shows the amino acid sequence encoded by the nucleic acid sequence of FIG. 46 (i.e., SEQ ID NO:50). This amino acid sequence is the amino acid sequence of the HIV-1 PG9 scFab described in Example 11 below.

FIG. 48 shows the nucleic acid sequence encoding the HIV-1 4E10 single chain Fab (scFab) described in Example 13 below.

FIG. 49 shows the amino acid sequence encoded by the nucleic acid sequence of FIG. 48 (i.e., SEQ ID NO:52). This amino acid sequence is the amino acid sequence of the HIV-1 4E10 scFab described in Example 13 below.

FIG. 52 shows the nucleic acid sequence encoding the HIV-1 VRC01 IgG1 heavy chain described in Example 9 below.

FIG. 53 shows the amino acid sequence encoded by the nucleic acid sequence of FIG. 52 (i.e., SEQ ID NO:54). This amino acid sequence is the amino acid sequence of the HIV-1 VRC01 IgG1 heavy chain described in Example 9 below.

FIG. 54 shows the nucleic acid sequence encoding the HIV-1 VRC01 IgG light chain described in Example 9 below.

FIG. 55 shows the amino acid sequence encoded by the nucleic acid sequence of FIG. 54 (i.e., SEQ ID NO:56). This amino acid sequence is the amino acid sequence of the HIV-1 VRC01 IgG light chain described below in Example 9.

FIG. 56 shows the nucleic acid sequence encoding the heavy chain (VH-CH1) of the CHIKV-Env-Fab described below in Example 14.

FIG. 57 shows the amino acid sequence encoded by the nucleic acid sequence of FIG. 56 (i.e., SEQ ID NO:58). This amino acid sequence is the amino acid sequence of the heavy chain (VH-CH1) of the CHIKV-Env-Fab described in Example 14 below.

FIG. 58 shows the nucleic acid sequence encoding the light chain (VL-CL) of the CHIKV-Env-Fab described below in Example 14.

FIG. 59 shows the amino acid sequence encoded by the nucleic acid sequence of FIG. 58 (i.e., SEQ ID NO:60). This amino acid sequence is the amino acid sequence of the light chain (VL-CL) of the CHIKV-Env-Fab described in Example 14 below.

FIG. 60 shows the nucleic acid sequence encoding HIV-1 Env-4E10 Ig described in Example 12 below FIG. 61 shows the nucleic acid sequence encoding HIV-1 Env-PG9 Ig described in Example 10 below.

FIG. 62 shows the nucleic acid sequence encoding VRC01 IgG (SEQ ID NO:64)

DETAILED DESCRIPTION

Figure 3:
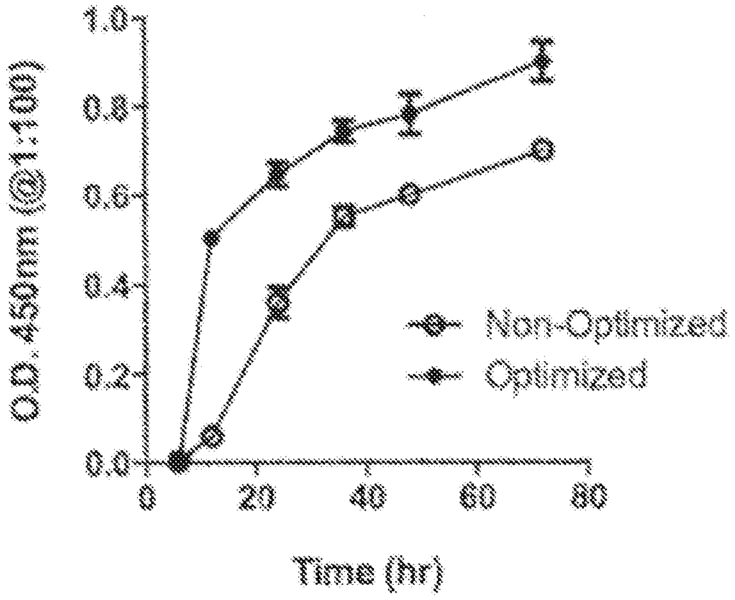
FIG. 3 shows a graph plotting time (hours) vs. OD 450 nm (1:100 dilution of tissue culture supernatant).

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom. The antibody may be a synthetic antibody as described herein.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell.

A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein or variant thereof and is generated in a subject. The synthetic antibody can be engineered to bind to a desired target molecule, thereby eliciting a biological effect. The desired target molecule can be an antigen, a receptor ligand, a receptor, including a ligand-binding site on the receptor, a ligand-receptor complex, a marker, including a marker for cancer, and any other molecule or target that can be bound by an antibody. In some embodiments, the recombinant nucleic acid sequence may have the nucleic acid sequence as set forth in SEQ ID NO:3, 4, 6, 7, 40, 42, 44, 50, 52, 54, 56, 58, 60, 62 63, 64, 65, 67, 69, 71, 73, 75, or 77. In some embodiments, the recombinant nucleic acid sequence may encode the amino acid sequence as set forth in SEQ ID NO:1, 2, 5, 41, 43, 45, 46, 47, 48, 49, 51, 53, 55, 57, 59, 61, 66, 68, 70, 72, 74, 76, or 78.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. For example, the nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the nucleic acid sequence as set forth in SEQ ID NO:3, 4, 6, 7, 40, 42, 44, 50, 52, 54, 56, 58, 60, 62 63, 64, 65, 67, 69, 71, 73, 75, or 77 or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof. For example, the amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence as set forth in SEQ ID NO:1, 2, 5, 41, 43, 45, 46, 47, 48, 49, 51, 53, 55, 57, 59, 61, 66, 68, 70, 72, 74, 76, or 78 or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOSITION

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (e.g., an antigen (which is discussed in more detail below), a ligand, including a ligand for a receptor, a receptor, including a ligand-binding site on the receptor, a ligand-receptor complex, and a marker, including a cancer marker) present in the subject. Such binding can neutralize the antigen, block recognition of the antigen by another molecule, for example, a protein or nucleic acid, and elicit or induce an immune response to the antigen.

The synthetic antibody can treat, prevent, and/or protect against disease in the subject administered the composition. The synthetic antibody by binding the antigen can treat, prevent, and/or protect against disease in the subject administered the composition. The synthetic antibody can promote survival of the disease in the subject administered the composition. The synthetic antibody can provide at least about 50%, 55%, 60%, 65%, 70%, 75%, 80%, 85%, 90%, 95%, or 100% survival of the disease in the subject administered the composition. In other embodiments, the synthetic antibody can provide at least about 65%, 66%, 67%, 68%, 69%, 70%, 71%, 72%, 73%, 74%, 75%, 76%, 77%, 78%, 79%, or 80% survival of the disease in the subject administered the composition.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the synthetic antibody in the subject. The composition can result in the generation of the synthetic antibody in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. RECOMBINANT NUCLEIC ACID SEQUENCE

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include at least one heterologous nucleic acid sequence or one or more heterologous nucleic acid sequences.

The recombinant nucleic acid sequence can be an optimized nucleic acid sequence. Such optimization can increase or alter the binding, and in particular, the biological effect (including neutralizing effect) of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include the heterologous nucleic acid sequence encoding the protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence. The 2A peptide sequence is a self-processing peptide derived from foot and mouth disease virus (FMDV).

In some embodiments, the protease cleavage site can include a combination (e.g., fusion) of the furin cleavage site followed by the 2A peptide sequence. An example of such a combination can be included in arrangement 2, which is described in more detail below, and can be seen, for example, in FIG. 69A. As discussed below in more detail, this combination of the furin cleavage site followed by the 2A peptide sequence can be positioned between the heterologous nucleic acid sequence encoding the heavy chain polypeptide and the heterologous nucleic acid sequence encoding the light chain polypeptide. Accordingly, this combination allows for separation of the heavy chain polypeptide and the light chain polypeptide into distinct polypeptides upon expression and may facilitate equimolar expression of the heavy and light chain polypeptides.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and W094/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

Figure 69:
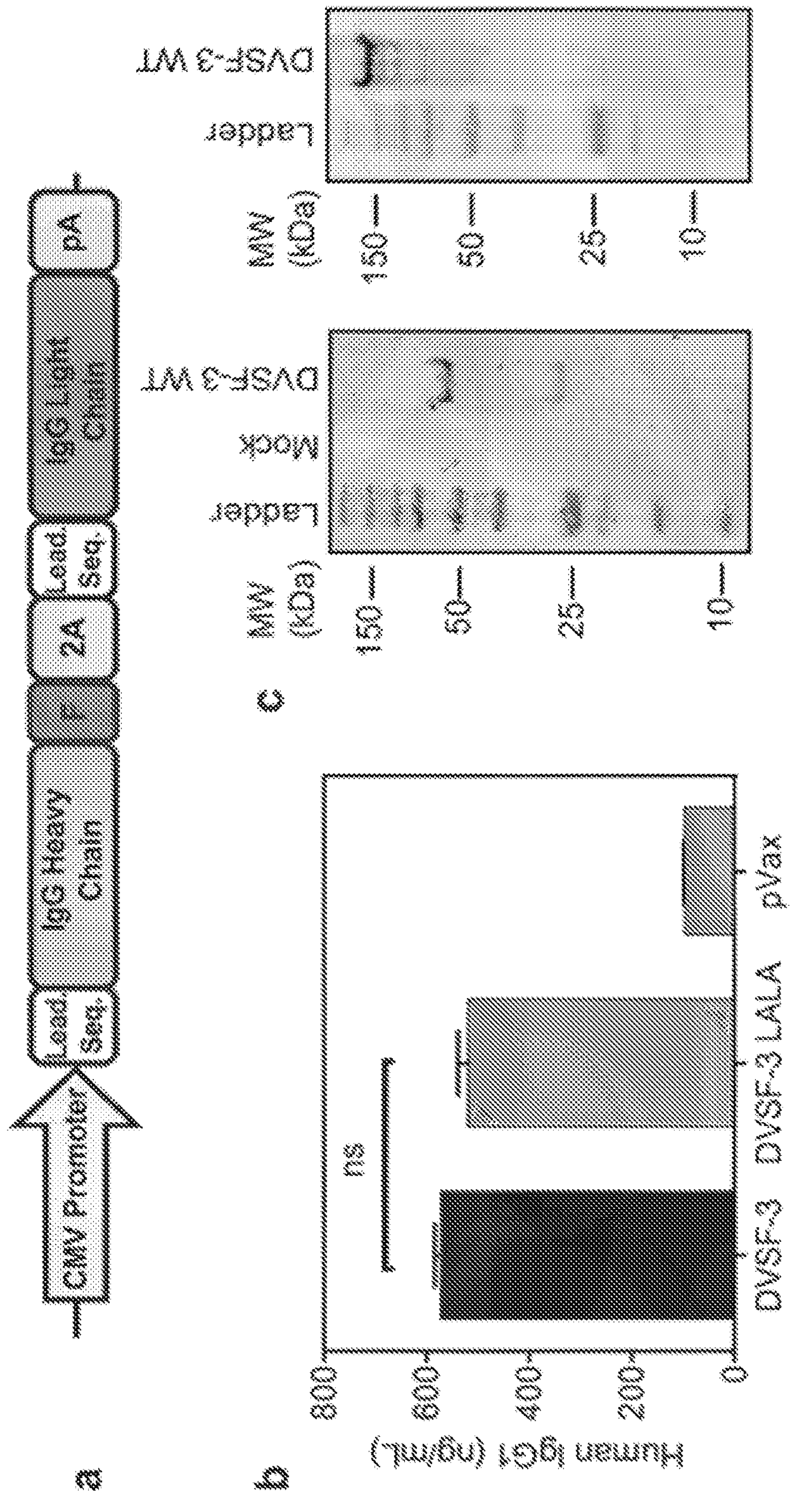
FIG. 69 shows the in vitro expression of human anti-DENV neutralizing mAbs delivered by a DNA construct encoding the antibody. (a) Schematic illustration of the DNA plasmid used for delivery; antibody heavy and light chain sequences are separated by a combination of furin and 2A cleavage sites. (b) ELISA quantification analysis of human IgG in supernatants of pDVSF-3 WT- or LALA-transfected 293T cells. (c) Western blot analysis of pDVSF-3 WT-transfected 293T supernatants containing DVSF-3 WT. Antibodies were purified by Protein A spin columns and separated by SDS-PAGE under reducing (left) and non-reducing (right) conditions. (d) Vero cells were either uninfected (Mock) or infected by DENV1, 2, 3, or 4, then fixed, permeabilized, and stained with supernatants of pDVSF-3 WT- or LALA-transfected 293T cells.

The recombinant nucleic acid sequence construct can include the heterologous nucleic acid sequence encoding the protease cleavage site and/or the linker sequence. As discussed above in more detail, in some embodiments, the protease cleavage site can include a combination (e.g., fusion) of the furin cleavage site followed by the 2A peptide sequence, for example, as shown in FIG. 69A.

If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression and may facilitate equimolar expression of the heavy and light chain polypeptides.

In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A fourth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the desired target molecule, e.g., the antigen, which is discussed in more detail below, a ligand, including a ligand for a receptor, a receptor, including a ligand-binding site on the receptor, a ligand-receptor complex, and a marker, including a cancer marker. In other embodiments, the heavy chain polypeptide and the light chain polypeptide can interact with one another such that assembly results in the synthetic antibody being more effective at binding its target molecule as compared to an antibody not assembled as described herein. In some embodiments, the heavy chain polypeptide and the light chain polypeptide can interact with one another such that assembly results in the synthetic antibody having a desired biological effect, e.g., neutralization, inhibition of a ligand binding to a receptor, and recruitment of immune cells to a cell targeted by the synthetic antibody. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAXI, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNA1 or pcDNA3 (Invitrogen, San Diego, Calif.), which may be used for protein production in mammalian cells such as Chinese hamster ovary (CHO) cells.

(3) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2

(New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(4) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, copending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. ANTIBODY

As described above, the recombinant nucleic acid sequence can encode the antibody, a fragment thereof, a variant thereof, or a combination thereof. The antibody can bind or react with a desired target molecule, which may be the antigen, which is described in more detail below, a ligand, including a ligand for a receptor, a receptor, including a ligand-binding site on the receptor, a ligand-receptor complex, and a marker, including a cancer marker.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the $F(ab')_2$ fragment, which comprises both antigen-binding sites. Accordingly, the antibody can be the Fab or $F(ab')_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject the subject. Such modifications are described below in more detail.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker, including a cancer marker.

b. Bifunctional Antibodies

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

5. ANTIGEN

The synthetic antibody is directed to the antigen or fragment or variant thereof. The antigen can be a nucleic acid sequence, an amino acid sequence, or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof.

The antigen can be from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV).

In some embodiments, the antigen is foreign. In some embodiments, the antigen is a self-antigen.

a. Foreign Antigens

In some embodiments, the antigen is foreign. A foreign antigen is any non-self substance (i.e., originates external to the subject) that, when introduced into the body, is capable of stimulating an immune response.

(1) Viral Antigens

The foreign antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from human immunodeficiency virus (HIV), Chikungunya virus (CHIKV), dengue fever virus, papilloma viruses, for example, human papillomoa virus (HPV), polio virus, hepatitis viruses, for example, hepatitis A virus (HAV), hepatitis B virus (HBV), hepatitis C virus (HCV), hepatitis D virus (HDV), and hepatitis E virus (HEV), smallpox virus (Variola major and minor), vaccinia virus, influenza virus, rhinoviruses, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, lassa virus, arenavirus, or cancer causing virus.

(a) Human Immunodeficiency Virus (HIV) Antigen

The viral antigen may be from Human Immunodeficiency Virus (HIV) virus. In some embodiments, the HIV antigen can be a subtype A envelope protein, subtype B envelope protein, subtype C envelope protein, subtype D envelope protein, subtype B Nef-Rev protein, Gag subtype A, B, C, or D protein, MPol protein, a nucleic acid or amino acid sequences of Env A, Env B, Env C, Env D, B Nef-Rev, Gag, or any combination thereof.

A synthetic antibody specific for HIV can include a Fab fragment comprising the amino acid sequence of SEQ ID NO:48, which is encoded by the nucleic acid sequence of SEQ ID NO:3, and the amino acid sequence of SEQ ID NO:49, which is encoded by the nucleic acid sequence of SEQ ID NO:4. The synthetic antibody can comprise the amino acid sequence of SEQ ID NO:46, which is encoded by the nucleic acid sequence of SEQ ID NO:6, and the amino acid sequence of SEQ ID NO:47, which is encoded by the nucleic acid sequence of SEQ ID NO:7. The Fab fragment comprise the amino acid sequence of SEQ ID NO:51, which is encoded by the nucleic acid sequence of SEQ ID NO:50. The Fab can comprise the amino acid sequence of SEQ ID NO:53, which is encoded by the nucleic acid sequence of SEQ ID NO:52.

A synthetic antibody specific for HIV can include an Ig comprising the amino acid sequence of SEQ ID NO:5. The Ig can comprise the amino acid sequence of SEQ ID NO:1, which is encoded by the nucleic acid sequence of SEQ ID NO:62. The Ig can comprise the amino acid sequence of SEQ ID NO:2, which is encoded by the nucleic acid sequence of SEQ ID NO:63. The Ig can comprise the amino acid sequence of SEQ ID NO:55, which is encoded by the nucleic acid sequence of SEQ ID NO:54, and the amino acid sequence of SEQ ID NO:57, which is encoded by the nucleic acid sequence SEQ ID NO:56.

(b) Chikungunya Virus

The viral antigen may be from Chikungunya virus. Chikungunya virus belongs to the alphavirus genus of the Togaviridae family. Chikungunya virus is transmitted to humans by the bite of infected mosquitoes, such as the genus *Aedes*.

In one embodiment, a synthetic antibody specific for CHIKV can be encoded by the recombinant nucleic acid sequence that includes first and second recombinant nucleic acid constructs in arrangement 1 as described above in more detail. A synthetic antibody specific for CHIKV can include a Fab fragment comprising the amino acid sequence of SEQ ID NO:59, which is encoded by the nucleic acid sequence of SEQ ID NO:58, and the amino acid sequence of SEQ ID NO:61, which is encoded by the nucleic acid sequence of SEQ ID NO:60.

In another embodiment, a synthetic antibody specific for CHIKV can be encoded by the recombinant nucleic acid sequence that includes the recombinant nucleic acid construct in arrangement 2, which is described above in more detail. A synthetic antibody specific for CHIKV can include an immunoglobulin (Ig) comprising the amino acid sequence of SEQ ID NO:66, which is encoded by the nucleic acid sequence of SEQ ID NO:65.

The synthetic antibody specific for CHIKV can provide protection against early and late exposures to CHIKV. The synthetic antibody specific for CHIKV can provide protection against different routes of exposure to CHIKV, for example, but not limited to, subcutaneous or intranasal routes. The synthetic antibody specific for CHIKV can provide protection against CHIKV infection, thereby resulting in survival of the infection.

(c) Dengue Virus

The viral antigen may be from Dengue virus. The Dengue virus antigen may be one of three proteins or polypeptides (C, prM, and E) that form the virus particle. The Dengue virus antigen may be one of seven other proteins or polypeptides (NS1, NS2a, NS2b, NS3, NS4a, NS4b, NS5) which are involved in replication of the virus. The Dengue virus may be one of five strains or serotypes of the virus, including DENV-1, DENV-2, DENV-3 and DENV-4. The antigen may be any combination of a plurality of Dengue virus antigens.

In one embodiment, a synthetic antibody for DENV can be encoded by the recombinant nucleic acid sequence that includes the recombinant nucleic acid construct in arrangement 2, which is described above in more detail. A synthetic antibody specific for Dengue virus can include a Ig comprising the amino acid sequence of SEQ ID NO:45, which is encoded by the nucleic acid sequence of SEQ ID NO:44. In another embodiment, a synthetic antibody specific for Dengue virus can include a Ig comprising the amino acid sequence of SEQ ID NO:68, which is encoded by the nucleic acid sequence of SEQ ID NO:67. In another embodiment, a synthetic antibody specific for Dengue virus can include a Ig comprising the amino acid sequence of SEQ ID NO:72, which is encoded by the nucleic acid sequence of SEQ ID NO:71. In still another embodiment, a synthetic antibody specific for Dengue virus can include a Ig comprising the amino acid sequence of SEQ ID NO:76, which is encoded by the nucleic acid sequence of SEQ ID NO:75.

In some embodiments, the synthetic antibody specific for Dengue virus can include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation, or LA substitution. The one or more amino acids substitutions may include replacing two leucine residues, each with an alanine residue, in the constant region of the antibody and also known herein as LALA, LALA mutation, or LALA substitution. The presence of the LALA substitution may prevent or block the antibody from binding to FcγR1a, and thus, the antibody does not enhance or cause ADE, but still neutralizes DENV.

In some embodiments, the synthetic antibody specific for Dengue virus and containing the LALA substitution can include an Ig comprising the amino acid sequence of SEQ ID NO:70, which is encoded by the nucleic acid sequence of SEQ ID NO:69. In other embodiments, the synthetic antibody specific for Dengue virus and containing the LALA substitution can include an Ig comprising the amino acid sequence of SEQ ID NO:74, which is encoded by the nucleic acid sequence of SEQ ID NO:73. In still other embodiments, the synthetic antibody specific for Dengue virus and containing the LALA substitution can include an Ig comprising the amino acid sequence of SEQ ID NO:78, which is encoded by the nucleic acid sequence of SEQ ID NO:77.

In some embodiments, the synthetic antibody specific for Dengue virus can be a combination of anti-Dengue antibodies, for example, two or more, three or more, or four or more antibodies. Such a combination may provide neutralization of multiple serotypes of DENV.

(d) Hepatitis Antigen

The viral antigen may include a hepatitis virus antigen (i.e., hepatitis antigen), or a fragment thereof, or a variant thereof. The hepatitis antigen can be an antigen or immunogen from one or more of hepatitis A virus (HAV), hepatitis B virus (HBV), hepatitis C virus (HCV), hepatitis D virus (HDV), and/or hepatitis E virus (HEV).

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof.

In some embodiments, the hepatitis antigen can be an antigen from HBV genotype A, HBV genotype B, HBV genotype C, HBV genotype D, HBV genotype E, HBV genotype F, HBV genotype G, or HBV genotype H.

(e) Human Papilloma Virus (HPV) Antigen

The viral antigen may comprise an antigen from HPV. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(f) RSV Antigen

The viral antigen may comprise a RSV antigen. The RSV antigen can be a human RSV fusion protein (also referred to herein as "RSV F," "RSV F protein," and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer, or trimer of the RSV F protein, or a fragment or variant thereof.

The RSV F protein can be in a prefusion form or a postfusion form. The postfusion form of RSV F elicits high titer neutralizing antibodies in immunized animals and protects the animals from RSV challenge.

The RSV antigen can also be human RSV attachment glycoprotein (also referred to herein as "RSV G," "RSV G protein," and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from the RSV subtype B isolate H5601, the RSV subtype B isolate H1068, the RSV subtype B isolate H5598, the RSV subtype B isolate H1123, or a fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, the RSV M2-2 protein from the RSV Long strain, the RSV L protein from the RSV Long strain, the RSV G protein from the RSV subtype B isolate H5601, the RSV G protein from the RSV subtype B isolate H1068, the RSV G protein from the RSV subtype B isolate H5598, the RSV G protein from the RSV subtype B isolate H1123, or fragment thereof, or variant thereof.

(g) Influenza Antigen

The viral antigen may comprise an antigen from influenza virus. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be derived from multiple strains of influenza A serotype H1, serotype H2, a hybrid sequence derived from different sets of multiple strains of influenza A serotype H1, or derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be derived from hemagglutinin antigen sequences from a plurality of influenza A virus strains of one serotype such as a plurality of influenza A virus strains of serotype H1 or of serotype H2. The antigen may be a hybrid hemagglutinin antigen sequence derived from combining two different hemagglutinin antigen sequences or portions thereof. Each of two different hemagglutinin antigen sequences may be derived from a different set of a plurality of influenza A virus strains of one serotype such as a plurality of influenza A virus strains of serotype H1. The antigen may be a hemagglutinin antigen sequence derived from hemagglutinin antigen sequences from a plurality of influenza B virus strains.

In some embodiments, the influenza antigen can be H1 HA, H2 HA, H3 HA, H5 HA, or a BHA antigen.

(h) Ebola Virus

The viral antigen may be from Ebola virus. Ebola virus disease (EVD) or Ebola hemorrhagic fever (EHF) includes any of four of the five known ebola viruses including Bundibugyo virus (BDBV), Ebola virus (EBOV), Sudan virus (SUDV), and Taï Forest virus (TAFV, also referred to as Côte d'Ivoire Ebola virus (Ivory Coast Ebolavirus, CIEBOV).

(2) Bacterial Antigens

The foreign antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis*, methicillin-resistant *Staphylococcus aureus* (MRSA), or *Clostridium difficile*. The bacterium can be *Mycobacterium tuberculosis*.

(a) *Mycobacterium tuberculosis* Antigens

The bacterial antigen may be a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

(3) Parasitic Antigens

The foreign antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing any one of the following diseases: Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be *Acanthamoeba, Anisakis, Ascaris lumbricoides*, Botfly, *Balantidium coli*, Bedbug, *Cestoda* (tapeworm), Chiggers, *Cochliomyia hominivorax*, Entamoeba histolytica, *Fasciola hepatica, Giardia lamblia*, Hookworm, *Leishmania, Linguatula serrata*, Liver fluke, Loa loa, *Paragonimus*-lung fluke, Pinworm, *Plasmodium falciparum*, Schistosoma, *Strongyloides stercoralis*, Mite, Tapeworm, *Toxoplasma gondii, Trypanosoma*, Whipworm, or *Wuchereria bancrofti*.

(a) Malaria Antigen

The foreign antigen may be a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be one of *P. falciparum* immunogens CS; LSA1; TRAP; CelTOS; and Ama1. The immunogens may be full length or immunogenic fragments of full length proteins.

In other embodiments, the malaria antigen can be TRAP, which is also referred to as SSP2. In still other embodiments, the malaria antigen can be CelTOS, which is also referred to as Ag2 and is a highly conserved *Plasmodium* antigen. In further embodiments, the malaria antigen can be Ama1, which is a highly conserved *Plasmodium* antigen. In some embodiments, the malaria antigen can be a CS antigen.

In other embodiments, the malaria antigen can be a fusion protein comprising a combination of two or more of the PF proteins set forth herein. For example, fusion proteins may comprise two or more of CS immunogen, ConLSA1 immunogen, ConTRAP immunogen, ConCelTOS immunogen, and ConAma1 immunogen linked directly adjacent to each other or linked with a spacer or one or more amino acids in between. In some embodiments, the fusion protein comprises two PF immunogens; in some embodiments the fusion protein comprises three PF immunogens, in some embodiments the fusion protein comprises four PF immunogens, and in some embodiments the fusion protein comprises five PF immunogens. Fusion proteins with two PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five PF immunogens may comprise CS or CS-alt, LSA1, TRAP, CelTOS and Ama1.

(4) Fungal Antigens

The foreign antigen can be a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii, dermatophyte, Fusarium* species, *Histoplasma capsulatum, Mucoromycotina, Pneumocystis jirovecii, Sporothrix schenckii, Exserohilum*, or *Cladosporium*.

b. Self Antigens

In some embodiments, the antigen is a self antigen. A self antigen may be a constituent of the subject's own body that is capable of stimulating an immune response. In some embodiments, a self antigen does not provoke an immune response unless the subject is in a disease state, e.g., an autoimmune disease.

Self antigens may include, but are not limited to, cytokines, antibodies against viruses such as those listed above including HIV and Dengue, antigens affecting cancer progression or development, and cell surface receptors or transmembrane proteins.

(1) WT-1

The self-antigen antigen can be Wilm's tumor suppressor gene 1 (WT1), a fragment thereof, a variant thereof, or a combination thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug. Mutation of WT1 can lead to tumor or cancer formation, for example, Wilm's tumor or tumors expressing WT1.

(2) EGFR

The self-antigen may include an epidermal growth factor receptor (EGFR) or a fragment or variation thereof. EGFR (also referred to as ErbB-1 and HER1) is the cell-surface receptor for members of the epidermal growth factor family (EGF-family) of extracellular protein ligands. EGFR is a member of the ErbB family of receptors, which includes four closely related receptor tyrosine kinases: EGFR (ErbB-1), HER2/c-neu (ErbB-2), Her 3 (ErbB-3), and Her 4 (ErbB-4). Mutations affecting EGFR expression or activity could result in cancer.

The antigen may include an ErbB-2 antigen. Erb-2 (human epidermal growth factor receptor 2) is also known as Neu, HER2, CD340 (cluster of differentiation 340), or p185 and is encoded by the ERBB2 gene. Amplification or over-expression of this gene has been shown to play a role in the development and progression of certain aggressive types of breast cancer. In approximately 25-30% of women with breast cancer, a genetic alteration occurs in the ERBB2 gene, resulting in the production of an increased amount of HER2 on the surface of tumor cells. This overexpression of HER2 promotes rapid cell division and thus, HER2 marks tumor cells.

A synthetic antibody specific for HER2 can include a Fab fragment comprising an amino acid sequence of SEQ ID NO:41, which is encoded by the nucleic acid sequence of SEQ ID NO:40, and an amino acid sequence of SEQ ID NO:43, which is encoded by the nucleic acid sequence of SEQ ID NO:42.

(3) Cocaine

The self-antigen may be a cocaine receptor antigen. Cocaine receptors include dopamine transporters.

(4) PD-1

The self-antigen may include programmed death 1 (PD-1). Programmed death 1 (PD-1) and its ligands, PD-L1 and PD-L2, deliver inhibitory signals that regulate the balance between T cell activation, tolerance, and immunopathology. PD-1 is a 288 amino acid cell surface protein molecule including an extracellular IgV domain followed by a transmembrane region and an intracellular tail.

(5) 4-1BB

The self-antigen may include 4-1BB ligand. 4-1BB ligand is a type 2 transmembrane glycoprotein belonging to the TNF superfamily. 4-1BB ligand may be expressed on activated T Lymphocytes. 4-1BB is an activation-induced T-cell costimulatory molecule. Signaling via 4-1BB upregulates survival genes, enhances cell division, induces cytokine production, and prevents activation-induced cell death in T cells.

(6) CTLA4

The self-antigen may include CTLA-4 (Cytotoxic T-Lymphocyte Antigen 4), also known as CD152 (Cluster of differentiation 152). CTLA-4 is a protein receptor found on the surface of T cells, which lead the cellular immune attack on antigens. The antigen may be a fragment of CTLA-4, such as an extracellular V domain, a transmembrane domain, and a cytoplasmic tail, or combination thereof.

(7) IL-6

The self-antigen may include interleukin 6 (IL-6). IL-6 stimulates the inflammatory and auto-immune processes in many diseases including, but not limited to, diabetes, atherosclerosis, depression, Alzheimer's Disease, systemic lupus erythematosus, multiple myeloma, cancer, Behcet's disease, and rheumatoid arthritis.

(8) MCP-1

The self-antigen may include monocyte chemotactic protein-1 (MCP-1). MCP-1 is also referred to as chemokine (C—C motif) ligand 2 (CCL2) or small inducible cytokine A2. MCP-1 is a cytokine that belongs to the CC chemokine family. MCP-1 recruits monocytes, memory T cells, and dendritic cells to the sites of inflammation produced by either tissue injury or infection.

(9) Amyloid beta

The self-antigen may include amyloid beta (Aβ) or a fragment or a variant thereof. The Aβ antigen can comprise an Aβ(X-Y) peptide, wherein the amino acid sequence from amino acid position X to amino acid Y of the human sequence Aβ protein including both X and Y, in particular to the amino acid sequence from amino acid position X to amino acid position Y of the amino acid sequence DAEFRHDSGYEVHHQKLVFFAEDVGSNKGAIIGLMVGGVVIATVIVI (corresponding to amino acid positions 1 to 47; the human query sequence) or variants thereof. The Aβ antigen can comprise an Aβ polypeptide of Aβ(X-Y) polypeptide wherein X can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 and Y can be 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. The Aβ polypeptide can comprise a fragment that is at least 15, at least 16, at least 17, at least 18, at least 19, at least 20, at least 21, at least 22, at least 23, at least 24, at least 25, at least 30, at least 35, at least 36, at least 37, at least 38, at least 39, at least 40, at least 41, at least 42, at least 43, at least 44, at least 45, or at least 46 amino acids.

(10) IP-10

The self-antigen may include interferon (IFN)-gamma-induced protein 10 (IP-10). IP-10 is also known as small-inducible cytokine B10 or C—X—C motif chemokine 10 (CXCL10). CXCL10 is secreted by several cell types, such as monocytes, endothelial cells and fibroblasts, in response to IFN-γ.

(11) PSMA

The self-antigen may include prostate-specific membrane antigen (PSMA). PSMA is also known as glutamate carboxypeptidase II (GCPII), N-acetyl-L-aspartyl-L-glutamate peptidase I (NAALADase I), NAAG peptidase, or folate hydrolase (FOLH). PMSA is an integral membrane protein highly expressed by prostate cancer cells.

c. Other Antigens

In some embodiments, the antigen is an antigen other than the foreign antigen and/or the self-antigen.

(a) HIV-1 VRC01

The other antigen can be HIV-1 VRC01. HIV-1 VCR01 is a neutralizing CD4-binding site-antibody for HIV. HIV-1 VCR01 contacts portions of HIV-1 including within the gp120 loop D, the CD4 binding loop, and the V5 region of HIV-1.

(b) HIV-1 PG9

The other antigen can be HIV-1 PG9. HIV-1 PG9 is the founder member of an expanding family of glycan-dependent human antibodies that preferentially bind the HIV (HIV-1) envelope (Env) glycoprotein (gp) trimer and broadly neutralize the virus.

(c) HIV-1 4E10

The other antigen can be HIV-1 4E10. HIV-1 4E10 is a neutralizing anti-HIV antibody. HIV-1 4E10 is directed against linear epitopes mapped to the membrane-proximal external region (MPER) of HIV-1, which is located at the C terminus of the gp41 ectodomain.

(d) DV-SF1

The other antigen can be DV-SF1. DV-SF1 is a neutralizing antibody that binds the envelope protein of the four Dengue virus serotypes.

(e) DV-SF2

The other antigen can be DV-SF2. DV-SF2 is a neutralizing antibody that binds an epitope of the Dengue virus. DV-SF2 can be specific for the DENV4 serotype.

(f) DV-SF3

The other antigen can be DV-SF3. DV-SF3 is a neutralizing antibody that binds the EDIII A strand of the Dengue virus envelope protein.

6. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 U.S.C. 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. METHOD OF TREATMENT

Also provided herein is a method of treating, protecting against, and/or preventing disease in a subject in need thereof by generating the synthetic antibody in the subject. The method can include administering the composition to the subject. Administration of the composition to the subject can be done using the method of delivery described above.

Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

The present invention has multiple aspects, illustrated by the following non-limiting examples.

11. EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

A high expression system for in vivo immunoglobulin (Ig) generation was constructed. In particular, Ig heavy and light chain sequences were modified in order to improve in vivo expression of the fully assembled Ig molecule, which included 2 heavy and 2 light chain polypeptides. Constructs of gp120IgG-heavy and light chain molecules were created and inserted separately in the pVAX1 vector (Life Technologies, Carlsbad, Calif.). This antibody has defined properties that allow it to be used for characterization studies as described below. Several modifications were included when creating the constructs to optimize expression of the Ig in vivo. Optimization included codon optimization and the introduction of a kozak sequence (GCC ACC). The nucleic acid sequences of the optimized constructs for the heavy and light chains of the Ig are set forth in SEQ ID NO:6 and SEQ ID NO:7, respectively (FIGS. 1 and 2, respectively). In FIGS. 1 and 2, underlining and double underling mark the BamHI (GGA TCC) and XhoI (CTC GAG) restriction enzymes sites used to clone the constructs into the pVAX1 vector while bold marks the start (ATG) and stop (TGA TAA) codons. SEQ ID NO:6 encodes the amino acid sequence set forth in SEQ ID NO:46, i.e., the amino acid sequence of the IgG heavy chain (FIG. 42). SEQ ID NO:7 encodes the amino acid sequence set forth in SEQ ID NO:47, i.e., the amino acid sequence of the IgG light chain (FIG. 43).

Cells were transfected with either native Ig constructs (i.e., not optimized) or constructs containing SEQ ID NOS:6 and 7 (i.e., optimized). After transfection, IgG secretion was measured from the transfected cells and the kinetics of IgG synthesis are shown in FIG. 3. As shown in FIG. 3, both the non-optimized and optimized constructs expressed the heavy and light chains of the Ig to form IgG, but the optimized constructs resulted in quicker accumulation of IgG antibody. Cells transfected with the plasmid containing SEQ ID NOS:6 and 7 (i.e., optimized Ig sequences) showed greater production of fully assembled Ig molecules than did cells transfected with the plasmid containing non-optimized Ig sequences. Accordingly, the optimization or modification of the constructs substantially increased Ig expression. In other words, the constructs containing SEQ ID NOS:6 and 7 provided substantially higher expression of Ig as compared to the native constructs because of the optimization or modification used to create SEQ ID NOS:6 and 7. These data also demonstrated that the heavy and light chains of an Ig can be efficiently assembled in vivo from a plasmid system.

Figure 4:
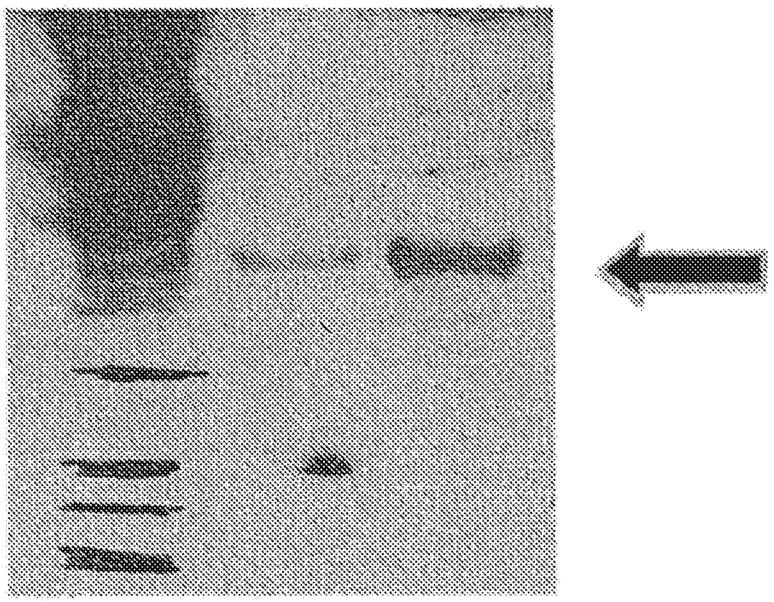
FIG. 4 shows an image of a Western blot.

To further examine the constructs containing SEQ ID NOS:6 and 7, mice were administered plasmid containing the sequences set forth in SEQ ID NOS:6 and 7. In particular, the plasmid was administered using electroporation. After administration, induction of immune response (i.e., IgG level) in the immunized mice was evaluated by Western Blot (i.e., sera from the mice was used to detect the gp120 antigen). As shown in FIG. 4, mice administered the plasmid containing SEQ ID NOS:6 and 7 resulted in strong antibody production because binding of the antibody was observed in the Western blot analysis. Only one administration was required to observe this antibody production.

In summary, these data indicated that nucleic acid sequences encoding Ig heavy and light chains, when included in an expression vector such as pVAX1, resulted in the expression of assembled IgG (i.e., heavy and light chains came together to form an antibody that bound its antigen) in transfected cells and mice administered the expression vector. These data further indicated that optimization or modification of the nucleic acid sequences encoding the Ig heavy and light chains significantly increased Ig production.

Example 2

Materials and Methods for Examples 3-7

Cells and Reagents.

293T and TZM-B1 cells were maintained in Dulbecco's Modified Eagle's medium (DMEM; Gibco-Invitrogen, CA) supplemented with 10% fetal bovine serum (FBS) and antibiotics and passaged upon confluence. Recombinant HIV-1 p24 and gp120 Env (rgp120) proteins were acquired from Protein Science Inc. and peroxidase-conjugated streptavidin from Jackson Laboratory. Cell lines and other reagents listed were obtained from the AIDS Research and Reference Reagent Program, Division of AIDS, NIAID, NIH.

Animals and Protein and Plasmid Administration and Delivery.

Female BALB/c mice (8 weeks of age) were purchased from Taconic Farms (Germantown, N.Y.). For these administrations, 25 μg of plasmid DNA in 50 μl volume (pVax1 or pHIV-1Env-Fab) was injected intramuscularly (IM) followed by EP mediated enhanced delivery by the MID-EP system (CELLECTRA®; Inovio Pharmaceuticals, Blue Bell, Pa.). Pulsing parameters for delivery were: 3 pulses of 0.5 Amp constant current, 1 second apart and 52 ms in length. Each animal received a single administration of either experimental or control plasmid formulations. For the protein immunization analysis, HIV-1 recombinant gp120 (rgp120) from the JRFL strain (purchased from Immune Technology Corp, N.Y.) was used. In the protein immunization study, a single 25 μg dose of the rgp120 was mixed with TiterMax adjuvant and injected subcutaneously. Sera from the pHIV-1 Env Fab or rgp120-administered mice were collected at different time points depending on the particular analysis.

Construction of HIV-1Env-Fab Plasmid DNA.

The HIV-1 Env-Fab sequences (VH and VL) from the anti-Env VRC01 human mAb were generated by use of synthetic oligonucleotides with several modifications. The heavy chain (VH-CH1) is encoded by the nucleic acid sequence set forth in SEQ ID NO:3, and the light chain (VL-CL) is encoded by the nucleic sequence set forth in SEQ ID NO:4 (FIGS. 9 and 10, respectively). In FIGS. 9 and 10, underlining and double underlining mark the HindIII (AAG CTT) and XhoI (CTC GAG) restriction enzyme sites used to clone the encoding nucleic acid sequences into pVAX1 while bold marks the start (ATG) and stop (TGA or TAA) codons. SEQ ID NO:3 encodes the amino acid sequence set forth in SEQ ID NO:48, i.e., the amino acid sequence of the VH-CH1 of HIV-1 Env-Fab (FIG. 44). SEQ ID NO:4 encodes the amino acid sequence set forth in SEQ ID NO:49, i.e., the amino acid sequence of the VL-CL of HIV-1 Env-Fab (FIG. 45).

An efficient IgE leader sequence was incorporated into the Env antigen gene sequences in order to improve expression. The resulting modified and enhanced HIV-1Env-Fab DNA immunogens were codon- and RNA-optimized, followed by cloning into the pVax1 expression vector by GenScript (Piscataway, N.J.), with subsequent large-scale production of these constructs. The VH and VL genes (SEQ ID NOs:3 and 4, respectively) were inserted between the BamH1 and Xho1 restriction sites. Purified plasmid DNA was then formulated in water for subsequent administration into mice. As a negative control plasmid, pIgG-E1M2, which generates an "irrelevant"/control Ig, was used.

HIV-1Env-Fab Expression and Immunoblot Analysis.

The 293T cell line was utilized for expression analysis using the non-liposomal FuGENE6 transfection reagent (Promega, WI), by methods as recommended by the manufacturer. Briefly, cells were seeded at 50-70% confluence ($1\text{-}3\times10^5$ cells/2 mL per well in 35 mm culture dish) 24 hours before subsequent transfection with 5 μg of the pVax1 control or pHIV-1Env-Fab. Supernatants were collected at various time points up to 70 hours and assessed for levels of specific Fab molecules by standard ELISA methods. Supernatants from pVax1 transfected cells were used as a negative control. In addition, 293T cells were transfected with a gene for the HIV gp160 Env protein.

Further confirmation of recognition of native HIV-1 Env protein by the generated Fab was performed by immunoblot analysis. For this study, rgp120, described above, underwent electrophoresis on 12% SDS-PAGE. The gel was blotted onto a nitrocellulose membrane (Millipore, Bedford, Mass.) and blocked with 5% w/v nonfat dry milk in PBS-T (0.05%). The nitrocellulose was then subsequently cut into individual strips for analysis. Sera from pHIV-1 Env Fab administered mice, collected 48 hours after administration, were diluted 1:100 in PBS and reacted with individual nitrocellulose strips for 1 hour. Subsequently, strips were washed 4 times with Tris-buffered saline-0.2% Tween, reacted with a peroxidase-coupled antiserum against mouse IgG (Jackson Laboratories, ME), and incubated with diaminobenzidine substrate (Sigma, St. Louis, Mo.), allowing for the visualization of proper binding of the generated HIV-1 Env Fab to gp120.

Ig Binding Analysis—ELISA.

Confirmation of binding of DNA plasmid generated Fab or anti-rgp120 antibody to rgp120 by ELISA was evaluated. Ig binding assays were carried out with sera from individual animals administered either pHIV-1 Env Fab, pVax1 or rgp120 protein. Again, for this basic Ig immunoassay analysis, sera samples were collected 48 hours after the single DNA plasmid administration. Briefly, 96-well high-binding polystyrene plates (Corning, N.Y.) plates were coated overnight at 4° C. with clade B HIV MN rgp120 (2 μg/mL), diluted in PBS. The following day, plates were washed with PBS-T (PBS, 0.05% Tween 20), blocked for 1 hour with 3% BSA in PBS-T, and incubated with 1:100 dilutions of serum from immunized and naïve mice for 1 hour at 37° C. Bound IgG was detected using goat anti-mouse IgG-HRP (Research Diagnostics, N.J.) at a dilution of 1:5,000. Bound enzyme were detected by the addition of the chromogen substrate solution TMB (R&D Systems), and read at 450 nm on a Biotek EL312e Bio-Kinetics reader. All sera samples were tested in duplicate. An additional immunoassay analysis was performed which quantified the Fab concentrations in sera from pHIV-1 Env Fab administered mice using a commercial IgG1 quantitation ELISA kit. This analysis was performed by manufacturer's specifications.

Flow Cytometric Analysis (FACS).

For flow cytometry analyses (FACS), 293T cells were transfected with either a concensus clade A Env plasmid (pCon-Env-A) or an optimized clade A plasmid (pOpt-Env-A) expressing an Env from a primary viral isolate (Q23Env17). Transfection was performed by standard methods. After confirmation of transfection, cells were washed with ice-cold buffer A (PBS/0.1% BSA/0.01% NaN3) and incubated for 20 min at 4° C. with a 1:100 dilution of primary Ig (either purified VRC01 or sera from mice injected with either pHIV-1 Env Fab or control pIgG-E1M2 plasmid, collected 48 hours after plasmid administration). This was followed by washing and incubation for another 20 min with 50 μl of a 1:100 diluted fluorescent-labeled secondary Igs conjugated to phycoerythrin (PE). Cells were then washed and immediately analyzed on a flow cytometer (Becton Dickinson FACS). All incubations and washes were performed at 4° C. with ice-cold buffer A. Cells were gated on singlets and live cells. To assess GFP expression GFP-positive cells was performed with a FACS-LSR instrument using CellQuest software (BD Bioscience). Data were analyzed with Flow Jo software.

Single-Cycle HIV-1 Neutralization Assay.

Fab mediated HIV-1 neutralization analysis was measured with a TZM-BI (HeLa cell derived) based assay in which a reduction in luciferase gene expression as used as an endpoint for neutralization, following a single round of infection with Env-pseudotyped virus in the presence or absence of experimental or control sera. The TZM-B1 cells were engineered to express CD4 and CCR5 and contained reporter genes for firefly luciferase. In this assay, sera from mice administered pVax1 only or pHIV-1Env Fab were diluted 1:50 in wells followed by addition of pseudotyped HIV-1 Ba126, Q23Env17, SF162S or ZM53M cell free virus, at a multiplicity of infection (MOI) of 0.01. Both Ba126 and SF162S are clade B tier 1 viruses, with this tier status indicating that the viruses had high or above average sensitivity to neutralization. Q23Env17 and ZM53M are clade A, Tier 1 and clade C, Tier 2 viruses, respectively. Tier 2 status indicated that the virus had average or moderate sensitivity to neutralization. Subsequently in this assay, $10^4$ TZM-BL cells were added to each well, incubated for 48 hours, lysed and followed by subsequent addition of 100 μl of Bright-Glo substrate (Luciferase Assay System, Promega, WI), followed by luciferase quantitation using a luminometer. The readout of this assay was RLU (relative light units). The percentages of RLU reduction were calculated as (1−(mean RLU of experimental samples-controls)/mean RLU from controls-no addition control wells))×100. HIV-1 neutralization was then expressed as percent decrease in RLU, which was indicative of the percent inhibition of infection.

Example 3

Generation of Anti-HIV-1 Env-Fab Expressing Constructs

Figure 5A:
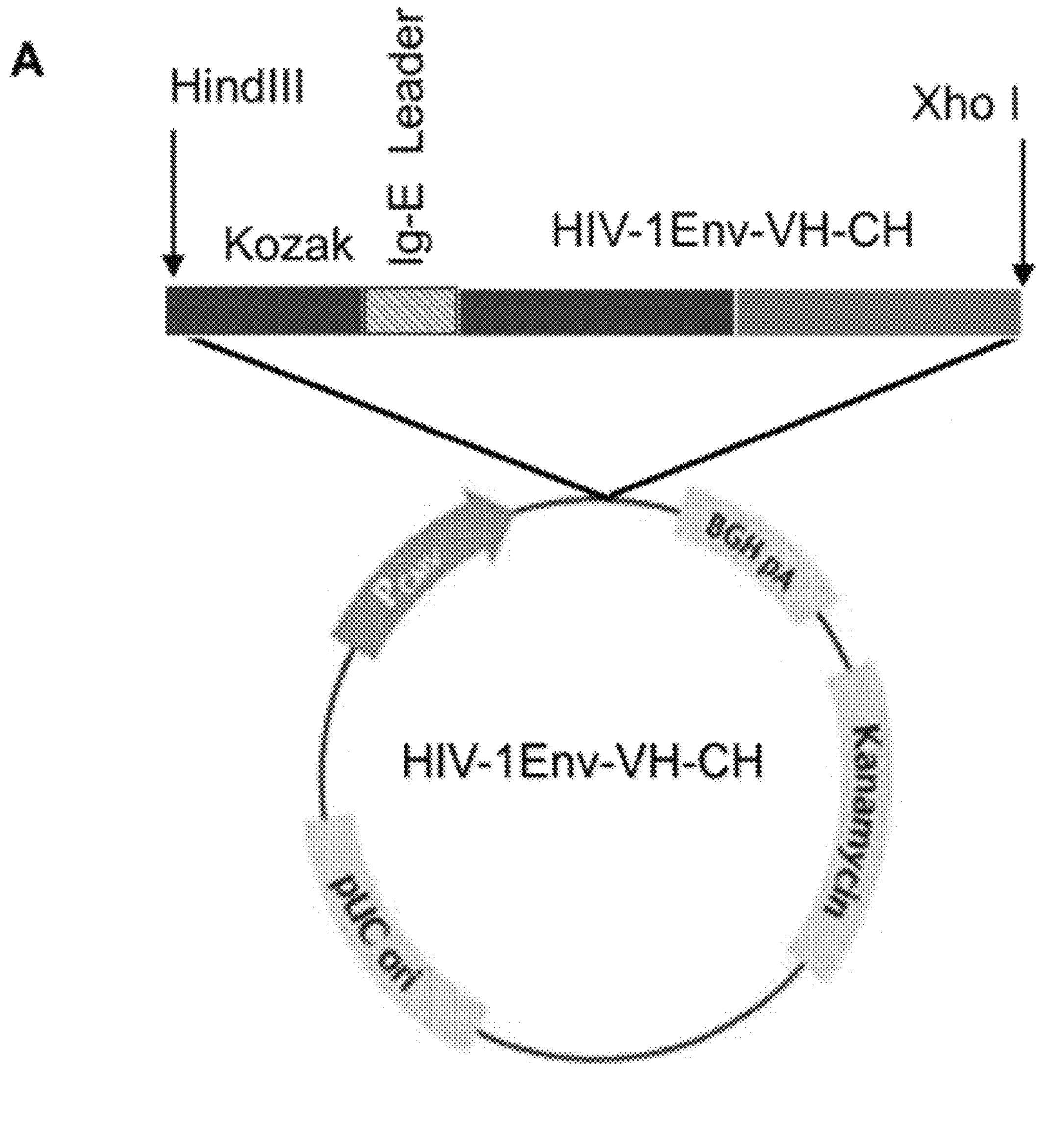
FIG. 5 shows generation and confirmation of expression of pHIV-1Env-Fab. (A & B) Circular plasmid map of pHIV-1 Env Fab anti-gp120 Fab expressing construct were designed using VRC01 heavy (H) and light (L) variable chain Ig genes. Several modifications were included when constructing the Fab plasmids in order to increase the level of expression. The Fab VL and VH fragment genes, as shown, were cloned separately between the BamH1 and Xho1 restriction sites of the pVax1 vector. (C) In vitro expression of pHIV-1 Env Fab. The graph indicated the temporal kinetics of expression of the pHIV-1 Env Fab after transfection of 293T cells. The values indicated, indicative of expression, are mean OD450 nm±SD of triplicate wells. As a control 293T cells were also transfected with the pVax1 backbone.
Figure 5B:
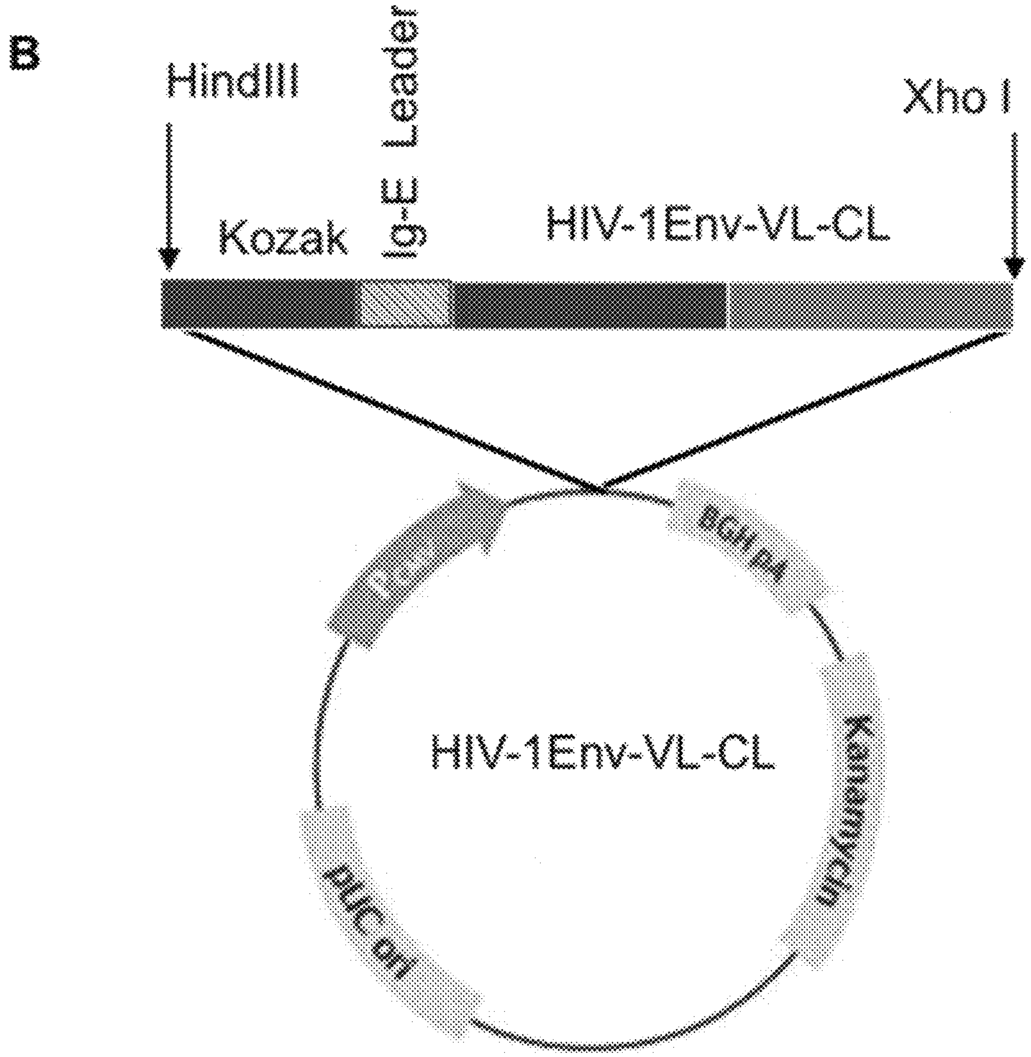

The cDNAs for both the VH and VL-Ig (immunoglobulin) chains coding sequences for the anti-HIV-1 Envelope broadly neutralizing human mAb VRC01 were obtained from the VRC (Vaccine Research Center, NIH) through the NIH AIDS Research and Reference Reagent Program and subsequently cloned into a pVax1 vector. Several modifications, as indicated in Example 2 above, were incorporated into the expression vectors in order to maximize and optimize the production of biologically active Ig molecules. Specifically, these modifications included codon and RNA optimization and stabilization, enhanced leader sequence utilization, plasmid production at high concentrations and facilitated in vivo plasmid delivery through EP. The constructs generated were placed under the control of an immediate early promoter from the human cytomegalovirus (CMV), which is important for proper and efficient expression in mammalian cells and tissues. The schematic maps of the construct used in this study are indicated in FIGS. 5A and 5B.

Figure 11:
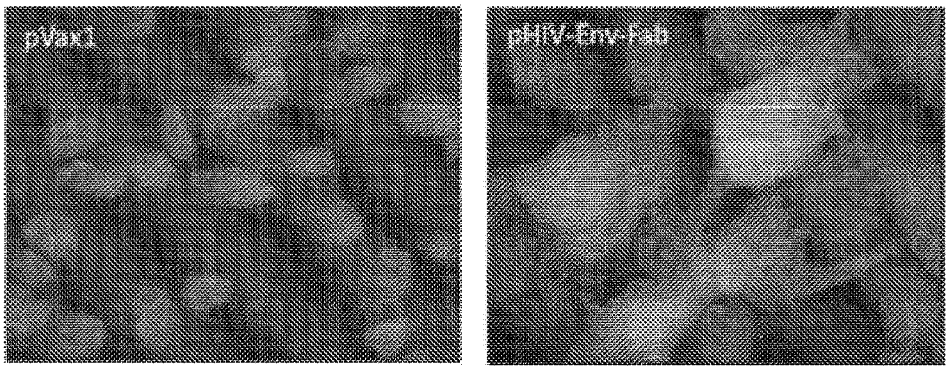
FIG. 11 shows immunofluorescence of cells transfected with a plasmid encoding HIV Env. The cells were stained with preparations from pVAX1 (left panel) or pHIV-Env-Fab (right panel).

Additionally, anti-HIV-1 Env Fab was prepared from pHIV-Env-Fab and used to stain cells transfected with a plasmid encoding HIV Env. pVAX1 was used as a control. As shown in FIG. 11, immunofluorescence staining demonstrated that the vector pHIV-Env-Fab allowed for the preparation of anti-HIV-1 Env Fab because the anti-HIV-1 Env Fab stained the cells transfected with the plasmid encoding HIV Env. Accordingly, the anti-HIV-1 Env Fab was specific for binding to the HIV Env glycoprotein.

Example 4

Ig Production by Transfected Cells

Figure 5C:
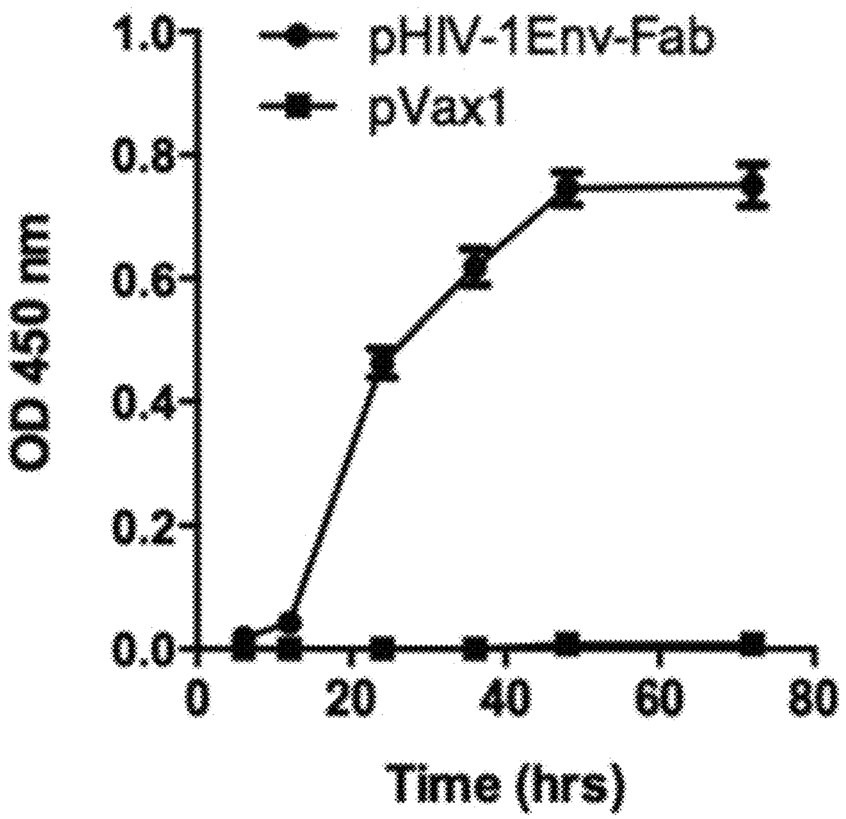

To evaluate the expression of pHIV-1Env-Fab, the constructs were transfected into 293T cells. An ELISA immunoassay, using a consensus HIV-1 clade B gp120 protein, confirmed the presence of the anti-HIV-1 Env-Fab in the supernatant from the transfected 293 T cells as early as 24 hours post transfection (FIG. 5C). High OD450 nm values (i.e. ranging from approximately 0.5 to 0.8) were detected in cell extracts from 24 to 72 hours post transfection and subsequently reached a peak and plateau at 48 hours. These results confirmed the specificity of the anti-HIV-1 Env Fab for the HIV Env glycoprotein. Statistical analysis of the data presented in FIG. 5C was as follows: OD450 nm values for sera from pHIV-1 Env-Fab injected mice were significant ($p<0.05$, student t test) compared to pVax1 control from the 22 through 72 hour time points measurements.

Example 5

In Vivo Characterization of HIV-1 Env Fab

To demonstrate in vivo Fab production from the DNA plasmids, mice were administered the pHIV-1 Env Fab by the intramuscular route followed by enhanced delivery through EP. A single injection of the DNA plasmids was delivered and sera was collected at 12 hours and at days 1, 2, 3, 4 7 and 10 following administration. Sera (at a dilution of 1:100 dilution) were then subsequently evaluated for Ig/Fab levels by ELISA analysis, as shown in FIG. 6A. Data in FIG. 6A are presented (from individual mice in both the pVax1 and HIV-1 Env-Fab groups) as OD450 nm, which was proportional to the level of Ig/Fab. These data demonstrated that the relative levels of Fab after single administration of pHIV-1Env-Fab became detectable on day 1 and subsequently increased over time. For comparative purposes, a single administration/immunization of rgp120, as described above in Example 2, was made into Balb/C mice with subsequent sera collection and analysis (at 1:100 dilution) over time by ELISA in order to determine the extent and longevity of specific anti-gp120 antibody levels. FIG. 6B show the results.

In this protein delivery study, antigen specific Ig levels over background were only detectable 10 days after immunization. This was in contrast to the Fab levels elicited by pHIV-1 Env Fab administration (FIG. 6A) where OD450 nm values attained at least 0.1 OD450 nm units by day 1 post administration and plateaued at day 10 at levels between 0.28 and 0.35 OD units. Therefore, the delivery of pHIV-1 Env Fab resulted in a more rapid generation of specific Fab than conventional protein immunization. This finding underscored the potential clinical utility of this DNA plasmid delivery method for generation of biologically active Ig.

Additional analyses were performed to ensure the quality as well as quantity of the recombinant Fab produced by the DNA delivery technology. Specifically, immunoblot analysis was performed using electrophoresed and blotted recombinant HIV-1 gp120 protein and probed with sera from pHIV-1Env-Fab mice 48 hours post administration (FIG. 6C). The blot indicated a band appropriate for the molecular weight of gp120 protein confirming that it was functional and able to bind to gp120. Likewise, human Fab quantitation, by ELISA, was performed and presented as a function of time (i.e. days) after plasmid administration (FIG. 6D). The results indicate that the levels of Fab generated peaked at 2-3 μg/ml. These results demonstrated the correct polypeptide assembly of the VH and VL chains of the generated VRC01 based Fab, as well as the ability to recognize and bind specifically to the HIV-1 Env protein.

Figure 6:
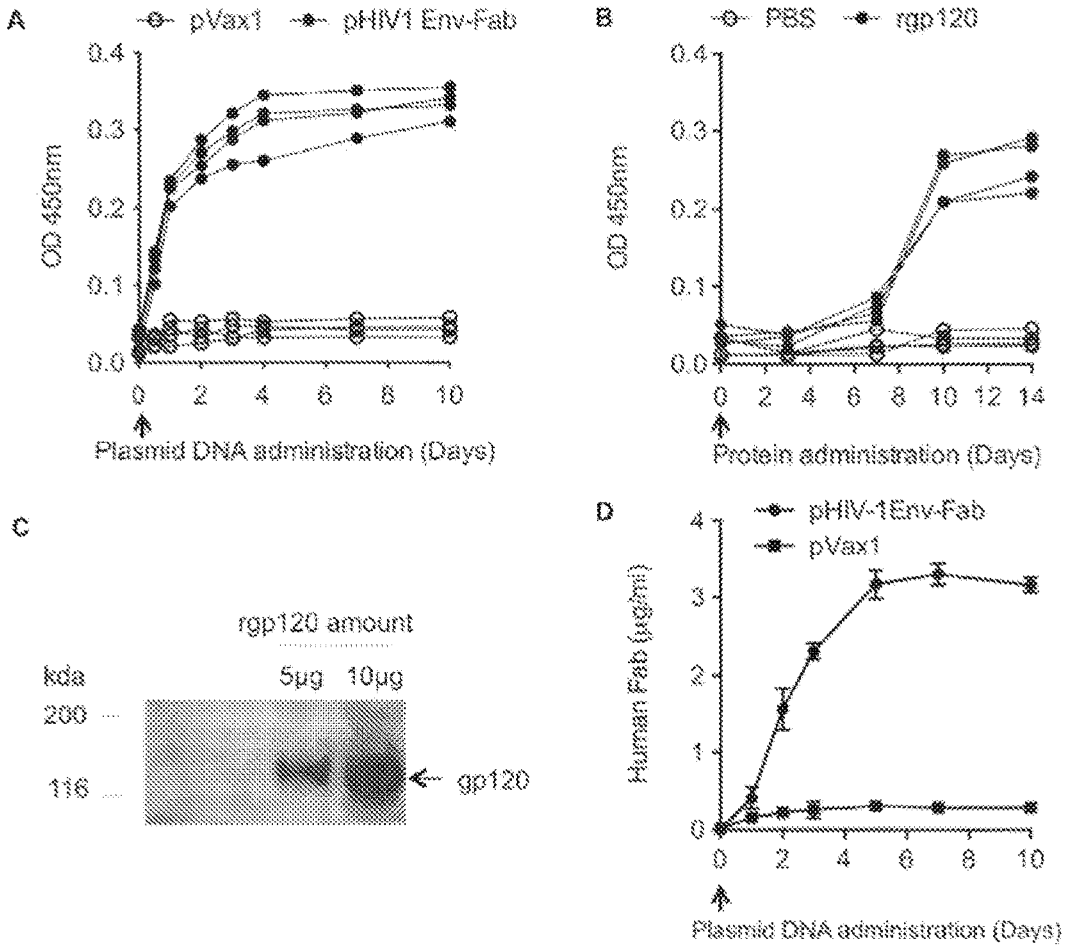
FIG. 6 shows measurement of temporal generation of anti HIV Env specific Fab by pHIV-1 Env Fab. (A) Time course of generation of anti-HIV1 Fab. After administration of pHIV-1 Env Fab, production of the specific Fab was measured over 10 days in the sera at a final dilution of 1:100 by ELISA and presented as OD450 nm. Sera from pVax1 administered mice were used as a negative control. (B) Comparative measurement of anti-gp120 antibody responses after immunization with recombinant gp120 (rgp120). As described in Example 2, mice were immunized with a single injection of rgp120 followed by measurement of production of anti-gp120 antibodies up to 10 days and presented as OD450 nm values. PBS was used as a negative control injection for this study. (C) Confirmation of HIV1 Env-Fab binding by immunoblot analysis. As indicated in Example, either 5 or 10 μg of gp120 were subjected to SDS-PAGE and nitrocellulose blotting followed by incubation of the blots with sera from pHIV-1 Env Fab administered mice. The immunoblot indicated that the experimental sera recognized bound rgp120, confirming the specificity of the generated Fab. (D) Temporal quantitation of human IgG1Fab, measured as IgG1 in mouse sera following pHIV-1Env-Fab administration. IgG1 was measured by a standard ELISA kit, at the time points indicated, and expressed as Fab (μg/mL)±SD. Sera from pVax1-administered mice were used as a negative control. Sera samples were analyzed at the time points indicated on the x-axis. The arrow shown in the graphs displayed in (A), (B) and (D) indicate the point of DNA plasmid administration.

Statistical analyses of the presented data in FIG. 6 are as follows. For data summarized in FIG. 6A, OD450 nm values for the sera from the pHIV-1 Env-Fab injected mice were statistically elevated ($p<0.05$, student t test) compared to the sera from pVax1 injected mice from the days 1 through 10 measurement time points. For data summarized in FIG. 6B, OD450 nm values from the rpg120 group were significantly elevated ($p<0.05$, student t test) compared to PBS control from the day 10 through 14 time point measurements. For data summarized in FIG. 6D, OD450 nm values from pHIV-1 Env-Fab injected mice were significantly elevated ($p<0.05$, student t test) from the day 2 through 10 time point measurements.

Example 6

Figure 7A:
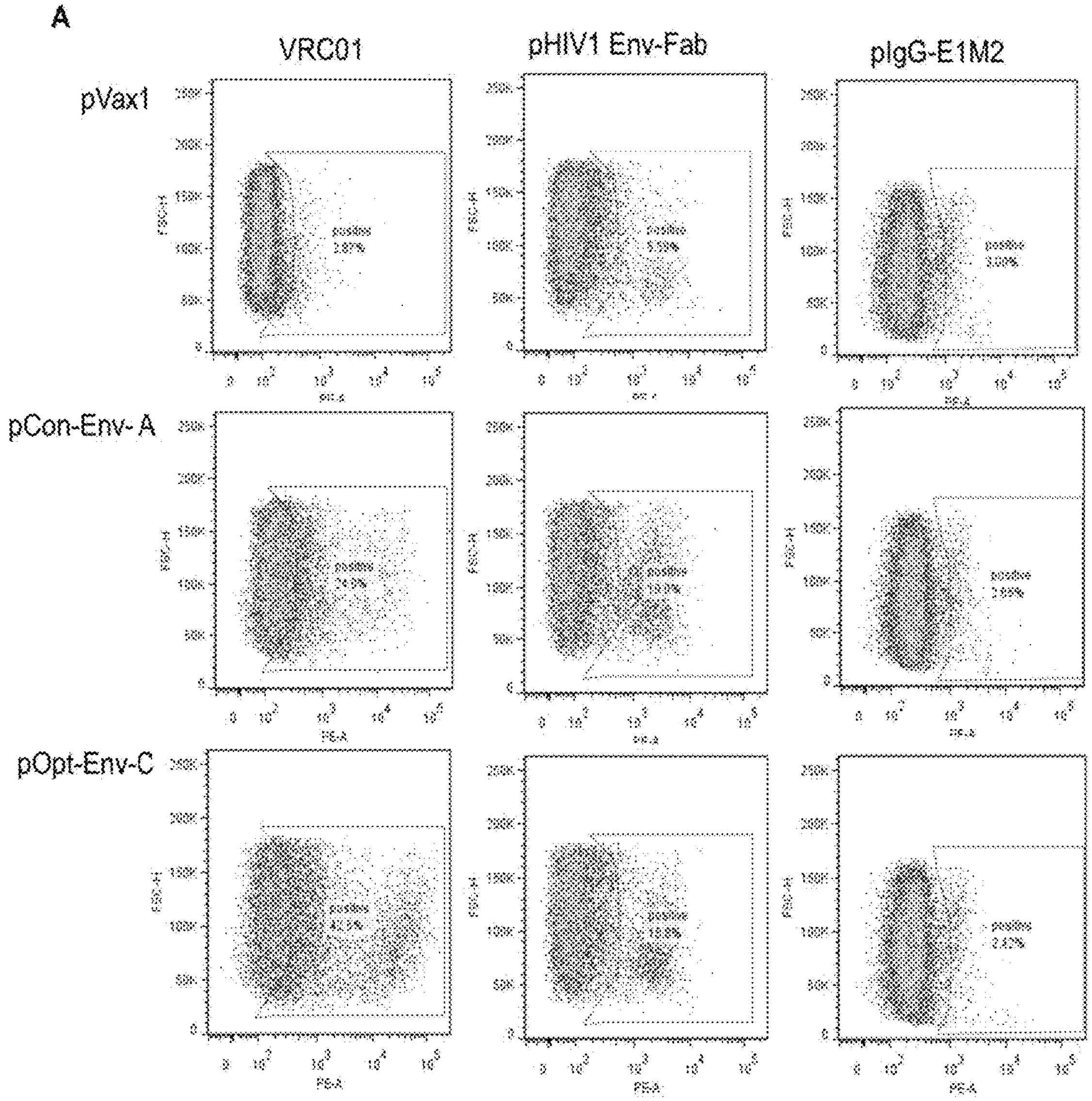
FIG. 7 shows FACS binding analysis HIV1 Env Fab to clade A HIV Env glycoprotein. (A) FACS scans indicating binding of anti-HIV1Env-Fab to HIV-1 clade A Env glycoprotein. DNA expressing either a consensus (pCon-Env-A) or "optimized" (pOpt-Env-A) HIV-1 clade A envelope was transfected into 293T cells. Two days post transfection, cells were stained with either purified native VRC01 Ig, sera generated from pHIV-1 Env Fab (collected 48 hours after a single plasmid administration) or control Ig generated from pIgG-E1M2 administration. Sera and VRC01 antibody were diluted 1:4 or 1:100, respectively in 50 μl of PBS and incubated at room temperature for 30 minutes. Cells were then stained with the appropriate secondary phycoerythrin (PE) conjugated Igs and subsequently gated for FACS analysis as singlet and live cells. The percent binding of positive cells was indicated in each of the scans. (B) Graphical representation of the FACS binding data. The number of stained cells (i.e. indicative of expression levels) in each of the Ig/sera tested groups was divided by the background staining values and presented as percent of specific binding on the y-axis as a function of the different HIV clade A Env preparations tested.

Binding of Fab/Igs to Cells Expressing Different HIV-1 Env Proteins: FACS Based Analysis Sera from the mice administered pHIV-1Env-Fab were also used to test binding of the generated Fab to different HIV-Env proteins transiently expressed by 293T cells. The native form of the VRC01-mAb was used as a positive control, to ensure proper expression and detection of the Env proteins on the surface of the cells. As indicated earlier, the "irrelevant/unrelated" Ig (Ig-E1M2) was used as a negative control. As demonstrated in FIGS. 7A and 7B, there was essentially only background staining by different Igs/Fabs to pVax1 (i.e. lacking the Env insert) transfected cells. However, for both the purified VRC01 mAb and sera from pHIV-1Env-Fab administered mice there was significant positive staining of transfected cells expressing either the consensus clade A Env plasmid (pCon-Env-A) as well as an optimized clade C plasmid (pOpt-Env-A) expressing and Env from the primary HIV-1 isolate pQ23Env17. Moreover, sera from pIg-E1M2 administered mice failed to demonstrate staining of any of the HIV1 Env transfected cells above background levels. FACS analysis indicating these results are provided in FIG. 7A. A representative graph showing the data from the FACS analysis (i.e., FIG. 7A) for this experiment was provided in FIG. 7B.

Figure 7B:
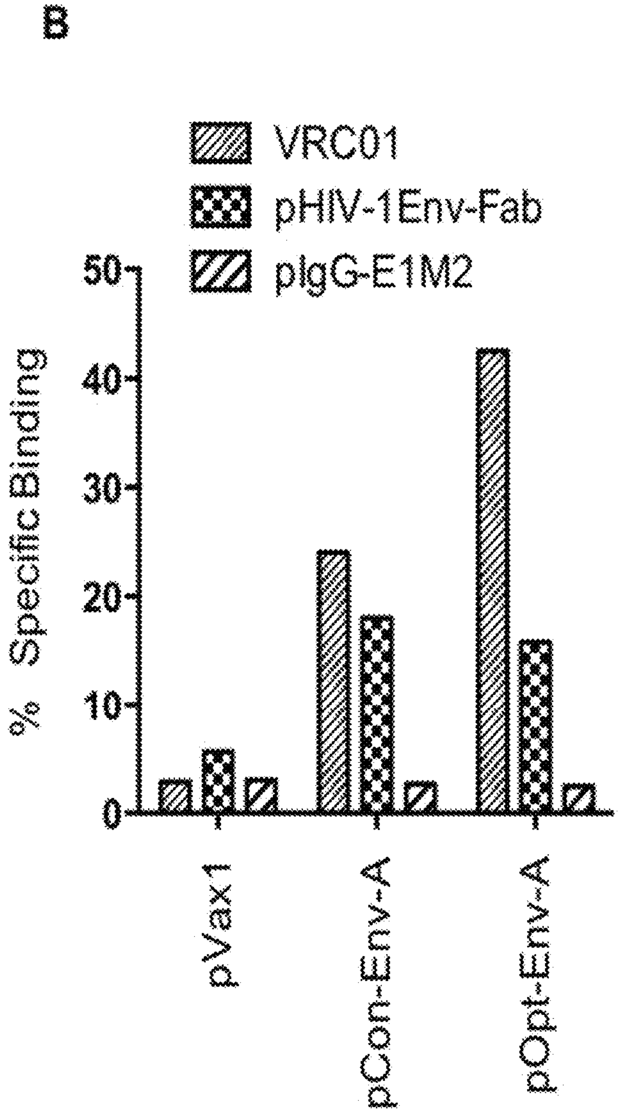

Statistical analyses of data presented in FIG. 7B are as follows. There was no significant difference ($p<0.05$, student t test) in specific binding between native VRC01 antibody and sera from pHIV-1 Env-Fab injected mice to the envelope glycoprotein generated by pCon-Env-A. However, binding of VRC01 antibody to the envelope glycoprotein generated by pOpt-Env-A was significantly higher ($p<0.05$, student t test) than binding by sera from pHIV-1 Env-Fab injected mice.

Example 7

HIV Neutralizing Activity of Ig Produced by pHIV-1 Env Fab

Figure 12:
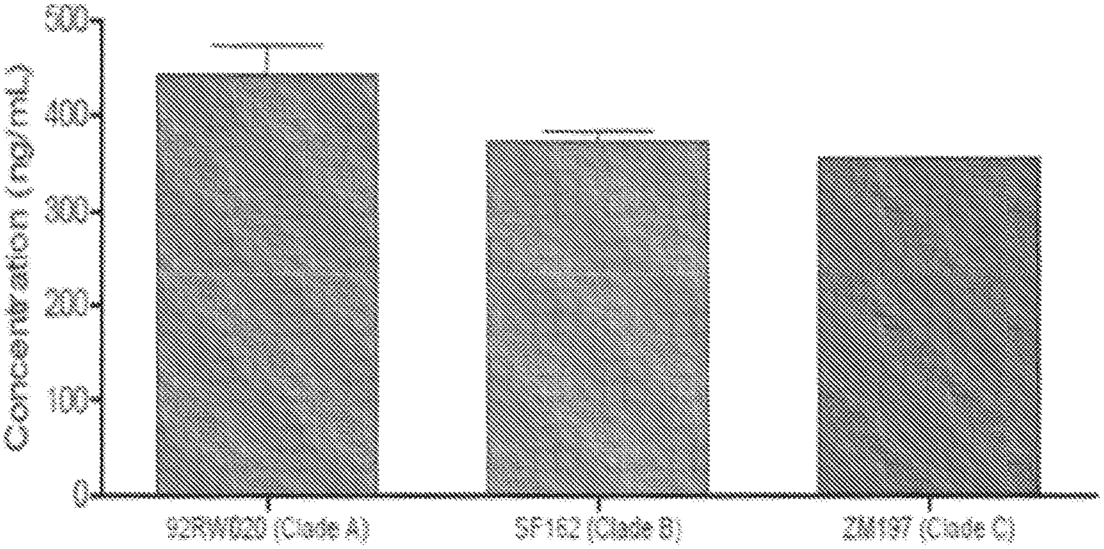
FIG. 12 shows a graph plotting type of antigen vs. sera concentration (ng/mL).

Sera from mice administered pHIV-1Env-Fab were used to test binding of the HIV-Env Fab to HIV-1 Env proteins expressed in transiently transfected to 293T cells. Sera was obtained from the mice 6 days after administration of pHIV-1Env-Fab. Specifically, cells were transfected with a plasmid from which HIV-1 Env from a Clade A, B or C strain was expressed. The clade A, B, and C strains were 92RW020, SF162, and ZM197. As shown in FIG. 12, sera from mice administered pHIV-1Env-Fab bound the HIV-1 Env from the clade A, B, and C HIV-1 strains, thereby indicating that the sera contained an antibody (i.e., HIV-Env Fab) that was cross-reactive with HIV-1 Env from multiple subtypes of HIV-1.

In order to assess the potential HIV-1 neutralizing activity of the HIV-Env Fab produced in this study, a luminescence based neutralization assay based using TZM-B1 target cells was performed. The TZM-B1 target cells were infected with the 4 different pseudotyped HIV viral isolates in the absence or presence of the experimental sera and control, as described in Example 2 above.

Figure 8:
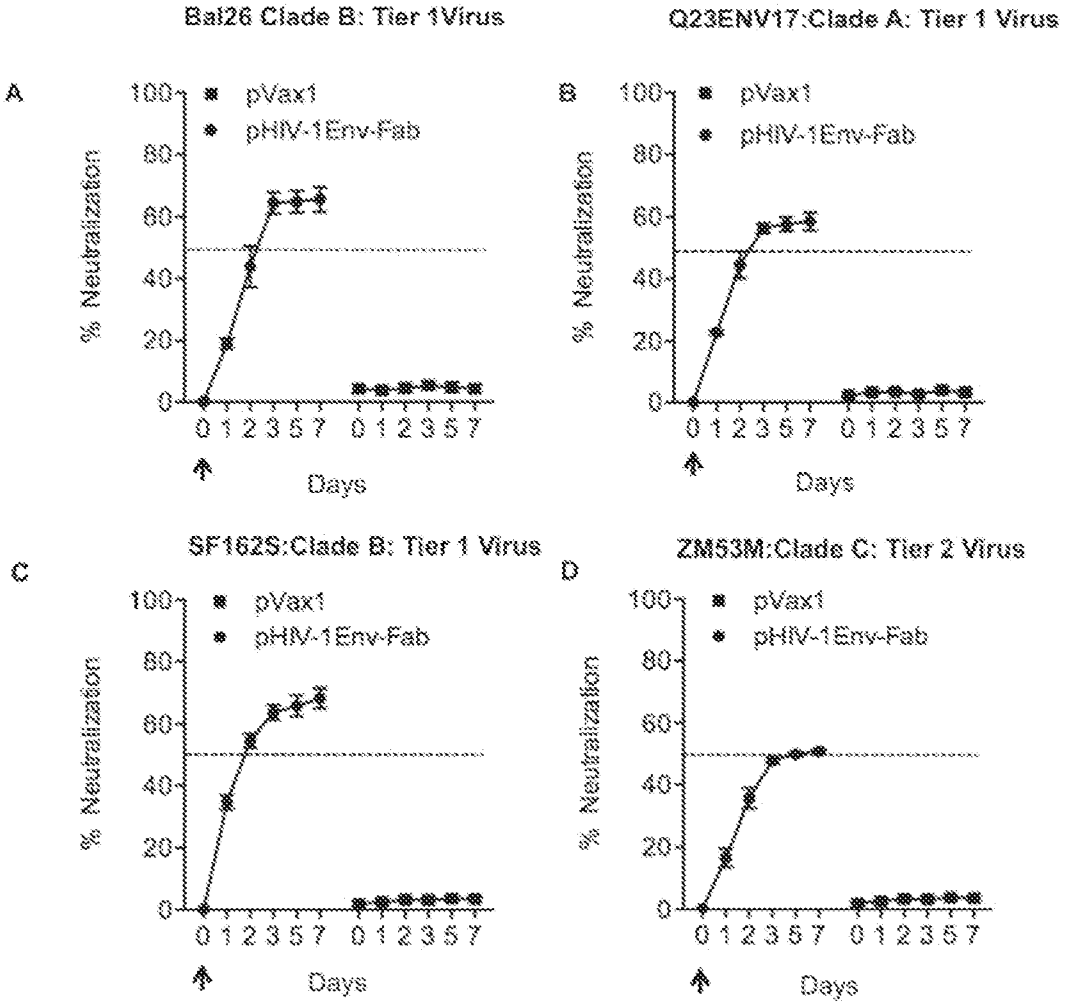
FIG. 8 shows time course of neutralization of HIV-1 by sera from pHIV-1Env-Fab administered mice. Sera used for analysis of neutralization activity sera were collected at the time points indicated in the graphs. The neutralization analysis was conducted in TZM-BL cells using a panel of HIV-1 pseudotyped viruses: Ba126 (Panel A; clade B, Tier 1), Q23Env17 (Panel B; clade A, Tier 1), SF162S (Panel C; clade B, Tier 1), and ZM53M (Panel D; clade C, Tier 2). Cells were infected at an MOI of 0.01 as delineated in Example 2 and incubated in the presence of sera (final dilution of 1:50) containing Fab generated from pHIV-1 Env Fab administration. Percent neutralization values are shown, the calculation of which was described in Example 2. As well, horizontal lines are provided in each of the graphs, indicating the approximate time points at which the experimental sera mediated 50% viral neutralization.

FIG. 8 depicts the neutralization curves for sera from pHIV-1 Env Fab injected mice against the HIV pseudotyped viruses. Specifically tested were the HIV-1 tier 1 viruses Ba126 and SF162S (both clade B), as well as Q23Env (clade A). In addition, sera were also tested against the HIV-1 clade C tier 2 virus ZM53M. The data are presented as percent neutralization/inhibition of HIV infection. The hatched horizontal lines in the graphs indicated the 50% neutralization/inhibition level in the assay. A positive neutralization control mAb (data not shown) was utilized in this study to confirm the utility and validity of this assay method. Briefly, the positive control neutralizing mAb was able to inhibit infection of the all four of the viral pseudotypes by at least 50%.

Sera from the pHIV-1 Env Fab administered mice demonstrated an increase in HIV neutralizing activity over time following plasmid administration, with percent neutralization reaching at 50% by Day 2 for Ba125, Q23Env17 and SF162S. As well plateau percent neutralization for these 3 viruses was approximately 62, 60 and 70%, respectively. For the ZM53M, the 50% neutralization threshold was not reached until 3 days and plateau neutralization did not exceed 50%. This less robust neutralization profile, compared to the other 3 tested, was likely reflective of it being a less neutralizable Tier 2 virus. In sum, the Fab generated in this study was able to effectively neutralize a range of HIV isolates. Statistical analyses of data presented in FIG. 8 are as follows. Based on Kruskal-Wallis non-parametric analysis, only HIV neutralization levels for the ZM53M Clade C virus (FIG. 8D), induced by sera from pHIV-1 Env-Fab injected mice, was significantly different from the other viruses tested (FIGS. 8A, 8B, and 8C). This difference was in time (days) required to achieve 50% neutralization as well as in the maximally attained level of neutralization.

In summary of Examples 3-7, the sera concentration of VRC01 Fab in pHIV-1 Env Fab administered mice peaked at 2-3 μg/mL at day 12 post-injection. This range was comparable to a number of monoclonal antibodies currently licensed by the FDA, indicating that our antibody approach produced significant and biologically relevant levels of antibodies in this small animal model. In particular, Ustekinumab (trade name: Stelara) and Golimumab (Simponi), two antibodies indicated for use against autoimmune diseases such as plaque psoriasis and arthritis, have mean±SD serum concentrations of 0.31±0.33 μg/mL and 1.8±1.1 μg/mL, respectively. Furthermore, the TNF inhibitor Adalimumab (Humira) has a mean rough serum concentration of around 6 μg/mL. In this regard, the data described in Examples 4-8 demonstrated that delivery of DNA encoding the antibody to the organism resulted in the being assembled in vivo such that significant and biologically relevant levels of the antibody were present in the organism.

These data also demonstrated the ability to more rapidly produce Fabs in vivo, after a single EP enhanced administration of pHIV-1Env Fab, compared to Igs produced by conventional protein administration (FIGS. 6A and 6B). In addition, the ability to generate functional protective Ig-like molecules against difficult vaccine targets was addressed. To date, inducing HIV-1 neutralizing antibodies following active vaccination has been incredibly difficult, and during primary infection, neutralizing antibodies do not develop until years after transmission. With this DNA plasmid approach, neutralization titers were observed within 1-2 days post delivery with peak neutralizing Fab sera concentrations (3.31±0.13 μg/mL) occurring one-week post-administration (FIG. 6D). This level of Ig was relatively similar to the 8.3 μg/mL concentration that has been demonstrated to provide complete protection from infection in a recent study. These data demonstrated the rapid induction of biologically active Ig fragments.

These data also showed the neutralizing antibody titer and the responses against HIV-1 primary isolates that were elicited by HIV-1 Env-Fab DNA administration. Sera were tested against a panel of different viral tier 1, and 2 viral isolates that represent examples from clades A, B and C. The results indicated generation of potent neutralizing activity against these viruses (FIG. 8).

Accordingly, this DNA plasmid-based method generated specific and biologically active Fab or Ig molecules in vivo, bypassed the need to use conventional antigen-based vaccination for antibody generation, and obviated the need to generate and purify Igs made in vitro.

Example 8

Construction of a Plasmid Encoding a Human Ig Antibody

Figure 13:
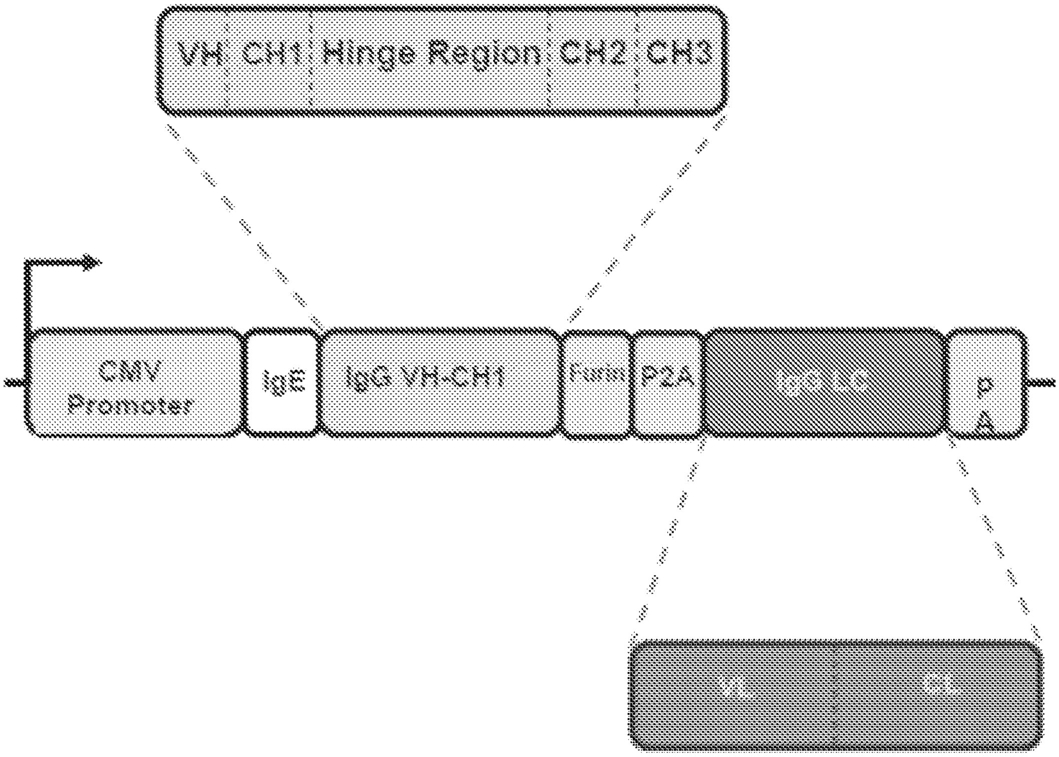
FIG. 13 shows a schematic of a construct encoding a synthetic human IgG1 antibody.

As described above, a Fab was generated from the VRC01 antibody, namely HIV-Env Fab, which was generated in vivo upon administration of the encoding nucleic acid to the subject. To further extend these studies, nucleic acid sequence was created that encoded an IgG1 antibody derived from the VRC01 antibody. As shown in the schematic in FIG. 13, this nucleic acid sequence encoded IgG heavy and light chains separated by a furin cleavage site and a nucleic acid sequence encoding P2A peptide sequence. The P2A peptide sequence increases the efficiency of cleavage by the protease, thereby resulting in discrete polypeptides after cleavage.

Figure 14:
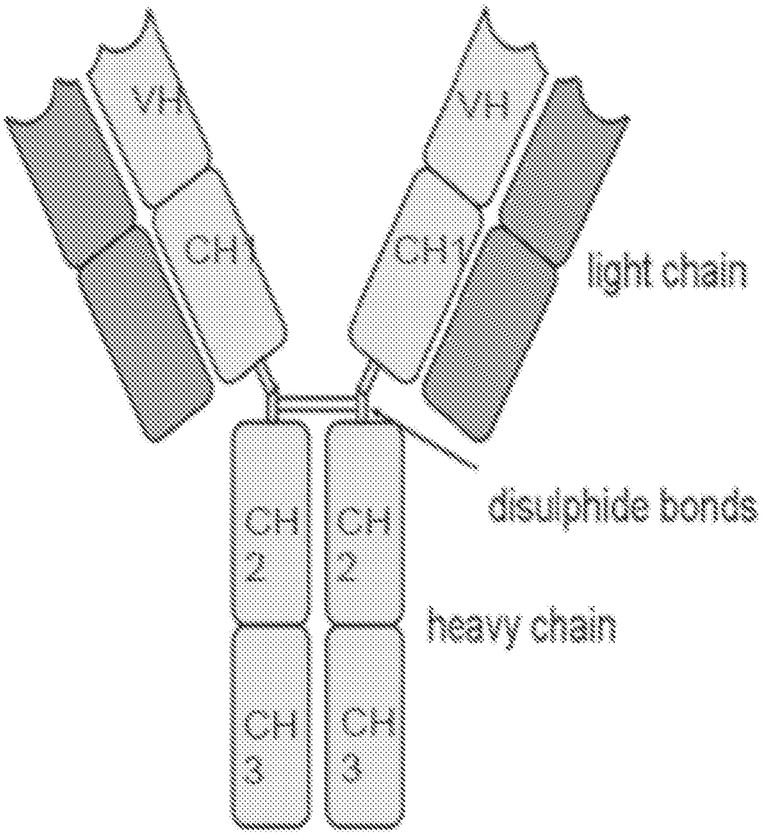
FIG. 14 shows a schematic of the assembled antibody (upon expression) that is encoded by the construct of FIG. 13.

The IgG heavy chain included the variable heavy (VH), constant heavy 1 (CH1), hinge, constant heavy 2 (CH2), and constant heavy 3 (CH3) regions. The IgG light chain included the variable light (VL) and constant light (CL) regions. This construct was placed under the control of a cytomegalovirus (CMV) promoter, for example, in the expression vector pVAX1. This construct resulted in the production of fully assembled IgG antibody (as shown in FIG. 14) that was reactive gp120 (i.e., the antigen recognized by the VRC01 antibody). This fully assembled IgG is referred to herein as VRC01 IgG. The amino acid sequence of the VRC01 IgG (before cleavage by furin) is shown in FIG. 15 and is set forth in SEQ ID NO:5.

In particular, the amino acid sequence of the VRC01 IgG (before cleavage by furin; SEQ ID NO:5 and FIG. 15) has the following structure: an immunoglobulin E1 (IgE1) signal peptide, variable heavy region (VH), constant heavy region 1 (CH1), hinge region, constant heavy region 2 (CH2), constant heavy region 3 (CH3), furin cleavage site, GSG linker, P2A peptide, IgE1 signal peptide, variable light region (VL), and constant light region (CL, specifically kappa). The sequence of each portion of the structure (all which are contained within SEQ ID NO:15 in the order described above and shown in FIG. 13) is provided below.

```
IgE1 Signal Peptide of VRC-1 IgG-
                                        (SEQ ID NO: 8)
MDWTWILFLVAAATRVHS.

Variable Heavy Region of VRC01 IgG-
                                        (SEQ ID NO: 9)
QVQLVQSGGQMKKPGESMRISCRASGYEFIDCTLNWIRLAPGKR

PEWMGWLKPRGGAVNYARPLQGRVTMTRDVYSDTAFLELRSLTV

DDTAVYFCTRGKNCDYNWDFEHWGRGTPVIVSSPSTKG.

Constant Heavy region 1 (CH1) of VRC01 IgG-
                                       (SEQ ID NO: 10)
PSVFPLAPSSKSTSGGTAALGCLVKDYFPEPVTVSWNSGALTSG

VHTFPAVLQSSGLYSLSSVVTVPSSSLGTQTYICNVNHKPSNTK

VDKKAEPKSC.

Hinge Region of VRC01 IgG
                                       (SEQ ID NO: 11)
EPKSCDKT HTCPPCP.

Constant Heavy Region 2 (CH2) of VRC01 IgG-
                                       (SEQ ID NO: 12)
APELLGGPSVFLFPPKPKDTLMISRTPEVTCVVVDVSHEDPEVK

FNWYVDGVEVHNAKTKPREEQYNSTYRVVSVLTVLHQDWLNGKE

YKCKVSNKALPAPIEKTISKAK.

Constant Heavy Region 3 (CH3) of VRC01 IgG-
                                       (SEQ ID NO: 13)
GQPREPQVYTLPPSRDELTKNQVSLTCLVKGFYPSDIAVEWESN

GQPENNYKTTPPVLDSDGSFFLYSKLTVDKSRWQQGNVFSCSVM

HEALHNHYTQKSLSLSPGK

Furin Cleavage Site of VRC01 IgG-
                                       (SEQ ID NO: 14)
RGRKRRS.

GSG Linker and P2A Peptide of VRC01 IgG-
                                       (SEQ ID NO: 15)
GSGATNFSLLKQAGDVEENPGP.

IgE1 Signal Peptide of VRC01 IgG-
                                        (SEQ ID NO: 8)
MDWTWILFLVAAATRVHS.

Variable Light Region (VL) of VRC01 IgG-
                                       (SEQ ID NO: 16)
EIVLTQSPGTLSLSPGETAIISCRTSQYGSLAWYQQRPGQAPRL

VIYSGSTRAAGIPDRFSGSRWGPDYNLTISNLESGDFGVYYCQQ

YEFFGQGTKVQVDIKR.

Constant Light Region (CL, kappa) of VRC01 IgG-
                                       (SEQ ID NO: 17)
TVAAPSVFIFPPSDEQLKSGTASVVCLLNNFYPREAKVQWKVDN

ALQSGNSQESVTEQDSKDSTYSLSSTLTLSKADYEKHKVYACEV

THQGLRSPVTKSFNRGEC.
```

Example 9

HIV-1 VRC01 IgG Encoded by Two Plasmids

Figure 50:
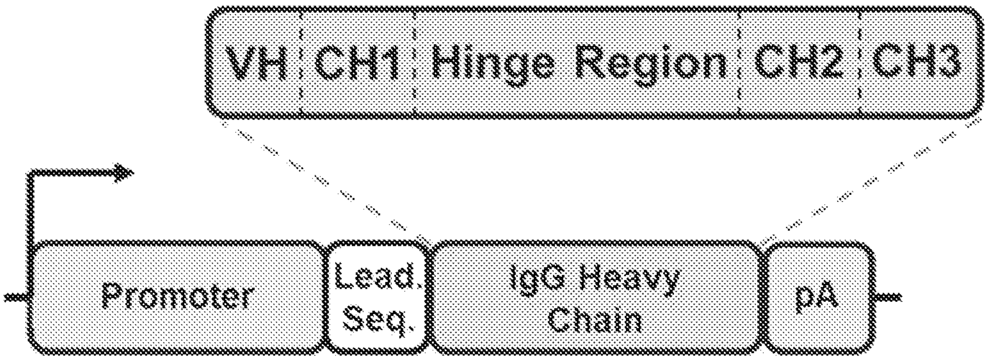
FIG. 50 shows a schematic illustrating a construct encoding the variable heavy region (VH), variable heavy constant region 1 (CH1), hinge region, variable heavy constant region 2 (CH2), variable heavy constant 3 (CH3) of an immunoglobulin G (IgG) heavy chain. The nucleic acid sequence encoding the IgG heavy chain is preceded by a leader sequence.
Figure 51:
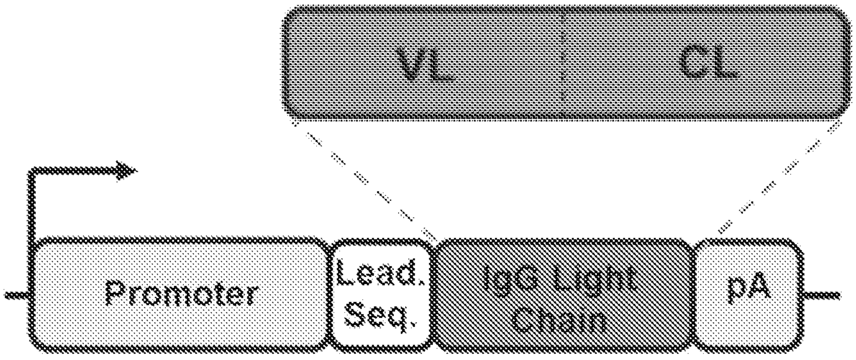
FIG. 51 shows a schematic illustrating a construct encoding the variable light region (VL) and variable light constant region (CL) of an IgG light chain. The nucleic acid sequence encoding the IgG light chain is preceded by a leader sequence.

As described above in Examples 2-8, a Fab (each chain expressed from a separate plasmid) was generated from the VRC01 antibody, namely HIV-Env Fab, and an IgG (expressed from a single plasmid) was generated from the VRC01 antibody, namely VRC01 IgG. To further extend these studies, an IgG was generated from the VRC01 antibody, in which the heavy chain (i.e., variable heavy region (VH), constant heavy region 1 (CH1), hinge region, constant heavy region 2 (CH2), and constant heavy region 3 (CH3)) and the light chain (i.e., variable light region (VL) and constant light region (CL)) were encoded by separate constructs (FIGS. 50 and 51). This IgG is referred to herein as HIV-1 VRC01 IgG.

Each construct also included a leader sequence for optimizing secretion of the antibody once generated in vivo. Each construct was cloned into the BamHI and XhoI sites of the pVAX1 vector, thereby placing the construct under the control of a cytomegalovirus (CMV) promoter (FIGS. 50 and 51). Accordingly, to form or generate the VRC01 IgG in vivo a mixture of plasmids has to be administered to the subject, namely a plasmid containing the construct encoding the heavy chain and a plasmid containing the construct encoding the light chain.

Additionally, each construct was further optimized. Optimization included addition of a kozak sequence (GCC ACC) and codon optimization. The nucleic acid sequence encoding the IgG1 heavy chain of the HIV-1 VRC01 IgG is set forth in SEQ ID NO:54 and FIG. 52. In FIG. 52, underlining and double underling mark the BamHI (GGA TCC) and XhoI (CTC GAG) restriction enzyme sites used to clone the nucleic acid sequence into the pVAX1 vector while bold marks the start (ATG) and stop (TGA TAA) codons. SEQ ID NO:54 encodes the amino acid sequence set forth in SEQ ID NO:55 and FIG. 53, i.e., the amino acid sequence of the IgG1 heavy chain of the HIV-1 VRC01 IgG.

The nucleic acid sequence encoding the IgG light chain of the HIV-1 VRC01 IgG is set forth in SEQ ID NO:56 and FIG. 54. In FIG. 54, underlining and double underling mark the BamHI (GGA TCC) and XhoI (CTC GAG) restriction enzyme sites used to clone the nucleic acid sequence into the pVAX1 vector while bold marks the start (ATG) and stop (TGA TAA) codons. SEQ ID NO:56 encodes the amino acid sequence set forth in SEQ ID NO:57 and FIG. 55, i.e., the amino acid sequence of the IgG light chain of the HIV-1 VRC01 IgG.

Example 10

HIV-1 Env-PG9 Ig

Figure 16A:
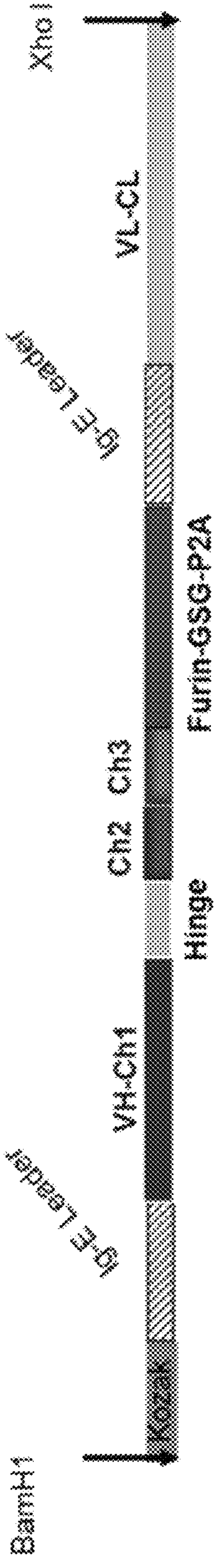
FIG. 16 shows (A) a schematic of the construct encoding HIV-1 Env-PG9 Ig; (B) a schematic of the vector containing the construct of (A); and (C) an image of a stained gel.
Figure 16B:
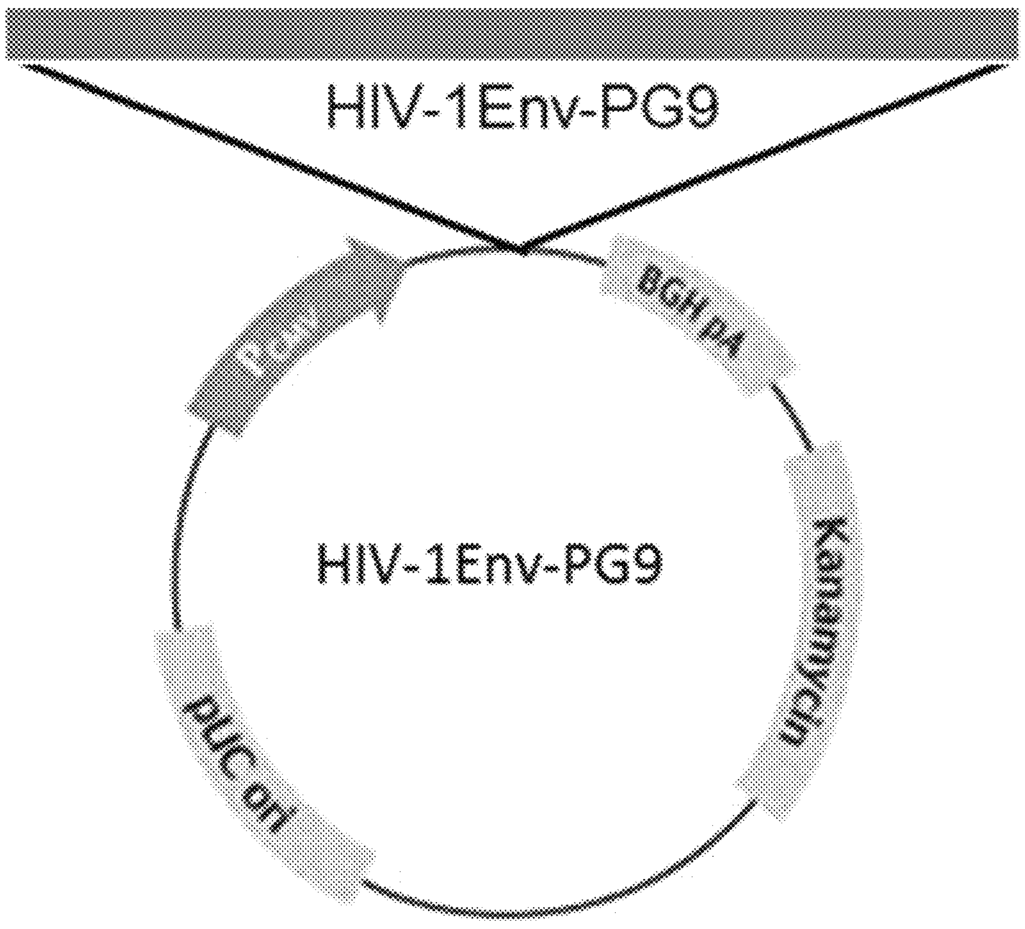
Figure 16C:
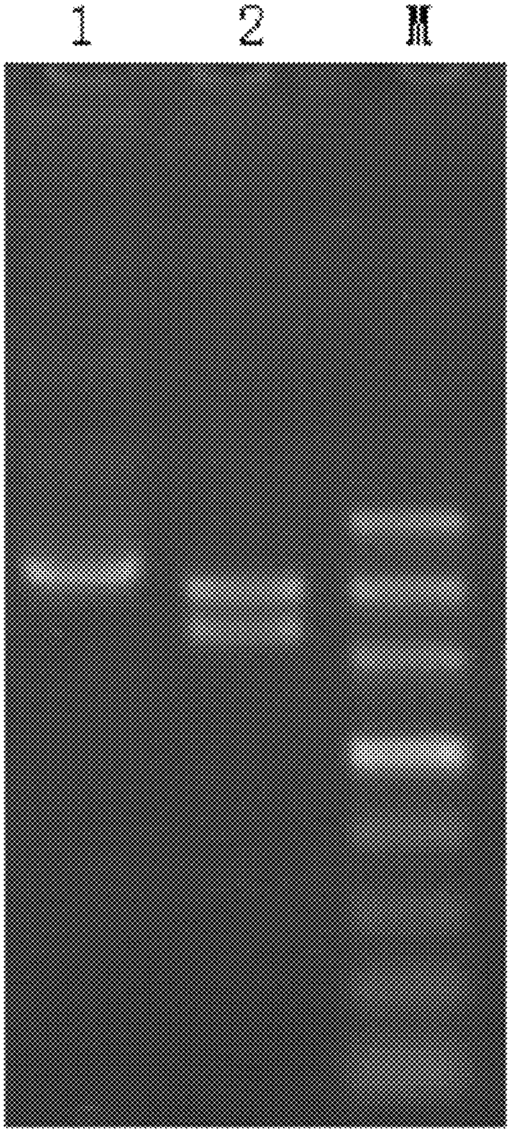

In addition to VRC01 IgG, another construct was created that encoded IgG that was reactive to HIV-1 Env. This construct was HIV-1 Env-PG9, which was optimized and cloned into an expression vector (FIGS. 16A and 16B). Optimization included introduction of a kozak sequence (e.g., GCC ACC), a leader sequence, and codon optimization. Creation of the expression vector containing the nucleic acid sequence encoding HIV-1 Env-PG9 Ig was confirmed by restriction enzyme digestion as shown in FIG. 16C. In FIG. 16C, lane 1 was undigested expression vector, lane 2 was the expression vector digested with BamHI and Xho1, and lane M was the Marker.

The nucleic acid sequence encoding HIV-1 Env-PG9 Ig is set forth in SEQ ID NO:63 and FIG. 61. In FIG. 61, underlining and double underlining mark the BamHI (GGA TCC) and XhoI (CTC GAG) restriction enzyme sites used to clone the nucleic acid sequence into the pVAX1 vector while bold marks the start (ATG) and stop (TGA TAA) codons. SEQ ID NO:63 encodes the amino acid sequence set forth in SEQ ID NO:2 and FIG. 18, i.e., the amino acid sequence of HIV-1 ENv-PG9 Ig (before cleavage by furin).

In this amino acid sequence, a signal peptide is linked by peptide bond to each of the heavy and light chains to improve secretion of the antibody generated in vivo. Additionally, a nucleic acid sequence encoding the P2A peptide is located between the nucleic acid sequences encoding the heavy and light chains to allow for more efficient cleavage of the translated polypeptide into separate polypeptides containing the heavy or light chain.

In particular, the amino acid sequence of the HIV-1 Env-PG9 Ig (before cleavage by furin; SEQ ID NO:2 and FIG. 18) has the following structure: human IgG heavy chain signal peptide, variable heavy region (VH), constant heavy region 1 (CH1), hinge region, constant heavy region 2 (CH2), constant heavy region 3 (CH3), furin cleavage site, GSG linker, P2A peptide, human lambda light chain signal peptide, variable light region (VL), and constant light region (CL, specifically lamba). The sequence of each portion of the structure (all which are contained within SEQ ID NO:2 in the order described above) is provided below.

```
Human IgG Heavy Chain Signal Peptide of HIV-1
Env-PG9-
                                        (SEQ ID NO: 18)
MDWTWRILFLVAAATGTHA.

Variable Heavy Region of HIV-1 Env-PG9 Ig-
                                        (SEQ ID NO: 19)
EFGLSWVFLVAFLRGVQCQRLVESGGGVVQPGSSLRLSCAASG

FDFSRQGMHWVRQAPGQGLEWVAFIKYDGSEKYHADSVWGRLS

ISRDNSKDTLYLQMNSLRVEDTATYFCVREAGGPDYRNGYNYY

DFYDGYYNYHYMDVWGKGTTVTVSS.

Constant Heavy region 1 (CH1) of HIV-1
Env-PG9 Ig-
                                        (SEQ ID NO: 20)
ASTKGPSVFPLAPSSKSTSGGTAALGCLVKDYFPEPVTVSWNS

GALTSGVHTFPAVLQSSGLYSLSSVVTVPSSSLGTQTYICNVN

HKPSNTKVDKRV.

Hinge Region of HIV-1 Env-PG9 Ig-
                                        (SEQ ID NO: 21)
EPKSCDKTHTCPPCP.

Constant Heavy Region 2 (CH2) of HIV-1
Env-PG9 Ig-
                                        (SEQ ID NO: 22)
APELLGGPSVFLFPPKPKDTLMISRTPEVTCVVVDVSHEDPEV

KFNWYVDGVEVHNAKTKPREEQYNSTYRVVSVLTVLHQDWLNG

KEYKCKVSNKALPAPIEKTISKAK.

Constant Heavy Region 3 (CH3) of HIV-1
Env-PG9 Ig-
                                        (SEQ ID NO: 23)
GQPREPQVYTLPPSRDELTKNQVSLTCLVKGFYPSDIAVEWES

NGQPENNYKTTPPVLDSDGSFFLYSKLTVDKSRWQQGNVFSCS

VMHEALHNHYTQKSLSLSPGK.
```

-continued

Furin Cleavage Site of HIV-1 Env-PG9 Ig-
(SEQ ID NO: 24)
RGRKRRS.

GSG Linker and P2A Peptide of HIV-1
Env-PG9 Ig-
(SEQ ID NO: 25)
GSGATNFSLLKQAGDVEENPGP.

Human Lamba Light Chain Signal Peptide of
HIV-1 Env-PG9 Ig-
(SEQ ID NO: 26)
MAWTPLFLFLLTCCPGGSNS.

Variable Light Region (VL) of HIV-1
Env-PG9 Ig-
(SEQ ID NO: 27)
QSALTQPASVSGSPGQSITISCNGTSNDVGGYESVSWYQQHPG

KAPKVVIYDVSKRPSGVSNRFSGSKSGNTASLTISGLQAEDEG

DYYCKSLTSTRRRVFGTGTKLTVL.

Constant Light Region (CL, lamba) of HIV-1
Env-PG9 Ig-
(SEQ ID NO: 28)
GQPKAAPSVTLFPPSSEELQANKATLVCLISDFYPGAVTVAWK

ADSSPVKAGVETTTPSKQSNNKYAASSYLSLTPEQWKSHKSYS

CQVTHEGSTVEKTVAPTECS.

Example 11

HIV-1 PG9 Single Chain Fab (scFab)

In addition to HIV-1 Env-PG9 Ig described above, a single chain Fab (i.e., VH/CH1 and VL/CL encoded by a nucleic sequence that is transcribed into a single transcript and translated into a single polypeptide) was created based upon the PG9 antibody (referred to herein as HIV-1 PG9 scFab). The nucleic acid sequence encoding HIV-1 PG9 scFab is set forth in SEQ ID NO:50 and FIG. 46. In FIG. 46, underlining and double underlining mark the BamHI (GGA TCC) and XhoI (CTC GAG) that were used to clone this nucleic acid sequence into the pVAX1 vector while bold marks the start (ATG) and stop (TGA TAA) codons. The nucleic acid sequence set forth in SEQ ID NO:50 was an optimized nucleic acid sequence, i.e., inclusion of a kozak sequence (GCC ACC), codon optimization, and leader sequence. The leader sequence was located at the 5' end of the construct, i.e., preceding the single chain Fab, and thus, the signal peptide encoded by the linker sequence was linked by a peptide bond to the amino terminus of the single chain Fab. The nucleic acid sequence set forth in SEQ ID NO:50 also included a linker sequence that was positioned between the nucleic acid sequence encoding the VH/CH1 and the nucleic acid sequence encoding the VL/CL. Accordingly, in the polypeptide encoded by SEQ ID NO:50, the amino acid sequence encoded by the linker sequence kept the VH/CH1 and VL/CL together. SEQ ID NO:50 encoded the amino acid sequence set forth in SEQ ID NO:51 and FIG. 47, i.e., the amino acid sequence of the HIV-1 PG9 scFab.

Example 12

HIV-1 Env-4E10 Ig

Figure 17A:
FIG. 17 shows (A) a schematic of the construct encoding HIV-1 Env-4E10 Ig; (B) a schematic of the vector containing the construct of (A); and (C) an image of a stained gel.
Figure 17B:
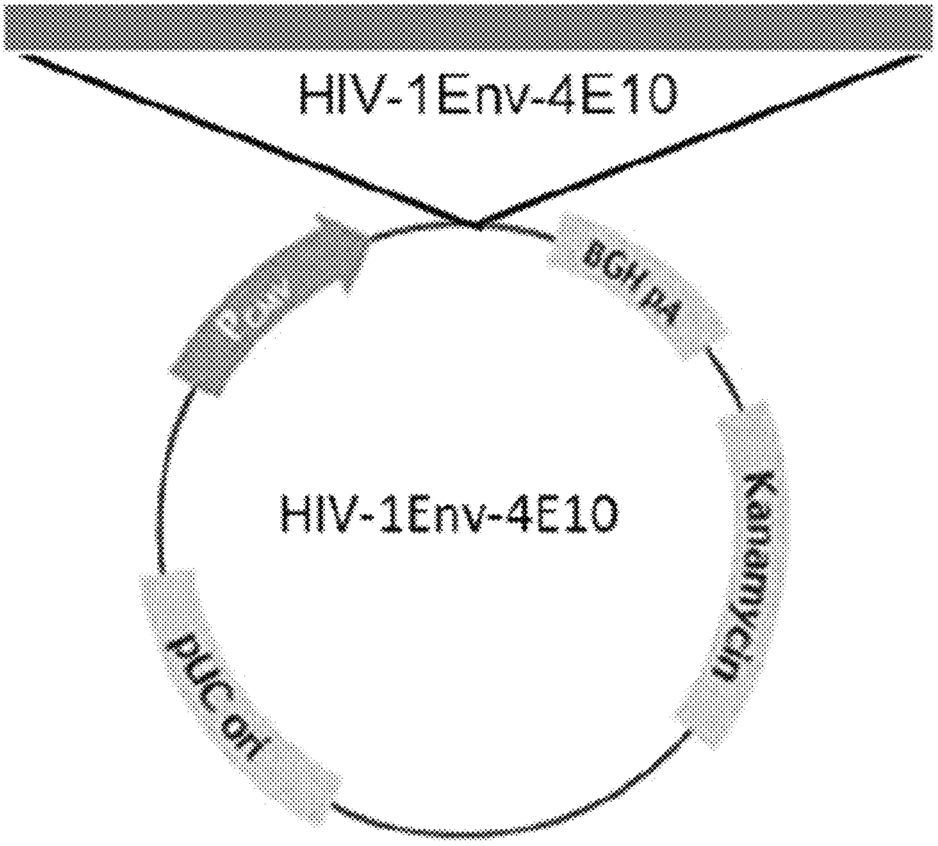
Figure 17C:
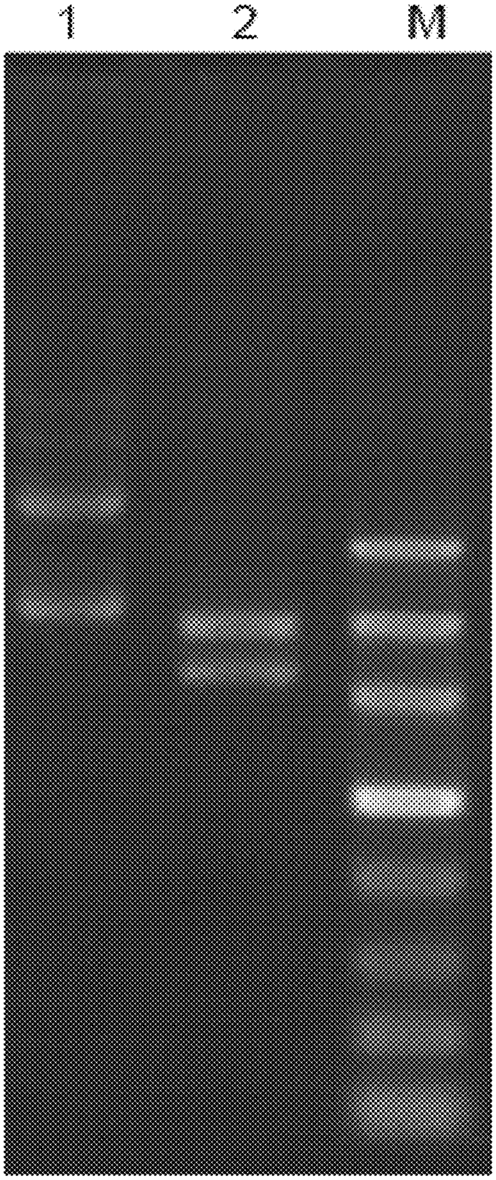

In addition to VRC01 IgG and HIV-1 Env-PG9 Ig, another construct was created that encoded IgG that was reactive to HIV-1 Env. This construct was HIV-1 Env-4E10, which was optimized and cloned into an expression vector (FIGS. 17A and 17B). Optimization included introduction of a kozak sequence (e.g., GCC ACC), a leader sequence, and codon optimization. Creation of the expression vector containing the nucleic acid sequence encoding HIV-1 Env-4E10 Ig was confirmed by restriction enzyme digestion as shown in FIG. 17C. In FIG. 17C, lane 1 was undigested expression vector, lane 2 was the expression vector digested with BamHI and Xho1, and lane M was the Marker.

The nucleic acid sequence encoding HIV-1 Env-4E10 Ig is set forth in SEQ ID NO:62 and FIG. 60. In FIG. 60, underlining and double underlining mark the BamHI (GGA TCC) and XhoI (CTC GAG) restriction enzyme sites used to clone the nucleic acid sequence into the pVAX1 vector while bold marks the start (ATG) and stop (TGA TAA) codons. SEQ ID NO:62 encodes the amino acid sequence set forth in SEQ ID NO:1 and FIG. 19, i.e., the amino acid sequence of HIV-1 ENv-4E10 Ig (before cleavage by furin).

In this amino acid sequence, a signal peptide is linked by peptide bond to each of the heavy and light chains to improve secretion of the antibody generated in vivo. Additionally, a nucleic acid sequence encoding the P2A peptide is located between the nucleic acid sequences encoding the heavy and light chains to allow for more efficient cleavage of the translated polypeptide into separate polypeptides containing the heavy or light chain.

In particular, the amino acid sequence of the HIV-1 Env-4E10 Ig (before cleavage by furin; SEQ ID NO:1 and FIG. 19) has the following structure: human IgG heavy chain signal peptide, variable heavy region (VH), constant heavy region 1 (CH1), hinge region, constant heavy region 2 (CH2), constant heavy region 3 (CH3), furin cleavage site, GSG linker, P2A peptide, human kappa light chain signal peptide, variable light region (VL), and constant light region (CL, specifically kappa). The sequence of each portion of the structure (all which are contained within SEQ ID NO:1 in the order described above) is provided below.

Human IgG Heavy Chain Signal Peptide of HIV-1
Env-4E10 Ig-
(SEQ ID NO: 29)
MDWTWRILFLVAAATGTHA.

Variable Heavy Region of HIV-1 Env-4E10 Ig-
(SEQ ID NO: 30)
QVQLVQSGAEVKRPGSSVTVSCKASGGSFSTYALSWVRQAPGRGLEW

MGGVIPLLTITNYAPRFQGRITITADRSTSTAYLELNSLRPEDTAVY

YCAREGTTGWGWLGKPIGAFAHWGQGTLVTVSS.

Constant Heavy region 1 (CH1) of HIV-1
Env-4E10 Ig-
(SEQ ID NO: 31)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKV.

Hinge Region of HIV-1 Env-4E10 Ig-
(SEQ ID NO: 32)
EPKSCDKTHTCPPCP.

-continued

Constant Heavy Region 2 (CH2) of HIV-1
Env-4E10 Ig-
(SEQ ID NO: 33)
APELLGGPSVFLFPPKPKDTLMISRTPEVTCVVVDVSHEDPEVKFNW

YVDGVEVHNAKTKPREEQYNSTYRVVSVLTVLHQDWLNGKEYKCKVS

NKALPAPIEKTISKAK.

Constant Heavy Region 3 (CH3) of HIV-1
Env-4E10 Ig-
(SEQ ID NO: 34)
GQPREPQVYTLPPSRDELTKNQVSLTCLVKGFYPSDIAVEWESNGQP

ENNYKTTPPVLDSDGSFFLYSKLTVDKSRWQQGNVFSCSVMHEALHN

HYTQKSLSLSPGK.

Furin Cleavage Site of HIV-1 Env-4E10 Ig-
(SEQ ID NO: 35)
RGRKRRS.

GSG Linker and P2A Peptide of HIV-1
Env-4E10 Ig-
(SEQ ID NO: 36)
GSGATNFSLLKQAGDVEENPGP.

Human Kappa Light Chain Signal Peptide of HIV-1
Env-4E10 Ig-
(SEQ ID NO: 37)
MVLQTQVFISLLLWISGAYG.

Variable Light Region (VL) of HIV-1
Env-4E10 Ig-
(SEQ ID NO: 38)
EIVLTQSPGTQSLSPGERATLSCRASQSVGNNKLAWYQQRPGQAPRL

LIYGASSRPSGVADRFSGSGSGTDFTLTISRLEPEDFAVYYCQQYGQ

SLSTFGQGTKVE.

Constant Light Region (CL, kappa) of HIV-1
Env-4E10 Ig-
(SEQ ID NO: 39)
KRTVAAPSVFIFPPSDEQLKSGTASVVCLLNNFYPREAKVQWKVDNA

LQSGNSQESVTEQDSKDSTYSLSSTLTLSKADYEKHKVYACEVTHQG

LSSPVTKSFNRGE.

Example 13

HIV-1 4E10 ScFab

In addition to HIV-1 Env-PG9 Ig described above, a single chain Fab (i.e., VH/CH1 and VL/CL encoded by a nucleic sequence that is transcribed into a single transcript and translated into a single polypeptide) was created based upon the 4E10 antibody (referred to herein as HIV-1 4E10 scFab). The nucleic acid sequence encoding HIV-1 4E10 scFab is set forth in SEQ ID NO:52 and FIG. 48. In FIG. 48, underlining and double underlining mark the BamHI (GGA TCC) and XhoI (CTC GAG) that were used to clone this nucleic acid sequence into the pVAX1 vector while bold marks the start (ATG) and stop (TGA TAA) codons. The nucleic acid sequence set forth in SEQ ID NO:52 was an optimized nucleic acid sequence, i.e., inclusion of a kozak sequence (GCC ACC), codon optimization, and leader sequence. The leader sequence was located at the 5' end of the construct, i.e., preceding the single chain Fab, and thus, the signal peptide encoded by the linker sequence was linked by a peptide bond to the amino terminus of the single chain Fab. The nucleic acid sequence set forth in SEQ ID NO:52 also included a linker sequence that was positioned between the nucleic acid sequence encoding the VH/CH1 and the nucleic acid sequence encoding the VL/CL. Accordingly, in the polypeptide encoded by SEQ ID NO:52, the amino acid sequence encoded by the linker sequence kept the VH/CH1 and VL/CL together. SEQ ID NO:52 encoded the amino acid sequence set forth in SEQ ID NO:53 and FIG. 49, i.e., the amino acid sequence of the HIV-1 4E10 scFab.

Example 14

CHIKV-Env-Fab

As described above, an Fab reactive to HIV-1 Env was assembled or generated in vivo upon delivery of the nucleic acid sequences encoding the heavy (VH-CH1) and light (VL-CL) chains of HIV-1Env Fab to the cell or mouse. To determine if Fabs reactive to other antigens could be generated in vivo upon delivery of encoding nucleic acid sequences to the cell or subject, constructs were created that encoded the heavy (VH-CH1) and light (VL-CL, lamba type) chains of an antibody reactive to an envelope protein (Env) of the Chikungunya virus (CHIKV). Generation of these constructs are described here in Example 14 and also below in Examples 17 and 18.

Figure 20A:
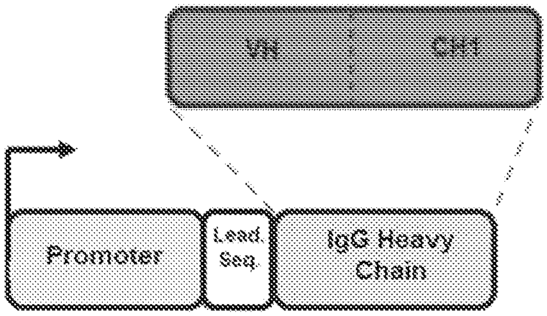
FIG. 20 shows (A) a schematic of a construct encoding the heavy (VH-CH1) chain of CHIKV-Env-Fab; and (B) a schematic of a construct encoding the heavy (VL-CL) chain of CHIKV-Env-Fab.
Figure 20B:
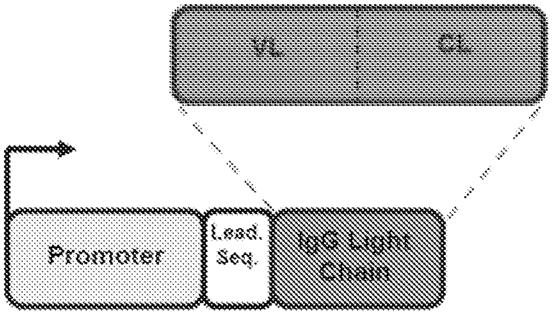
Figure 21:
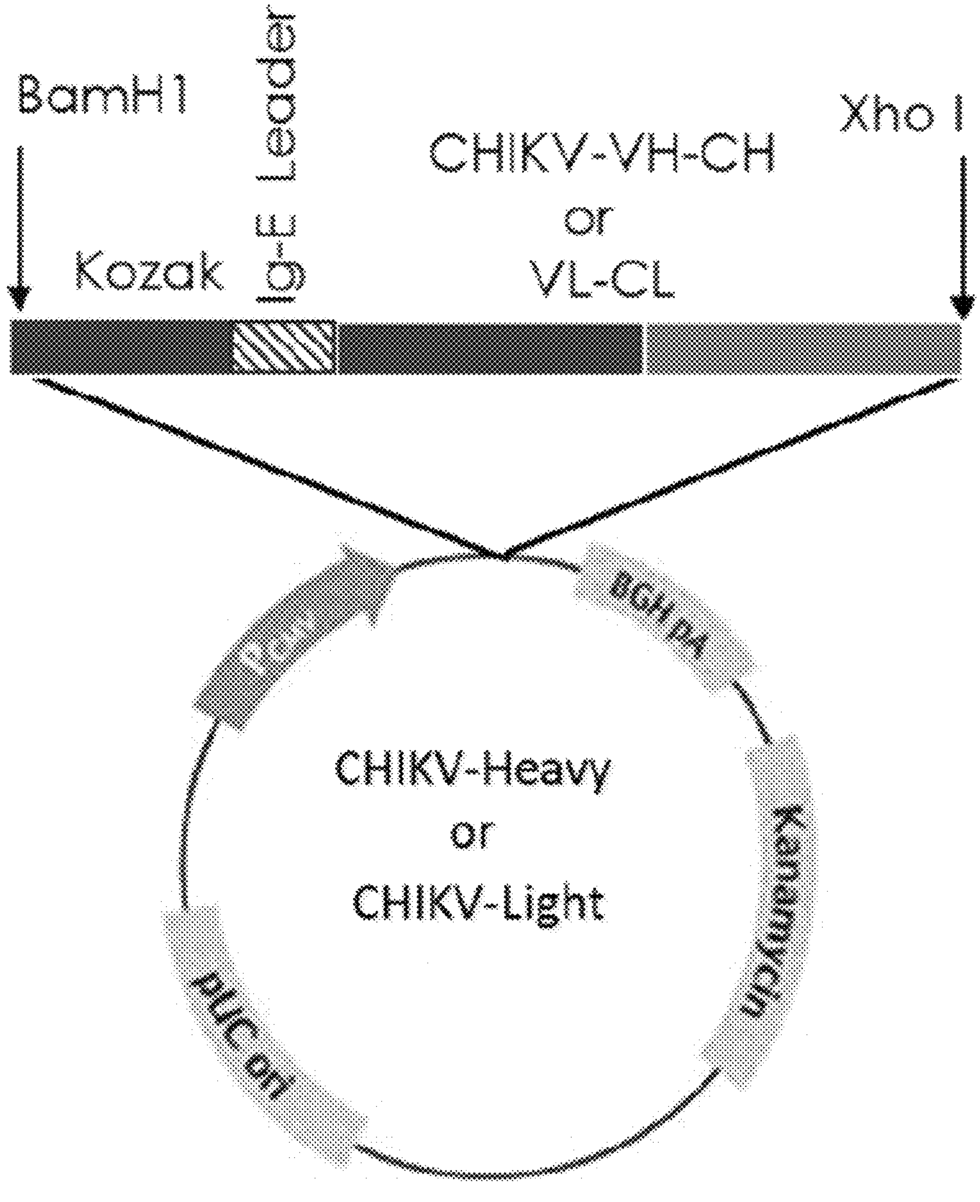
FIG. 21 shows a schematic of an expression vector containing the construct encoding the heavy (VH-CH1) or light (VL-CL) chain of CHIKV-Env-Fab.

Each construct included a leader sequence and a kozak sequence as shown in FIGS. 20A, 20B, and 21. The constructs encoding the VH-CH1 and VL-CL were cloned into an expression vector and thus, placed under the control of the cytomegalovirus (CMV) promoter (FIG. 21). The expression vectors containing the constructs encoding the VH-CH1 and VL-CL were known as CHIKV-H and CHIV-L, respectively. Together, a mixture of the CHIKV-H and CHIKV-L vectors was known as pCHIKV-Env-Fab and this generated CHIKV-Env-Fab in vivo (i.e., upon introduction into a cell or subject). In other words, both vectors were required to generate the CHIKV-Env-Fab in vivo as described in more detail below.

The constructs were also optimized for expression. In particular, a leader sequence was included in each construct to increase the efficiency of secretion of the CHIKV-Env-Fab upon generation of the CHIKV-Env-Fab in vivo. Each construct was also codon optimized and included a kozak sequence (GCC ACC). The nucleic acid sequence encoding the heavy chain (VH-CH1) of the CHIKV-Env-Fab is set forth in SEQ ID NO:58 and FIG. 56. In FIG. 56, underlining and double underling mark the BamHI (GGA TCC) and XhoI (CTC GAG) restriction enzyme sites used to clone the nucleic acid sequence into the pVAX1 vector while bold marks the start (ATG) and stop (TGA TAA) codons. SEQ ID NO:58 encodes the amino acid sequence set forth in SEQ ID NO:59 and FIG. 57, i.e., the amino acid sequence of the heavy chain (VH-CH1) of the CHIKV-Env-Fab.

The nucleic acid sequence encoding the light chain (VL-CL) of the CHIKV-Env-Fab is set forth in SEQ ID NO:60 and FIG. 58. In FIG. 58, underlining and double underling mark the BamHI (GGA TCC) and XhoI (CTC GAG) restriction enzyme sites used to clone the nucleic acid sequence into the pVAX1 vector while bold marks the start (ATG) and stop (TGA TAA) codons. SEQ ID NO:60 encodes the amino acid sequence set forth in SEQ ID NO:61 and FIG. 59, i.e., the amino acid sequence of the light chain (VL-CL) of the CHIKV-Env-Fab.

Figure 22:
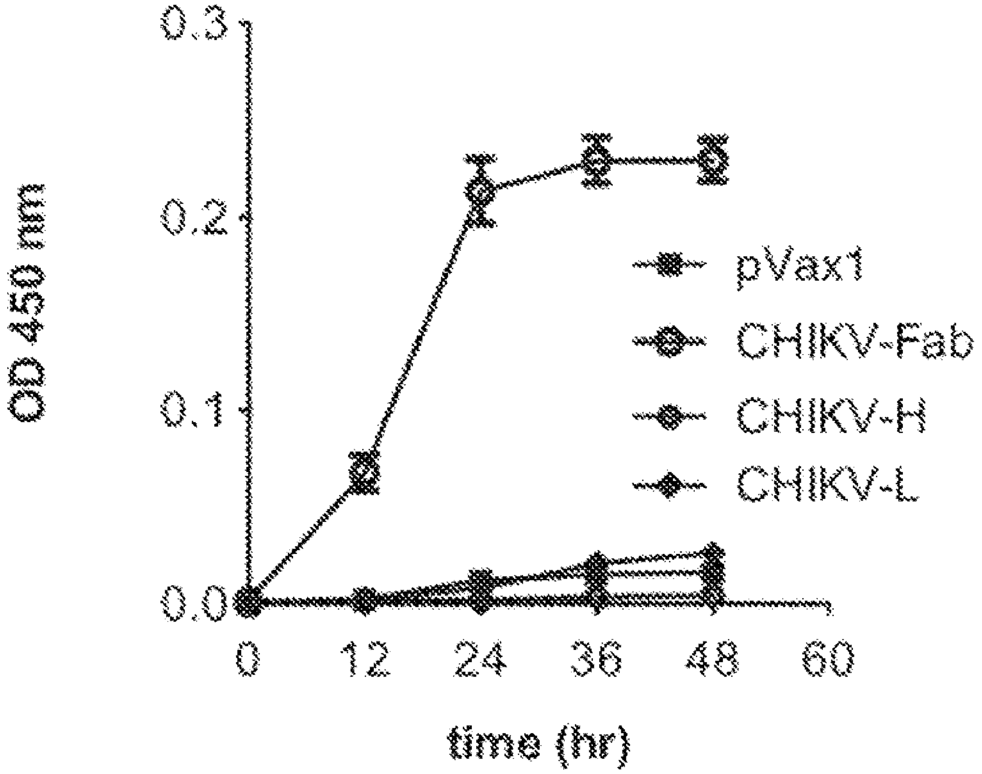
FIG. 22 shows a graph plotting time in hours (hr) vs. OD450 nm.

To measure the temporal kinetics of CHIKV-Env-Fab generation in vivo, cells were transfected with pVAX1, CHIKV-H, CHIKV-L, or pCHIKV-Env-Fab. After transfection, ELISA was used to measure the level of CHIKV-Env-Fab generation over time. As shown in FIG. 22, cells transfected with pVAX1, CHIKV-H, or CHIKV-L did not produce antibody that was reactive with the CHIKV Env antigen. In contrast, cells transfected with pCHIKV-Env-Fab produced antibody (i.e., CHIKV-Env-Fab, also known as CHIKV-Fab) that was reactive to the CHIKV Env antigen. Accordingly, these data indicated that delivery of nucleic acid sequences encoding the heavy (VH-CH1) and light (VL-CL) of the CHIKV-Env-Fab resulted in the generation of a Fab that bound or was reactive to the CHIKV-Env antigen.

Figure 23:
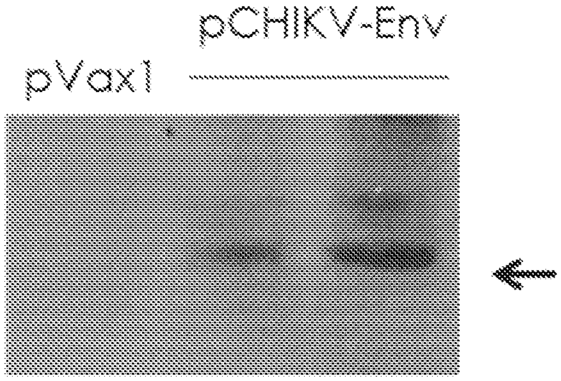
FIG. 23 shows an image of an immunoblot.

Additionally, CHIKV-Env-Fab was used in a Western blot of lysates obtained from cells transfected with pCHIKV-Env, which is a plasmid that encodes the CHIKV-Env antigen. As shown in the FIG. 23, the CHIKV-Env antigen was detected via the CHIKV-Env-Fab, indicating that this Fab bound to the antigen.

Figure 24:
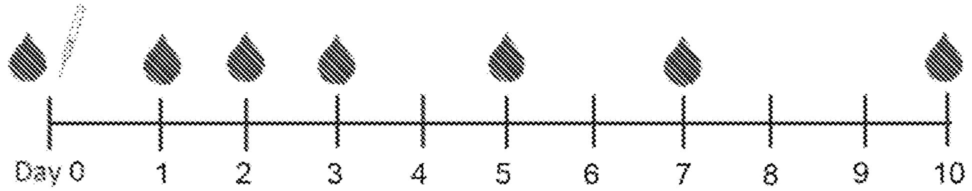
FIG. 24 shows a schematic of the timing of DNA administration and obtaining the pre-bleed and bleeds.
Figure 25:
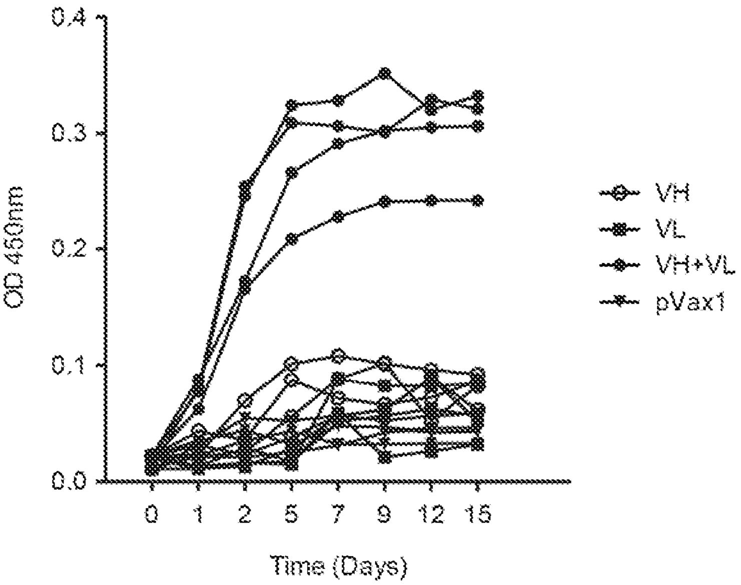
FIG. 25 shows a graph plotting time in days vs. OD450 nm.

To further examine the generation or assembly of CHIKV-Env-Fab in vivo, mice were administered pCHIKV-Env-Fab (i.e., 12.5 μg CHIKV-H and 12.5 μg CHIKV-L). Additionally, a second, third, and fourth group of mice were administered 25 μg pVAX1, CHIKV-H, and CHIKV-L, respectively, and served as controls. Specifically, the plasmids were administered to the respective groups of mice on day 0 after obtaining a pre-bleed sample. Bleeds were taken on day 1, day 2, day 3, day 5, day 7, and day 10 (FIG. 24). ELISA measurements were performed on these bleeds to determine the levels of antibody reactive to the CHIKV-Env antigen. As shown in FIG. 25, mice administered pCHIKV-Env-Fab resulted in the generation of antibody (i.e., CHIKV-Env-Fab) that was reactive to the CHIKV-Env antigen. Mice administered pVAX1, CHIKV-H or CHIKV-L did not generate antibodies having significant reactivity with the CHIKV-Env antigen. Accordingly, these data further demonstrated that upon delivery of nucleic acid sequences encoding the heavy (VH-CH1) and light (VL-CL) chains of the CHIKV-Env-Fab, this Fab was generated in vivo (i.e., in the mice) and was reactive to its antigen (i.e., CHIKV-Env), thereby demonstrating that the Fab was correctly assembled in vivo.

To determine if the CHIKV-Env-Fab could protect against CHIKV infection, C57BL/6 mice (2-3 weeks of age; about 20-25 grams in weight) were administered on day 0 pCHIKV-Env-Fab (50 μg) or pVAX1. 6 hours after administration of pCHIKV-Env-Fab, each mouse was inoculated with 7 log 10 PFU in a total volume of 25 μl by an intranasal route. Each subsequent day, body weight was determined for each mouse and a mouse was sacrificed if weight loss was more than 30%.

Figure 26:
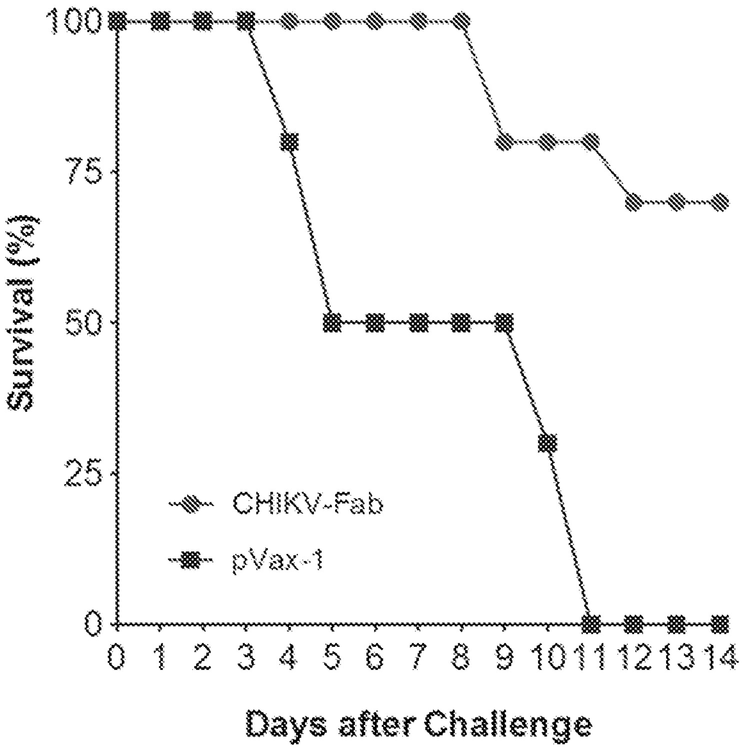
FIG. 26 shows a graph plotting days after challenge vs. percent survival.
Figure 27:
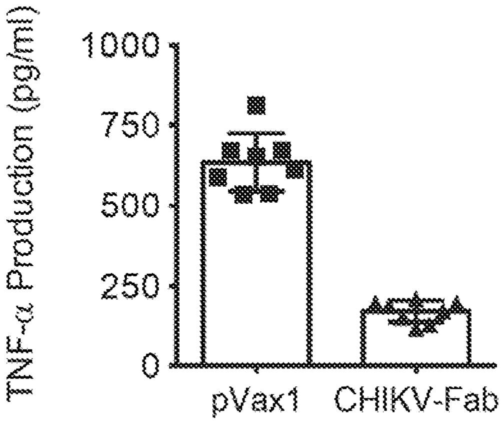
FIG. 27 shows a graph plotting mouse group vs. pg/mL of TNF-α.
Figure 28:
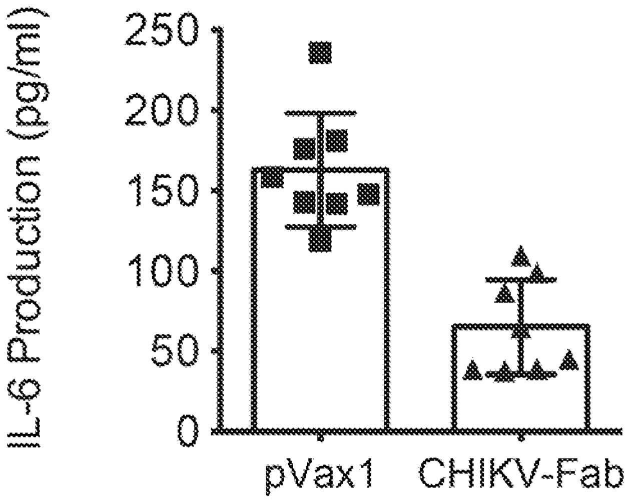
FIG. 28 shows a graph plotting mouse group vs. pg/mL of IL-6.
Figure 29:
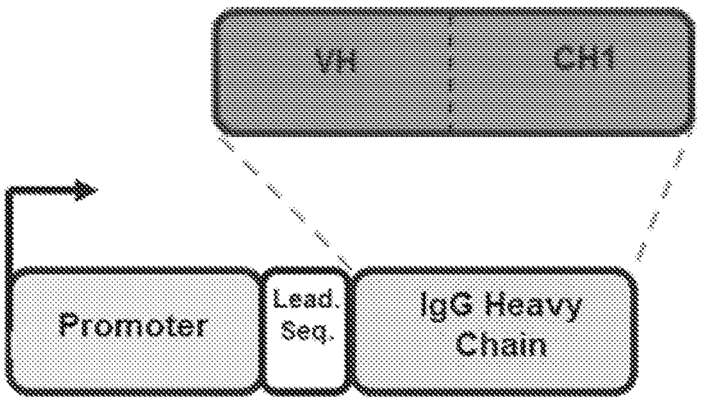
FIG. 29 shows a schematic illustrating a construct encoding a VH-CH1 and under the control of a promoter.

As shown in FIG. 26, about 75% of the mice administered pCHIKV-Env-Fab survived CHIKV infection as of day 14 of study while by day 14, all of mice that were administered pVAX1 were dead. Additionally, mice administered pCHIKV-Env-Fab were associated with lower levels of the cytokines TNF-α and IL-6 as compared to the mice administered pVAX1 (FIGS. 27 and 28). TNF-α and IL-6 levels were measured in sera obtained from the mice. These surviving mice exhibited no signs of pathology, body weight loss, and had lower levels of the cytokines TNF-α and IL-6. Accordingly, these data indicated that the pCHIKV-Env-Fab administration protected the mice from CHIKV infection and promoted survival of CHIKV infection. In other words, in vivo generation of CHIKV-Env-Fab in the mice protected against and promoted survival of CHIKV infection.

Example 15

Anti-Her-2 Fab

Figure 30:
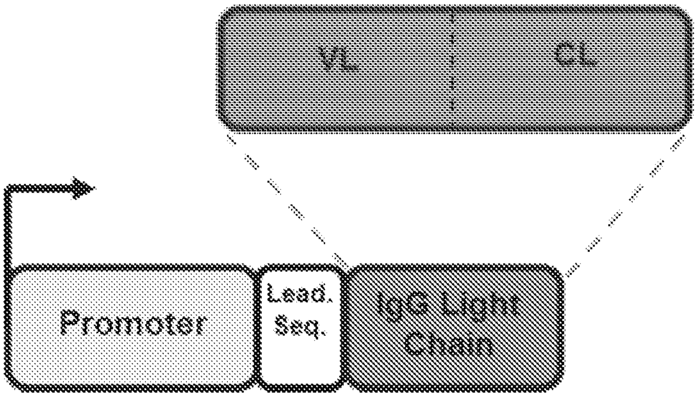
FIG. 30 shows a schematic illustrating a construct encoding a VL-CL and under the control of a promoter.
Figure 31:
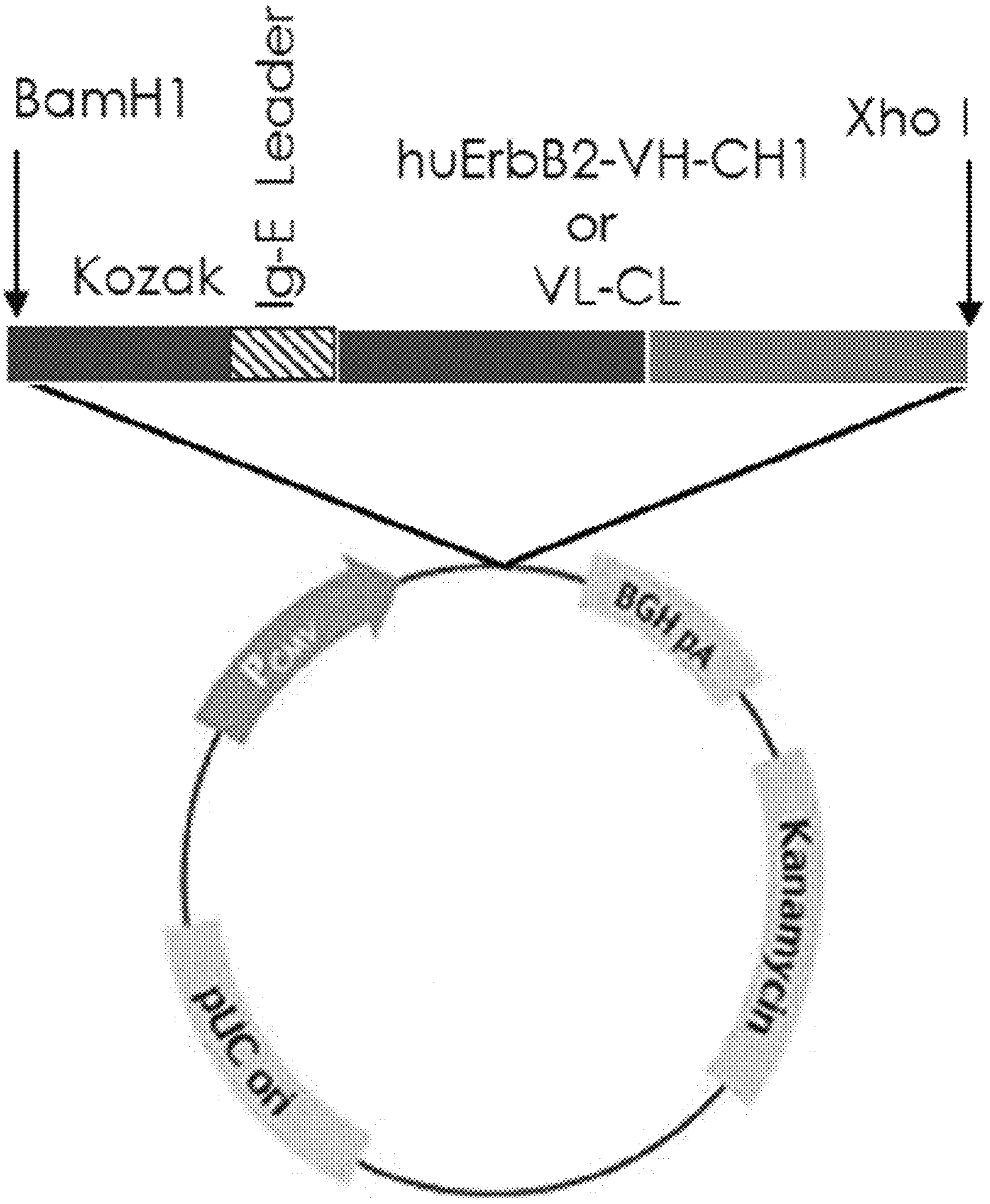
FIG. 31 shows a schematic illustrating the construct encoding a VH-CH1 or VL-CL of the anti-Her-2 Fab cloned into an expression vector.

As described above, an Fab (i.e., VH/CH1 and VL/CL) reactive to HIV-1 Env or CHIKV Env was assembled or generated in vivo upon delivery of the nucleic acid sequences encoding the heavy (VH-CH1) and light (VL-CL) chains of the HIV-1Env Fab or CHIKV Env-Fab to the cell or mouse. To determine if Fabs reactive to a self antigen (i.e., an antigen endogenous to the subject being administered the nucleic acid sequences encoding the Fab) could be generated in vivo upon delivery of encoding nucleic acid sequences to the cell or subject, constructs were created that encoded the heavy (VH-CH1) and light (VL-CL, kappa type) chains of an antibody reactive to human epidermal growth factor receptor 2 (Her-2; also known as Erb2). Each construct included a leader sequence and a kozak sequence (GCC ACC), which preceded the nucleic acid sequence encoding the VH-CH1 or VL-CL of the anti-Her-2 Fab as shown in FIGS. 28, 30, and 31. Accordingly, these constructs were optimized due to the introduction of the leader sequence and kozak sequence, and were further optimized for codon usage.

The constructs encoding the VH-CH1 and VL-CL were cloned into the pVAX1 expression vector, namely between the BamHI and XhoI restriction sites and thus, were placed under the control of the cytomegalovirus (CMV) promoter. In particular, the constructs encoding the VH-CH1 and VL-CL were cloned into two separate pVAX1 vectors, and thus, the resulting two plasmids were required to generate the anti-Her-2 Fab in vivo.

The nucleic acid sequence encoding the VH-CH1 of the anti-Her-2 Fab is set forth in SEQ ID NO:40 and FIG. 32. In FIG. 32, underlining and double underling mark the BamHI (GGA TCC) and XhoI (CTC GAG) restriction enzyme sites, respectively, used to clone the nucleic acid sequence into the pVAX1 vector while bold marks the start (ATG) and stop (TGA TAA) codons. SEQ ID NO:40 encodes the amino acid sequence set forth in SEQ ID NO:41, i.e., the amino acid sequence of the VH-CH1 of the anti-Her-2 Fab (FIGS. 32 and 33).

The nucleic acid sequence encoding the VL-CL of the anti-Her-2 Fab is set forth in SEQ ID NO:42 and FIG. 34. In FIG. 34, underlining and double underlining mark the BamHI (GGA TCC) and Xho (CTC GAG) restriction enzyme sites, respectively, used to cloned the nucleic acid sequence into the pVAX1 vector while bold marks the start (ATG) and stop (TGA TAA) codons. SEQ ID NO:42 encodes the amino acid sequence set forth in SEQ ID NO:43, i.e., the amino acid sequence of the VL-CL of the anti-Her-2 Fab (FIGS. 34 and 35).

Figure 36:
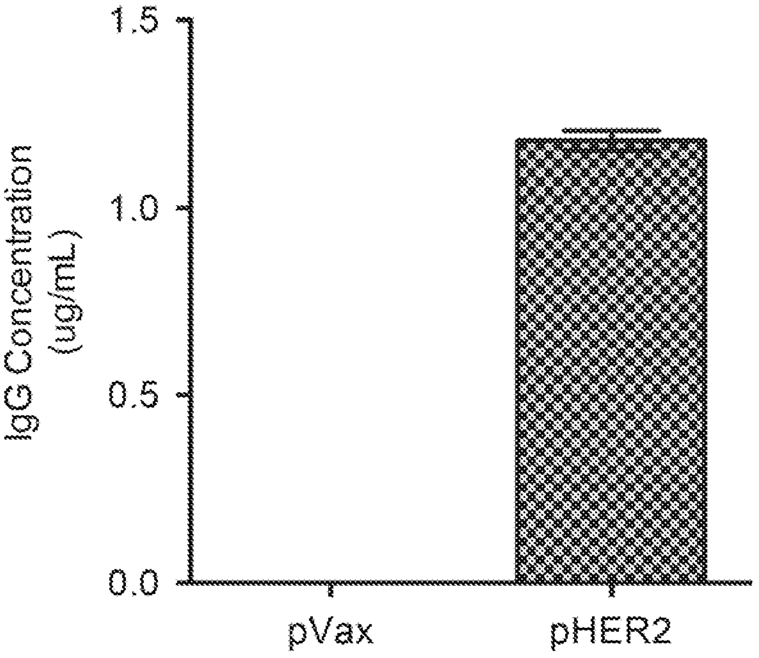
FIG. 36 shows a graph plotting type of transfected cell vs. IgG concentration (ng/mL).

To determine whether a mixture of the plasmids encoding the VH-CH1 and VL-CL of the anti-Her-2 Fab generated the anti-Her-2 Fab in vivo, 293T cells were transfected with a mixture of the plasmids encoding the heavy (VH-CH1) and light (VL and CL) of anti-Her-2 Fab or pVAX1. After transfection, total IgG concentration was measured as shown in FIG. 36. In FIG. 36, error bars represented the standard deviation. These data indicated that the anti-Her-2 Fab was generated in vivo upon introduction of the two plasmids, each encoding the VH-CH1 or VL-CL of anti-Her-2 Fab.

Example 16

Anti-Dengue Virus Human IgG

Figure 37:
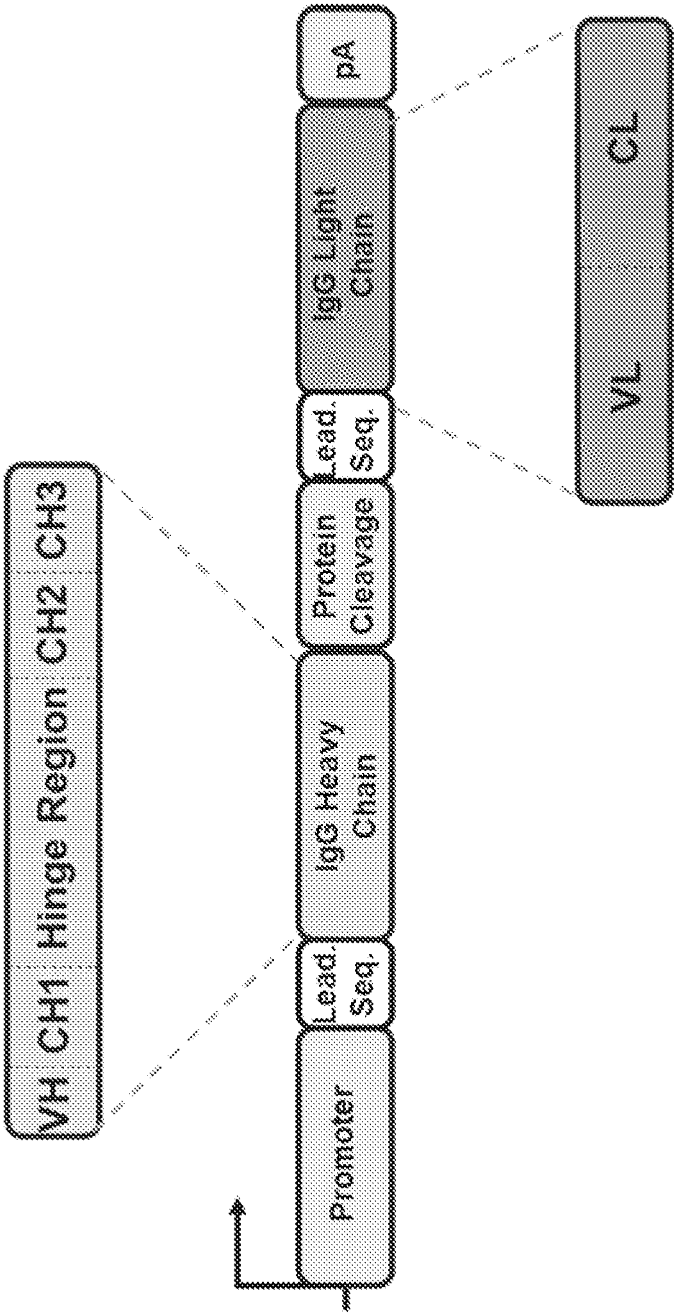
FIG. 37 shows a schematic illustrating a construct encoding the variable heavy region (VH), variable heavy constant region 1 (CH1), hinge region, variable heavy constant region 2 (CH2), variable heavy constant 3 (CH3) of an immunoglobulin G (IgG) heavy chain and encoding the variable light region (VL) and variable light constant region (CL) of an IgG light chain. The heavy and light chains of the IgG are separated by a protease cleavage site and each is preceded by a signal peptide (encoded by leader sequence).

A single plasmid system was created to generate an anti-Dengue virus (DENV) human IgG antibody in vivo. Specifically, a construct was generated as shown in the schematic of FIG. 37. Specifically, a leader sequence was placed upstream of the nucleic acid sequence encoding the IgG heavy chain (i.e., variable heavy region (VH), constant heavy region 1 (CH1), hinge region, constant heavy region 2 (CH2), and constant heavy region 3 (CH3)). In turn, a sequence encoding a protease cleavage site was placed downstream of the nucleic acid sequence encoding the IgG heavy chain. A nucleic acid sequence encoding the IgG light chain (i.e., variable light region (VL) and constant light region (CL)) was located after the sequence encoding the protease cleavage site (i.e., furin cleavage site). The signal peptides encoded by this construct were cognate signal peptides, thereby providing proper secretion of the antibody upon expression. Additionally, upon expression a single transcript is translated into a single polypeptide, which is then processed by the protease into the polypeptides corresponding to the heavy and light chains of the anti-DENV human IgG. These heavy and light chain polypeptides then assemble into a functional anti-DENV human IgG, i.e., an antibody that binds its cognate antigen.

This construct was cloned into the expression vector pVAX1 (namely the BamHI and XhoI sites), thereby placing it under the control of a promoter. This construct encoding the anti-Dengue virus human IgG has the nucleic acid sequence set forth in SEQ ID NO:44 (FIG. 38), which has been optimized for expression. In FIG. 38, underlining and double underlining mark the BamH1 (GGA TCC) and Xho1 (CTC GAG) restriction enzyme sites used to clone the construct into the pVAX 1 vector while bolds marks the start (ATG) and stop (TGA TAA) codons. Optimization included inclusion of a kozak sequence (GCC ACC) and codon optimization. SEQ ID NO:44 encodes the amino acid sequence set forth in SEQ ID NO:45 and FIG. 39, i.e., the amino acid sequence of the anti-DENV human IgG before cleavage by the protease to separate the heavy and light chains into two separate polypeptides.

Figure 40:
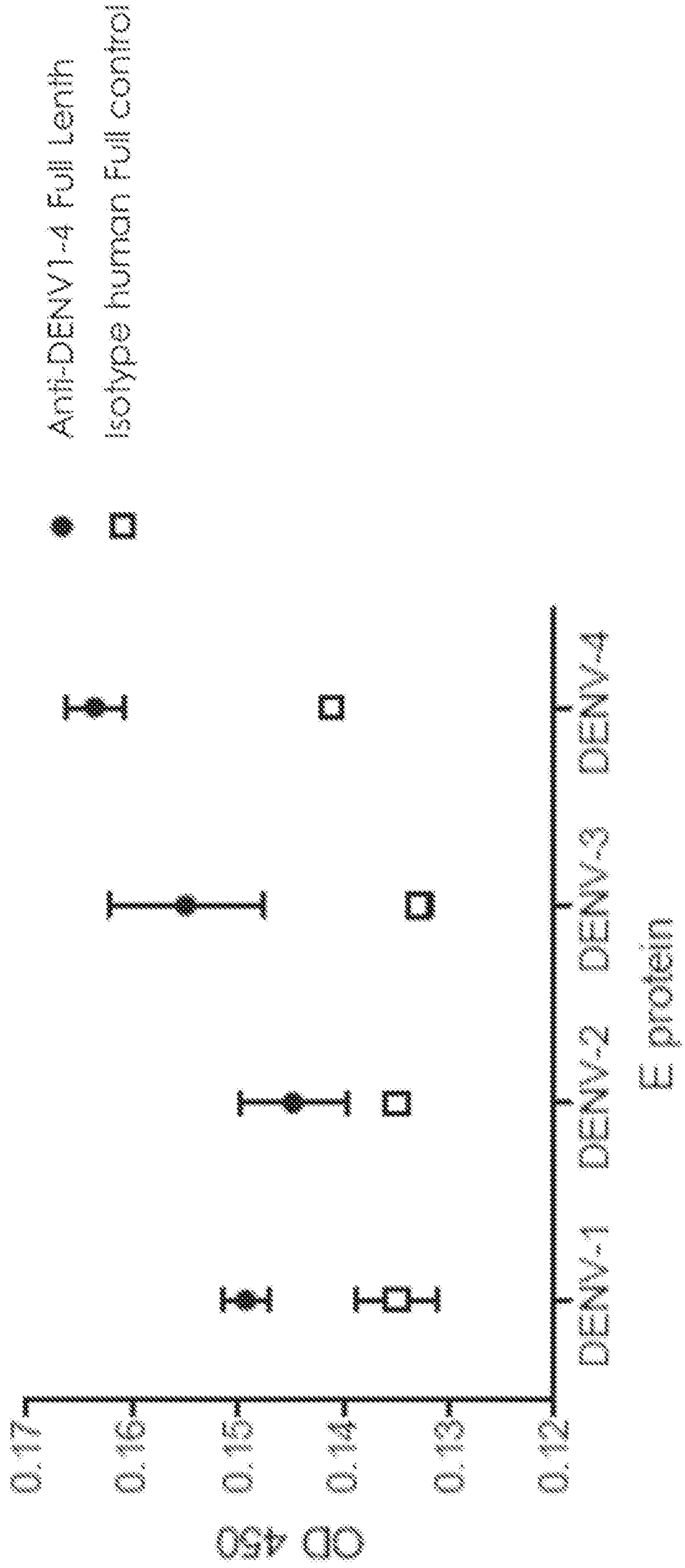
FIG. 40 shows a graph plotting mouse group vs. OD 450 nm.

The plasmid containing the nucleic acid sequence encoding the anti-Dengue virus human IgG was administered to mice to determine if the anti-Dengue virus human IgG was generated in vivo (i.e., in the mice). After administration of the plasmid, sera were obtained from the mice and analyzed via ELISA to determine whether the sera contained antibody that was reactive to the Dengue E protein from four Dengue virus serotypes, namely DENV-1, DENV-2, DENV-3, and DENV-4. As shown in FIG. 40, sera from mice administered the plasmid containing the nucleic acid sequence encoding the anti-DENV human IgG was reactive to the DENV E protein from serotypes DENV-1, -2, -3, and -4. An isotypic antibody was used as a positive control. Accordingly, these data indicated that upon introduction of the plasmid into mice, the nucleic acid sequence encoding the anti-DENV human IgG was transcribed and translated into a polypeptide that was processed to yield polypeptides containing the heavy and light chains of the anti-DENV human IgG. These polypeptides assembled into the anti-DENV human IgG, thereby providing a functional antibody that bound or was reactive to the DENV E protein.

Figure 41:
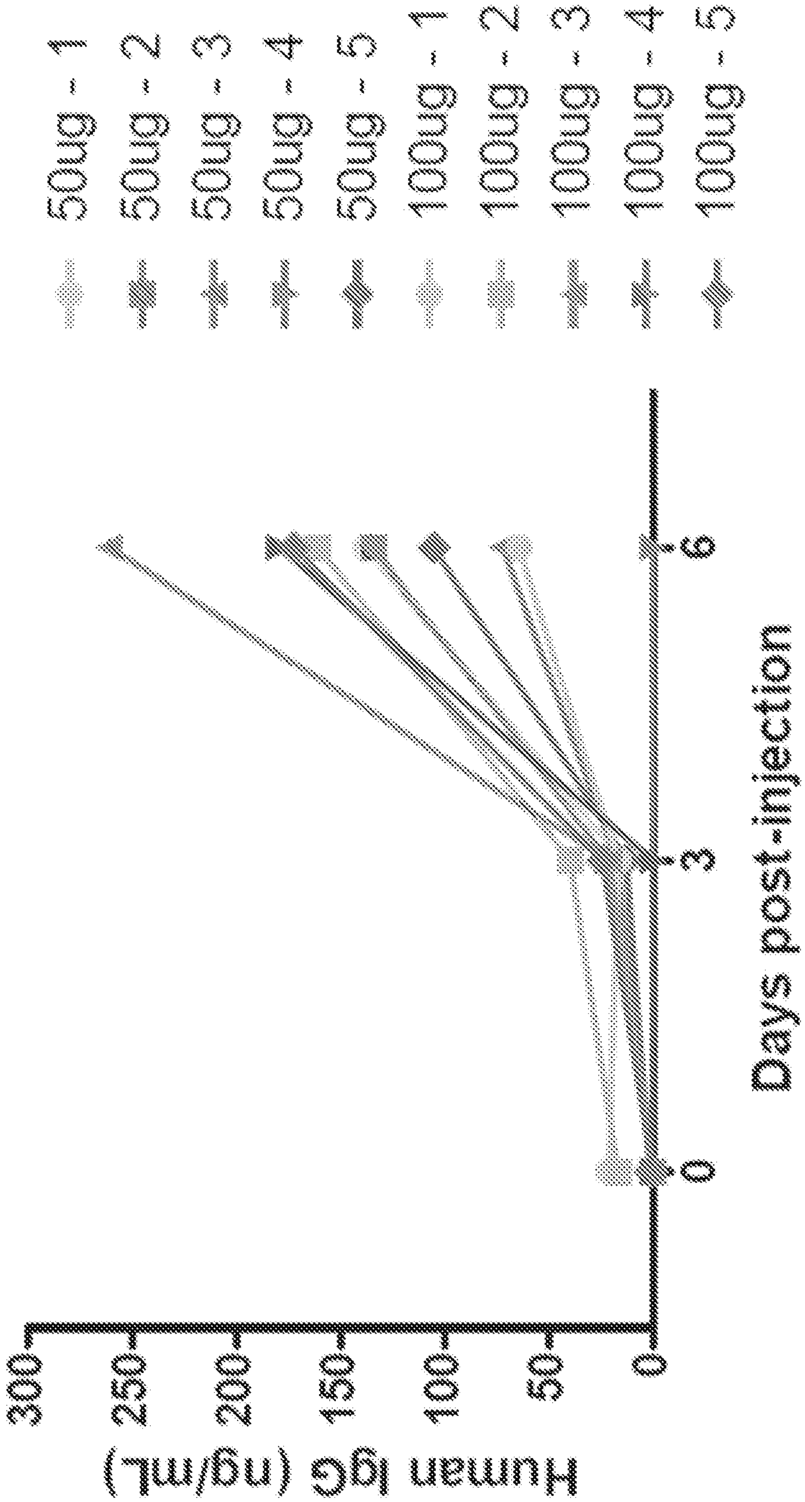
FIG. 41 shows a graph plotting days post-injection vs. human IgG concentration (ng/mL).

To further examine the generation of anti-DENV human IgG in vivo by administration of a single plasmid, mice were administered via injection the plasmid containing the nucleic acid sequence encoding the anti-DENV human IgG. Specifically, mice were administered 50 μg or 100 μg of the plasmid and 5 mice were in each group. On day 3 and day 6 post-injection, the mice were examined for seroconversion. As shown in FIG. 41, mice from both groups were seropositive for anti-DENV IgG antibodies. In particular, the mice administered 50 μg of the plasmid had about 110 ng/mL of human IgG and the mice administered 100 μg of the plasmid had about 170 ng/mL of human IgG. Accordingly, these data further demonstrated the generation of anti-DENV human IgG in vivo after administration of a plasmid encoding the same. These data also demonstrated that anti-DENV human IgG antibody production occurred in less than 1 week, thereby allowing for rapid production of anti-DENV human IgG.

Example 17

Materials and Methods for Examples 18-25

Optimized DNA plasmid(s) encoding either a Fab fragment (CHIKV-Fab) or full-length antibody (CHIKV-IgG) targeting the CHIKV envelope (Env) protein were designed and compared. Intramuscular delivery of either DNA construct into mice resulted in rapid production of their encoded antibodies as well as protective efficacy from early and late exposures to CHIKV. Sera from CHIKV-IgG immunized mice also neutralized multiple clinical CHIKV isolates ex vivo. Single immunizations with CHIKV-IgG demonstrated significantly better protection from early viral exposure than antigen-inducing DNA plasmids as well as comparable levels of protection from late exposure to CHIKV. These studies are described in more detail below.

Cells.

Human Embryonic Kidney (HEK) 293T cells and Vero cells were maintained in Dulbecco's Modified Eagle's Medium (Gibco-Invitrogen) supplemented with 10% fetal bovine serum (FBS), 100 IU of penicillin per ml, 100 ug of streptomycin per ml and 2 mM L-glutamine Construction of the CHIKV-Fab and CHIKV-IgG.

To construct the anti-CHIKV Env antibody expressing plasmid, the variable heavy (VH) and variable light (VL) chain segments of the antibody were generated by use of synthetic oligonucleotides with several modifications. For cloning the Fab fragment or full length antibody, a single open reading frame was assembled containing the heavy and light chains, an inserted furin cleavage site and a P2A self-processing peptide site in between heavy and light chain. This was incorporated in order to express a full-length antibody from a single open reading frame. In both plasmids, a leader sequence was incorporated into each gene in order to enhance expression. The resulting sequences were modified and enhanced with codon and RNA optimization and were cloned into the pVax1 expression vector and the resulting constructs were produced on a large scale for this study (GenScript, NJ). The purified plasmid DNA was formulated in water for subsequent administration into mice. An empty control pVax1 expression vector was used as a negative control. Specifically, the DNA for the variable light (VL) and variable heavy (VH) (i.e. Fab) chains or full immunoglobulin (Ig) used in this study were generated from an anti-Env specific CHIKV neutralizing human monoclonal antibody/hybridoma.

Construction of the CHIKV Fab is also described above in Example 14 and below in Example 18.

Construction of the CHIKV Ig is also described below in Example 18. The nucleic acid sequence encoding the CHIKV Ig is set forth in SEQ ID NO:65. SEQ ID NO:65 encodes the amino acid sequence set forth in SEQ ID NO:66.

Measurement of Expression of Anti-CHIKV Env Antibody from CHIKV Fab or CHIKV-IgG by Western Blot Analysis.

The human 293T cell line was utilized for expression analysis using the TurboFectin 8.0 transfection reagent (OriGene). These cells were seeded at 50-70% confluence ($1\text{-}3\times10^5$ cells per well in 2 mL total media volume) in a 35 mm culture dish for 24 hours. After 24 hours, cells were transfected with 10 μg of pVax1 control vector, CHIKV-Fab (5 μg of VH and 5 μg of VL DNA) or CHIKV-IgG (10 μg). Supernatant was collected at 48 hours post-transfection and assessed for anti-CHIKV antibody levels by ELISA using CHIKV-Env recombinant protein as the coating antigen. Supernatant from the pVax1 sample was used as a negative control.

Western blot analysis was performed to confirm specific binding of the antibody produced by transfection with CHIKV-Fab or CHIKV-IgG. To generate a source of CHIKV envelope protein, 293T cells were transfected with 10 μg of DNA plasmids expressing the CHIKV-Env. Two days post transfection cells were lysed and electrophoresed on a 12% SDS-PAGE gel. The gel was transferred onto a nitrocellulose membrane using iBlot2 (Life Technologies). Samples were separated on a poly-acrylamide gel (12% NuPAGE Novex, Invitrogen) and transferred to a PDF membrane (Invitrogen). Membranes were blocked using a commercial buffer (Odyssey Blocking Buffer, LiCor Biosciences) and incubated overnight at 4° C. with specific primary antibodies raised in mice as well as β-actin (Santa Cruz). IRDye800 and IRD700 goat anti-rabbit or anti-mouse secondary antibodies were used for detection (LiCor Biosciences).

Virus-Specific Binding Assay: Immunofluorescence Analysis.

Chamber slides (Nalgene Nunc, Naperville, Ill.) were seeded with Vero cells ($1\times10^4$) from stock cultures. Cells were grown until they reach approximately 80% confluency after which cells were infected for 2 h with CHIKV at a multiplicity of infection (m.o.i.) of 1. After adsorbing for 2 h at 37° C., the virus inoculum was aspirated and the cell sheets were rinsed three times with Iscove-10% FBS medium. Twenty-four hours post infection, the cells were washed twice with PBS and fixed with cold methanol for 20 min at room temperature and then allowed to air dry. Antibody binding was detected by addition of immune sera (1:100 dilution) from the CHIKV-Fab administered mice for 90 min at 37° C. in a humidified chamber. After washing thrice with PBS, the cells were incubated for 60 min at 37° C. with a FITC-conjugated goat anti-human IgG (Santa Cruz Biotechnology Inc.,). The additional nuclear staining with 4',6-diamidino-2-phenylindole (DAPI) at room temperature for 20 minutes. 1×PBS washes were performed after each incubation step. The samples were subsequently mounted onto glass slides using DABCO and were viewed under a confocal microscope (LSM710; Carl Zeiss). The resulting images were analysed using the Zen software (Carl Zeiss). Further, immune reactivity of CHIK-IgG immunized sera were tested in HIV-1 GFP pseudotyped with CHIKV-Env virus infected Vero cells to test the binding activity by flow cytometry.

Antibody Quantification Analysis by ELISA.

ELISA assays were performed with sera from mice administered CHIKV-Fab, CHIKV-IgG or pVax1 in order to measure the antibody construct's expression kinetics and capacity to bind to its target antigen, CHIKV-Env. Sera samples were collected from plasmid-injected mice at various time points. For quantification of total human Fab in the collected sera samples, ninety-six well high binding polystyrene plates (Corning) were coated with 1 μg/well of goat anti-human IgG-Fab fragment antibody (Bethyl Laboratories) overnight at 4° C. To measure the antibody construct's capacity to bind its target antigen, the CHIKV Env protein, ELISA plates were coated with recombinant CHIKV Env protein overnight at 4° C. The following day, plates were washed with PBS-T (PBS, 0.05% Tween 20) and blocked with 3% BSA in PBS-T for 1 hour at room temperature. After another wash, samples were diluted at 1:100 in 1% FBS in PBS-T, added to the plate, and incubated for 1 hour at room temperature. Plates were washed, and HRP-conjugated goat anti-human kappa light chain (Bethyl Laboratories) was added for 1 hour at room temperature. Plates were then read at 450 nm using a Biotek EL312e Bio-Kinetics reader. Samples were detected with SIGMAFAST OPD (Sigma-Aldrich). For quantification, a standard curve was generated using purified human IgG/kappa (Bethyl Laboratories). All sera samples were tested in duplicate.

CHIKV-Env Pseudotype Production and FACS Analysis.

CHIKV-Env GFP pseudotypes were produced by using 5 μg of pNL4-3env-GFP and 10 μg of plasmid-encoding CHIKV viral envelope. Pseudotyped VSVs were produced. Pseudovirions were concentrated by ultracentrifuge concentration at 28,000 rpm in a Sorvall Lynx 400 superspeed centrifuge (Thermo Scientific) through a 20% sucrose cushion for 1.5 h at 4° C. The pellets were resuspended overnight in HBSS at 4° C. After p24 ELISA analysis, lentiviral pseudovirions were normalized to contain an equal number of viral particles. Cells were seeded at $2.5\times10^4$ in 48-well plates 24 h prior to infection. Cells were detached 18 hours post infection, fixed with 1% PFA in PBS for 10 minutes, and permeabilized with 0.1% (w/v) saponin detergent solution. CHIKV infected cells were incubated with sera from pCHIKV-IgG administered mice and Alexa 594 conjugated goat anti-human IgG secondary antibody (Life Technologies). Infection was evaluated with flow cytometry (Becton-Dickinson) and analyzed using FlowJo software.

IgG Administration in Mice and CHIKV Challenge Study.

B6.Cg-Foxn1$^{nu}$/J (The Jackson Laboratory) mice were used for the Fab and full length IgG generation, quantification and functional characterization. Mice were injected with a total volume of 50 μl of either pVax1 DNA (100 μg), CHIKV-Fab DNA (50 mg of VH and 50 μg of VL) or CHIKV-IgG (100 μg) in the quadriceps muscle. Administration of the DNA plasmids was followed immediately by optimized EP-mediated delivery (CELLECTRA®; Inovio Pharmaceuticals, Inc.,). The pulsing parameters for EP delivery were 3 pulses of 0.5 Amp constant current, 1 second apart and 52 milliseconds in length.

For CHIKV challenge study, BALB/c mice were injected intramuscularly with 100 μl total volume of CHIKV-Fab or CHIKV-IgG or empty control pVax1 plasmids (100 μg), immediately followed with Opt-EP mediated delivery. Two days after DNA delivery, mice were challenged with a total of $1\times10^7$ PFU (25 μl) of CHIKV-Del-03 (JN578247) (41) via the subcutaneous route in the dorsal side of each hind foot. Foot swelling (height by breadth) was measured using a digital caliper daily from 0 to 14 dpi. Mice were monitored daily for survival and signs of infection (i.e. body weight and lethargy) over a three week post-challenge observation period. Animals that lost more than 30% body mass were euthanized and serum samples were collected for cytokine quantification and other immune analysis. Blood samples were collected at days 7 to 14 postchallenge from tail bleedings and viremia was analyzed by plaque assay (PFU/ml). Two independent experiments were performed.

Immune Cytokine Analysis.

Sera were collected from CHIKV-Fab or CHIKV-Ig injected and virally challenged mice (at day 10 post challenge). TNF-β, IL-1β, IP-10 and IL-6 serum cytokine levels were measured using ELISA kits according to the manufacturer's instructions (R&D Systems).

CHIKV Neutralization Assay.

Virus neutralizing antibody titers in sera of mice administered with CHIKV-Fab or CHIKV-IgG were determined Briefly, Vero cells (American Type Culture Collection) were plated at 15,000 cells per well in a 96 well plate (Nunc). Serial two-fold dilutions of heat-inactivated mice sera were prepared in triplicate in 96-wells plate and 100 TCID50 of CHIKV viral isolates suspension was added to each well. After one hour of incubation at 37° C., samples were added to Vero cell monolayers and incubated for 3 days. Vero cell monolayers were subsequently fixed and stained with 0.05% crystal violet, 20% methanol (Sigma-Aldrich). Neutralization titers were determined by taking the reciprocal of the last dilution where the Vero cell monolayer remained fully intact and expressed as the reciprocal of the highest serum dilution still giving 100% suppression of cytopathic effect. Graphs and statistics were generated with the GraphPad Prism 5 software package (GraphPad Software). Nonlinear regression fitting with sigmoidal dose-response (variable slope) was used to determine the IC50.

Statistical Analysis.

Statistical analyses, using either a student t-test or the nonparametric Spearman's correlation test, were performed using Graph Pad Prism software (Prism Inc.). Correlations between the variables in the control and experimental groups were statistically evaluated using the Spearman rank correlation test. For all the tests, p values less than 0.05 were considered significant.

Example 18

Construct and Functionality of CHIKV Monoclonal Antibodies

Figure 63:
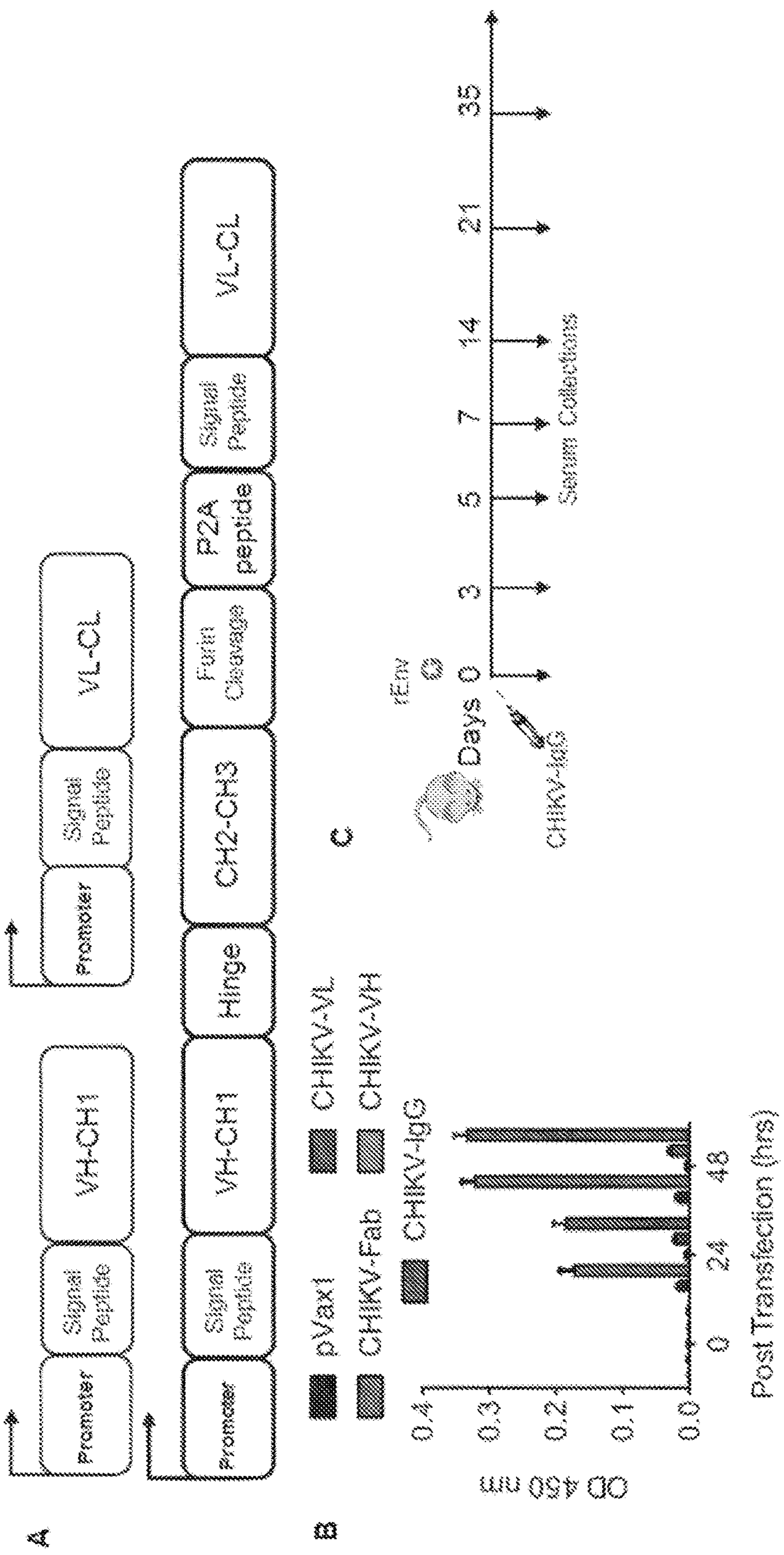
FIG. 63 shows the schematic design of antibody expressing plasmids and confirmation of expression and binding kinetics of antibodies following a single EP mediated injection of the CHIKV-Fab expression plasmid. (A) The variable light and heavy (VL and VH) IgG fragment genes of a selected anti-CHIKV human monoclonal were cloned separately for CHIKV-Fab and CHIKV-IgG into optimized DNA plasmid vectors. (B) DNA plasmids encoding the anti-CHIKV VL and VH-Fab genes or CHIKV-IgG were transfected together into 293T cells in order to determine their respective in vitro expression by ELISA. Cells transfected with an empty control pVax1 plasmid served as a negative control. (C) In vivo expression of anti-CHIKV-IgG antibodies following EP mediated delivery. Mice (B6.Cg-Foxn $1^{nu}$/J) were administrated single intramuscular injections of CHIKV-IgG plasmids (total 100 μg) followed by EP (n=5 mice per group). Injection of an empty pVax1 vector was used a negative control. (D) Specific binding to the CHIKV-Env antigen was measured through ELISA assays with collected sera from CHIKV-IgG and recombinant CHIKV-Env immunized mice and presented as OD 450 nm values for individual mice at different time points. (E) Sera levels of human IgG concentration were measured at various time points in mice injected intramuscularly with CHIKV-IgG as described in Example 17. (F) Evaluation of antibody binding affinity and specificity. Binding affinity functionality of sera from CHIKV-IgG injected mice (Day 14) to target proteins was tested by Western blot using the cell lysates from the CHIKV-infected cells as described in the Examples, below.

The CHIKV-Fab and full length IgG constructs were optimized for increased expression. FIG. 63A illustrates the design of the optimized anti-CHIKV-Fab and CHIKV-IgG plasmids. For CHIKV-Fab, the VH and VL genes were then separately cloned into pVax1 plasmid vectors as described above in Examples 14 and 17.

To examine the expression and functionality of CHIKV-Fab and IgG, these antibodies were produced in vitro. Specifically, human 293T cells were transfected with equal amounts of both heavy and light chain plasmids of the CHIKV-Fab or the plasmid of the CHIKV-IgG, and supernatant from transfected cells were collected at 48 hours post-transfection. As indicated in FIG. 63B, only cells transfected with CHIKV-Fab plasmids or CHIKV-IgG plasmid produced measurable levels of the anti-CHIKV antibodies as measured by the binding ELISA using recombinant CHIKV envelope protein and indicating that the two-plasmid design of CHIKV-Fab or single full length IgG generated properly assembled and functional CHIKV antibodies in vitro.

Example 19

Enhanced In Vivo Expression Kinetics and Quantification of CHIKV-IgG Following EP-Mediated Delivery To characterize this DNA delivery approach for monoclonal antibody delivery, the effect of the ability of CHIKV-IgG to produce functional CHIKV antibodies in vivo was tested. This test used the full length IgG construct described above in Examples 17 and 18. B6.Cg-Foxn1$^{nu}$/J mice were administered the IgG plasmid or pVax1 vector by IM injection, followed immediately by EP as indicated in FIG. 63C. In addition to the CHIKV-IgG for the comparative purposes, single administration of recombinant CHIKV-Env protein was also immunized in mice. Sera from all mice were collected at various time points during the experiment as indicated, and target antigen binding to the CHIKV envelope protein was measured by ELISA. Mice administered CHIKV-IgG plasmid produced detectable levels of antibodies capable of binding to the CHIKV envelope protein and elicited by day 1-3 post administration, where recombinant CHIKV-Env immunized mice showed by day 8 post administration (FIG. 63D) and This result indicated the rapid generation of IgG via this plasmid delivery as compared to protein administration.

Furthermore, a single administration of CHIKV-IgG plasmid with EP in mice resulted in the rapid generation of human CHIKV-Abs detectable in serum. Serum levels of CHIKV-Abs attained 600-800 ng/mL by day 5, peaked at 1300-1600 ng/mL on day 14 and were sustained at levels >800 ng/mL thru day 35 (FIG. 63E). To examine the expression of CHIKV-IgG produced by the plasmid in vivo, the binding specificity of the anti-CHIKV antibodies produced from the immunized mice was confirmed by Western blot analysis using recombinant CHIKV protein, indicating that the IgG-plasmid design of CHIKV-IgG generated properly cleaved and assembled functional CHIKV-IgG antibodies in vivo (FIG. 63F). These experiments provided evidence that the DNA delivered CHIKV-monoclonal antibodies were stable not only in vitro but also over multiple-day time courses in animals.

Example 20

Figures 64A, 64B:
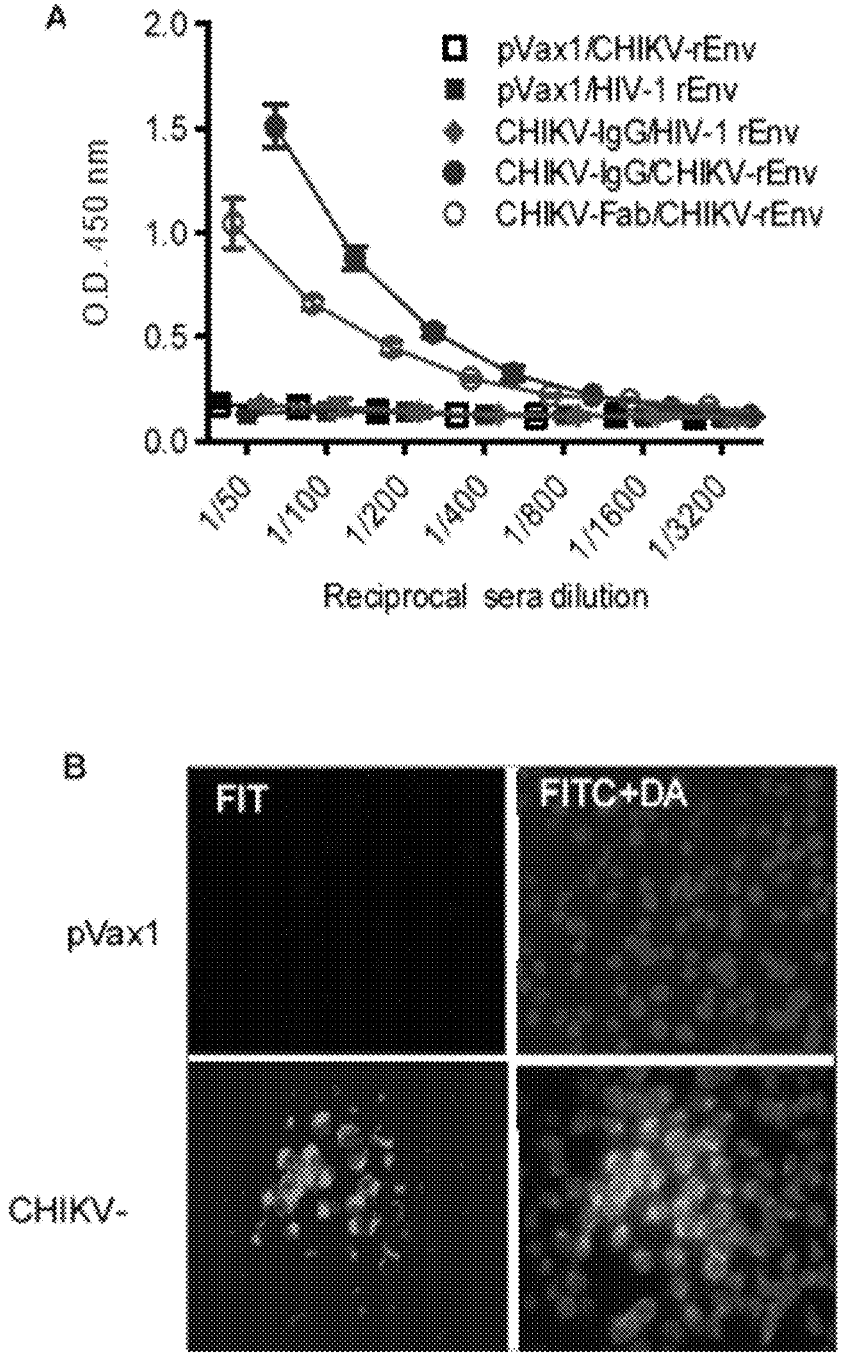
FIG. 64 shows the expression and binding kinetics of IgG following a single electroporation mediated injection of the CHIKV-IgG expression plasmid. (A) Sera from CHIKV-Fab administered mice were specific for the CHIKV-Env antigen. ELISA plates were coated with recombinant CHIKV-Env or HIV-1 Env (subtype B; MN) protein and sera from mice injected with CHIKV-IgG or pVax1 were obtained as indicated after the first injection. Specific binding to the CHIKV-Env antigen was measured through ELISA assays with collected sera and presented as OD 450 nm values for individual mice at different time points. (B) Immunofluorescence assay (IFA) results demonstrated that CHIKV-Fab generated from CHIKV-Fab administered mice was capable of binding to the CHIKV-Env glycoprotein. CHIKV infected Vero cells were fixed at 24 hrs post infection and followed by an immunofluorescence assay to detect CHIKV-Env antigen expression. Cell nuclei were stained with DAPI. Moderate amounts of CHIKV-Env protein expression were observed in Vero cells with CHIKV-Fab antibody. pVax1 immunized mice sera was used as a negative control. (C) FACS analysis of binding of sera from plasmid injected mice to CHIKV-infected cells. The x-axis indicated GFP staining using the lentiviral GFP pseudovirus complemented with CHIKV-Env. The y-axis demonstrated staining of the tested human IgG produced in mice. Double-positive cells were an indication/measurement of sera binding to the CHIKV infected cells.
Figure 64C:
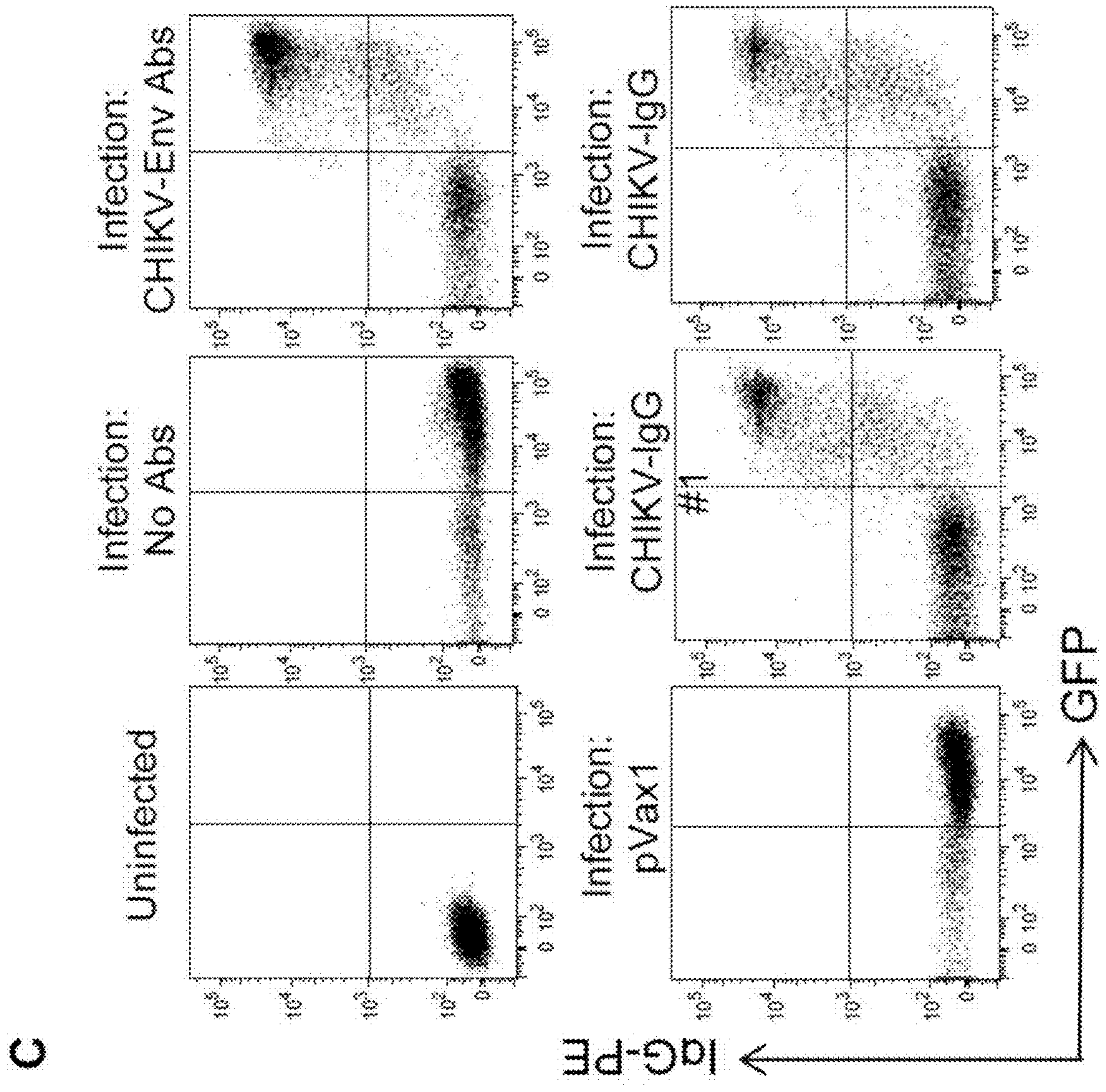
Figure 65:
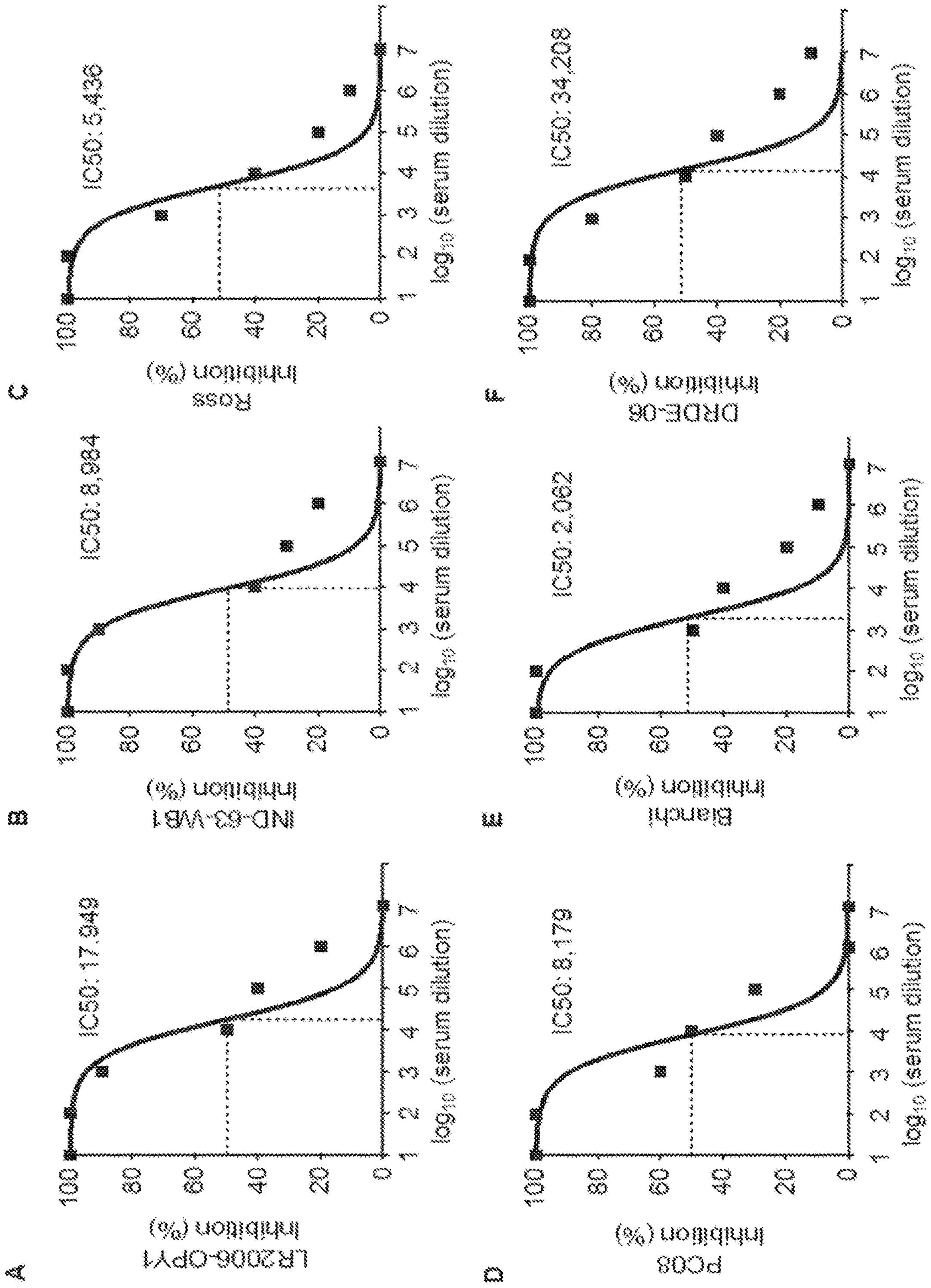
FIG. 65 shows that sera from mice injected with CHIKV-IgG plus EP exhibited neutralizing activity against multiple CHIKV strains. (A-F) Shows the neutralizing activity of sera from mice administered CHIKV-IgG with EP that was measured against six different CHIKV viral strains: Ross, LR2006-OPY1, IND-63-WB1, PC-08, B448-China and Bianchi. Neutralizing antibody (nAb) titers were plotted as the highest dilution of serum that resulted in at least 50% inhibition of CPE in Vero cells. Similar results were observed in 2 independent experiments with at least 10 mice per group for each experiment. IC-50 values were performed with Prism GraphPad software.

Characterization of Binding Specificity and Immunohistochemistry of CHIKV-Infected Cells The above study in Example 19 was expanded and infection was used to characterize the therapeutic potential of the DNA delivery anti-CHIKV monoclonal antibodies. CHIKV-abs bind specifically to CHIKV-Env and not to other proteins. The specificity and target binding properties of CHIKV-Abs were assessed by binding ELISA, FACS analysis and immunohistochemistry using the CHIKV infected cells. Tested serial dilutions of sera from day 14 mice injected with plasmid(s) encoding CHIKV-IgG or CHIKV-Fab antibodies demonstrated that the detected antibodies could specifically bind to its target antigen, i.e. CHIKV-Env protein, and not another viral protein, i.e., recombinant HIV-1 envelope protein (FIG. 64A). To further analyze the binding specificity of the anti-CHIKV-IgG antibody produced in vivo, sera from mice were incubated with fixed Vero cells that had been infected with CHIKV virus Immunofluorescence imaging highlighted the presence of bound anti-CHIKV-IgG on cells expressing the CHIKV envelope protein but not in mouse serum from construct pVax1 only mice (FIG. 64B). In addition, in vivo produced antibody binding specificity for the infected cells was analysed by FACS (FIG. 64C). Experimental sera samples, from CHIKV-IgG administered mice bound the CHIKV-Env target antigen.

Example 21

Sera from CHIKV-IgG Injected Mice Demonstrated Broad Neutralizing Activity Against Clinical CHIKV Isolates To assess the potential anti-CHIKV activity of sera collected from CHIKV-Ig administered mice, neutralizing activity was measured against multiple CHIKV isolates, specifically CHIKV strains Ross, LR2006-OPY1, IND-63WB1, Ross, PC08, Bianchi and DRDE-06. $IC_{50}$ values (the highest dilution of serum that resulted in at least 50% inhibition) were determined for each viral isolate (FIGS. 65A-65F). Sera from CHIKV-IgG injected mice effectively neutralized all six viral isolates tested, demonstrating that a single injection of the DNA encoding CHIKV-IgG produced neutralizing titers of the human anti-CHIKV Ig in mice. The results indicated that the antibody generated from administration of CHIKV-IgG exhibited relevant biological activity after in vivo delivery.

Example 22

Figure 66:
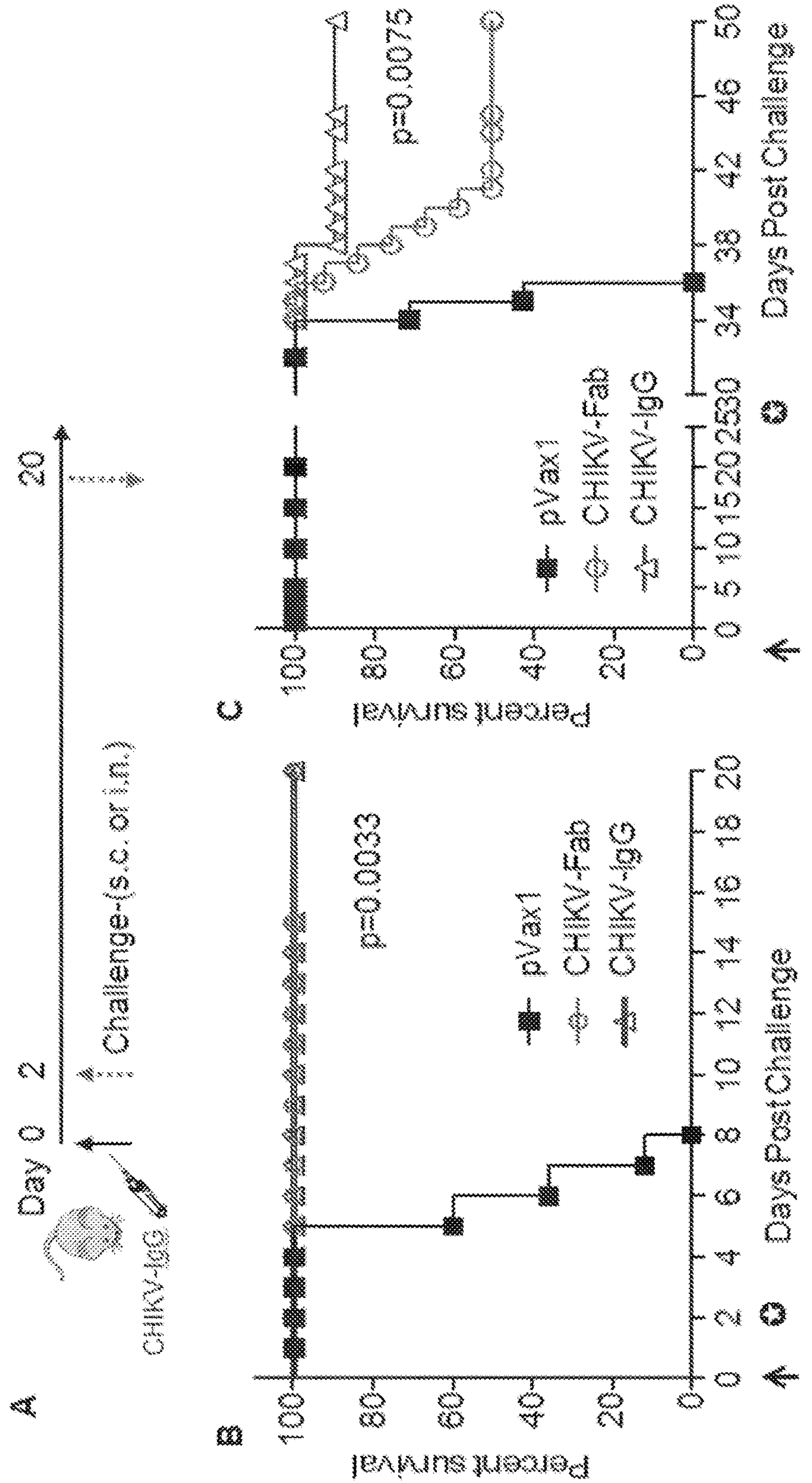
FIG. 66 shows the durability of anti-CHIKV-Env IgG and serum and mucosal IgG responses following immunization with CHIKV-Fab as well as IgG expression and challenge studies. (A) Schematic representation of IgG plasmid immunizations and CHIKV-challenge. (B-C) BALB/c mice were injected with pVax1, CHIKV-IgG or CHIKV-Fab on day 0 and challenged on day 2 (B) or day 30 (C) with CHIKV-Del-03 (JN578247) CHIKV strain ($1\times10^7$ PFU in a total volume of 25 ul). Mice were monitored daily and survival rates were recorded for 20 days after the viral challenge. (D-E) Protection of mice from a different route of CHIKV viral infection. Two groups of mice were immunized with 100 ug of CHIKV-IgG by intramuscular (IM) injection and were challenged on day 2 with subcutaneous (s.c) (D) and another group of mice were challenged by intranasal (i.n). (E) Inoculation with CHIKV. Mice were monitored daily and survival rates were recorded for 20 days after the viral challenge. ↑ indicated DNA administration; ✪ indicated virus challenge. Each group consisted of 10 mice and the results were representative of 2 independent experiments.

CHIKV-IgG Contributed High Levels of Virus-Specific Antibody Activity and Protected Mice from CHIKV Challenge To determine if the CHIKV-IgG construct provided protection from early exposure to CHIKV, groups of mice were injected with either CHIKV-IgG or CHIKV-Fab plasmids on day 0, and then challenged with virus on day 2. A third group of mice received empty pVax1 plasmid to serve as a negative control. Survival and weight changes were recorded for 20 days. All mice injected with pVax1 plasmid died within a week of viral challenge (FIG. 66A). In challenged mice, 100% survival was observed in mice administered either CHIKV-IgG or CHIKV-Fab during the 20-day post-challenge observation period. This indicates that both of the CHIKV constructs confered protective immunity against CHIKV as early as post-delivery (FIG. 66B).

Next, whether CHIKV-IgG and CHIKV-Fab produced long-lasting protective immunity was assessed. Groups of mice were challenged with CHIKV virus 30 days after single injections with CHIKV-IgG plasmid, CHIKV-Fab plasmids or the pVax1 plasmid. Mice were then monitored for survival over a period of 20 days. The mice injected with CHIKV-Fab had a 50% survival whereas 90% survival was observed in mice injected with CHIKV-IgG during the post challenge observation period. These results indicated that both of the CHIKV-IgG and CHIKV-Fab constructs provided long-lasting protective immunity in vivo, although protection conferred by CHIKV-IgG may be more persistent and long lasting than that noted with CHIKV-Fab injection ($p=0.0075$) (FIG. 66C).

Mosquito-borne virus like CHIKV can cause severe encephalitis in humans. Different modes of viral challenge such as intranasal, subcutaneous and footpad infection of mice with the CHIKV have resulted in high mortality within 6-9 days of infection. In addition, CHIKV causes high mortality within 6-9 days following infection of mice with various degrees of pathogenesis. Accordingly, an experiment was conducted to compare the efficacy of CHIKV-antibody therapy against viral infection with intranasal and subcutaneous viral challenge. Twenty mice in each group, i.e., one group with pVax1 and one group with CHIKV-IgG plasmid, received single immunization and half of the mice in each groups were challenged through intranasal administered of CHIKV (in 25 Ξl of PBS) and rest of the mice were challenged by subcutaneous injection with CHIKV on day 2. The protective efficacy of CHIKV-IgG was measured by determining the weight loss, hind limb weakness and lethargy. Whether challenged subcutaneously (FIG. 66D) ($p<0.0024$) or intranasally (FIG. 66E) ($p<0.0073$), CHIKV-IgG provided significant protection from CHIKV infection as compared to control mice. Mice receiving the subcutaneous challenge had a delay in mean weight loss relative to the intranasal challenge. Taken together with the above data, the results indicated that the DNA delivered CHIKV-IgG generated broadly reactive neutralizing antibody responses that protected against traditional (subcutaneous) as well as mucosal CHIKV challenge.

Example 23

Evaluation of Immediate and Persistent CHIKV Specific IgG Upon Viral Challenge After demonstrating that CHIKV-IgG generated an equally rapid, yet more persistent, protective immune response than the CHIKV-Fab construct in vivo, the protective efficacy generated by CHIKV-IgG was compared to the CHIKV-Env plasmid, a DNA vaccine plasmid that expresses a full-length CHIKV envelope protein. Whereas such DNA vaccine strategies rely on the host immune system to recognize and respond to a target antigen, the CHIKV-IgG construct confered protective immunity independent from the host immune response. Considering this difference, it was determined if the CHIKV-IgG construct provided a more immediate source of protective humoral immunity from early exposure to CHIKV.

Figure 67:
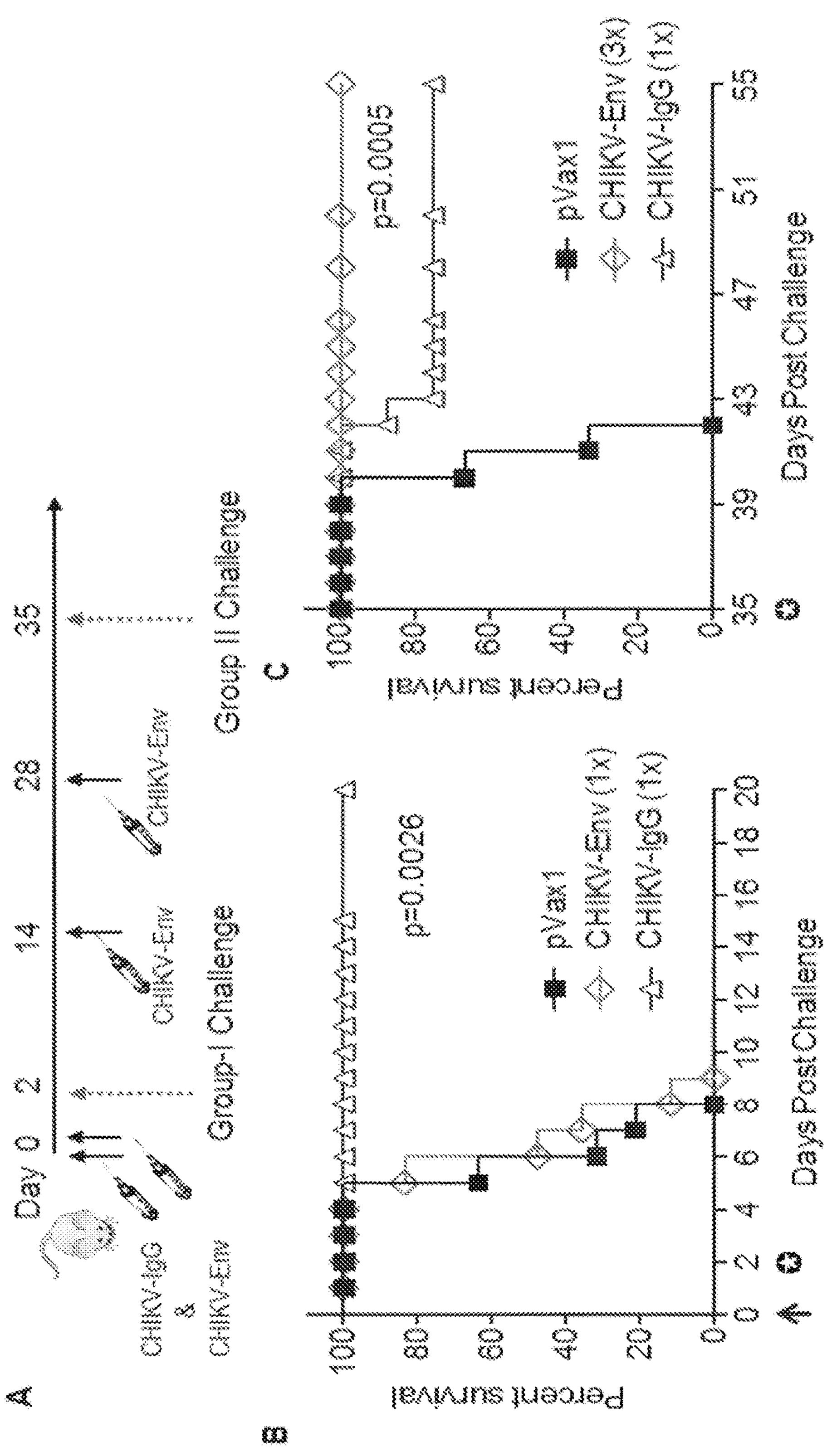
FIG. 67 shows protection both immediate and persistent via CHIKV-challenge studies. (A) Schematic representation of CHIKV-IgG vaccination and challenge studies. Group I challenge: BALB/c mice were injected with CHIKV-IgG, CHIKV-Env, or pVax1 on day 0 and challenged on day 2 with CHIKV-Del-03 (JN578247) viral strain ($1\times10^7$ PFU in a total volume of 25 ul). Group II challenge: BALB/c mice were given either single CHIKV-IgG immunization on day 0 or multiple CHIKV-Env immunizations on indicated days, and then challenged on day 35 under the same conditions as the Group I challenge. ↑ indicated DNA administration; ✪ indicated virus challenge. For each study, mice were monitored for 20 days, and survival rates were recorded. (B) Survival curve of mice from Group I challenge study. Note that 100% survival was recorded in CHIKV-IgG-immunized mice. (C) Survival curve of mice from Group II challenge study. (D) Concentrations of anti-CHIKV human IgG levels were measured at indicated time points following immunization with CHIKV-IgG plus EP. (E) Induction of persistent and systemic anti-CHIKV-Env antibodies following CHIKV-IgG and CHIKV-Env immunization in mice.

Therefore, groups of mice were given a single administration of CHIKV-IgG, CHIKV-Env, or pVax1, and then challenged with CHIKV two days post-plasmid immunization (FIG. 67A). All mice administered CHIKV-Env or pVax1 died within six days of viral challenge, whereas 100% survival was observed in mice immunized with CHIKV-IgG (FIG. 67B). This illustrated that protective immunity was conferred much earlier post-administration by CHIKV-IgG than CHIKV-Env, a antigen-generating DNA vaccine.

The duration of anti-CHIKV responses generated by CHIKV-IgG and CHIKV-Env were subsequently evaluated. Different immunization regimens were utilized to ensure induction of a robust immune response by CHIKV-Env. Thus, mice were given either a single immunization of CHIKV-IgG on day 0, or multiple immunizations with CHIKV-Env (days 0, 14, and 28) prior to viral challenge on day 35. A third group of mice received a single immunization of pVax1 on day 0 and viral challenge on day 35 (FIG. 67A, group II). 100% survival was recorded for mice that received the multi-booster immunization regimen with CHIKV-Env (FIG. 67C), which markedly contrasted the survival rate of mice previously immunized with a single injection of the same DNA vaccine (FIG. 67B). These findings were consistent with the kinetics of an adaptive immune response, which takes approximately two weeks to develop following antigen exposure and often require multiple rounds of antigen exposure to generate protective immunity.

Furthermore, 90% survival was noted in CHIKV-IgG inoculated mice during the 20-day observation period ($p=0.0005$) (FIG. 67C); the figure shows <80% survival in CHIKV-IgG immunized mice by day 43. However, how different levels of human IgG detected in the mouse serum at early and late time points after plasmid/vaccine administration could influence the above challenge outcomes was evaluated. Anti-CHIKV Env specific human IgG was detectable within 48 hours of single injection of CHIKV-IgG construct, and peak levels were measured by 14 days post-injection (~1400 ng/mL). The human IgG was still detectable 45 days post-injection at levels above the initially measured values on day 2. This decreased protection corresponded to measured sera levels of anti-CHIKV IgG (FIG.

67D). Diminishing levels of protective antibodies were likely due to normal clearance of the antibody, indicating that the level of CHIKV-IgG may wane to levels below protection after extended periods of time if not re-administered. In summary, these findings indicated that a single injection of CHIKV-IgG generated a protective response that was similar in quality and persistence to DNA vaccine-induced immune responses that require multiple booster immunizations.

Example 24

Induction of Persistent and Systemic Anti-CHIKV-Env Antibodies Following CHIKV-IgG and CHIKV-Env Immunization Given that both CHIKV-IgG and CHIKV-Env protective responses were seen in mice immunized with CHIKV-IgG construct and CHIKV-Env construct, an additional study was conducted to evaluate the antibody levels. BALB/c mice were immunized with CHIKV-IgG DNA at 0 days or with CHIKV-Env DNA at 0, 14 and 21 days. FIG. 67E shows the levels of anti-CHIKV IgG at indicated time points from mice immunized with either CHIKV-IgG DNA or CHIKV-Env DNA. The anti-CHIKV human IgG was measured in CHIKV-IgG-immunized mice and anti-CHIKV mouse IgG was measured in CHIKV-Env-immunized mice. The results showed an early detection and rapid increase of human IgG in CHIKV-IgG-immunized mice. Titres of mouse IgG elicited by CHIKV-Env reach similar peak levels within two weeks of immunization, but exhibited a slower level of antibody production.

Example 25

Figure 68:
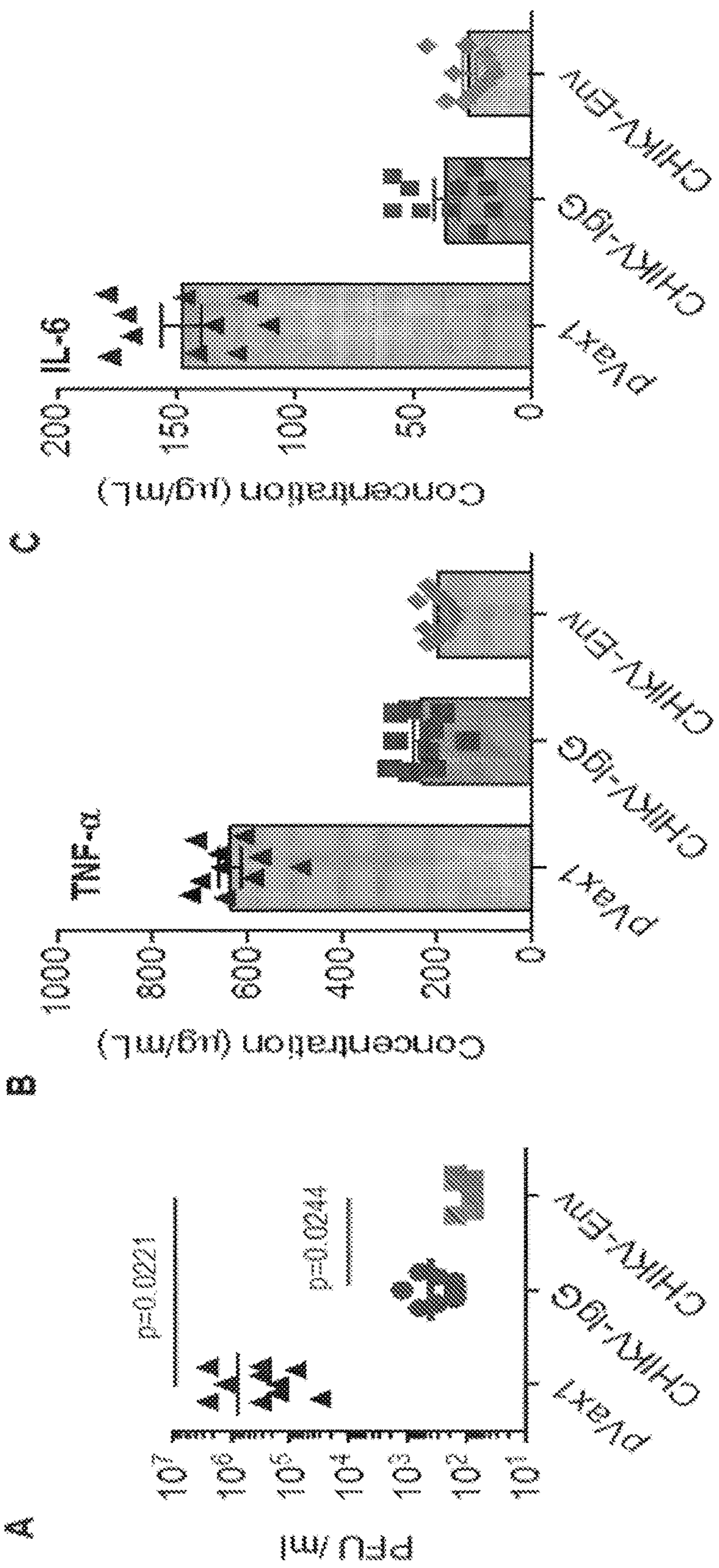
FIG. 68 shows the ex vivo cytokine production in response to infection with CHIKV. (A) Viral titers in CHIKV-IgG and CHIKV-Env administered mice from Group II challenge study on day 45 (i.e. 10 days post-challenge). Each data point represented the average viral titers from 10 mice. A group of pVax1 immunized mice served as a control. Viral loads were significantly reduced in both CHIKV-IgG ($p=0.0244$) and CHIKV-Env ($p=0.0221$) compared to pVax1 mice. (B & C) Characterization of serum pro-inflammatory cytokines levels (TNF-α and IL-6) from CHIKV infected mice. Cytokine levels were measured in mice at day 45 (15 days post-challenge) by specific ELISA assays. Mice injected with CHIKV-IgG or CHIKV-Env had similar and significantly lower sera levels of TNF-α and IL-6 than the control group ($p<0.0001$). Data represented the average of 3 wells per mouse ($n=10$ per group). (D) T-cell responses in splenocytes of mice immunized with CHIKV-IgG or CHIKV-Env immunization of mice, and then stimulated with CHIKV-specific peptides. The data shown were representative of at least 2 separate experiments.

Reduction in CHIKV Viral Loads and Cytokine Levels Resulting in the Control of Infection CHIKV viral load and pro-inflammatory cytokines may correlate to CHIKV-associated disease severity. Thus, the ability of CHIKV-IgG to suppress these associated-disease markers (i.e., viral load and pro-inflammatory cytokines) at early and late time points post-viral challenge was assessed. Sera from mice immunized with either CHIKV-IgG DNA or CHIKV-Env DNA exhibited significantly reduced viral loads in comparison to pVax1 control animals (p=0.0244 and 0.0221 respectively) (FIG. 68A). CHIKV-IgG-immunized mice showed comparable levels of viral load reduction to CHIKV-Env mice. Selected pro-inflammatory cytokines were also measured (TNF-α and IL-6) from CHIKV-IgG-immunized mice and CHIKV-Env immunized mice on $5^{th}$ post-viral challenge. In comparison to pVax1-immunized animals, CHIKV-IgG and CHIKV-Env immunized animals exhibited reduced sera levels of both cytokines to similar levels at early and late time points (FIGS. 68B and 68C). As sera levels of CHIKV virus, TNF-α, and IL-6 correlate with disease severity, these findings indicated that single immunizations with CHIKV-IgG DNA provided a durable level of protection from CHIKV-associated pathology at levels comparable to DNA vaccines such as CHIKV-Env.

As CTL may be important in eliminating virus-infected cells, further analyses were carried out to assess the induced T-cell responses by CHIKV-ENV and CHIKV-IgG. IFN-γ producing cells were detected in all immunized mice. FIG. 68D was a measure of T cell responses from mice previously immunized with CHIKV-IgG DNA or CHIKV-Env DNA. The results showed that CHIKV-Env elicited strong T cell responses as measured by IFN-γ levels, whereas CHIKV-IgG did not.

In summary, the studies in Examples 14 and 17-25 demonstrated rapid production of the encoded antibody within 48 hours post-injection in vivo. The produced antibody was also sustained for several weeks within the receipt animal. Mice injected with CHIKV-IgG DNA were fully protected from lethal CHIKV challenge (100% protection). Viremia and pro-inflammatory cytokine levels were also reduced in these protected mice and CHIKV-associated disease pathologies were suppressed.

In particular, in these CHIKV-Fab and CHIKV-IgG studies, rapid production of the full length IgG was noted within the first 48 to 72 hours after administration. The kinetics and level of production were similar between the Fab and IgG versions of the antibody at early time points, which was critical for infectious disease prevention. Both forms of antibody modalities protected mice against a lethal CHIKV challenge two days post-immunization. However, differences in protection were apparent when mice were challenged at a later time point (30 days post-immunization) following vaccine delivery: 90% of mice immunized with CHIKV-IgG survived, whereas 50% survival was recorded in CHIKV-Fab immunized mice. Thus, although both antibody constructs have identical antigen specificity and rapid expression following delivery, the full length IgG demonstrated a longer half-life than the Fab construct, which proved essential in sustaining protective immunity.

A DNA based vaccine for CHIKV infection, termed CHIKV-Env, was also compared to the encoded antibodies. When mice were injected with a single dose of either CHIKV-IgG or CHIKV-Env and challenged with virus two days later, all mice in the CHIKV-IgG injection group survived, which contrasted with the CHIKV-Env group, where no mice survived infection. However, complete protection was observed with CHIKV-ENV following a full immunization regimen (three inoculations over a three week period). A similar level of protection was seen in mice administered a single dose of CHIKV-IgG, though this protection waned to 75% survival over an extended period of time.

Example 26

Delivery of Cross-Reactive Neutralizing Antibodies Against DENV

Optimized DNA plasmids encoding the heavy and light chains of the anti-DENV antibody DV87.1, a human IgG1 mAb that has the ability to neutralize DENV1-3, were designed and constructed. Specifically, two optimized plasmids were constructed: pDVSF-3 WT, which encoded for the heavy and light chains of DV87.1, and pDVSF-3 LALA, which encoded for an Fc region-modified version of DV87.1 with abrogated FcγR binding by way of two leucine-to-alanine (LALA) mutations in the CH2 region. This was done to eliminate antibody-dependent enhancement. The heavy and light chain genes in each construct were separated by a furin cleavage site and a P2A self-processing peptide. Each transgene was genetically optimized, synthesized, and subcloned into a modified pVax1 mammalian expression vector (FIG. 69A).

The antibody DVSF-3 WT was encoded by the nucleic acid sequence set forth in SEQ ID NO:75. SEQ ID NO:75 encoded the amino acid sequence set forth in SEQ ID NO:76. The nucleic acid sequence of SEQ ID NO:75 was contained in the plasmid pDVSF-3 WT.

The antibody DVSF-3 LALA was encoded by the nucleic acid sequence set forth in SEQ ID NO:77. SEQ ID NO:77 encoded the amino acid sequence set forth in SEQ ID NO:78. The nucleic acid sequence of SEQ ID NO:77 was contained in the plasmid pDVSF-3 LALA.

The plasmids were transfected into human embryonic kidney (HEK) 293T cells, and secreted antibody levels in the supernatant were quantified after 48 hours by enzyme-linked immunosorbent assay (ELISA) (FIG. 69B). Both pDVSF-3 WT and pDVSF-3 LALA resulted in 600 ng/mL of human IgG, confirming that the plasmids expressed human IgG, and that the LALA mutation had no effect on antibody expression levels in vitro. To confirm proper antibody assembly, DVSF-3 and DVSF-3 LALA antibodies were collected from supernatants of transfected HEK293T cells and separated by SDS-PAGE gel for Western blot analysis (FIG. 69C). The heavy and light chain proteins were at their expected molecular weights, indicating proper protein cleavage and antibody assembly.

Figure 72:
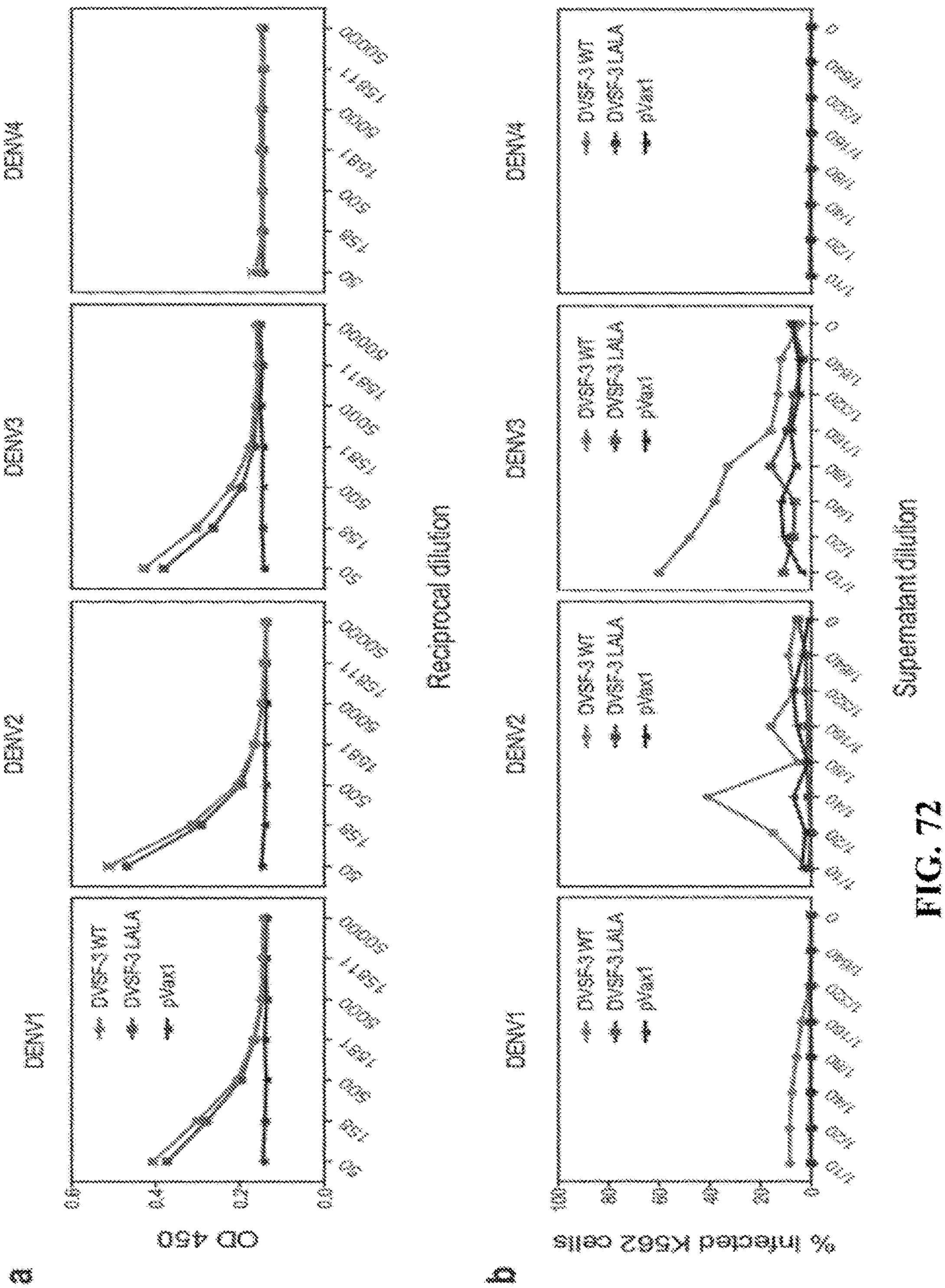
FIG. 72 shows the in vitro functional analysis of pDVSF-3 WT and LALA-encoded antibodies. (a) ELISA binding analysis of human IgG in supernatants of pDVSF-3 WT- or LALA-transfected 293T cells against purified recombinant DENV E proteins. (b) Antibody-dependent enhancement was assessed by incubating DENV1, 2, 3, or 4 with serial dilutions of supernatants of pDVSF-3 WT- or LALA-transfected 293T cells before addition to K562 cells. The percentage of infected cells is shown.
Figure 75:
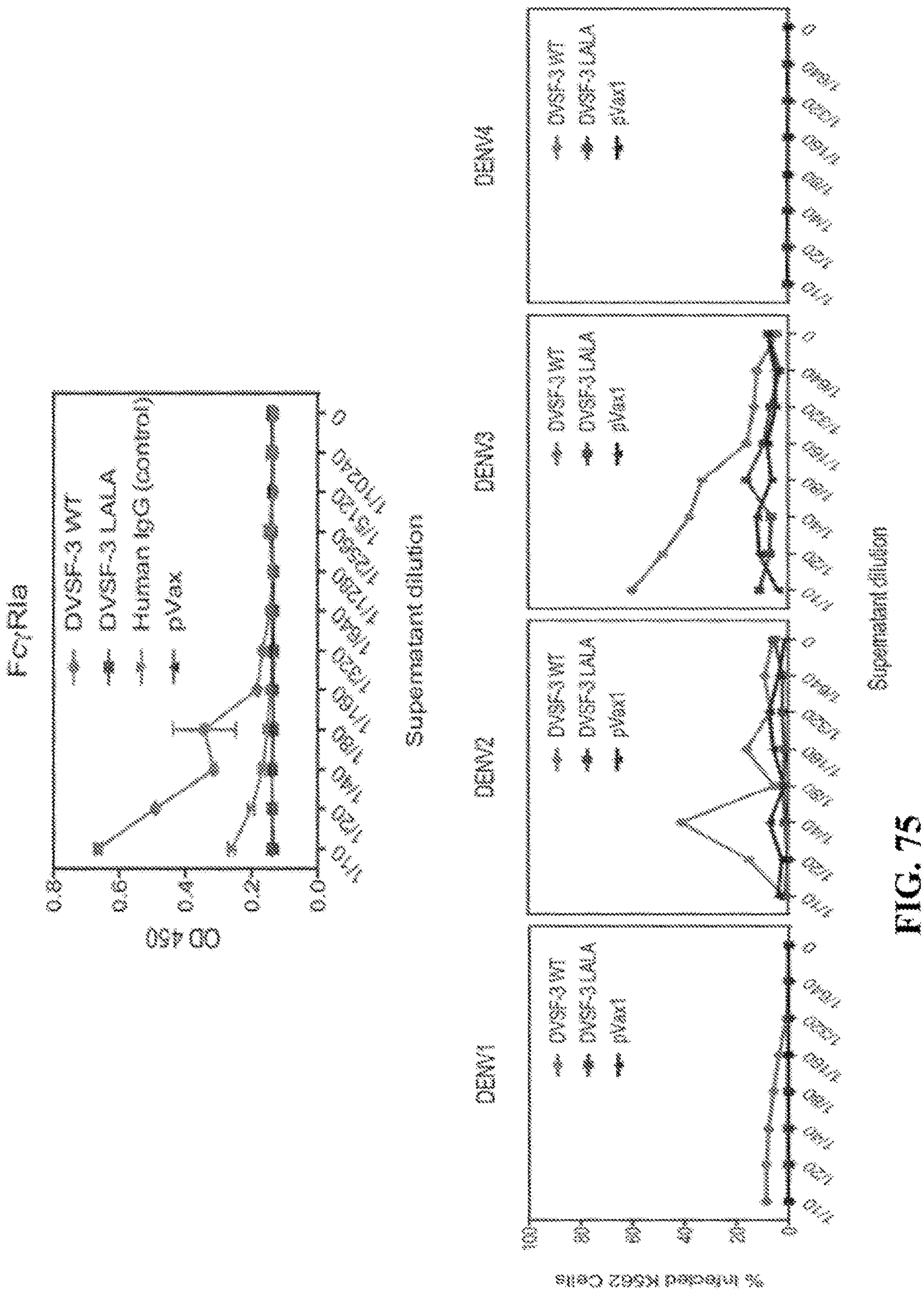
FIG. 75 shows in the top panel that DVSF-3 WT bound to human FcγR1a, whereas DVSF-3 LALA did not bind FcγR1a. The bottom 4 panels show the results of the antibody-dependent enhancement assay: incubation of DENV-1, -2, -3, or -4 with DVSF-3 LALA did not lead to human monocyte (K562 cell line) infection, whereas DVSF-3 WT did enhance infection for DENV-1, -2, and -3.

To assess the biological activity of the antibodies, a binding ELISA assay that measured whether the antibody-containing supernatant bound to recombinant DENV1-3 E proteins was performed. The supernatants of HEK293T cells that secreted either DVSF-3 WT or DVSF-3 LALA antibodies were able to recognize DENV1-3 E proteins, while DENV4 went unrecognized, as expected (FIG. 72). Additionally, DVSF-3 WT- and DVSF-3 LALA-containing supernatants were able to stain Vero cells infected with DENV1-3, whereas Vero cells infected with DENV4 were not stained by the supernatants (FIG. 69D). Each construct showed in vitro neutralization of DENV1-3 (data not shown), but DVSF-3 WT enhanced DENV infection of FcγR-bearing human K562 cells, whereas DVSF-3 LALA had no such ADE activity in vitro (FIGS. 72B and 75 (bottom panel)). Additionally, DVSF-3 bound to human FcγR1a whereas DVSF-3 LALA did not bind FcγR1a (FIG. 75 (top panel)).

In order to investigate antibody production kinetics in vivo, the duration of DNA plasmid-encoded human IgG expression in nude mice, which would model antibody expression in an immune-accommodating host, was determined. The mice were injected intramuscularly with 100 ug of a DNA plasmid encoding another human IgG1 anti-DENV antibody, DVSF-1 WT, followed immediately by EP. DVSF-1 antibody was encoded by the nucleic acid sequence set forth in SEQ ID NO:67. SEQ ID NO:67 encoded the amino acid sequence set forth in SEQ ID NO:68.

Figure 70:
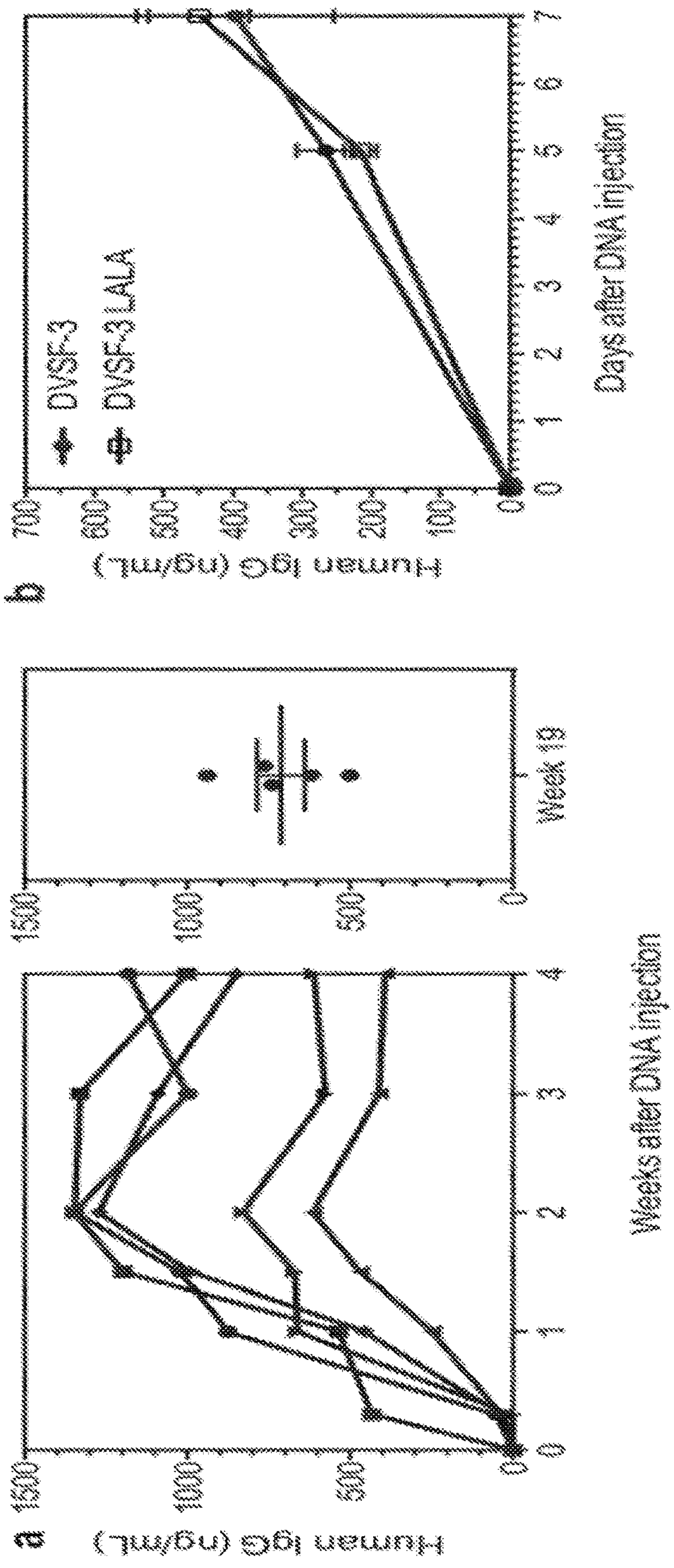
FIG. 70 shows the results in long-term expression of neutralizing DENV antibodies in mouse serum. (a) Total serum-detectable levels of human IgG were measured by ELISA after a single intramuscular injection of DNA plasmid encoding the anti-DENV human IgG antibody DVSF-1 into Foxn1/NuJ immunodeficient mice. Human IgG levels between weeks 0-4 (left) and at week 19 (right). Each line (left) or dot (right) represented an individual mouse ($n=5$). (b) Total human IgG in serum was measured by ELISA after intramuscular injection of pDVSF-3 WT or pDVSF-3 LALA plasmids in 129/Sv mice ($n=4$-5 per group). (c) Vero cells were either uninfected (Mock) or infected by DENV1, 2, 3, or 4, then fixed, permeabilized, and stained with 129/Sv mouse serum taken at days 0 or 7 post-DNA injection of either pDVSF-3 WT or pDVSF-3 LALA ($n=5$ per group). (d) Neutralization was assessed by incubating DENV1, 2, 3, or 4 with serial dilutions of 129/Sv mouse serum taken at day 7 post-DNA injection of either pDVSF-3 WT or pDVSF-3 LALA ($n=5$ per group) before addition to Vero cells. The percentage of infected cells is shown.

Human IgG concentrations in the serum were detectable within 5 days of injection, with peak levels of about 1000 ng/mL at two weeks post-injection (FIG. 70A, left panel). Duration of human IgG expression lasted at least 19 weeks (FIG. 70A, right panel), thereby illustrating the sustained expression levels attainable with the DNA plasmids.

Given that the mouse DENV challenge model used mice from the 129/Sv background, the antibody-encoding DNA plasmid constructs were studied to determine production of serum-detectable levels of DVSF-3 WT or LALA in this background strain. Serum from 129/Sv mice receiving either pDVSF-3 WT or pDVSF-3 LALA showed comparable human IgG levels (FIG. 70B) and stained Vero cells infected with DENV1-3 (FIG. 70C). Additionally, both WT and LALA-containing serum were capable of neutralizing DENV1-3 (FIG. 70D).

To assess whether mice expressing DNA plasmid-encoded anti-DENV neutralizing mAbs would be protected from DENV challenge, the AG129 mouse model was employed. This mouse model lacked type I and type II interferon (IFN) receptors and, upon DENV infection, recapitulated many aspects of human disease. These mice also exhibited ADE, with low doses of serotype-specific as well as cross-reactive antibodies both enhancing infection. For these studies, mice were infected with the mouse-adapted DENV2 strain S221, which, in the presence of sub-neutralizing amounts of the anti-DENV mAb 2H2, caused antibody-enhanced severe disease and acute lethality (4-6 days post-infection) in AG129 mice at sublethal doses.

Figure 73:
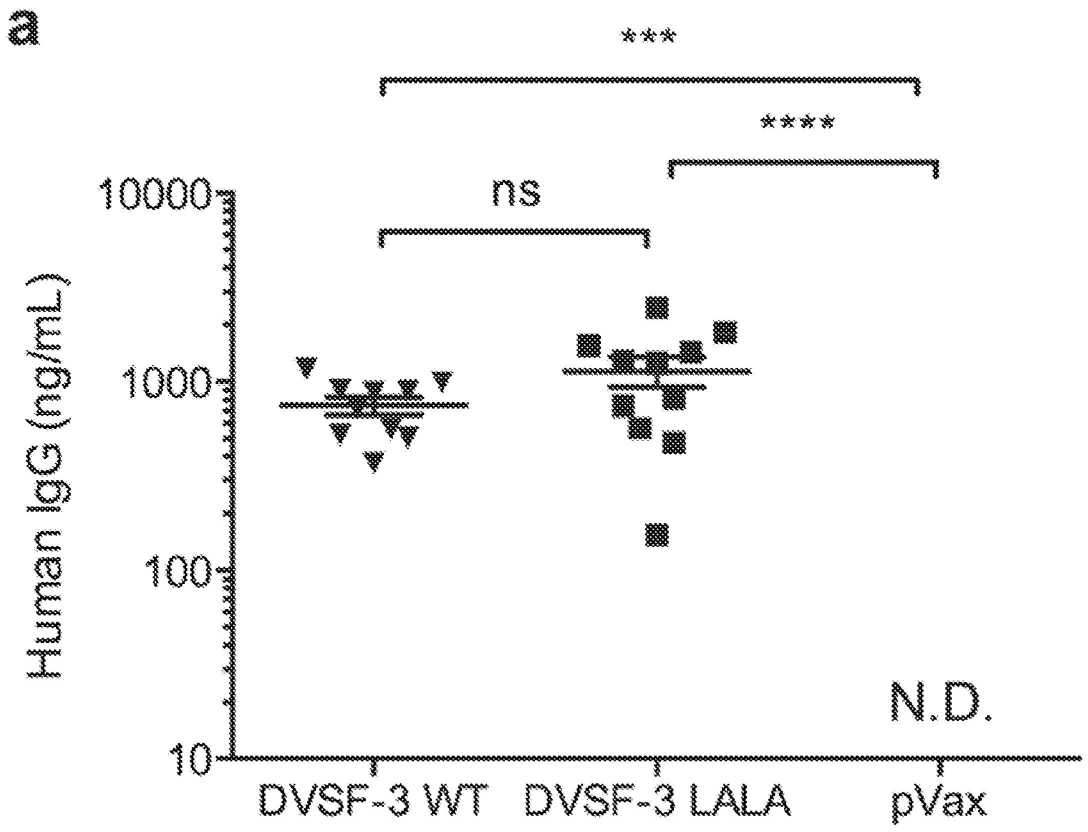
FIG. 73 shows the pre-challenge levels of anti-DENV human IgG levels in AG129 mice after delivery of the DNA construct encoding the antibody. (a) Total human IgG of DVSF-3 WT or DVSF-3 LALA in serum was measured by ELISA 4 days after DNA intramuscular injection (one day before DENV2 challenge) and EP of respective plasmids in AG129 mice ($n=5$-6 per group; $p\leq 0.0005$ for comparison between pDVSF-3 WT and pVax; $p\leq 0.0001$ for comparison between pDVSF-3 LALA and pVax).

To determine whether AG129 mice expressing pDVSF-3 LALA would be protected against virus-only infection and antibody-dependent enhanced disease (ADE), AG129 mice were given a single intramuscular injection of pDVSF-3 WT or pDVSF-3 LALA followed immediately by EP. Negative controls received a single intramuscular injection of pVax1 empty vector followed by EP. Five days later, the mice were challenged with a sub-lethal dose ($1\times10^9$ GE) of DENV2 S221 in the presence (ADE) or absence (virus-only infection) of exogenous anti-DENV mAb 2H2. Mice in the pDVSF-3 WT, pDVSF-3 LALA, and pVax1 cohorts had mean human IgG concentrations of 750 ng/mL, 1139 ng/mL, and undetectable levels, respectively, one day before challenge (FIG. 73; $p\leq0.0930$ for comparison between pDVSF-3 WT and pDVSF-3 LALA).

Figure 71:
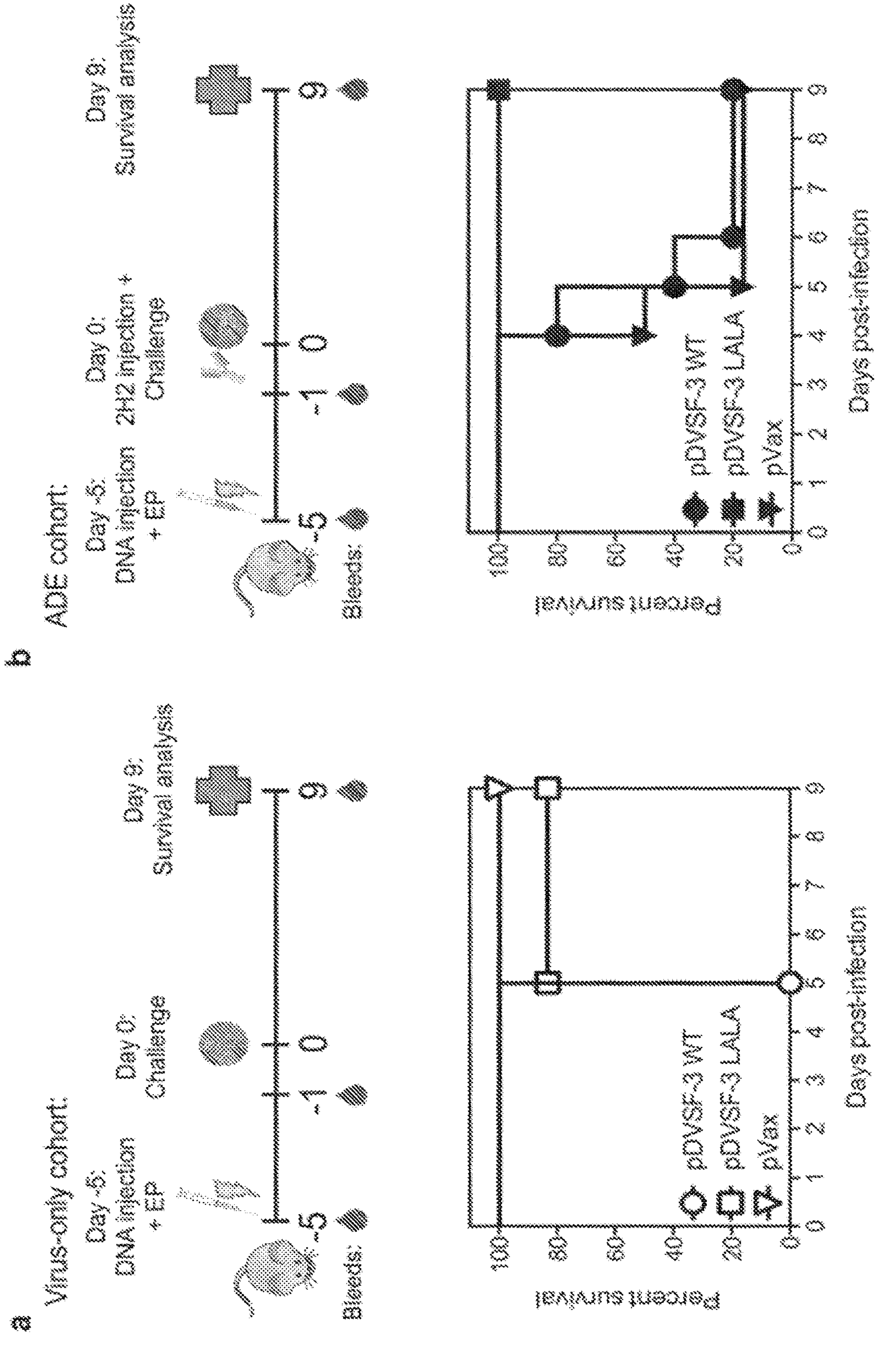
FIG. 71 shows that delivery of the DNA construct encoding the antibody protected against virus-only and antibody-enhanced disease. (a) Virus-only challenge: AG129 mice received an intramuscular injection of either pDVSF-3 WT, pDVSF-3 LALA, or pVax empty vector five days prior to challenge with a sublethal dose of DENV2 S221 ($n=5$-6 per group; $p\leq 0.0084$ for comparison between pDVSF-3 LALA and pDVSF-3 WT). (b) Antibody-dependent enhancement challenge: AG129 mice received an intramuscular injection of either pDVSF-3 WT, pDVSF-3 LALA, or pVax empty vector five days prior to administration of an enhancing dose of the non-neutralizing anti-DENV mAb 2H2. Thirty minutes later, mice were challenged with a sublethal dose of DENV2 5221 ($n=5$-6 per group; $p\leq 0.0072$ for comparison between pDVSF-3 LALA and pDVSF-3 WT). A Kaplan-Meier survival curve is shown in (a-b).

Under virus-only infection conditions, pDVSF-3 WT-treated mice were expected to experience ADE and acute lethality, as immune complexes formed by DVSF-3 WT antibodies with DENV should lead to increased infection. Conversely, pVax1- and pDVSF-3 LALA-treated mice were expected to be protected from severe disease. Indeed, five of six pDVSF-3 LALA-treated mice and all five pVax1 mice were protected from severe disease; all pDVSF-3 WT-treated mice succumbed to disease by day 5 (FIG. 71A; $p\leq0.0084$ for comparison between pDVSF-3 LALA and pDVSF-3 WT), demonstrating the protective capacity of pDVSF-3 LALA against virus-only infection.

Under ADE conditions, both pDVSF-3 WT- and pVax1-treated mice were expected to experience acute lethality due to enhanced infection, whereas pDVSF-3 LALA-treated mice should be protected from severe disease. All five mice receiving pDVSF-3 LALA survived under ADE conditions, while those receiving either pDVSF-3 WT or pVax1 empty vector succumbed to acute, antibody-enhanced disease within 4-5 days (FIG. 71B; $p\leq0.0072$ for comparison between pDVSF-3 LALA and pDVSF-3 WT). Taken together, these data showed that injection of pDVSF-3 LALA protected against severe disease in both virus-only and ADE conditions.

In summary, a single intramuscular injection of a DNA plasmid encoding a modified human anti-DENV 1-3 neutralizing antibody was capable of protecting mice against virus-only and antibody-enhanced DENV disease. The protection conferred by neutralizing anti-DENV mAbs expressed by this DNA delivery method was rapid, with complete survival in mice challenged less than a week after pDVSF-3 LALA administration. Further, plasmid-encoded antibody delivery provided protection within 5 days after delivery, which was significantly more rapid than vaccine-driven protection.

Example 27

Formulation with DVSF-1 and DVSF-3 Constructs

Figure 74:
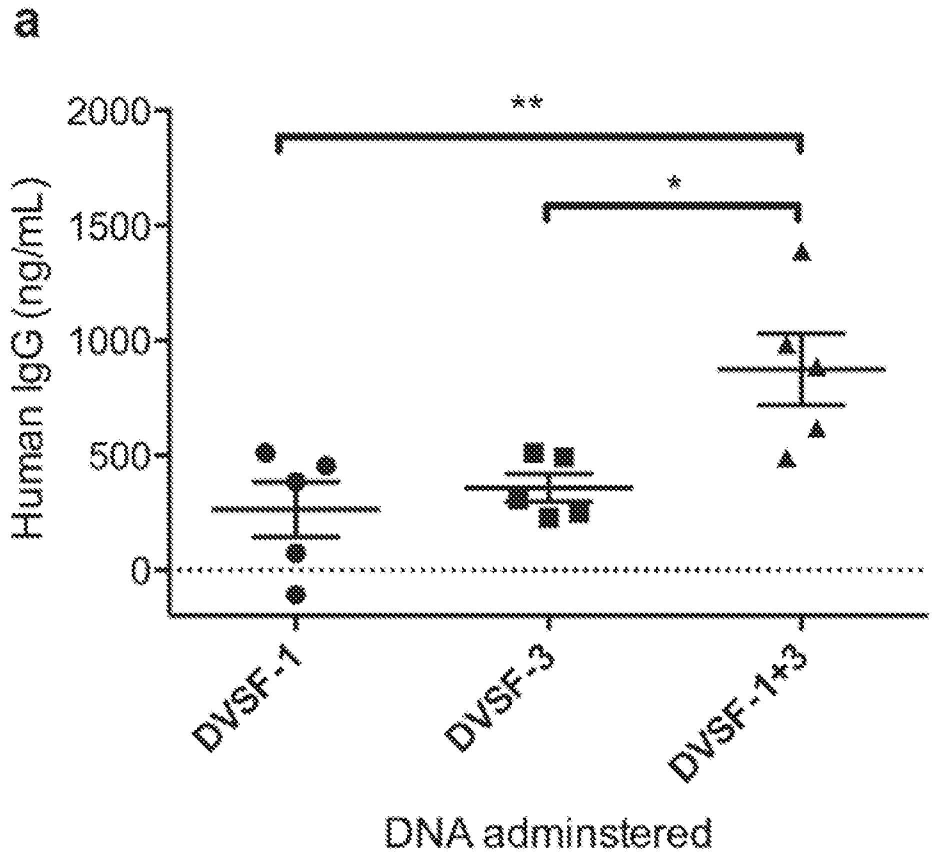
FIG. 74 shows the delivery of multiple DENV antibody-encoding plasmids in mice produced increased DENV1-4 antisera. (a) Total human IgG of DVSF-3 WT, DVSF-1 WT, or DVSF-3 WT and DVSF-1 WT in serum was measured by ELISA 7 days after DNA intramuscular injection and EP of respective plasmids in 129/Sv mice ($n=5$ per group; $p\leq 0.0088$ for comparison between pDVSF-1 WT and pDVSF-1+3; $p\leq 0.0240$ for comparison between pDVSF-3 WT and pDVSF-1+3).

DENV serotypes may escape neutralization. Accordingly, a study was performed to examine an antibody cocktail targeting multiple epitopes on the DENV virion for prophylaxis. 129/Sv mice were injected with pDVSF-3 WT (anti-DENV1-3) in one leg and pDVSF-1 WT (anti-DENV1-4) in the other. Mice injected with both plasmids had significantly higher serum human antibody levels at day 7 compared to mice receiving a single plasmid (FIG. 74; p≤0.0088 for comparison between pDVSF-1 WT and pDVSF-1+3; p≤0.0240 for comparison between pDVSF-3 WT and pDVSF-1+3). Furthermore, sera from mice injected with both plasmids stained Vero cells infected with all four DENV serotypes (data not shown).

Example 28

Anti-DENV Antibodies

As described above, constructs were generated that produced DVSF-1 (i.e., WT), DVSF-3 WT and DVSF-3 LALA. Additional constructs were generated that produced DVSF-1 LALA, DVSF-2 WT, and DVSF-2 LALA.

As described above, DVSF-3 WT was encoded by the nucleic acid sequence set forth in SEQ ID NO:75. SEQ ID NO:75 encoded the amino acid sequence set forth in SEQ ID NO:76. DVSF-3 WT antibody neutralized DENV1-3 (data not shown).

As also described above, DVSF-3 LALA was encoded by the nucleic acid sequence set forth in SEQ ID NO:77. SEQ ID NO:77 encoded the amino acid sequence set forth in SEQ ID NO:78.

DVSF-1 WT was encoded by the nucleic acid sequence set forth in SEQ ID NO:67. SEQ ID NO:67 encoded the amino acid sequence set forth in SEQ ID NO:68. DVSF-1 WT antibody neutralized DENV1-4 (data not shown).

DVSF-1 LALA was encoded by the nucleic acid sequence set forth in SEQ ID NO:69. SEQ ID NO:69 encoded the amino acid sequence set forth in SEQ ID NO:70.

DVSF-2 WT was encoded by the nucleic acid sequence set forth in SEQ ID NO:71. SEQ ID NO:71 encoded the amino acid sequence set forth in SEQ ID NO:72. DVSF-2 WT antibody neutralized DENV4 (data not shown).

DVSF-2 LALA was encoded by the nucleic acid sequence set forth in SEQ ID NO:73. SEQ ID NO:73 encoded the amino acid sequence set forth in SEQ ID NO:74.

12. CLAUSES

For reasons of completeness, various aspects of the invention are set out in the following numbered clauses:

Clause 1. A method of generating a synthetic antibody in a subject, the method comprising administering to the subject a composition comprising a recombinant nucleic acid sequence encoding an antibody or fragment thereof, wherein the recombinant nucleic acid sequence is expressed in the subject to generate the synthetic antibody.

Clause 2. The method of clause 1, wherein the antibody comprises a heavy chain polypeptide, or fragment thereof, and a light chain polypeptide, or fragment thereof.

Clause 3. The method of clause 2, wherein the heavy chain polypeptide, or fragment thereof, is encoded by a first nucleic acid sequence and the light chain polypeptide, or fragment thereof, is encoded by a second nucleic acid sequence.

Clause 4. The method of clause 3, wherein the recombinant nucleic acid sequence comprises the first nucleic acid sequence and the second nucleic acid sequence.

Clause 5. The method of clause 4, wherein the recombinant nucleic acid sequence further comprises a promoter for expressing the first nucleic acid sequence and the second nucleic acid sequence as a single transcript in the subject.

Clause 6. The method of clause 5, wherein the promoter is a cytomegalovirus (CMV) promoter.

Clause 7. The method of clause 5, wherein the recombinant nucleic acid sequence further comprises a third nucleic acid sequence encoding a protease cleavage site, wherein the third nucleic acid sequence is located between the first nucleic acid sequence and second nucleic acid sequence.

Clause 8. The method of clause 7, wherein the protease of the subject recognizes and cleaves the protease cleavage site.

Clause 9. The method of clause 8, wherein the recombinant nucleic acid sequence is expressed in the subject to generate an antibody polypeptide sequence, wherein the antibody polypeptide sequence comprises the heavy chain polypeptide, or fragment thereof, the protease cleavage site, and the light chain polypeptide, or fragment thereof, wherein the protease produced by the subject recognizes and cleaves the protease cleavage site of the antibody polypeptide sequence thereby generating a cleaved heavy chain polypeptide and a cleaved light chain polypeptide, wherein the synthetic antibody is generated by the cleaved heavy chain polypeptide and the cleaved light chain polypeptide.

Clause 10. The method of clause 4, wherein the recombinant nucleic acid sequence comprises a first promoter for expressing the first nucleic acid sequence as a first transcript and a second promoter for expressing the second nucleic acid sequence as a second transcript, wherein the first transcript is translated to a first polypeptide and the second transcript is translated into a second polypeptide, wherein the synthetic antibody is generated by the first and second polypeptide.

Clause 11. The method of clause 10, wherein the first promoter and the second promoter are the same.

Clause 12. The method of clause 11, wherein the promoter is a cytomegalovirus (CMV) promoter.

Clause 13. The method of clause 2, wherein the heavy chain polypeptide comprises a variable heavy region and a constant heavy region 1.

Clause 14. The method of clause 2, wherein the heavy chain polypeptide comprises a variable heavy region, a constant heavy region 1, a hinge region, a constant heavy region 2 and a constant heavy region 3.

Clause 15. The method of clause 2, wherein the light chain polypeptide comprises a variable light region and a constant light region.

Clause 16. The method of clause 1, wherein the recombinant nucleic acid sequence further comprises a Kozak sequence.

Clause 17. The method of clause 1, wherein the recombinant nucleic acid sequence further comprises an immunoglobulin (Ig) signal peptide.

Clause 18. The method of clause 17, wherein the Ig signal peptide comprises an IgE or IgG signal peptide.

Clause 19. The method of clause 1, wherein the recombinant nucleic acid sequence comprises a nucleic acid sequence encoding at least one amino acid sequence of SEQ ID NOs:1, 2, 5, 41, 43, 45, 46, 47, 48, 49, 51, 53, 55, 57, 59, 61, 66, 68, 70, 72, 74, 76, and 78.

Clause 20. The method of clause 1, wherein the recombinant nucleic acid sequence comprises at least one nucleic acid sequence of SEQ ID NOs:3, 4, 6, 7, 40, 42, 44, 50, 52, 54, 56, 58, 60, 62 63, 64, 65, 67, 69, 71, 73, 75, and 77.

Clause 21. A method of generating a synthetic antibody in a subject, the method comprising administering to the subject a composition comprising a first recombinant nucleic acid sequence encoding a heavy chain polypeptide, or fragment thereof, and a second recombinant nucleic acid sequence encoding a light chain polypeptide, or fragment thereof, wherein the first recombinant nucleic acid sequence is expressed in the subject to generate a first polypeptide and the second recombinant nucleic acid is expressed in the subject to generate a second polypeptide, wherein the synthetic antibody is generated by the first and second polypeptides.

Clause 22. The method of clause 21, wherein the first recombinant nucleic acid sequence further comprises a first promoter for expressing the first polypeptide in the subject and wherein the second recombinant nucleic acid sequence further comprises a second promoter for expressing the second polypeptide in the subject.

Clause 23. The method of clause 22, wherein the first promoter and second promoter are the same.

Clause 24. The method of clause 23, wherein the promoter is a cytomegalovirus (CMV) promoter.

Clause 25. The method of clause 21, wherein the heavy chain polypeptide comprises a variable heavy region and a constant heavy region 1.

Clause 26. The method of clause 21, wherein the heavy chain polypeptide comprises a variable heavy region, a constant heavy region 1, a hinge region, a constant heavy region 2 and a constant heavy region 3.

Clause 27. The method of clause 21, wherein the light chain polypeptide comprises a variable light region and a constant light region.

Clause 28. The method of clause 21, wherein the first recombinant nucleic acid sequence and the second recombinant nucleic acid sequence further comprise a Kozak sequence.

Clause 29. The method of clause 21, wherein the first recombinant nucleic acid sequence and the second recombinant nucleic acid sequence further comprise an immunoglobulin (Ig) signal peptide.

Clause 30. The method of clause 29, wherein the Ig signal peptide comprises an IgE or IgG signal peptide.

Clause 31. A method of preventing or treating a disease in a subject, the method comprising generating a synthetic antibody in a subject according to the method of clause 1 or 21.

Clause 32. The method of clause 31, wherein the synthetic antibody is specific for a foreign antigen.

Clause 33. The method of clause 32, wherein the foreign antigen is derived from a virus.

Clause 34. The method of clause 33, wherein the virus is Human immunodeficiency virus (HIV), Chikungunya virus (CHIKV) or Dengue virus.

Clause 35. The method of clause 34, wherein the virus is HIV.

Clause 36. The method of clause 35, wherein the recombinant nucleic acid sequence comprises a nucleic acid sequence encoding at least one amino acid sequence of SEQ ID NOs:1, 2, 5, 46, 47, 48, 49, 51, 53, 55, and 57.

Clause 37. The method of clause 35, wherein the recombinant nucleic acid sequence comprises at least one nucleic acid sequence of SEQ ID NOs:3, 4, 6, 7, 50, 52, 55, 56, 62, 63, and 64.

Clause 38. The method of clause 34, wherein the virus is CHIKV.

Clause 39. The method of clause 38, wherein the recombinant nucleic acid sequence comprises a nucleic acid sequence encoding at least one amino acid sequence of SEQ ID NOs:59, 61, and 66.

Clause 40. The method of clause 38, wherein the recombinant nucleic acid sequence comprises at least one nucleic acid sequence of SEQ ID NOs:58, 60, and 65.

Clause 41. The method of clause 34, wherein the virus is Dengue virus.

Clause 42. The method of clause 41, wherein the recombinant nucleic acid sequence comprises a nucleic acid sequence encoding at least one amino acid sequence of SEQ ID NOs:45, 68, 70, 72, 74, 76, and 78.

Clause 43. The method of clause 41, wherein the recombinant nucleic acid sequence comprises at least one nucleic acid sequence of SEQ ID NOs:44, 67, 69, 71, 73, 75, and 77.

Clause 44. The method of clause 31, wherein the synthetic antibody is specific for a self-antigen.

Clause 45. The method of clause 44, wherein the self-antigen is Her2.

Clause 46. The method of clause 45, wherein the recombinant nucleic acid sequence comprises a nucleic acid sequence encoding at least one amino acid sequence of SEQ ID NOs:41 and 43.

Clause 47. The method of clause 45, wherein the recombinant nucleic acid sequence comprises at least one nucleic acid sequence of SEQ ID NOs:40 and 42.

Clause 48. A product produced by any one of the methods of clauses 1-47.

Clause 49. The product of clause 48, wherein the product is single DNA plasmid capable of expressing a functional antibody.

Clause 50. The product of clause 48, wherein the product is comprised of two distinct DNA plasmids capable of expressing components of a functional antibody that combine in vivo to form a functional antibody.

Clause 51. A method of treating a subject from infection by a pathogen, comprising: administering a nucleotide sequence encoding a synthetic antibody specific for the pathogen.

Clause 52. The method of clause 51, further comprising: administering an antigen of the pathogen to generate an immune response in the subject.

Clause 53. A nucleic acid molecule encoding a synthetic antibody comprising a nucleic acid sequence having at least about 95% identity over an entire length of the nucleic acid sequence selected from the group consisting of: (a) a nucleic acid sequence as set forth in SEQ ID NO:44; (b) a nucleic acid sequence as set forth in SEQ ID NO:67; (c) a nucleic acid sequence as set forth in SEQ ID NO:69; (d) a nucleic acid sequence as set forth in SEQ ID NO:71; (e) a nucleic acid sequence as set forth in SEQ ID NO:73; (f) a nucleic acid sequence as set forth in SEQ ID NO:75; (g) a nucleic acid sequence as set forth in SEQ ID NO:77; (h) a nucleic acid sequence as set forth in SEQ ID NO:58; (i) a nucleic acid sequence as set forth in SEQ ID NO:60; and (j) a nucleic acid sequence as set forth in SEQ ID NO:65.

Clause 54. The nucleic acid molecule of clause 53, wherein the nucleic acid sequence is selected from the group consisting of: (a) the nucleic acid sequence as set forth in SEQ ID NO:44; (b) the nucleic acid sequence as set forth in SEQ ID NO:67; (c) the nucleic acid sequence as set forth in SEQ ID NO:69; (d) the nucleic acid sequence as set forth in SEQ ID NO:71; (e) the nucleic acid sequence as set forth in SEQ ID NO:73; (f) the nucleic acid sequence as set forth in SEQ ID NO:75; (g) the nucleic acid sequence as set forth in SEQ ID NO:77; (h) the nucleic acid sequence as set forth in SEQ ID NO:58; (i) the nucleic acid sequence as set forth in SEQ ID NO:60; and (j) the nucleic acid sequence as set forth in SEQ ID NO:65.

Clause 55. A nucleic acid molecule encoding a synthetic antibody comprising a nucleic acid sequence encoding a protein having at least about 95% identity over an entire length of the amino acid sequence selected from the group consisting of: (a) an amino acid sequence as set forth in SEQ ID NO:45; (b) an amino acid sequence as set forth in SEQ ID NO:68; (c) an amino acid sequence as set forth in SEQ ID NO:70; (d) an amino acid sequence as set forth in SEQ ID NO:72; (e) an amino acid sequence as set forth in SEQ ID NO:74; (f) an amino acid sequence as set forth in SEQ ID NO:76; (g) an amino acid sequence as set forth in SEQ ID NO:78; (h) an amino acid sequence as set forth in SEQ ID NO:59; (i) an amino acid sequence as set forth in SEQ ID NO:61; and (j) an amino acid sequence as set forth in SEQ ID NO:66.

Clause 56. The nucleic acid molecule of clause 55, wherein the nucleic acid encodes a protein having the amino acid sequence selected from the group consisting of: (a) the amino acid sequence as set forth in SEQ ID NO:45; (b) the amino acid sequence as set forth in SEQ ID NO:68; (c) the amino acid sequence as set forth in SEQ ID NO:70; (d) the amino acid sequence as set forth in SEQ ID NO:72; (e) the amino acid sequence as set forth in SEQ ID NO:74; (f) the amino acid sequence as set forth in SEQ ID NO:76; (g) the amino acid sequence as set forth in SEQ ID NO:78; (h) the amino acid sequence as set forth in SEQ ID NO:59; (i) the amino acid sequence as set forth in SEQ ID NO:61; and (j) the amino acid sequence as set forth in SEQ ID NO:66.

Clause 57. The nucleic acid molecule of any one of clauses 53-56, wherein the nucleic acid sequence encodes a light chain polypeptide, a heavy chain polypeptide, both a light chain polypeptide and a heavy chain polypeptide, or fragments thereof.

Clause 58. The nucleic acid molecule of clause 57, wherein when the nucleic acid sequence encodes a light chain polypeptide and a heavy chain polypeptide, the nucleic acid sequence also encodes a protease cleavage site.

Clause 59. The nucleic acid molecule of clause 58, wherein the protease cleavage site is located between the light chain polypeptide and the heavy chain polypeptide and wherein the protease cleavage site includes a furin cleavage site and 2A peptide sequence.

Clause 60. The nucleic acid molecule of any one of clauses 53-56, wherein the nucleic acid molecule further encodes an immunoglobulin (Ig) signal peptide.

Clause 61. The nucleic acid molecule of clause 60, wherein the Ig signal peptide comprises an IgE signal peptide.

Clause 62. The nucleic acid molecule of any one of clauses 53-56, wherein the nucleic acid molecule comprises an expression vector.

Clause 63. A composition comprising the nucleic acid molecule of any one of clauses 53-56.

Clause 64. The composition of clause 63 further comprising a pharmaceutically acceptable excipient.

Clause 65. A method of preventing a disease in a subject in need thereof, the method comprising administering the nucleic acid molecule of any one of clauses 53-56 to the subject.

Clause 66. The method of clause 65, wherein the disease is infection by Chikagunya virus (CHIKV) or Dengue virus (DENV).

Clause 67. The method of clause 66, wherein when the disease is infection by CHIKV, the nucleic acid sequence is selected from the group consisting of: (a) the nucleic acid sequence as set forth in SEQ ID NO:58; (b) the nucleic acid sequence as set forth in SEQ ID NO:60; and (c) the nucleic acid sequence as set forth in SEQ ID NO:65.

Clause 68. The method of clause 66, wherein when the disease is infection by DENV, the nucleic acid sequence is selected from the group consisting of: (a) the nucleic acid sequence as set forth in SEQ ID NO:44; (b) the nucleic acid sequence as set forth in SEQ ID NO:67; (c) the nucleic acid sequence as set forth in SEQ ID NO:69; (d) the nucleic acid sequence as set forth in SEQ ID NO:71; (e) the nucleic acid sequence as set forth in SEQ ID NO:73; (f) the nucleic acid sequence as set forth in SEQ ID NO:75; and (g) the nucleic acid sequence as set forth in SEQ ID NO:77.

Clause 69. The method of clause 66, wherein when the disease is infection by CHIKV, the amino acid sequence is selected from the group consisting of: (a) the amino acid sequence as set forth in SEQ ID NO:59; (b) the amino acid sequence as set forth in SEQ ID NO:61; and (c) the amino acid sequence as set forth in SEQ ID NO:66.

Clause 70. The method of clause 66, wherein when the disease is infection by DENV, the amino acid sequence is selected from the group consisting of: (a) the amino acid sequence as set forth in SEQ ID NO:45; (b) the amino acid sequence as set forth in SEQ ID NO:68; (c) the amino acid sequence as set forth in SEQ ID NO:70; (d) the amino acid sequence as set forth in SEQ ID NO:72; (e) the amino acid sequence as set forth in SEQ ID NO:74; (f) the amino acid sequence as set forth in SEQ ID NO:76; and (g) the amino acid sequence as set forth in SEQ ID NO:78.

Clause 71. The method of clause 65, wherein administering includes at least one of electroporation and injection.

Clause 72. A method of treating a disease in a subject in need thereof, the method comprising administering the nucleic acid molecule of any one of clauses 53-56 to the subject.

Clause 73. The method of clause 72, wherein the disease is infection by Chikagunya virus (CHIKV) or Dengue virus (DENV).

Clause 74. The method of clause 73, wherein when the disease is infection by CHIKV, the nucleic acid sequence is selected from the group consisting of: (a) the nucleic acid sequence as set forth in SEQ ID NO:58; (b) the nucleic acid sequence as set forth in SEQ ID NO:60; and (c) the nucleic acid sequence as set forth in SEQ ID NO:65.

Clause 75. The method of clause 73, wherein when the disease is infection by DENV, the nucleic acid sequence is selected from the group consisting of: (a) the nucleic acid sequence as set forth in SEQ ID NO:44; (b) the nucleic acid sequence as set forth in SEQ ID NO:67; (c) the nucleic acid sequence as set forth in SEQ ID NO:69; (d) the nucleic acid sequence as set forth in SEQ ID NO:71; (e) the nucleic acid sequence as set forth in SEQ ID NO:73; (f) the nucleic acid sequence as set forth in SEQ ID NO:75; and (g) the nucleic acid sequence as set forth in SEQ ID NO:77.

Clause 76. The method of clause 73, wherein when the disease is infection by CHIKV, the amino acid sequence is selected from the group consisting of: (a) the amino acid sequence as set forth in SEQ ID NO:59; (b) the amino acid sequence as set forth in SEQ ID NO:61; and (c) the amino acid sequence as set forth in SEQ ID NO:66.

Clause 77. The method of clause 73, wherein when the disease is infection by DENV, the amino acid sequence is selected from the group consisting of: (a) the amino acid sequence as set forth in SEQ ID NO:45; (b) the amino acid sequence as set forth in SEQ ID NO:68; (c) the amino acid sequence as set forth in SEQ ID NO:70; (d) the amino acid sequence as set forth in SEQ ID NO:72; (e) the amino acid sequence as set forth in SEQ ID NO:74; (f) the amino acid sequence as set forth in SEQ ID NO:76; and (g) the amino acid sequence as set forth in SEQ ID NO:78.

Clause 78. The method of clause 72, wherein administering includes at least one of electroporation and injection.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding a synthetic antibody comprising a nucleic acid sequence having at least about 95% identity over an entire length of the nucleic acid sequence selected from the group consisting of:
(a) a nucleic acid sequence as set forth in SEQ ID NO:67;
(b) a nucleic acid sequence as set forth in SEQ ID NO:69;
(c) a nucleic acid sequence as set forth in SEQ ID NO:71;
(d) a nucleic acid sequence as set forth in SEQ ID NO:73;
(e) a nucleic acid sequence as set forth in SEQ ID NO:75;
(f) a nucleic acid sequence as set forth in SEQ ID NO:77;
(g) a nucleic acid sequence as set forth in SEQ ID NO:65.

2. The nucleic acid molecule of claim 1, wherein the nucleic acid sequence is selected from the group consisting of:
(a) the nucleic acid sequence as set forth in SEQ ID NO:67;
(b) the nucleic acid sequence as set forth in SEQ ID NO:69;
(c) the nucleic acid sequence as set forth in SEQ ID NO:71;
(d) the nucleic acid sequence as set forth in SEQ ID NO:73;
(e) the nucleic acid sequence as set forth in SEQ ID NO:75;
(f) the nucleic acid sequence as set forth in SEQ ID NO:77; and
(g) the nucleic acid sequence as set forth in SEQ ID NO:65.

3. A nucleic acid molecule encoding a synthetic antibody comprising a nucleic acid sequence encoding a protein having at least about 95% identity over an entire length of the amino acid sequence selected from the group consisting of:
(a) an amino acid sequence as set forth in SEQ ID NO:68;
(b) an amino acid sequence as set forth in SEQ ID NO:70;
(c) an amino acid sequence as set forth in SEQ ID NO:72;
(d) an amino acid sequence as set forth in SEQ ID NO:74;
(e) an amino acid sequence as set forth in SEQ ID NO:76;
(f) an amino acid sequence as set forth in SEQ ID NO:78; and
(g) an amino acid sequence as set forth in SEQ ID NO:66.

4. The nucleic acid molecule of claim 3, wherein the nucleic acid encodes a protein having the amino acid sequence selected from the group consisting of:
(a) an amino acid sequence as set forth in SEQ ID NO:68;
(b) an amino acid sequence as set forth in SEQ ID NO:70;
(c) an amino acid sequence as set forth in SEQ ID NO:72;
(d) an amino acid sequence as set forth in SEQ ID NO:74;
(e) an amino acid sequence as set forth in SEQ ID NO:76;
an amino acid sequence as set forth in SEQ ID NO:78; and
(g) an amino acid sequence as set forth in SEQ ID NO:66.

5. The nucleic acid molecule of claim 1, wherein the nucleic acid sequence encodes a light chain polypeptide, a heavy chain polypeptide, both a light chain polypeptide and a heavy chain polypeptide, or fragments thereof.

6. The nucleic acid molecule of claim 5, wherein when the nucleic acid sequence encodes a light chain polypeptide and a heavy chain polypeptide, the nucleic acid sequence also encodes a protease cleavage site.

7. The nucleic acid molecule of claim 6, wherein the protease cleavage site is located between the light chain polypeptide and the heavy chain polypeptide and wherein the protease cleavage site includes a furin cleavage site and 2A peptide sequence.

8. The nucleic acid molecule of claim 1, wherein the nucleic acid molecule further encodes an immunoglobulin (Ig) signal peptide.

9. The nucleic acid molecule of claim 8, wherein the Ig signal peptide comprises an IgE signal peptide.

10. The nucleic acid molecule of claim 1, wherein the nucleic acid molecule comprises an expression vector.

11. A composition comprising the nucleic acid molecule of claim 1.

12. The composition of claim 11 further comprising a pharmaceutically acceptable excipient.

13. A method of preventing a disease in a subject in need thereof, the method comprising administering the nucleic acid molecule of claim 1.

14. The method of claim 13, wherein the disease is infection by Chikungunya virus (CHIKV) or Dengue virus (DENV).

15. The method of claim 14, wherein when the disease is infection by CHIKV, the nucleic acid sequence is the nucleic acid sequence as set forth in SEQ ID NO:65.

16. The method of claim 14, wherein when the disease is infection by DENV, the nucleic acid sequence is selected from the group consisting of:
(a) the nucleic acid sequence as set forth in SEQ ID NO:67;
(b) the nucleic acid sequence as set forth in SEQ ID NO:69;
(c) the nucleic acid sequence as set forth in SEQ ID NO:71;
(d) the nucleic acid sequence as set forth in SEQ ID NO:73;
(e) the nucleic acid sequence as set forth in SEQ ID NO:75; and
(f) the nucleic acid sequence as set forth in SEQ ID NO:77.

17. The method of claim 14, wherein when the disease is infection by CHIKV, the amino acid sequence is the amino acid sequence as set forth in SEQ ID NO:66.

18. The method of claim 14, wherein when the disease is infection by DENV, the amino acid sequence is selected from the group consisting of:
(a) the amino acid sequence as set forth in SEQ ID NO:68;
(b) the amino acid sequence as set forth in SEQ ID NO:70;
(c) the amino acid sequence as set forth in SEQ ID NO:72;
(d) the amino acid sequence as set forth in SEQ ID NO:74;
(e) the amino acid sequence as set forth in SEQ ID NO:76; and
(f) the amino acid sequence as set forth in SEQ ID NO:78.

19. The method of claim 13, wherein administering includes at least one of electroporation and injection.

20. A method of treating a disease in a subject in need thereof, the method comprising administering the nucleic acid molecule of claim 1 to the subject.

21. The method of claim 20, wherein the disease is infection by Chikungunya virus (CHIKV) or Dengue virus (DENV).

22. The method of claim 21, wherein when the disease is infection by CHIKV, the nucleic acid sequence is the nucleic acid sequence as set forth in SEQ ID NO:65.

23. The method of claim 21, wherein when the disease is infection by DENV, the nucleic acid sequence is selected from the group consisting of:
(a) the nucleic acid sequence as set forth in SEQ ID NO:67;

(b) the nucleic acid sequence as set forth in SEQ ID NO:69;
(c) the nucleic acid sequence as set forth in SEQ ID NO:71;
(d) the nucleic acid sequence as set forth in SEQ ID NO:73;
(e) the nucleic acid sequence as set forth in SEQ ID NO:75; and
(f) the nucleic acid sequence as set forth in SEQ ID NO:77.

24. The method of claim 21, wherein when the disease is infection by CHIKV, the amino acid sequence is the nucleic acid sequence as set forth in SEQ ID NO:66.

25. The method of claim 21, wherein when the disease is infection by DENV, the amino acid sequence is selected from the group consisting of:
(a) the amino acid sequence as set forth in SEQ ID NO:68;
(b) the amino acid sequence as set forth in SEQ ID NO:70;
(c) the amino acid sequence as set forth in SEQ ID NO:72;
(d) the amino acid sequence as set forth in SEQ ID NO:74;
(e) the amino acid sequence as set forth in SEQ ID NO:76; and
(f) the amino acid sequence as set forth in SEQ ID NO:78.

26. The method of claim 20, wherein administering includes at least one of electroporation and injection.

27. A method of generating an anti-CHIKV synthetic antibody or anti-DENV synthetic antibody in a cell, the method comprising administering to the cell a composition comprising a recombinant nucleic acid sequence encoding an anti-CHIKV or anti-DENV antibody or an antigen binding fragment thereof, wherein the recombinant nucleic acid sequence is expressed in the cell to generate the synthetic antibody, wherein the anti-CHIKV or anti-DENV antibody comprises an amino acid sequence having at least about 95% identity over an entire length of the amino acid sequence selected from the group consisting of:
(a) an amino acid sequence as set forth in SEQ ID NO:68;
(b) an amino acid sequence as set forth in SEQ ID NO:70;
(c) an amino acid sequence as set forth in SEQ ID NO:72;
(d) an amino acid sequence as set forth in SEQ ID NO:74;
(e) an amino acid sequence as set forth in SEQ ID NO:76;
(f) an amino acid sequence as set forth in SEQ ID NO:78; and
(g) an amino acid sequence as set forth in SEQ ID NO:66.

28. The method of claim 27, wherein the anti-CHIKV or anti-DENV antibody comprises an amino acid sequence selected from the group consisting of
(a) an amino acid sequence as set forth in SEQ ID NO:68;
(b) an amino acid sequence as set forth in SEQ ID NO:70;
(c) an amino acid sequence as set forth in SEQ ID NO:72;
(d) an amino acid sequence as set forth in SEQ ID NO:74;
(e) an amino acid sequence as set forth in SEQ ID NO:76;
(f) an amino acid sequence as set forth in SEQ ID NO:78; and
(g) an amino acid sequence as set forth in SEQ ID NO:66.

29. The method of claim 27, wherein the recombinant nucleic acid sequence comprises a nucleic acid sequence having at least about 95% identity over an entire length of the nucleic acid sequence selected from the group consisting of:
(a) a nucleic acid sequence as set forth in SEQ ID NO:69;
(b) a nucleic acid sequence as set forth in SEQ ID NO:71;
(c) a nucleic acid sequence as set forth in SEQ ID NO:73;
(d) a nucleic acid sequence as set forth in SEQ ID NO:75;
(e) a nucleic acid sequence as set forth in SEQ ID NO:77; and
(f) a nucleic acid sequence as set forth in SEQ ID NO:65.

30. The method of claim 29, wherein the recombinant nucleic acid sequence comprises a nucleic acid sequence selected from the group consisting of:
(a) the nucleic acid sequence as set forth in SEQ ID NO:67;
(b) the nucleic acid sequence as set forth in SEQ ID NO:69;
(c) the nucleic acid sequence as set forth in SEQ ID NO:71;
(d) the nucleic acid sequence as set forth in SEQ ID NO:73;
(e) the nucleic acid sequence as set forth in SEQ ID NO:75;
(f) the nucleic acid sequence as set forth in SEQ ID NO:77; and
(g) the nucleic acid sequence as set forth in SEQ ID NO:65.

31. A composition comprising two or more recombinant nucleic acid sequences, wherein each recombinant nucleic acid sequence encodes an antibody, wherein the antibody comprises an amino acid sequence having at least about 95% identity over an entire length of an amino acid sequence selected from the group consisting of:
(a) an amino acid sequence as set forth in SEQ ID NO:68;
(b) an amino acid sequence as set forth in SEQ ID NO:70;
(c) an amino acid sequence as set forth in SEQ ID NO:72;
(d) an amino acid sequence as set forth in SEQ ID NO:74;
(e) an amino acid sequence as set forth in SEQ ID NO:76;
(f) an amino acid sequence as set forth in SEQ ID NO:78.

* * * * *

SEQUENCE LISTING

```
<160> NUMBER OF SEQ ID NOS: 78

<210> SEQ ID NO 1
<211> LENGTH: 738
<212> TYPE: PRT
<213> ORGANISM: Artificial Sequence
<220> FEATURE:
<223> OTHER INFORMATION: Amino Acid Sequence of HIV-1 Env-4E10 Ig

<400> SEQUENCE: 1

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Arg
            20                  25                  30

Pro Gly Ser Ser Val Thr Val Ser Cys Lys Ala Ser Gly Gly Ser Phe
        35                  40                  45

Ser Thr Tyr Ala Leu Ser Trp Val Arg Gln Ala Pro Gly Arg Gly Leu
    50                  55                  60

Glu Trp Met Gly Gly Val Ile Pro Leu Leu Thr Ile Thr Asn Tyr Ala
65                  70                  75                  80

Pro Arg Phe Gln Gly Arg Ile Thr Ile Thr Ala Asp Arg Ser Thr Ser
                85                  90                  95

Thr Ala Tyr Leu Glu Leu Asn Ser Leu Arg Pro Glu Asp Thr Ala Val
            100                 105                 110

Tyr Tyr Cys Ala Arg Glu Gly Thr Thr Gly Trp Gly Trp Leu Gly Lys
        115                 120                 125

Pro Ile Gly Ala Phe Ala His Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
```

-continued

```
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys Arg Gly Arg Lys
465                 470                 475                 480

Arg Arg Ser Gly Ser Gly Ala Thr Asn Phe Ser Leu Leu Lys Gln Ala
                485                 490                 495

Gly Asp Val Glu Glu Asn Pro Gly Pro Met Val Leu Gln Thr Gln Val
            500                 505                 510

Phe Ile Ser Leu Leu Leu Trp Ile Ser Gly Ala Tyr Gly Glu Ile Val
        515                 520                 525

Leu Thr Gln Ser Pro Gly Thr Gln Ser Leu Ser Pro Gly Glu Arg Ala
    530                 535                 540

Thr Leu Ser Cys Arg Ala Ser Gln Ser Val Gly Asn Asn Lys Leu Ala
545                 550                 555                 560

Trp Tyr Gln Gln Arg Pro Gly Gln Ala Pro Arg Leu Leu Ile Tyr Gly
                565                 570                 575

Ala Ser Ser Arg Pro Ser Gly Val Ala Asp Arg Phe Ser Gly Ser Gly
            580                 585                 590

Ser Gly Thr Asp Phe Thr Leu Thr Ile Ser Arg Leu Glu Pro Glu Asp
        595                 600                 605

Phe Ala Val Tyr Tyr Cys Gln Gln Tyr Gly Gln Ser Leu Ser Thr Phe
    610                 615                 620

Gly Gln Gly Thr Lys Val Glu Lys Arg Thr Val Ala Ala Pro Ser Val
625                 630                 635                 640

Phe Ile Phe Pro Pro Ser Asp Glu Gln Leu Lys Ser Gly Thr Ala Ser
                645                 650                 655

Val Val Cys Leu Leu Asn Asn Phe Tyr Pro Arg Glu Ala Lys Val Gln
            660                 665                 670

Trp Lys Val Asp Asn Ala Leu Gln Ser Gly Asn Ser Gln Glu Ser Val
        675                 680                 685

Thr Glu Gln Asp Ser Lys Asp Ser Thr Tyr Ser Leu Ser Ser Thr Leu
    690                 695                 700

Thr Leu Ser Lys Ala Asp Tyr Glu Lys His Lys Val Tyr Ala Cys Glu
705                 710                 715                 720
```

Val Thr His Gln Gly Leu Ser Ser Pro Val Thr Lys Ser Phe Asn Arg
725 730 735

Gly Glu

<210> SEQ ID NO 2
<211> LENGTH: 768
<212> TYPE: PRT
<213> ORGANISM: Artificial Sequence
<220> FEATURE:
<223> OTHER INFORMATION: Amino Acid Sequence of HIV-1 Env-PG9 Ig

<400> SEQUENCE: 2

Met Asp Trp Thr Trp Arg Ile Leu Phe Leu Val Ala Ala Ala Thr Gly
1 5 10 15

Thr His Ala Glu Phe Gly Leu Ser Trp Val Phe Leu Val Ala Phe Leu
20 25 30

Arg Gly Val Gln Cys Gln Arg Leu Val Glu Ser Gly Gly Gly Val Val
35 40 45

Gln Pro Gly Ser Ser Leu Arg Leu Ser Cys Ala Ala Ser Gly Phe Asp
50 55 60

Phe Ser Arg Gln Gly Met His Trp Val Arg Gln Ala Pro Gly Gln Gly
65 70 75 80

Leu Glu Trp Val Ala Phe Ile Lys Tyr Asp Gly Ser Glu Lys Tyr His
85 90 95

Ala Asp Ser Val Trp Gly Arg Leu Ser Ile Ser Arg Asp Asn Ser Lys
100 105 110

Asp Thr Leu Tyr Leu Gln Met Asn Ser Leu Arg Val Glu Asp Thr Ala
115 120 125

Thr Tyr Phe Cys Val Arg Glu Ala Gly Gly Pro Asp Tyr Arg Asn Gly
130 135 140

Tyr Asn Tyr Tyr Asp Phe Tyr Asp Gly Tyr Tyr Asn Tyr His Tyr Met
145 150 155 160

Asp Val Trp Gly Lys Gly Thr Thr Val Thr Val Ser Ser Ala Ser Thr
165 170 175

Lys Gly Pro Ser Val Phe Pro Leu Ala Pro Ser Ser Lys Ser Thr Ser
180 185 190

Gly Gly Thr Ala Ala Leu Gly Cys Leu Val Lys Asp Tyr Phe Pro Glu
195 200 205

Pro Val Thr Val Ser Trp Asn Ser Gly Ala Leu Thr Ser Gly Val His
210 215 220

Thr Phe Pro Ala Val Leu Gln Ser Ser Gly Leu Tyr Ser Leu Ser Ser
225 230 235 240

Val Val Thr Val Pro Ser Ser Ser Leu Gly Thr Gln Thr Tyr Ile Cys
245 250 255

Asn Val Asn His Lys Pro Ser Asn Thr Lys Val Asp Lys Arg Val Glu
260 265 270

Pro Lys Ser Cys Asp Lys Thr His Thr Cys Pro Pro Cys Pro Ala Pro
275 280 285

Glu Leu Leu Gly Gly Pro Ser Val Phe Leu Phe Pro Pro Lys Pro Lys
290 295 300

Asp Thr Leu Met Ile Ser Arg Thr Pro Glu Val Thr Cys Val Val Val
305 310 315 320

Asp Val Ser His Glu Asp Pro Glu Val Lys Phe Asn Trp Tyr Val Asp
325 330 335

-continued

```
Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys Arg Gly Arg Lys Arg Arg Ser Gly Ser
            500                 505                 510

Gly Ala Thr Asn Phe Ser Leu Leu Lys Gln Ala Gly Asp Val Glu Glu
        515                 520                 525

Asn Pro Gly Pro Met Ala Trp Thr Pro Leu Phe Leu Phe Leu Leu Thr
    530                 535                 540

Cys Cys Pro Gly Gly Ser Asn Ser Gln Ser Ala Leu Thr Gln Pro Ala
545                 550                 555                 560

Ser Val Ser Gly Ser Pro Gly Gln Ser Ile Thr Ile Ser Cys Asn Gly
                565                 570                 575

Thr Ser Asn Asp Val Gly Gly Tyr Glu Ser Val Ser Trp Tyr Gln Gln
            580                 585                 590

His Pro Gly Lys Ala Pro Lys Val Val Ile Tyr Asp Val Ser Lys Arg
        595                 600                 605

Pro Ser Gly Val Ser Asn Arg Phe Ser Gly Ser Lys Ser Gly Asn Thr
    610                 615                 620

Ala Ser Leu Thr Ile Ser Gly Leu Gln Ala Glu Asp Glu Gly Asp Tyr
625                 630                 635                 640

Tyr Cys Lys Ser Leu Thr Ser Thr Arg Arg Arg Val Phe Gly Thr Gly
                645                 650                 655

Thr Lys Leu Thr Val Leu Gly Gln Pro Lys Ala Ala Pro Ser Val Thr
            660                 665                 670

Leu Phe Pro Pro Ser Ser Glu Glu Leu Gln Ala Asn Lys Ala Thr Leu
        675                 680                 685

Val Cys Leu Ile Ser Asp Phe Tyr Pro Gly Ala Val Thr Val Ala Trp
    690                 695                 700

Lys Ala Asp Ser Ser Pro Val Lys Ala Gly Val Glu Thr Thr Thr Pro
705                 710                 715                 720

Ser Lys Gln Ser Asn Asn Lys Tyr Ala Ala Ser Ser Tyr Leu Ser Leu
                725                 730                 735

Thr Pro Glu Gln Trp Lys Ser His Lys Ser Tyr Ser Cys Gln Val Thr
            740                 745                 750

His Glu Gly Ser Thr Val Glu Lys Thr Val Ala Pro Thr Glu Cys Ser
```

755 760 765

<210> SEQ ID NO 3
<211> LENGTH: 792
<212> TYPE: DNA
<213> ORGANISM: Artificial Sequence
<220> FEATURE:
<223> OTHER INFORMATION: Nucleic Acid Sequence Encoding the Heavy Chain (VH-CH1) of HIV-1 Env Fab

<400> SEQUENCE: 3
aagcttgccg ccaccatgga gactgataca ctgctgctgt gggtgctgct gctgtgggtg 60
ccagggtcaa ccggagatgg ggctcaggtc cagctggtcc agagcggcgg acagatgaag 120
aaacccggcg agagcatgag gatctcctgc agagcatctg gatacgagtt catcgactgt 180
accctgaact ggattaggct ggctcctgga aagagaccag agtggatggg gtggctgaaa 240
ccacgagggg gagcagtgaa ttacgcccgg cccctgcagg gacgagtgac catgaccagg 300
gacgtgtaca gcgataccgc cttcctggag ctgcggtccc tgacagtgga cgatactgct 360
gtctacttct gcacacgcgg aaagaactgt gactataatt gggattttga acactggggc 420
cggggaacac ccgtgatcgt cagctccccc agtactaagg gaccttcagt gtttccactg 480 gcccccctcta gtaaatccac ctctggaggg acagccgctc tgggatgcct ggtgaaagat 540
tatttccccg aacctgtgac cgtcagttgg aactcagggg ctctgacttc tggcgtgcac 600
acctttcctg cagtcctgca gtcaagcggg ctgtacagtc tgtcctctgt ggtcactgtg 660
cctagttcaa gcctgggcac tcagacctat atttgtaacg tgaatcataa gccatccaat 720
acaaaagtgg acaaaaaagc cgaacccaaa tcctgttacc cttatgatgt gcccgactac 780
gcctgactcg ag 792

<210> SEQ ID NO 4
<211> LENGTH: 756
<212> TYPE: DNA
<213> ORGANISM: Artificial Sequence
<220> FEATURE:
<223> OTHER INFORMATION: Light Chain (VL-CL) of HIV-1 Env Fab

<400> SEQUENCE: 4
aagcttgccg ccaccatgga aaccgataca ctgctgctgt gggtgctgct gctgtgggtg 60
ccaggaagta ccggggatgg ggctcaggtc cagattgtgc tgactcagtc ccctgggacc 120
ctgtctctga gtccaggcga gacagctatc atttcatgcc gaactagcca gtacggcagc 180
ctggcttggt atcagcagcg accaggacag gcaccacgac tggtcatcta ctcaggcagc 240
acaagggccg ctggcatccc cgacaggttc tccggcagca ggtgggggcc tgattacaac 300
ctgactatct ctaatctgga gagtggggac tttggcgtgt actattgcca gcagtatgag 360
ttcttcggcc agggaactaa ggtgcaggtg gacatcaaaa gaaccgtggc agccccatcc 420
gtcttcattt ttccccccttc tgatgagcag ctgaagtcag gcaccgccag cgtggtctgt 480
ctgctgaaca atttctaccc ccgggaagcc aaggtgcagt ggaaagtgga caacgctctg 540
cagagtggaa attcacagga gagcgtgacc gaacaggact ccaaggattc tacatatagt 600
ctgagcagca ccctgaccct gagtaaagca gattacgaga agcacaaagt gtatgcctgt 660
gaagtcacac atcagggcct gaggagcccc gtgactaaaa gtttcaaccg aggagagtgc 720 taccccttatg atgtgcccga ctacgcctaa ctcgag 756

<210> SEQ ID NO 5

<211> LENGTH: 731
<212> TYPE: PRT
<213> ORGANISM: Artificial Sequence
<220> FEATURE:
<223> OTHER INFORMATION: VRC01 IgG

<400> SEQUENCE: 5

```
Met Asp Trp Thr Trp Ile Leu Phe Leu Val Ala Ala Ala Thr Arg Val
1               5                   10                  15

His Ser Gln Val Gln Leu Val Gln Ser Gly Gly Gln Met Lys Lys Pro
            20                  25                  30

Gly Glu Ser Met Arg Ile Ser Cys Arg Ala Ser Gly Tyr Glu Phe Ile
        35                  40                  45

Asp Cys Thr Leu Asn Trp Ile Arg Leu Ala Pro Gly Lys Arg Pro Glu
    50                  55                  60

Trp Met Gly Trp Leu Lys Pro Arg Gly Gly Ala Val Asn Tyr Ala Arg
65                  70                  75                  80

Pro Leu Gln Gly Arg Val Thr Met Thr Arg Asp Val Tyr Ser Asp Thr
                85                  90                  95

Ala Phe Leu Glu Leu Arg Ser Leu Thr Val Asp Asp Thr Ala Val Tyr
            100                 105                 110

Phe Cys Thr Arg Gly Lys Asn Cys Asp Tyr Asn Trp Asp Phe Glu His
        115                 120                 125

Trp Gly Arg Gly Thr Pro Val Ile Val Ser Ser Pro Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Ala Glu Pro Lys
225                 230                 235                 240

Ser Cys Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380
```

```
Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys Arg Gly Arg Lys Arg Arg
465                 470                 475                 480

Ser Gly Ser Gly Ala Thr Asn Phe Ser Leu Leu Lys Gln Ala Gly Asp
                485                 490                 495

Val Glu Glu Asn Pro Gly Pro Met Asp Trp Thr Trp Ile Leu Phe Leu
            500                 505                 510

Val Ala Ala Ala Thr Arg Val His Ser Glu Ile Val Leu Thr Gln Ser
        515                 520                 525

Pro Gly Thr Leu Ser Leu Ser Pro Gly Glu Thr Ala Ile Ile Ser Cys
    530                 535                 540

Arg Thr Ser Gln Tyr Gly Ser Leu Ala Trp Tyr Gln Gln Arg Pro Gly
545                 550                 555                 560

Gln Ala Pro Arg Leu Val Ile Tyr Ser Gly Ser Thr Arg Ala Ala Gly
                565                 570                 575

Ile Pro Asp Arg Phe Ser Gly Ser Arg Trp Gly Pro Asp Tyr Asn Leu
            580                 585                 590

Thr Ile Ser Asn Leu Glu Ser Gly Asp Phe Gly Val Tyr Tyr Cys Gln
        595                 600                 605

Gln Tyr Glu Phe Phe Gly Gln Gly Thr Lys Val Gln Val Asp Ile Lys
    610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
            660                 665                 670

Ser Gly Asn Ser Gln Glu Ser Val Thr Glu Gln Asp Ser Lys Asp Ser
        675                 680                 685

Thr Tyr Ser Leu Ser Ser Thr Leu Thr Leu Ser Lys Ala Asp Tyr Glu
    690                 695                 700

Lys His Lys Val Tyr Ala Cys Glu Val Thr His Gln Gly Leu Arg Ser
705                 710                 715                 720

Pro Val Thr Lys Ser Phe Asn Arg Gly Glu Cys
                725                 730


<210> SEQ ID NO 6
<211> LENGTH: 819
<212> TYPE: DNA
<213> ORGANISM: Artificial Sequence
<220> FEATURE:
<223> OTHER INFORMATION: Optimized Nucleic Acid Sequence Encoding IgG
      Heavy Chain

<400> SEQUENCE: 6

ggatccgcca ccatggaaac cgacactctg ctgctgtggg tgctgctgct gtgggtgccc     60
```

ggctcaacag gcgacggcgc tcaggtccag ctggtccagt ctggagctgt gatcaagacc 120
cctggcagct ccgtcaaaat ttcttgcaga gcaagtggct acaacttccg ggactatagc 180
atccactggg tgcggctgat tcctgataag ggatttgagt ggatcggctg gatcaagcca 240
ctgtggggcg ctgtgtccta cgcaaggcag ctgcaggggc gcgtctccat gacacgacag 300
ctgtctcagg acccagacga tcccgattgg ggggtggcct acatggagtt cagtggactg 360
actcccgcag acaccgccga atatttttgc gtgcggagag gctcctgcga ctactgtggg 420
gatttcccat ggcagtattg gtgtcaggga actgtggtcg tggtctctag tgcatcaacc 480
aagggcccca gcgtgtttcc tctggcccca tcaagcaaaa gtacatcagg aggaactgca 540
gctctgggat gtctggtgaa ggattacttc cccgagcctg tgaccgtcag ctggaactcc 600
ggagcactga cctccggagt gcacacattt cccgctgtcc tgcagtcctc tgggctgtac 660
tctctgagtt cagtggtcac agtgcctagc tcctctctgg gcacccagac atatatctgc 720
aacgtcaatc ataagccaag taatactaaa gtggacaaga aagtcgaacc caaatcatgt 780 taccccctatg acgtgcctga ttatgcttga taactcgag 819

<210> SEQ ID NO 7
<211> LENGTH: 753
<212> TYPE: DNA
<213> ORGANISM: Artificial Sequence
<220> FEATURE:
<223> OTHER INFORMATION: Optimized Nucleic Acid Sequence Encoding IgG Light Chain

<400> SEQUENCE: 7
ggatccgcca ccatggagac tgatacactg ctgctgtggg tgctgctgct gtgggtgcct 60
ggctcaaccg gcgacggggc tcaggtccag attgtgctga cccagagccc tggcatcctg 120
tcactgagcc caggagagac cgcaacactg ttctgcaagg cctcccaggg cgggaacgct 180
atgacatggt accagaaacg gagaggacag gtgccccgac tgctgatcta tgacacttca 240
aggcgagcaa gcggagtgcc tgatcgattt gtcggcagcg gctctgggac agacttcttt 300
ctgactatta ataagctgga cagagaggat ttcgctgtgt actattgcca gcagtttgaa 360
ttctttggac tgggcagcga gctggaagtg cacaggaccg tcgccgctcc aagtgtgttc 420
atttttcccc ctagcgatga gcagctgaaa tccgggacag cctctgtggt ctgtctgctg 480
aacaatttct acccccgcga agcaaaggtg cagtggaaag tcgacaacgc cctgcagagt 540
ggcaattcac aggagagcgt gaccgaacag gactccaagg attctacata tagtctgagc 600
tccactctga ccctgtctaa agctgattac gagaagcaca aagtgtatgc atgcgaagtc 660
actcatcagg gcctgtctag tcctgtgacc aagagcttta accgagggga gtgttaccca 720
tatgacgtcc ccgattacgc ctgataactc gag 753

<210> SEQ ID NO 8
<211> LENGTH: 18
<212> TYPE: PRT
<213> ORGANISM: Artificial Sequence
<220> FEATURE:
<223> OTHER INFORMATION: IgE1 Signal Peptide of VRC-1 IgG

<400> SEQUENCE: 8

Met Asp Trp Thr Trp Ile Leu Phe Leu Val Ala Ala Ala Thr Arg Val
1 5 10 15

His Ser

-continued

<210> SEQ ID NO 9
<211> LENGTH: 126
<212> TYPE: PRT
<213> ORGANISM: Artificial Sequence
<220> FEATURE:
<223> OTHER INFORMATION: Variable Heavy Region of VRC01 IgG

<400> SEQUENCE: 9

```
Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser Pro Ser Thr Lys Gly
        115                 120                 125
```

<210> SEQ ID NO 10
<211> LENGTH: 98
<212> TYPE: PRT
<213> ORGANISM: Artificial Sequence
<220> FEATURE:
<223> OTHER INFORMATION: Constant Heavy region 1 (CH1) of VRC01 IgG

<400> SEQUENCE: 10

```
Pro Ser Val Phe Pro Leu Ala Pro Ser Ser Lys Ser Thr Ser Gly Gly
1               5                   10                  15

Thr Ala Ala Leu Gly Cys Leu Val Lys Asp Tyr Phe Pro Glu Pro Val
            20                  25                  30

Thr Val Ser Trp Asn Ser Gly Ala Leu Thr Ser Gly Val His Thr Phe
        35                  40                  45

Pro Ala Val Leu Gln Ser Ser Gly Leu Tyr Ser Leu Ser Ser Val Val
    50                  55                  60

Thr Val Pro Ser Ser Ser Leu Gly Thr Gln Thr Tyr Ile Cys Asn Val
65                  70                  75                  80

Asn His Lys Pro Ser Asn Thr Lys Val Asp Lys Lys Ala Glu Pro Lys
                85                  90                  95

Ser Cys
```

<210> SEQ ID NO 11
<211> LENGTH: 15
<212> TYPE: PRT
<213> ORGANISM: Artificial Sequence
<220> FEATURE:
<223> OTHER INFORMATION: Hinge Region of VRC01 IgG

<400> SEQUENCE: 11

```
Glu Pro Lys Ser Cys Asp Lys Thr His Thr Cys Pro Pro Cys Pro
1               5                   10                  15
```

<210> SEQ ID NO 12

<211> LENGTH: 110
<212> TYPE: PRT
<213> ORGANISM: Artificial Sequence
<220> FEATURE:
<223> OTHER INFORMATION: Constant Heavy Region 2 (CH2) of VRC01 IgG

<400> SEQUENCE: 12

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 13
<211> LENGTH: 107
<212> TYPE: PRT
<213> ORGANISM: Artificial Sequence
<220> FEATURE:
<223> OTHER INFORMATION: Constant Heavy Region 3 (CH3) of VRC01 IgG

<400> SEQUENCE: 13

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 14
<211> LENGTH: 7
<212> TYPE: PRT
<213> ORGANISM: Artificial Sequence
<220> FEATURE:
<223> OTHER INFORMATION: Furin Cleavage Site of VRC01 IgG

<400> SEQUENCE: 14

```
Arg Gly Arg Lys Arg Arg Ser
1               5
```

<210> SEQ ID NO 15
<211> LENGTH: 22
<212> TYPE: PRT
<213> ORGANISM: Artificial Sequence
<220> FEATURE:

<223> OTHER INFORMATION: GSG Linker and P2A Peptide of VRC01 IgG

<400> SEQUENCE: 15

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 16
<211> LENGTH: 104
<212> TYPE: PRT
<213> ORGANISM: Artificial Sequence
<220> FEATURE:
<223> OTHER INFORMATION: Variable Light Region (VL) of VRC01 IgG

<400> SEQUENCE: 16

```
Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100
```

<210> SEQ ID NO 17
<211> LENGTH: 106
<212> TYPE: PRT
<213> ORGANISM: Artificial Sequence
<220> FEATURE:
<223> OTHER INFORMATION: Constant Light Region (CL, kappa) of VRC01 IgG

<400> SEQUENCE: 17

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Arg Ser Pro
                85                  90                  95

Val Thr Lys Ser Phe Asn Arg Gly Glu Cys
            100                 105
```

<210> SEQ ID NO 18
<211> LENGTH: 19
<212> TYPE: PRT
<213> ORGANISM: Artificial Sequence
<220> FEATURE:
<223> OTHER INFORMATION: Human IgG Heavy Chain Signal Peptide of HIV-1

Env-PG9 Ig

<400> SEQUENCE: 18

```
Met Asp Trp Thr Trp Arg Ile Leu Phe Leu Val Ala Ala Ala Thr Gly
1               5                   10                  15

Thr His Ala


<210> SEQ ID NO 19
<211> LENGTH: 154
<212> TYPE: PRT
<213> ORGANISM: Artificial Sequence
<220> FEATURE:
<223> OTHER INFORMATION: Variable Heavy Region of HIV-1 Env-PG9 Ig

<400> SEQUENCE: 19

Glu Phe Gly Leu Ser Trp Val Phe Leu Val Ala Phe Leu Arg Gly Val
1               5                   10                  15

Gln Cys Gln Arg Leu Val Glu Ser Gly Gly Gly Val Val Gln Pro Gly
            20                  25                  30

Ser Ser Leu Arg Leu Ser Cys Ala Ala Ser Gly Phe Asp Phe Ser Arg
        35                  40                  45

Gln Gly Met His Trp Val Arg Gln Ala Pro Gly Gln Gly Leu Glu Trp
    50                  55                  60

Val Ala Phe Ile Lys Tyr Asp Gly Ser Glu Lys Tyr His Ala Asp Ser
65                  70                  75                  80

Val Trp Gly Arg Leu Ser Ile Ser Arg Asp Asn Ser Lys Asp Thr Leu
                85                  90                  95

Tyr Leu Gln Met Asn Ser Leu Arg Val Glu Asp Thr Ala Thr Tyr Phe
            100                 105                 110

Cys Val Arg Glu Ala Gly Gly Pro Asp Tyr Arg Asn Gly Tyr Asn Tyr
        115                 120                 125

Tyr Asp Phe Tyr Asp Gly Tyr Tyr Asn Tyr His Tyr Met Asp Val Trp
    130                 135                 140

Gly Lys Gly Thr Thr Val Thr Val Ser Ser
145                 150


<210> SEQ ID NO 20
<211> LENGTH: 98
<212> TYPE: PRT
<213> ORGANISM: Artificial Sequence
<220> FEATURE:
<223> OTHER INFORMATION: Constant Heavy region 1 (CH1) of HIV-1 Env-PG9
      Ig

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val
```

-continued

<210> SEQ ID NO 21
<211> LENGTH: 15
<212> TYPE: PRT
<213> ORGANISM: Artificial Sequence
<220> FEATURE:
<223> OTHER INFORMATION: Hinge Region of HIV-1 Env-PG9 Ig

<400> SEQUENCE: 21

Glu Pro Lys Ser Cys Asp Lys Thr His Thr Cys Pro Pro Cys Pro
1 5 10 15

<210> SEQ ID NO 22
<211> LENGTH: 110
<212> TYPE: PRT
<213> ORGANISM: Artificial Sequence
<220> FEATURE:
<223> OTHER INFORMATION: Constant Heavy Region 2 (CH2) of HIV-1 Env-PG9 Ig

<400> SEQUENCE: 22

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys
100 105 110

<210> SEQ ID NO 23
<211> LENGTH: 107
<212> TYPE: PRT
<213> ORGANISM: Artificial Sequence
<220> FEATURE:
<223> OTHER INFORMATION: Constant Heavy Region 3 (CH3) of HIV-1 Env-PG9 Ig

<400> SEQUENCE: 23

Gly Gln Pro Arg Glu Pro Gln Val Tyr Thr Leu Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly Lys
100 105

<210> SEQ ID NO 24
<211> LENGTH: 7
<212> TYPE: PRT
<213> ORGANISM: Artificial Sequence
<220> FEATURE:
<223> OTHER INFORMATION: Furin Cleavage Site of HIV-1 Env-PG9 Ig

<400> SEQUENCE: 24

```
Arg Gly Arg Lys Arg Arg Ser
1               5
```

<210> SEQ ID NO 25
<211> LENGTH: 22
<212> TYPE: PRT
<213> ORGANISM: Artificial Sequence
<220> FEATURE:
<223> OTHER INFORMATION: GSG Linker and P2A Peptide of HIV-1 Env-PG9 Ig

<400> SEQUENCE: 25

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 26
<211> LENGTH: 20
<212> TYPE: PRT
<213> ORGANISM: Artificial Sequence
<220> FEATURE:
<223> OTHER INFORMATION: Human Lamba Light Chain Signal Peptide of HIV-1
      Env-PG9 Ig

<400> SEQUENCE: 26

```
Met Ala Trp Thr Pro Leu Phe Leu Phe Leu Leu Thr Cys Cys Pro Gly
1               5                   10                  15

Gly Ser Asn Ser
            20
```

<210> SEQ ID NO 27
<211> LENGTH: 110
<212> TYPE: PRT
<213> ORGANISM: Artificial Sequence
<220> FEATURE:
<223> OTHER INFORMATION: Variable Light Region (VL) of HIV-1 Env-PG9 Ig

<400> SEQUENCE: 27

```
Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
        35                  40                  45

Val Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
            100                 105                 110
```

<210> SEQ ID NO 28
<211> LENGTH: 106

<212> TYPE: PRT
<213> ORGANISM: Artificial Sequence
<220> FEATURE:
<223> OTHER INFORMATION: Constant Light Region (CL, lamba) of HIV-1
Env-PG9 Ig

<400> SEQUENCE: 28

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 29
<211> LENGTH: 19
<212> TYPE: PRT
<213> ORGANISM: Artificial Sequence
<220> FEATURE:
<223> OTHER INFORMATION: Human IgG Heavy Chain Signal Peptide of HIV-1
Env-4E10 Ig

<400> SEQUENCE: 29

```
Met Asp Trp Thr Trp Arg Ile Leu Phe Leu Val Ala Ala Ala Thr Gly
1               5                   10                  15

Thr His Ala
```

<210> SEQ ID NO 30
<211> LENGTH: 127
<212> TYPE: PRT
<213> ORGANISM: Artificial Sequence
<220> FEATURE:
<223> OTHER INFORMATION: Variable Heavy Region of HIV-1 Env-4E10 Ig

<400> SEQUENCE: 30

```
Gln Val Gln Leu Val Gln Ser Gly Ala Glu Val Lys Arg Pro Gly Ser
1               5                   10                  15

Ser Val Thr Val Ser Cys Lys Ala Ser Gly Gly Ser Phe Ser Thr Tyr
            20                  25                  30

Ala Leu Ser Trp Val Arg Gln Ala Pro Gly Arg Gly Leu Glu Trp Met
        35                  40                  45

Gly Gly Val Ile Pro Leu Leu Thr Ile Thr Asn Tyr Ala Pro Arg Phe
    50                  55                  60

Gln Gly Arg Ile Thr Ile Thr Ala Asp Arg Ser Thr Ser Thr Ala Tyr
65                  70                  75                  80

Leu Glu Leu Asn Ser Leu Arg Pro Glu Asp Thr Ala Val Tyr Tyr Cys
                85                  90                  95

Ala Arg Glu Gly Thr Thr Gly Trp Gly Trp Leu Gly Lys Pro Ile Gly
            100                 105                 110

Ala Phe Ala His Trp Gly Gln Gly Thr Leu Val Thr Val Ser Ser
        115                 120                 125
```

<210> SEQ ID NO 31
<211> LENGTH: 98
<212> TYPE: PRT
<213> ORGANISM: Artificial Sequence
<220> FEATURE:
<223> OTHER INFORMATION: Constant Heavy region 1 (CH1) of HIV-1 Env-4E10 Ig

<400> SEQUENCE: 31

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 32
<211> LENGTH: 15
<212> TYPE: PRT
<213> ORGANISM: Artificial Sequence
<220> FEATURE:
<223> OTHER INFORMATION: Hinge Region of HIV-1 Env-4E10 Ig

<400> SEQUENCE: 32

```
Glu Pro Lys Ser Cys Asp Lys Thr His Thr Cys Pro Pro Cys Pro
1               5                   10                  15
```

<210> SEQ ID NO 33
<211> LENGTH: 110
<212> TYPE: PRT
<213> ORGANISM: Artificial Sequence
<220> FEATURE:
<223> OTHER INFORMATION: Constant Heavy Region 2 (CH2) of HIV-1 Env-4E10 Ig

<400> SEQUENCE: 33

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 34
<211> LENGTH: 107

<212> TYPE: PRT
<213> ORGANISM: Artificial Sequence
<220> FEATURE:
<223> OTHER INFORMATION: Constant Heavy Region 3 (CH3) of HIV-1 Env-4E10 Ig

<400> SEQUENCE: 34

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 35
<211> LENGTH: 7
<212> TYPE: PRT
<213> ORGANISM: Artificial Sequence
<220> FEATURE:
<223> OTHER INFORMATION: Furin Cleavage Site of HIV-1 Env-4E10 Ig

<400> SEQUENCE: 35

```
Arg Gly Arg Lys Arg Arg Ser
1               5
```

<210> SEQ ID NO 36
<211> LENGTH: 22
<212> TYPE: PRT
<213> ORGANISM: Artificial Sequence
<220> FEATURE:
<223> OTHER INFORMATION: GSG Linker and P2A Peptide of HIV-1 Env-4E10 Ig

<400> SEQUENCE: 36

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 37
<211> LENGTH: 20
<212> TYPE: PRT
<213> ORGANISM: Artificial Sequence
<220> FEATURE:
<223> OTHER INFORMATION: Human Kappa Light Chain Signal Peptide of HIV-1 Env-4E10 Ig

<400> SEQUENCE: 37

```
Met Val Leu Gln Thr Gln Val Phe Ile Ser Leu Leu Leu Trp Ile Ser
1               5                   10                  15

Gly Ala Tyr Gly
            20
```

<210> SEQ ID NO 38
<211> LENGTH: 106
<212> TYPE: PRT

<213> ORGANISM: Artificial Sequence
<220> FEATURE:
<223> OTHER INFORMATION: Variable Light Region (VL) of HIV-1 Env-4E10 Ig

<400> SEQUENCE: 38

Glu Ile Val Leu Thr Gln Ser Pro Gly Thr Gln Ser Leu Ser Pro Gly
1 5 10 15

Glu Arg Ala Thr Leu Ser Cys Arg Ala Ser Gln Ser Val Gly Asn Asn
20 25 30

Lys Leu Ala Trp Tyr Gln Gln Arg Pro Gly Gln Ala Pro Arg Leu Leu
35 40 45

Ile Tyr Gly Ala Ser Ser Arg Pro Ser Gly Val Ala Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Gln Ser Leu
85 90 95

Ser Thr Phe Gly Gln Gly Thr Lys Val Glu
100 105

<210> SEQ ID NO 39
<211> LENGTH: 107
<212> TYPE: PRT
<213> ORGANISM: Artificial Sequence
<220> FEATURE:
<223> OTHER INFORMATION: Constant Light Region (CL, kappa) of HIV-1 Env-4E10 Ig

<400> SEQUENCE: 39

Lys Arg Thr Val Ala Ala Pro Ser Val Phe Ile Phe Pro Pro Ser Asp
1 5 10 15

Glu Gln Leu Lys Ser Gly Thr Ala Ser Val Val Cys Leu Leu Asn Asn
20 25 30

Phe Tyr Pro Arg Glu Ala Lys Val Gln Trp Lys Val Asp Asn Ala Leu
35 40 45

Gln Ser Gly Asn Ser Gln Glu Ser Val Thr Glu Gln Asp Ser Lys Asp
50 55 60

Ser Thr Tyr Ser Leu Ser Ser Thr Leu Thr Leu Ser Lys Ala Asp Tyr
65 70 75 80

Glu Lys His Lys Val Tyr Ala Cys Glu Val Thr His Gln Gly Leu Ser
85 90 95

Ser Pro Val Thr Lys Ser Phe Asn Arg Gly Glu
100 105

<210> SEQ ID NO 40
<211> LENGTH: 744
<212> TYPE: DNA
<213> ORGANISM: Artificial Sequence
<220> FEATURE:
<223> OTHER INFORMATION: Nucleic Acid Sequence Encoding the VH-CH1 of anti-Her-2 Fab

<400> SEQUENCE: 40
ggatccgcca ccatggactg gacatggatt ctgtttctgg tcgccgccgc tacaagagtg 60
cattccgaag tgcagctggt cgagagtgga gggggactgg tgcagcccgg cggatctctg 120
cgactgagtt gcgccgcttc aggcttcacc tttacagact acaccatgga ttgggtgaga 180
caggcacctg gcaagggact ggagtgggtg gctgatgtca acccaaatag tgggggctca 240
atctacaacc agaggttcaa gggcaggttc accctgagcg tggacaggtc caaaaacact 300

```
ctgtatctgc agatgaattc tctgcgggct gaagataccg cagtctacta ttgcgcccgc    360

aatctgggcc caagcttcta ctttgactat tgggggcagg gcacactggt gactgtcagc    420

tccgcttcta caaagggacc aagcgtgttc ccactggcac cctctagtaa atccacctct    480

ggagggacag cagccctggg ctgtctggtg aaagactatt tccccgagcc tgtgactgtc    540

agctggaact ccggagcact gactagcgga gtgcacacct ttccagccgt cctgcagtca    600

agcggcctgt actccctgtc ctctgtggtc acagtgccta gttcaagcct gggaactcag    660

acctatattt gtaatgtgaa ccataaacca agcaatacaa aggtggacaa gaaggtggaa    720

ccaaaatcct gctgataact cgag                                           744
```

```
<210> SEQ ID NO 41
<211> LENGTH: 240
<212> TYPE: PRT
<213> ORGANISM: Artificial Sequence
<220> FEATURE:
<223> OTHER INFORMATION: Amino Acid Sequence of the VH-CH1 of anti-Her-2
      Fab

<400> SEQUENCE: 41

Met Asp Trp Thr Trp Ile Leu Phe Leu Val Ala Ala Ala Thr Arg Val
1               5                   10                  15

His Ser Glu Val Gln Leu Val Glu Ser Gly Gly Gly Leu Val Gln Pro
            20                  25                  30

Gly Gly Ser Leu Arg Leu Ser Cys Ala Ala Ser Gly Phe Thr Phe Thr
        35                  40                  45

Asp Tyr Thr Met Asp Trp Val Arg Gln Ala Pro Gly Lys Gly Leu Glu
    50                  55                  60

Trp Val Ala Asp Val Asn Pro Asn Ser Gly Gly Ser Ile Tyr Asn Gln
65                  70                  75                  80

Arg Phe Lys Gly Arg Phe Thr Leu Ser Val Asp Arg Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asn Leu Gly Pro Ser Phe Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240


<210> SEQ ID NO 42
<211> LENGTH: 720
<212> TYPE: DNA
<213> ORGANISM: Artificial Sequence
<220> FEATURE:
```

<223> OTHER INFORMATION: Nucleic Acid Sequence Encoding the VL-CL of anti-Her-2 Fab

<400> SEQUENCE: 42

```
ggatccgcca ccatggattg gacttggatt ctgttcctgg tcgccgccgc tacccgcgtg     60
cattccgata ttcagatgac tcagagcccc tcctcactgt cagccagcgt gggcgaccga    120
gtcaccatca catgcaaagc ttctcaggat gtgagtattg ggtcgcatg gtaccagcag     180
aagccaggca aagcacccaa gctgctgatc tattccgcct cttacaggta tacaggagtg    240
cccagcagat tcagtggctc aggaagcggg actgacttta ctctgaccat cagctccctg    300
cagcctgagg atttcgctac ctactattgc cagcagtact atatctaccc atataccttt    360
ggccagggaa caaaagtgga gatcaagcgg accgtggccg ctccctccgt cttcattttt    420
ccccccttctg acgaacagct gaagagcgga acagcaagcg tggtctgtct gctgaacaat    480
ttctaccctc gcgaggccaa agtgcagtgg aaggtcgata acgctctgca gtccgggaat    540
tctcaggaga gtgtgactga acaggactca aaagatagca cctattccct gtctagtaca    600
ctgactctga gcaaggcaga ctacgaaaag cacaaagtgt atgcctgtga ggtcacccac    660
caggggctgt caagtcccgt caccaagtcc ttcaatagag gcgaatgctg ataactcgag    720
```

<210> SEQ ID NO 43
<211> LENGTH: 232
<212> TYPE: PRT
<213> ORGANISM: Artificial Sequence
<220> FEATURE:
<223> OTHER INFORMATION: Amino Acid Sequence of the VL-CL of anti-Her-2 Fab

<400> SEQUENCE: 43

```
Met Asp Trp Thr Trp Ile Leu Phe Leu Val Ala Ala Ala Thr Arg Val
1               5                   10                  15

His Ser Asp Ile Gln Met Thr Gln Ser Pro Ser Ser Leu Ser Ala Ser
            20                  25                  30

Val Gly Asp Arg Val Thr Ile Thr Cys Lys Ala Ser Gln Asp Val Ser
        35                  40                  45

Ile Gly Val Ala Trp Tyr Gln Gln Lys Pro Gly Lys Ala Pro Lys Leu
    50                  55                  60

Leu Ile Tyr Ser Ala Ser Tyr Arg Tyr Thr Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys Gln Gln Tyr Tyr Ile Tyr
            100                 105                 110

Pro Tyr Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205
```

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 44
<211> LENGTH: 2241
<212> TYPE: DNA
<213> ORGANISM: Artificial Sequence
<220> FEATURE:
<223> OTHER INFORMATION: Nucleic Acid Sequence Encoding anti-DENV Human IgG

<400> SEQUENCE: 44
ggatccgcca ccatggactg gacttggagg attctgtttc tggtcgccgc cgctactggg 60
actcacgctc aggcacatct ggtcgaatct ggaggaggag tggtccagcc tggccgatcc 120
ctgcgactgt cttgcgcagc tagcgccttc aacttcagca caaacgcaat gcactgggtg 180
cgacaggcac caggcaaggg actggagtgg gtcgctgtga tctcatacga cggaagccat 240
aagtactatg cagattctgt gaaaggccgg ttcaccattt ccagggacaa ttctaagaac 300
accctgtatc tgcagatgaa tagcctgcgc gcagccgata ccgcagtgta ctattgcgca 360
actgtcggcg tgctgacctg gccagtgaac gccgaatact ttcaccattg gggacagggc 420
agtctggtct cagtgagctc cgcaagtact aagggaccat cagtgttccc actggcaccc 480
tctagtaaat ctactagtgg cgggaccgct gcactgggat gtctggtgaa ggactatttc 540
cccgagcctg tcaccgtgag ctggaattcc ggagccctga caagcggcgt ccacactttt 600
cccgctgtgc tgcagtcaag cggactgtac tccctgtcct ctgtggtcac tgtgcctagt 660
tcaagcctgg gcactcagac ctatatctgc aatgtgaacc acaagccctc taacaccaaa 720
gtcgacaaga aagtggaacc taagagctgt gataaaacac atacttgccc accttgtcca 780
gcaccagagc tgctgggagg accaagcgtg ttcctgtttc cacccaagcc taaagacaca 840
ctgatgatta gccggacacc tgaagtcact tgcgtggtcg tggacgtgtc ccacgaggac 900
cccgaagtca agtttaattg gtacgtggat ggcgtcgagg tgcataacgc caagaccaaa 960
ccccgggagg aacagtacaa tagcacatat agagtcgtgt ccgtcctgac tgtgctgcat 1020
caggattggc tgaatgggaa ggagtataag tgcaaagtgt ctaacaaggc tctgcctgca 1080
ccaatcgaga aaaccattag caaggctaaa ggccagccta gggaaccaca ggtgtacaca 1140
ctgcctccaa gtcgcgacga gctgaccaag aatcaggtct ccctgacatg tctggtgaaa 1200
ggcttctatc catcagatat cgccgtggag tgggaaagca acgggcagcc cgaaaacaat 1260
tacaagacca caccccctgt gctggactct gatggcagtt tctttctgta ttctaagctg 1320
accgtggaca aaagtagatg gcagcagggg aatgtctttt catgtagcgt gatgcacgag 1380
gccctgcaca accattacac acagaagtcc ctgtctctga gtcccggaaa gaggggccgc 1440
aaacggagat cagggagcgg agctactaat ttcagcctgc tgaaacaggc aggggatgtg 1500
gaggaaaacc ccggacctat ggcttggacc ccactgttcc tgtttctgct gacatgctgt 1560
cccgggggca gcaattctca gagtgtcctg acacagccac catcagtgag cggagcacca 1620
ggacagaggg tgaccatctc ctgcacaggc agcagcagca acattggcgc cgggtacgac 1680
gtgcattggt atcagcagct gcccggcacc gctcctaagc tgctgatctg tggcaacaat 1740
aaccgcccat ctggggtgcc cgatcgattc tccggctcta aaagtgggac ttcagccagc 1800
ctggctatta ccggcctgca ggccgaggac gaagctgatt actattgcca gagctacgac 1860

```
tcaagcctga ccggagtcgt gttcggagga ggaaccaagc tgacagtcct gggacagcct   1920

aaagccgctc caagcgtgac actgtttcct ccatcctctg aggaactgca ggcaaacaag   1980

gccaccctgg tgtgcctgat ttccgacttc taccccgggg cagtcactgt ggcttggaag   2040

gcagatagtt cacctgtcaa agccggagtg gagactacca caccatcaaa gcagagcaat   2100

aacaaatacg cagccagctc ctatctgtcc ctgacccctg agcagtggaa gtctcacaaa   2160

tcctattctt gccaggtcac tcacgaagga agcactgtgg agaaaactgt cgcaccaacc   2220

gaatgtagtt gataactcga g                                              2241


<210> SEQ ID NO 45
<211> LENGTH: 739
<212> TYPE: PRT
<213> ORGANISM: Artificial Sequence
<220> FEATURE:
<223> OTHER INFORMATION: Amino Acid Sequence of anti-DENV Human IgG

<400> SEQUENCE: 45

Met Asp Trp Thr Trp Arg Ile Leu Phe Leu Val Ala Ala Ala Thr Gly
1               5                   10                  15

Thr His Ala Gln Ala His Leu Val Glu Ser Gly Gly Gly Val Val Gln
            20                  25                  30

Pro Gly Arg Ser Leu Arg Leu Ser Cys Ala Ala Ser Ala Phe Asn Phe
        35                  40                  45

Ser Thr Asn Ala Met His Trp Val Arg Gln Ala Pro Gly Lys Gly Leu
    50                  55                  60

Glu Trp Val Ala Val Ile Ser Tyr Asp Gly Ser His Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Ala Asp Thr Ala Val
            100                 105                 110

Tyr Tyr Cys Ala Thr Val Gly Val Leu Thr Trp Pro Val Asn Ala Glu
        115                 120                 125

Tyr Phe His His Trp Gly Gln Gly Ser Leu Val Ser Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
```

-continued

```
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Ala Trp Thr Pro Leu Phe Leu Phe Leu
            500                 505                 510

Leu Thr Cys Cys Pro Gly Gly Ser Asn Ser Gln Ser Val Leu Thr Gln
        515                 520                 525

Pro Pro Ser Val Ser Gly Ala Pro Gly Gln Arg Val Thr Ile Ser Cys
    530                 535                 540

Thr Gly Ser Ser Ser Asn Ile Gly Ala Gly Tyr Asp Val His Trp Tyr
545                 550                 555                 560

Gln Gln Leu Pro Gly Thr Ala Pro Lys Leu Leu Ile Cys Gly Asn Asn
                565                 570                 575

Asn Arg Pro Ser Gly Val Pro Asp Arg Phe Ser Gly Ser Lys Ser Gly
            580                 585                 590

Thr Ser Ala Ser Leu Ala Ile Thr Gly Leu Gln Ala Glu Asp Glu Ala
        595                 600                 605

Asp Tyr Tyr Cys Gln Ser Tyr Asp Ser Ser Leu Thr Gly Val Val Phe
    610                 615                 620

Gly Gly Gly Thr Lys Leu Thr Val Leu Gly Gln Pro Lys Ala Ala Pro
625                 630                 635                 640

Ser Val Thr Leu Phe Pro Pro Ser Ser Glu Glu Leu Gln Ala Asn Lys
                645                 650                 655

Ala Thr Leu Val Cys Leu Ile Ser Asp Phe Tyr Pro Gly Ala Val Thr
            660                 665                 670

Val Ala Trp Lys Ala Asp Ser Ser Pro Val Lys Ala Gly Val Glu Thr
        675                 680                 685

Thr Thr Pro Ser Lys Gln Ser Asn Asn Lys Tyr Ala Ala Ser Ser Tyr
    690                 695                 700

Leu Ser Leu Thr Pro Glu Gln Trp Lys Ser His Lys Ser Tyr Ser Cys
705                 710                 715                 720
```

```
Gln Val Thr His Glu Gly Ser Thr Val Glu Lys Thr Val Ala Pro Thr
                725                 730                 735

Glu Cys Ser
```

<210> SEQ ID NO 46
<211> LENGTH: 265
<212> TYPE: PRT
<213> ORGANISM: Artificial Sequence
<220> FEATURE:
<223> OTHER INFORMATION: IgG Heavy Chain

<400> SEQUENCE: 46

```
Met Glu Thr Asp Thr Leu Leu Leu Trp Val Leu Leu Leu Trp Val Pro
1               5                   10                  15

Gly Ser Thr Gly Asp Gly Ala Gln Val Gln Leu Val Gln Ser Gly Ala
            20                  25                  30

Val Ile Lys Thr Pro Gly Ser Ser Val Lys Ile Ser Cys Arg Ala Ser
        35                  40                  45

Gly Tyr Asn Phe Arg Asp Tyr Ser Ile His Trp Val Arg Leu Ile Pro
    50                  55                  60

Asp Lys Gly Phe Glu Trp Ile Gly Trp Ile Lys Pro Leu Trp Gly Ala
65                  70                  75                  80

Val Ser Tyr Ala Arg Gln Leu Gln Gly Arg Val Ser Met Thr Arg Gln
                85                  90                  95

Leu Ser Gln Asp Pro Asp Asp Pro Asp Trp Gly Val Ala Tyr Met Glu
            100                 105                 110

Phe Ser Gly Leu Thr Pro Ala Asp Thr Ala Glu Tyr Phe Cys Val Arg
        115                 120                 125

Arg Gly Ser Cys Asp Tyr Cys Gly Asp Phe Pro Trp Gln Tyr Trp Cys
    130                 135                 140

Gln Gly Thr Val Val Val Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
                245                 250                 255

Tyr Pro Tyr Asp Val Pro Asp Tyr Ala
            260                 265
```

<210> SEQ ID NO 47
<211> LENGTH: 243
<212> TYPE: PRT
<213> ORGANISM: Artificial Sequence
<220> FEATURE:
<223> OTHER INFORMATION: IgG Light Chain

<400> SEQUENCE: 47

```
Met Glu Thr Asp Thr Leu Leu Leu Trp Val Leu Leu Leu Trp Val Pro
1               5                   10                  15
```

Gly Ser Thr Gly Asp Gly Ala Gln Val Gln Ile Val Leu Thr Gln Ser
20 25 30

Pro Gly Ile Leu Ser Leu Ser Pro Gly Glu Thr Ala Thr Leu Phe Cys
35 40 45

Lys Ala Ser Gln Gly Gly Asn Ala Met Thr Trp Tyr Gln Lys Arg Arg
50 55 60

Gly Gln Val Pro Arg Leu Leu Ile Tyr Asp Thr Ser Arg Arg Ala Ser
65 70 75 80

Gly Val Pro Asp Arg Phe Val Gly Ser Gly Ser Gly Thr Asp Phe Phe
85 90 95

Leu Thr Ile Asn Lys Leu Asp Arg Glu Asp Phe Ala Val Tyr Tyr Cys
100 105 110

Gln Gln Phe Glu Phe Phe Gly Leu Gly Ser Glu Leu Glu Val His Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys Tyr Pro Tyr Asp Val Pro
225 230 235 240

Asp Tyr Ala

<210> SEQ ID NO 48
<211> LENGTH: 256
<212> TYPE: PRT
<213> ORGANISM: Artificial Sequence
<220> FEATURE:
<223> OTHER INFORMATION: Amino Acid Sequence of the Heavy Chain (VH-CH1) of HIV-1 Env Fab

<400> SEQUENCE: 48

Met Glu Thr Asp Thr Leu Leu Leu Trp Val Leu Leu Leu Trp Val Pro
1 5 10 15

Gly Ser Thr Gly Asp Gly Ala Gln Val Gln Leu Val Gln Ser Gly Gly
20 25 30

Gln Met Lys Lys Pro Gly Glu Ser Met Arg Ile Ser Cys Arg Ala Ser
35 40 45

Gly Tyr Glu Phe Ile Asp Cys Thr Leu Asn Trp Ile Arg Leu Ala Pro
50 55 60

Gly Lys Arg Pro Glu Trp Met Gly Trp Leu Lys Pro Arg Gly Gly Ala
65 70 75 80

Val Asn Tyr Ala Arg Pro Leu Gln Gly Arg Val Thr Met Thr Arg Asp
85 90 95

Val Tyr Ser Asp Thr Ala Phe Leu Glu Leu Arg Ser Leu Thr Val Asp
100 105 110

Asp Thr Ala Val Tyr Phe Cys Thr Arg Gly Lys Asn Cys Asp Tyr Asn
115 120 125

```
Trp Asp Phe Glu His Trp Gly Arg Gly Thr Pro Val Ile Val Ser Ser
    130                 135                 140

Pro Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Ala Glu Pro Lys Ser Cys Tyr Pro Tyr Asp Val Pro Asp Tyr Ala
                245                 250                 255


<210> SEQ ID NO 49
<211> LENGTH: 244
<212> TYPE: PRT
<213> ORGANISM: Artificial Sequence
<220> FEATURE:
<223> OTHER INFORMATION: Amino Acid Sequence of the Light Chain (VL-CL)
      of HIV-1 Env Fab

<400> SEQUENCE: 49

Met Glu Thr Asp Thr Leu Leu Leu Trp Val Leu Leu Leu Trp Val Pro
1               5                   10                  15

Gly Ser Thr Gly Asp Gly Ala Gln Val Gln Ile Val Leu Thr Gln Ser
            20                  25                  30

Pro Gly Thr Leu Ser Leu Ser Pro Gly Glu Thr Ala Ile Ile Ser Cys
        35                  40                  45

Arg Thr Ser Gln Tyr Gly Ser Leu Ala Trp Tyr Gln Gln Arg Pro Gly
    50                  55                  60

Gln Ala Pro Arg Leu Val Ile Tyr Ser Gly Ser Thr Arg Ala Ala Gly
65                  70                  75                  80

Ile Pro Asp Arg Phe Ser Gly Ser Arg Trp Gly Pro Asp Tyr Asn Leu
                85                  90                  95

Thr Ile Ser Asn Leu Glu Ser Gly Asp Phe Gly Val Tyr Tyr Cys Gln
            100                 105                 110

Gln Tyr Glu Phe Phe Gly Gln Gly Thr Lys Val Gln Val Asp Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Arg Ser
    210                 215                 220

Pro Val Thr Lys Ser Phe Asn Arg Gly Glu Cys Tyr Pro Tyr Asp Val
```

-continued 225 230 235 240

Pro Asp Tyr Ala

<210> SEQ ID NO 50
<211> LENGTH: 1536
<212> TYPE: DNA
<213> ORGANISM: Artificial Sequence
<220> FEATURE:
<223> OTHER INFORMATION: Nucleic Acid Sequence Encoding HIV-1 PG9 Fab

<400> SEQUENCE: 50
ggatccgcca ccatggcaag acccctgtgc accctgctgc tgctgatggc aaccctggcc 60
ggagccctgg cacagagcgc cctgacccag cccgcaagcg tctccggctc accaggccag 120
agcatcacta ttagttgcaa cgggactagc aacgacgtgg gaggctatga gagtgtcagc 180
tggtaccagc agcatcccgg aaaagcacca aaagtggtca tctacgatgt cagtaaaagg 240
ccaagtgggg tctcaaatag gttctcaggg agtaaatctg ggaatacagc atctctgacc 300
atctccggac tgggcgcaga agatgaaggc gactactatt gcaaaagcct gacctcaacc 360
agacggcgag tctttgggac aggcaccaag ctgacagtcc tgacagtcgc tgccccctcc 420
gtcttcattt ttccaccttc agatgagcag ctgaaatctg gcactgcatc tgtggtctgc 480
ctgctgaaca acttctatcc acgagaggcc aaggtgcagt ggaaagtgga taacgcactg 540
cagtccggca atagtcagga aagcgtgact gagcaggatt ccaaggacag tacctatagc 600
ctgtccagta cactgaccct gtccaaggct gactacgaaa aacataaggt gtatgcatgt 660
gaagtgactc accagggact gaggtcacca gtcactaagt cttttaacag gggagagtgc 720
ggcgggggag gatctggagg cggcggctct ggagggggag gctcaggggg cggaggaagc 780
ggcggaggag ggtccggagg aggaggcagt cagagactgg tcgaaagcgg gggaggagtg 840
gtgcagcctg ggtcctcact gagactgtca tgcgctgcca gtggctttga tttttcacga 900
cagggaatgc attgggtcag gcaggcaccc ggacagggcc tggaatgggt cgccttcatt 960
aagtacgacg gaagcgagaa gtaccatgcc gactcagtgt ggggaaggct gagcatctca 1020
agggacaact caaaggacac cctgtacctg cagatgaata gcctgagagt ggaagatacc 1080
gctacttatt tctgcgtgcg agaggccgga gggccagatt accggaacgg gtacaattac 1140
tatgatttct acgacggcta ctacaattac cattatatgg atgtctgggg caaaggaact 1200
acagtcaccg tgagctccgc aagtactaag ggaccttccg tgtttcctct ggctcccagt 1260
tccaaaagta catccggagg aacagccgct ctgggatgtc tggtcaagga ctattttccc 1320
gagcccgtga ctgtctcctg gaacagcggg gctctgacaa gcggggtgca cacctttcct 1380
gccgtgctgc agtccagtgg gctgtacagt ctgtctagtg tcgtcactgt gccaagctca 1440
agtctgggga cccagacata catttgtaat gtgaaccata aaccctcaaa caccaaagtg 1500
gacaagaaag tggaacctaa aagctgataa ctcgag 1536

<210> SEQ ID NO 51
<211> LENGTH: 504
<212> TYPE: PRT
<213> ORGANISM: Artificial Sequence
<220> FEATURE:
<223> OTHER INFORMATION: Amino Acid Sequence of HIV-1 PG9 Fab

<400> SEQUENCE: 51

Met Ala Arg Pro Leu Cys Thr Leu Leu Leu Leu Met Ala Thr Leu Ala
1 5 10 15

-continued

```
Gly Ala Leu Ala Gln Ser Ala Leu Thr Gln Pro Ala Ser Val Ser Gly
            20                  25                  30

Ser Pro Gly Gln Ser Ile Thr Ile Ser Cys Asn Gly Thr Ser Asn Asp
        35                  40                  45

Val Gly Gly Tyr Glu Ser Val Ser Trp Tyr Gln Gln His Pro Gly Lys
    50                  55                  60

Ala Pro Lys Val Val Ile Tyr Asp Val Ser Lys Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gly Ala Glu Asp Glu Gly Asp Tyr Tyr Cys Lys Ser
            100                 105                 110

Leu Thr Ser Thr Arg Arg Arg Val Phe Gly Thr Gly Thr Lys Leu Thr
        115                 120                 125

Val Leu Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Arg
    210                 215                 220

Ser Pro Val Thr Lys Ser Phe Asn Arg Gly Glu Cys Gly Gly Gly Gly
225                 230                 235                 240

Ser Gly Gly Gly Gly Ser Gly Gly Gly Gly Ser Gly Gly Gly Gly Ser
                245                 250                 255

Gly Gly Gly Gly Ser Gly Gly Gly Gly Ser Gln Arg Leu Val Glu Ser
            260                 265                 270

Gly Gly Gly Val Val Gln Pro Gly Ser Ser Leu Arg Leu Ser Cys Ala
        275                 280                 285

Ala Ser Gly Phe Asp Phe Ser Arg Gln Gly Met His Trp Val Arg Gln
    290                 295                 300

Ala Pro Gly Gln Gly Leu Glu Trp Val Ala Phe Ile Lys Tyr Asp Gly
305                 310                 315                 320

Ser Glu Lys Tyr His Ala Asp Ser Val Trp Gly Arg Leu Ser Ile Ser
                325                 330                 335

Arg Asp Asn Ser Lys Asp Thr Leu Tyr Leu Gln Met Asn Ser Leu Arg
            340                 345                 350

Val Glu Asp Thr Ala Thr Tyr Phe Cys Val Arg Glu Ala Gly Gly Pro
        355                 360                 365

Asp Tyr Arg Asn Gly Tyr Asn Tyr Tyr Asp Phe Tyr Asp Gly Tyr Tyr
    370                 375                 380

Asn Tyr His Tyr Met Asp Val Trp Gly Lys Gly Thr Thr Val Thr Val
385                 390                 395                 400

Ser Ser Ala Ser Thr Lys Gly Pro Ser Val Phe Pro Leu Ala Pro Ser
                405                 410                 415

Ser Lys Ser Thr Ser Gly Gly Thr Ala Ala Leu Gly Cys Leu Val Lys
            420                 425                 430

Asp Tyr Phe Pro Glu Pro Val Thr Val Ser Trp Asn Ser Gly Ala Leu
```

-continued

```
        435                 440                 445

Thr Ser Gly Val His Thr Phe Pro Ala Val Leu Gln Ser Ser Gly Leu
    450                 455                 460

Tyr Ser Leu Ser Ser Val Val Thr Val Pro Ser Ser Ser Leu Gly Thr
465                 470                 475                 480

Gln Thr Tyr Ile Cys Asn Val Asn His Lys Pro Ser Asn Thr Lys Val
                485                 490                 495

Asp Lys Lys Val Glu Pro Lys Ser
            500


<210> SEQ ID NO 52
<211> LENGTH: 1503
<212> TYPE: DNA
<213> ORGANISM: Artificial Sequence
<220> FEATURE:
<223> OTHER INFORMATION: Nucleic Acid Sequence Encoding HIV-1 4E10 Fab

<400> SEQUENCE: 52

ggatccgcca ccatggcaag acctctgtgc actctgctgc tgctgatggc tactctggcc     60

ggggctctgg ctgagattgt cctgacccag tcccctggca ctcagtcact gtcccccggc    120

gagcgcgcaa ctctgtcctg cagagcaagc cagtccgtcg ggaacaacaa gctggcatgg    180

taccagcagc gcccaggaca ggcacccagg ctgctgatct acggagcaag ctcccggcct    240

agcggagtcg ctgatagatt ctccggaagc ggctccggga ccgatttcac tctgaccatc    300

tccaggctgg aacctgagga ttttgccgtg tattactgtc agcagtacgg gcagagcctg    360

tcaactttcg gccagggaac taaagtcgaa aagagaaccg tggccgcacc aagcgtcttt    420

atttttcccc ctagcgatga acagctgaaa tccgggactg cttccgtggt ctgcctgctg    480

aataacttct atccaagaga ggcaaaggtg cagtggaaag tggacaacgc cctgcagagc    540

ggaaactcac aggaatctgt gacagagcag gactccaagg atagcacata cagtctgtcc    600

tcaactctga ccctgtccaa agctgactat gagaagcata aagtctacgc atgtgaggtg    660

acccaccagg gactgaggtc ccccgtcact aagtccttca atagaggcga gtgcgggggc    720

gggggcagtg gcggaggggg aagtgggggc ggagggagtg gcggcggcgg gagtggcggc    780

ggcggctcag gggcggcgg ctcccaggtc cagctggtcc agagcggagc cgaggtcaag     840

agaccaggct cttcagtcac cgtgagctgc aaagccagcg gaggctcctt tagcacttac    900

gccctgtcat gggtgcggca ggccccaggc cgaggcctgg agtggatggg cggcgtgatc    960

cccctgctga ccattactaa ctatgcccct agatttggag gccggatcac catcacagct   1020

gacagatcca catccacagc ttacctggag ctgaacagtc tgaggcccga ggacactgca   1080

gtctactact gtgcacgaga aggcaccact ggatgggggt ggctggggaa gcccatcggg   1140

gcttttgcac attggggcgg agggacactg gtgactgtga gctctgccag cactaaaggg   1200

cccagtgtct tccctctggc cccaagttcc aagagtacat caggggggcac cgccgcactg  1260

gggtgtctgg tgaaggatta cttcccagag cccgtgacag tcagttggaa cagcggcgct   1320

ctgaccagtg gggtgcacac tttcccagcc gtgctgcaga gttcagggct gtactccctg   1380

tcctcagtgg tgactgtgcc ctcaagcagt ctggggactc agacttacat ttgtaatgtg   1440

aaccataaac cctcaaatac taaagtggac aaaaaagtgg aaccaaagag ctgataactc   1500

gag                                                                 1503


<210> SEQ ID NO 53
<211> LENGTH: 493
```

<212> TYPE: PRT
<213> ORGANISM: Artificial Sequence
<220> FEATURE:
<223> OTHER INFORMATION: Amino Acid Sequence of HIV-1 4E10 Fab

<400> SEQUENCE: 53

```
Met Ala Arg Pro Leu Cys Thr Leu Leu Leu Leu Met Ala Thr Leu Ala
1               5                   10                  15

Gly Ala Leu Ala Glu Ile Val Leu Thr Gln Ser Pro Gly Thr Gln Ser
            20                  25                  30

Leu Ser Pro Gly Glu Arg Ala Thr Leu Ser Cys Arg Ala Ser Gln Ser
        35                  40                  45

Val Gly Asn Asn Lys Leu Ala Trp Tyr Gln Gln Arg Pro Gly Gln Ala
    50                  55                  60

Pro Arg Leu Leu Ile Tyr Gly Ala Ser Ser Arg Pro Ser Gly Val Ala
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Gln Ser Leu Ser Thr Phe Gly Gln Gly Thr Lys Val Glu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Arg Ser Pro
    210                 215                 220

Val Thr Lys Ser Phe Asn Arg Gly Glu Cys Gly Gly Gly Gly Ser Gly
225                 230                 235                 240

Gly Gly Gly Ser Gly Gly Gly Gly Ser Gly Gly Gly Gly Ser Gly Gly
                245                 250                 255

Gly Gly Ser Gly Gly Gly Gly Ser Gln Val Gln Leu Val Gln Ser Gly
            260                 265                 270

Ala Glu Val Lys Arg Pro Gly Ser Ser Val Thr Val Ser Cys Lys Ala
        275                 280                 285

Ser Gly Gly Ser Phe Ser Thr Tyr Ala Leu Ser Trp Val Arg Gln Ala
    290                 295                 300

Pro Gly Arg Gly Leu Glu Trp Met Gly Gly Val Ile Pro Leu Leu Thr
305                 310                 315                 320

Ile Thr Asn Tyr Ala Pro Arg Phe Gly Gly Arg Ile Thr Ile Thr Ala
                325                 330                 335

Asp Arg Ser Thr Ser Thr Ala Tyr Leu Glu Leu Asn Ser Leu Arg Pro
            340                 345                 350

Glu Asp Thr Ala Val Tyr Tyr Cys Ala Arg Glu Gly Thr Thr Gly Trp
        355                 360                 365

Gly Trp Leu Gly Lys Pro Ile Gly Ala Phe Ala His Trp Gly Gly Gly
    370                 375                 380
```

```
Thr Leu Val Thr Val Ser Ser Ala Ser Thr Lys Gly Pro Ser Val Phe
385                 390                 395                 400

Pro Leu Ala Pro Ser Ser Lys Ser Thr Ser Gly Gly Thr Ala Ala Leu
                405                 410                 415

Gly Cys Leu Val Lys Asp Tyr Phe Pro Glu Pro Val Thr Val Ser Trp
            420                 425                 430

Asn Ser Gly Ala Leu Thr Ser Gly Val His Thr Phe Pro Ala Val Leu
        435                 440                 445

Gln Ser Ser Gly Leu Tyr Ser Leu Ser Ser Val Val Thr Val Pro Ser
    450                 455                 460

Ser Ser Leu Gly Thr Gln Thr Tyr Ile Cys Asn Val Asn His Lys Pro
465                 470                 475                 480

Ser Asn Thr Lys Val Asp Lys Lys Val Glu Pro Lys Ser
                485                 490
```

<210> SEQ ID NO 54
<211> LENGTH: 1446
<212> TYPE: DNA
<213> ORGANISM: Artificial Sequence
<220> FEATURE:
<223> OTHER INFORMATION: Nucleic Acid Sequence Encoding the HIV-1 VRC01
IgG1 Heavy Chain (VH/CH1/Hinge/CH2/CH3)

<400> SEQUENCE: 54

```
ggatccgcca ccatggattg gacatggatt ctgttcctgg tcgccgccgc aactagagtg     60

cattcacagg tgcagctggt gcagtcaggc gggcagatga agaaacccgg cgagagtatg    120

cgaatctcat gccgggctag cgggtacgaa ttcatcgact gtaccctgaa ctggattaga    180

ctggcacctg ggaagaggcc agagtggatg ggatggctga aacctagagg cggggcagtg    240

aattacgcca gaccactgca gggcagggtc actatgaccc gcgacgtgta ttctgatacc    300

gcattcctgg agctgcgaag tctgacagtc gacgatactg ccgtgtactt ctgcacacgg    360

ggcaagaact gtgactataa ttgggatttt gaacactggg gcagggggac acctgtcatt    420

gtgagctccc caagtactaa gggaccctca gtgtttcccc tggcccctto tagtaaaagt    480

acctcaggag gcacagccgc tctgggatgc ctggtgaagg attacttccc tgagccagtc    540

accgtgagtt ggaactcagg cgccctgaca agcggggtcc atacttttcc agctgtgctg    600

cagtcaagcg gctgtactc cctgtcctct gtggtcacag tgcccagttc aagcctggga    660

acacagactt atatctgtaa cgtcaatcac aagcctagca atactaaagt ggacaagaaa    720

gccgagccta agagctgcga accaaagtcc tgtgataaaa cccatacatg ccctccctgt    780

ccagctcctg aactgctggg cggcccatcc gtgttcctgt ttccacccaa gcccaaagac    840

accctgatga ttagcaggac tcctgaggtc acctgcgtgg tcgtggacgt gtcccacgag    900

gaccccgaag tcaagtttaa ctggtacgtg gatggcgtcg aagtgcataa tgccaagaca    960

aaaccccggg aggaacagta caactctacc tatagagtcg tgagtgtcct gacagtgctg   1020

caccaggact ggctgaacgg gaaggagtat aagtgcaaag tgtctaataa ggccctgcca   1080

gctcccatcg agaaaacaat ttccaaggca aaaggccagc caagggaacc ccaggtgtac   1140

actctgcctc catcccgcga cgagctgact aagaaccagg tctctctgac ctgtctggtg   1200

aaaggattct atccaagcga tatcgccgtg gagtgggaat ccaatggcca gcccgagaac   1260

aattacaaga ccacaccccc tgtgctggac agcgatggct ccttctttct gtattcaaag   1320

ctgaccgtgg ataaaagccg ctggcagcag gggaacgtct ttagctgctc cgtgatgcac   1380

gaagctctgc acaatcatta cacccagaag tctctgagtc tgtcacctgg caagtgataa   1440
```

ctcgag 1446

<210> SEQ ID NO 55
<211> LENGTH: 474
<212> TYPE: PRT
<213> ORGANISM: Artificial Sequence
<220> FEATURE:
<223> OTHER INFORMATION: Amino Acid Sequence of the HIV-1 VRC01 IgG1
Heavy Chain (VH/CH1/CH2/CH3)

<400> SEQUENCE: 55

Met Asp Trp Thr Trp Ile Leu Phe Leu Val Ala Ala Ala Thr Arg Val
1 5 10 15

His Ser Gln Val Gln Leu Val Gln Ser Gly Gly Gln Met Lys Lys Pro
20 25 30

Gly Glu Ser Met Arg Ile Ser Cys Arg Ala Ser Gly Tyr Glu Phe Ile
35 40 45

Asp Cys Thr Leu Asn Trp Ile Arg Leu Ala Pro Gly Lys Arg Pro Glu
50 55 60

Trp Met Gly Trp Leu Lys Pro Arg Gly Gly Ala Val Asn Tyr Ala Arg
65 70 75 80

Pro Leu Gln Gly Arg Val Thr Met Thr Arg Asp Val Tyr Ser Asp Thr
85 90 95

Ala Phe Leu Glu Leu Arg Ser Leu Thr Val Asp Asp Thr Ala Val Tyr
100 105 110

Phe Cys Thr Arg Gly Lys Asn Cys Asp Tyr Asn Trp Asp Phe Glu His
115 120 125

Trp Gly Arg Gly Thr Pro Val Ile Val Ser Ser Pro Ser Thr Lys Gly
130 135 140

Pro Ser Val Phe Pro Leu Ala Pro Ser Ser Lys Ser Thr Ser Gly Gly
145 150 155 160

Thr Ala Ala Leu Gly Cys Leu Val Lys Asp Tyr Phe Pro Glu Pro Val
165 170 175

Thr Val Ser Trp Asn Ser Gly Ala Leu Thr Ser Gly Val His Thr Phe
180 185 190

Pro Ala Val Leu Gln Ser Ser Gly Leu Tyr Ser Leu Ser Ser Val Val
195 200 205

Thr Val Pro Ser Ser Ser Leu Gly Thr Gln Thr Tyr Ile Cys Asn Val
210 215 220

Asn His Lys Pro Ser Asn Thr Lys Val Asp Lys Lys Ala Glu Pro Lys
225 230 235 240

Ser Cys Glu Pro Lys Ser Cys Asp Lys Thr His Thr Cys Pro Pro Cys
245 250 255

Pro Ala Pro Glu Leu Leu Gly Gly Pro Ser Val Phe Leu Phe Pro Pro
260 265 270

Lys Pro Lys Asp Thr Leu Met Ile Ser Arg Thr Pro Glu Val Thr Cys
275 280 285

Val Val Val Asp Val Ser His Glu Asp Pro Glu Val Lys Phe Asn Trp
290 295 300

Tyr Val Asp Gly Val Glu Val His Asn Ala Lys Thr Lys Pro Arg Glu
305 310 315 320

Glu Gln Tyr Asn Ser Thr Tyr Arg Val Val Ser Val Leu Thr Val Leu
325 330 335

His Gln Asp Trp Leu Asn Gly Lys Glu Tyr Lys Cys Lys Val Ser Asn
340 345 350

```
Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 56
<211> LENGTH: 708
<212> TYPE: DNA
<213> ORGANISM: Artificial Sequence
<220> FEATURE:
<223> OTHER INFORMATION: Nucleic Acid Sequence Encoding the HIV-1 VRC01 IgG Light Chain (VL/CL)

<400> SEQUENCE: 56

```
ggatccgcca ccatggattg gacttggatt ctgttcctgg tggcagccgc taccagagtc      60

cattccgaaa ttgtgctgac ccagtctccc ggaacactgt ctctgagtcc tggcgagaca     120

gccatcattt cctgtaggac ttctcagtac gggagtctgg catggtatca gcagcgacca     180

ggacaggctc ctcgactggt catctactca ggaagcactc gggcagccgg cattcccgac     240

cgattctccg ggtctcggtg gggacctgat tacaacctga ccatctcaaa tctggaaagc     300

ggagactttg gcgtgtacta ttgccagcag tatgagttct ttgggcaggg aaccaaggtc     360

caggtggaca tcaaacgcac agtcgctgca ccaagcgtgt tcatctttcc accctcagat     420

gaacagctga agtccggcac cgcctctgtg gtgtgcctgc tgaacaattt ctacccccgg     480

gaggcaaagg tccagtggaa agtggacaac gccctgcagt ctggcaatag tcaggagtca     540

gtgactgaac aggacagcaa ggattccacc tattctctgt cctctactct gaccctgagc     600

aaagctgatt acgagaagca caaagtgtat gcatgtgagg tcacccacca gggactgcgg     660

tcacccgtca ccaagagctt caatcgcgga gagtgttgat aactcgag                  708
```

<210> SEQ ID NO 57
<211> LENGTH: 228
<212> TYPE: PRT
<213> ORGANISM: Artificial Sequence
<220> FEATURE:
<223> OTHER INFORMATION: Amino Acid Sequence of the HIV-1 VRC01 IgG Light Chain (VL/CL)

<400> SEQUENCE: 57

```
Met Asp Trp Thr Trp Ile Leu Phe Leu Val Ala Ala Ala Thr Arg Val
1               5                   10                  15

His Ser Glu Ile Val Leu Thr Gln Ser Pro Gly Thr Leu Ser Leu Ser
            20                  25                  30

Pro Gly Glu Thr Ala Ile Ile Ser Cys Arg Thr Ser Gln Tyr Gly Ser
        35                  40                  45
```

```
Leu Ala Trp Tyr Gln Gln Arg Pro Gly Gln Ala Pro Arg Leu Val Ile
    50                  55                  60

Tyr Ser Gly Ser Thr Arg Ala Ala Gly Ile Pro Asp Arg Phe Ser Gly
65                  70                  75                  80

Ser Arg Trp Gly Pro Asp Tyr Asn Leu Thr Ile Ser Asn Leu Glu Ser
                85                  90                  95

Gly Asp Phe Gly Val Tyr Tyr Cys Gln Gln Tyr Glu Phe Phe Gly Gln
            100                 105                 110

Gly Thr Lys Val Gln Val Asp Ile Lys Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Arg Ser Pro Val Thr Lys Ser Phe Asn
    210                 215                 220

Arg Gly Glu Cys
225


<210> SEQ ID NO 58
<211> LENGTH: 744
<212> TYPE: DNA
<213> ORGANISM: Artificial Sequence
<220> FEATURE:
<223> OTHER INFORMATION: Nucleic Acid Sequence Encoding the Heavy Chain
      (VH-CH1) of the CHIKV-Env-Fab

<400> SEQUENCE: 58

ggatccgcca ccatggattg gacatggagg attctgtttc tggtcgccgc cgctactgga     60

actcacgctc aggtgcagct ggtgcagtca gggtccgaac tgaagaaacc aggggcatct    120

gtgaaggtca gttgcaaagc ctcaggctac accctgacac ggtatgccat gacttgggtg    180

cgccaggctc ctggacaggg actggagtgg atgggctgga tcaacactta caccggaaat    240

ccaacttatg tgcaggggtt caccggccga ttcgtgtttt ctctggacac ttccgtctct    300

accgcctttc tgcacattac aagtctgaag gcagaggaca ctgccgtgta cttctgcgct    360

agggaaggcg gagcaagagg ctttgattat tggggccagg gaaccctggt gacagtcagc    420

tccgccagca caaagggacc ctccgtgttc ccactggctc cctctagtaa aagtacatca    480

gggggcactg ccgctctggg atgtctggtc aaagattact tccccgaacc tgtgaccgtc    540

agctggaact ccggagctct gaccagcggg gtgcatacat ttcccgcagt cctgcagtca    600

agcggactgt actccctgtc ctctgtggtc acagtgccta gttcaagcct ggggacacag    660

acttatatct gtaatgtgaa ccataagcca agcaacacca aagtggacaa aaaagtggaa    720

cctaagagct gctgataact cgag                                            744


<210> SEQ ID NO 59
<211> LENGTH: 240
<212> TYPE: PRT
<213> ORGANISM: Artificial Sequence
```

<220> FEATURE:
<223> OTHER INFORMATION: Amino Acid Sequence of the Heavy Chain (VH-CH1)
of the CHIKV-Env-Fab

<400> SEQUENCE: 59

Met Asp Trp Thr Trp Arg Ile Leu Phe Leu Val Ala Ala Ala Thr Gly
1 5 10 15

Thr His Ala Gln Val Gln Leu Val Gln Ser Gly Ser Glu Leu Lys Lys
20 25 30

Pro Gly Ala Ser Val Lys Val Ser Cys Lys Ala Ser Gly Tyr Thr Leu
35 40 45

Thr Arg Tyr Ala Met Thr Trp Val Arg Gln Ala Pro Gly Gln Gly Leu
50 55 60

Glu Trp Met Gly Trp Ile Asn Thr Tyr Thr Gly Asn Pro Thr Tyr Val
65 70 75 80

Gln Gly Phe Thr Gly Arg Phe Val Phe Ser Leu Asp Thr Ser Val Ser
85 90 95

Thr Ala Phe Leu His Ile Thr Ser Leu Lys Ala Glu Asp Thr Ala Val
100 105 110

Tyr Phe Cys Ala Arg Glu Gly Gly Ala Arg Gly Phe Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Ser Ser Lys Ser Thr Ser Gly Gly Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Ser Leu Gly Thr Gln Thr Tyr Ile Cys Asn Val Asn His
210 215 220

Lys Pro Ser Asn Thr Lys Val Asp Lys Lys Val Glu Pro Lys Ser Cys
225 230 235 240

<210> SEQ ID NO 60
<211> LENGTH: 738
<212> TYPE: DNA
<213> ORGANISM: Artificial Sequence
<220> FEATURE:
<223> OTHER INFORMATION: Nucleic Acid Sequence Encoding the Light Chain
(VL-CL) of the CHIKV-Env-Fab

<400> SEQUENCE: 60
ggatccgcca ccatggcatg gaccccactg ttcctgttcc tgctgacttg ttgtcctggc 60
gggagcaatt cacagagcgt cctgacccag cccccttctg tgtccggagc accaggacag 120
cgagtcacaa tctcttgcac tggaagctcc tctaacattg gggccagcca cgacgtgcat 180
tggtaccagc agctgccagg gaccgctccc acactgctga tctatgtgaa ctctaatagg 240
cctagtggcg tcccagatag attttcaggg agcaagtccg gcacctctgc tagtctggca 300
attacaggac tgcaggctga ggacgaagca gattactatt gccagagtta cgactcaaac 360
ctgtcaggca gcgcagtgtt cggaggagga actaagctga ccgtcctggg acagcccaaa 420
gccgctcctt ctgtgaccct gtttcccccct agttcagagg aactgcaggc caacaaggct 480
actctggtgt gtctgatctc cgacttctac cctggagcag tgaccgtcgc atggaaggcc 540

```
gatagctccc cagtgaaagc tggggtcgag accacaactc ccagcaagca gtccaacaac    600
aagtacgcag cctctagtta tctgtcactg acacctgaac agtggaagag ccacaaatcc    660
tattcttgcc aagtgactca tgagggcagt accgtggaaa agacagtcgc cccaactgag    720
tgttcctgat aactcgag                                                  738

<210> SEQ ID NO 61
<211> LENGTH: 238
<212> TYPE: PRT
<213> ORGANISM: Artificial Sequence
<220> FEATURE:
<223> OTHER INFORMATION: Amino Acid Sequence of the Light Chain (VL-CL)
      of the CHIKV-Env-Fab

<400> SEQUENCE: 61

Met Ala Trp Thr Pro Leu Phe Leu Phe Leu Leu Thr Cys Cys Pro Gly
1               5                   10                  15

Gly Ser Asn Ser Gln Ser Val Leu Thr Gln Pro Pro Ser Val Ser Gly
            20                  25                  30

Ala Pro Gly Gln Arg Val Thr Ile Ser Cys Thr Gly Ser Ser Ser Asn
        35                  40                  45

Ile Gly Ala Ser His Asp Val His Trp Tyr Gln Gln Leu Pro Gly Thr
    50                  55                  60

Ala Pro Thr Leu Leu Ile Tyr Val Asn Ser Asn Arg Pro Ser Gly Val
65                  70                  75                  80

Pro Asp Arg Phe Ser Gly Ser Lys Ser Gly Thr Ser Ala Ser Leu Ala
                85                  90                  95

Ile Thr Gly Leu Gln Ala Glu Asp Glu Ala Asp Tyr Tyr Cys Gln Ser
            100                 105                 110

Tyr Asp Ser Asn Leu Ser Gly Ser Ala Val Phe Gly Gly Gly Thr Lys
        115                 120                 125

Leu Thr Val Leu Gly Gln Pro Lys Ala Ala Pro Ser Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Ser Ser Pro Val Lys Ala Gly Val Glu Thr Thr Thr Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Lys Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 62
<211> LENGTH: 2238
<212> TYPE: DNA
<213> ORGANISM: Artificial Sequence
<220> FEATURE:
<223> OTHER INFORMATION: Nucleic Acid Sequence Encoding HIV-1 Env-4E10
      Ig

<400> SEQUENCE: 62
ggatccgcca ccatggattg gacatggagg attctgtttc tggtcgccgc cgctacagga     60
actcacgccc aggtgcagct ggtgcagtca ggagccgaag tgaagcgacc aggcagctcc    120
```

-continued

```
gtcactgtgt cctgcaaagc atctggcgga tcattcagca cctacgccct gagctgggtg    180
agacaggctc ctggacgagg actggaatgg atgggaggcg tcatcccact gctgacaatt    240
actaactacg ccccccgatt tcagggcagg atcaccatta cagcagaccg ctccacttct    300
accgcctatc tggagctgaa tagcctgaga ccagaagata ccgcagtgta ctattgcgcc    360
cgggagggaa ccacaggatg gggatggctg ggaaagccca tcggggcttt cgcacactgg    420
ggccagggaa ccctggtcac agtgtctagt gccagcacaa agggcccctc cgtgtttccc    480
ctggctcctt caagcaaaag tacttcagga gggaccgccg ctctgggatg tctggtgaag    540
gactacttcc ctgagccagt caccgtgtcc tggaactctg gcgctctgac ctccggagtg    600
catacatttc ccgcagtcct gcagtcctct gggctgtact ctctgagttc agtggtcact    660
gtgcctagct cctctctggg cacacagact tatatctgca acgtgaatca caagccctcc    720
aataccaaag tcgacaagaa agtggaacct aagtcttgtg ataaaaccca tacatgccca    780
ccttgtccag cacctgagct gctgggcgga ccttccgtgt tcctgtttcc acccaagcca    840
aaagacacac tgatgattag ccggacacct gaagtgactt gtgtggtcgt ggacgtcagc    900
cacgaggacc ccgaagtgaa gttcaactgg tacgtggatg gcgtcgaggt gcataatgcc    960
aagaccaaac ccagggagga acagtacaac tctacttata gggtcgtgag tgtcctgacc   1020
gtgctgcacc aggactggct gaacgggaag gagtataagt gcaaagtgtc caataaggcc   1080
ctgccagctc ccatcgagaa aacaatttct aaggctaaag gccagccacg cgaaccccag   1140
gtgtacactc tgcctcccag cagggacgag ctgaccaaga accaggtgag tctgacatgt   1200
ctggtcaaag gcttctatcc aagcgatatc gccgtggagt gggaatccaa tggacagccc   1260
gaaaacaatt acaagactac ccccccctgtg ctggacagtg atggatcatt ctttctgtat   1320
tccaagctga ccgtggacaa atctcgctgg cagcagggga acgtctttag ctgctccgtg   1380
atgcacgagg ccctgcacaa tcattacaca cagaagtctc tgagtctgtc accaggcaag   1440
cggggacgca aaaggagaag cgggtccggc gctactaact tcagcctgct gaaacaggca   1500
ggggatgtgg aggaaaatcc tggcccaatg gtcctgcaga cccaggtgtt tatctcactg   1560
ctgctgtgga ttagcggggc ttatggcgaa atcgtgctga ctcagagccc cggaacccag   1620
tctctgagtc ctggggagcg cgctacactg agctgtcgag catcacagag cgtggggaac   1680
aataagctgg catggtacca gcagaggcct ggccaggctc caagactgct gatctatggc   1740
gcaagttcac ggcctagcgg agtggcagac cgcttctccg gatctgggag tggcaccgat   1800
tttactctga ccattagcag gctggagcca gaagacttcg ctgtgtacta ttgccagcag   1860
tacggccagt cactgagcac atttggacag gggactaagg tcgaaaaaag aaccgtggca   1920
gccccaagtg tcttcatttt tccaccctca gacgagcagc tgaagagtgg aacagcctca   1980
gtcgtgtgtc tgctgaacaa tttctacccc agggaggcca aggtccagtg gaaagtggat   2040
aacgctctgc agagcggcaa ttcccaggag tctgtgacag aacaggacag taaggattca   2100
acttatagcc tgagctccac actgactctg tccaaagcag attacgagaa gcacaaagtg   2160
tatgcctgcg aagtcaccca tcagggactg tctagtcctg tgacaaagtc ttttaacaga   2220
ggggagtgat aactcgag                                                 2238
```

<210> SEQ ID NO 63
<211> LENGTH: 2328
<212> TYPE: DNA
<213> ORGANISM: Artificial Sequence
<220> FEATURE:

-continued

<223> OTHER INFORMATION: Nucleic Acid Sequence Encoding HIV-1 Env-PG9 Ig

<400> SEQUENCE: 63

```
ggatccgcca ccatggactg gacttggagg attctgtttc tggtcgccgc cgcaactgga     60
actcacgctg aatttggact gtcatgggtc tttctggtgg cctttctgcg aggggtccag    120
tgccagaggc tggtggagtc cggaggagga gtggtccagc caggcagctc cctgcgactg    180
agttgtgccg cttcagggtt cgacttttct agacagggca tgcactgggt gcggcaggca    240
ccaggacagg gactggagtg ggtggctttc atcaagtacg acggaagtga aaaatatcat    300
gccgattcag tgtgggggcg gctgtcaatt agccgcgaca actccaagga taccctgtac    360
ctgcagatga attctctgag ggtcgaggac acagctactt atttctgcgt gagggaagca    420
ggcggacctg attacagaaa cggtataat tactatgact tttacgatgg ctactataac    480
taccactata tggacgtgtg gggcaaggga accacagtca cagtgtctag tgcatcaact    540
aaaggcccaa gcgtgtttcc cctggcccct tcaagcaagt ccacttctgg aggaaccgca    600
gcactgggat gtctggtgaa ggattacttc cctgagccag tcaccgtgag ttggaactca    660
ggcgccctga ctagcggagt ccataccttt cctgctgtgc tgcagtcctc tgggctgtac    720
agcctgagtt cagtggtcac agtgccaagc tcctctctgg gcacccagac atatatctgc    780
aacgtgaatc acaagcctag caatactaag gtcgacaaaa gagtggaacc aaagagctgt    840
gataaaactc atacctgccc accttgtcca gcacctgagc tgctgggagg gccttccgtg    900
ttcctgtttc cacccaagcc aaaagacacc ctgatgatta gccggacacc agaagtcact    960
tgcgtggtcg tggacgtgag ccacgaggac cccgaagtca agtttaactg gtacgtggat   1020
ggcgtcgagg tgcataatgc taagacaaaa ccacgggagg aacagtacaa ctccacatat   1080
cgcgtcgtgt ctgtcctgac tgtgctgcac caggactggc tgaacggcaa ggagtataag   1140
tgcaaagtgt ccaataaggc actgccagcc cccatcgaga aaaccatttc taaggccaaa   1200
ggccagccac gagaacccca ggtgtacaca ctgcctccaa gtagggacga gctgactaag   1260
aaccaggtct ctctgacctg tctggtgaaa ggcttctatc cctctgatat cgctgtggag   1320
tgggaaagta atggacagcc tgaaaacaat tacaagacta ccccccctgt gctggacagc   1380
gatggcagct tcttcctgta tagcaagctg accgtggaca aatccagatg gcagcagggg   1440
aacgtcttta gttgctcagt gatgcacgag gcactgcaca atcattacac ccagaaaagc   1500
ctgtccctgt ctcctggcaa gaggggaaga aaaaggagaa gtgggtcagg cgcaacaaac   1560
ttcagcctgc tgaagcaggc cggagatgtg gaggaaaatc ctgggccaat ggcttggacc   1620
cccctgttcc tgtttctgct gacatgctgt cctggcggaa gcaactccca gtctgcactg   1680
acacagccag caagtgtgtc agggagccca ggacagagca tcaccatttc ctgtaacggc   1740
acaagcaatg acgtcggggg ctacgagtcc gtgtcttggt atcagcagca tcctggaaag   1800
gccccaaaag tcgtgatcta cgatgtcagc aaacgcccct ctggggtgag taaccgattc   1860
agtggatcaa agagcgggaa taccgcttct ctgacaatta gtggcctgca ggcagaggac   1920
gaaggagatt actattgcaa atcactgaca agcactcggc gccgagtctt cggaaccggg   1980
acaaagctga ctgtgctggg ccagcccaaa gctgcaccta gcgtgaccct gtttccaccc   2040
agttcagagg aactgcaggc taataaggca acactggtgt gtctgatctc cgacttctac   2100
cctggcgctg tcactgtggc ctggaaggct gatagctccc cagtcaaagc aggagtggaa   2160
acaactaccc cctccaagca gtctaacaac aagtacgccg cttctagtta tctgtcactg   2220
actcccgagc agtggaagag ccacaaatcc tattcttgcc aggtgaccca tgagggctcc   2280
```

actgtcgaaa agaccgtggc ccctacagag tgttcttgat aactcgag 2328

<210> SEQ ID NO 64
<211> LENGTH: 2217
<212> TYPE: DNA
<213> ORGANISM: Artificial Sequence
<220> FEATURE:
<223> OTHER INFORMATION: Nucleic Acid Sequence Encoding VRC01 IgG

<400> SEQUENCE: 64
ggatccgcca ccatggattg gacatggatt ctgttcctgg tcgccgccgc aactagagtg 60
cattcacagg tgcagctggt gcagtcaggc gggcagatga agaaacccgg cgagagtatg 120
cgaatctcat gccgggctag cgggtacgaa ttcatcgact gtaccctgaa ctggattaga 180
ctggcacctg ggaagaggcc agagtggatg ggatggctga aacctagagg cggggcagtg 240
aattacgcca gaccactgca gggcagggtc actatgaccc gcgacgtgta ttctgatacc 300
gcattcctgg agctgcgaag tctgacagtc gacgatactg ccgtgtactt ctgcacacgg 360
ggcaagaact gtgactataa ttgggatttt gaacactggg gcagggggac acctgtcatt 420
gtgagctccc caagtactaa gggaccctca gtgtttcccc tggccccttc tagtaaaagt 480
acctcaggag gcacagccgc tctgggatgc ctggtgaagg attacttccc tgagccagtc 540
accgtgagtt ggaactcagg cgccctgaca agcggggtcc atacttttcc agctgtgctg 600
cagtcaagcg ggctgtactc cctgtcctct gtggtcacag tgcccagttc aagcctggga 660
acacagactt atatctgtaa cgtcaatcac aagcctagca atactaaagt ggacaagaaa 720
gccgagccta agagctgcga accaaagtcc tgtgataaaa cccatacatg ccctccctgt 780
ccagctcctg aactgctggg cggcccatcc gtgttcctgt ttccacccaa gcccaaagac 840
accctgatga ttagcaggac tcctgaggtc acctgcgtgg tcgtggacgt gtcccacgag 900
gaccccgaag tcaagtttaa ctggtacgtg gatggcgtcg aagtgcataa tgccaagaca 960
aaaccccggg aggaacagta caactctacc tatagagtcg tgagtgtcct gacagtgctg 1020
caccaggact ggctgaacgg gaaggagtat aagtgcaaag tgtctaataa ggccctgcca 1080
gctcccatcg agaaaacaat ttccaaggca aaaggccagc caagggaacc ccaggtgtac 1140
actctgcctc catcccgcga cgagctgact aagaaccagg tctctctgac ctgtctggtg 1200
aaaggattct atccaagcga tatcgccgtg gagtgggaat ccaatggcca gcccgagaac 1260
aattacaaga ccacaccccc tgtgctggac agcgatggct ccttctttct gtattcaaag 1320
ctgaccgtgg ataaaagccg ctggcagcag gggaacgtct ttagctgctc cgtgatgcac 1380
gaagctctgc acaatcatta cacccagaag tctctgagtc tgtcacctgg caagagggga 1440
cgaaaacgga gaagcggcag cggagctaca aacttcagcc tgctgaaaca ggcaggcgac 1500
gtggaggaaa atcctgggcc aatggattgg acttggattc tgttcctggt ggcagccgct 1560
accagagtcc attccgaaat tgtgctgacc cagtctcccg gaacactgtc tctgagtcct 1620
ggcgagacag ccatcatttc ctgtaggact tctcagtacg ggagtctggc atggtatcag 1680
cagcgaccag gacaggctcc tcgactggtc atctactcag gaagcactcg ggcagccggc 1740
attcccgacc gattctccgg gtctcggtgg ggacctgatt acaacctgac catctcaaat 1800
ctggaaagcg gagactttgg cgtgtactat tgccagcagt atgagttctt tgggcaggga 1860
accaaggtcc aggtggacat caaacgcaca gtcgctgcac caagcgtgtt catctttcca 1920
ccctcagatg aacagctgaa gtccggcacc gcctctgtgg tgtgcctgct gaacaatttc 1980

-continued

```
taccccccggg aggcaaaggt ccagtggaaa gtggacaacg ccctgcagtc tggcaatagt   2040

caggagtcag tgactgaaca ggacagcaag gattccacct attctctgtc ctctactctg   2100

accctgagca aagctgatta cgagaagcac aaagtgtatg catgtgaggt cacccaccag   2160

ggactgcggt cacccgtcac caagagcttc aatcgcggag agtgttgata actcgag      2217
```

<210> SEQ ID NO 65
<211> LENGTH: 2223
<212> TYPE: DNA
<213> ORGANISM: Artificial Sequence
<220> FEATURE:
<223> OTHER INFORMATION: CHIKV snapi nucleic acid sequence

<400> SEQUENCE: 65

```
ggatccgcca ccatggactg gacttggatt ctgtttctgg tcgccgccgc tacccgagtg     60

cattcacagg tgcagctgca gcagcctggg gccgctctgg tgaagccagg agctagcgca    120

atgatgtcct gcaaagcctc tggctacact ttcacctcct attggatcac ctgggtgaag    180

cagcgacctg gacagggact ggagtggatc ggcgacatct acccaggcac cgggagaaca    240

atctacaagg aaaaattcaa gacaaaagcc acactgactg tggacaccag ctcctctaca    300

gcttttatgc agctgaacag cctgacttcc gaggatagcg ccgtgtacta ttgcgcaaga    360

ggatacggct ctccttacta tgccctggac tattgggggc agggaactag cgtcaccgtg    420

agttcagcat ctaccaaggg accaagcgtg ttcccactgg cacctagctc caaatccact    480

tctggcggga ccgccgctct gggatgtctg gtgaaggatt acttccctga gccagtcaca    540

gtgagttgga actcaggggc tctgaccagc ggagtccaca catttcctgc agtgctgcag    600

tctagtggac tgtactccct gtcaagcgtg gtcactgtcc catcctctag tctgggcacc    660

cagacatata tctgcaacgt gaatcacaag ccatccaata ccaaagtcga taagaaagtg    720

gagcccaagt cttgtgacaa aactcatacc tgccctccct gtccagcacc tgaactgctg    780

ggaggcccaa gcgtgttcct gtttccaccc aagcctaaag acaccctgat gattagcagg    840

acaccagagg tcacttgcgt ggtcgtggac gtgagccacg aagaccccga ggtcaagttc    900

aactggtacg tggatggcgt cgaagtgcat aatgccaaga caaaaccccg ggaggaacag    960

tacaactcaa cctatcgggt cgtgagcgtc ctgacagtgc tgcaccagga ctggctgaac   1020

ggaaaggagt acaagtgcaa agtgtctaat aaggccctgc cagctcccat cgaaaaaacc   1080

attagcaagg ctaaaggcca gccaagagag ccccaggtgt acacactgcc tccatcaagg   1140

gacgaactga caaagaacca ggtcagcctg acttgtctgg tgaaaggctt ctatcccagc   1200

gatatcgcag tggaatggga gtccaatggg cagcctgaga acaattacaa gaccacaccc   1260

cctgtgctgg acagcgatgg gtccttcttt ctgtattcca agctgacagt ggataaatct   1320

cggtggcagc agggaaacgt ctttagttgc tcagtgatgc acgaagccct gcacaatcat   1380

tacactcaga agagcctgtc cctgtctccc ggaaagaggg gccgcaaacg gagaagtggc   1440

tcaggggcaa ccaacttctc tctgctgaaa caggccggcg atgtggagga aaatcctggg   1500

ccaatggact ggacatggat tctgttcctg gtggcagccg ctacaagggt ccattccgac   1560

attgtgctga ctcagtctcc tgcaagtctg gccgtgtctc agggacagcg agcaaccatc   1620

agttgtaagg ctagccagtc cgtcgactac gatggggaca gttacgtgaa ctggtatcag   1680

cagaagcctg gacagtcccc aaaactgctg atctatgatg ctagtaatct ggagtcaggc   1740

attcccgcac gattctctgg aagtggctca gggacagact tcaccctgaa cattcaccct   1800

gtcgaggaag aggacgtggc tacctactat tgccaggaaa gcaatgagga cccccgcact   1860
```

```
ttcgggggag gcaccaagct ggagatcaaa cgaactgtcg cagcccccag cgtgttcatc   1920

tttccaccct cagacgaaca gctgaagagc ggaaccgcat ccgtggtgtg cctgctgaac   1980

aacttctacc cccgcgaggc caaggtccag tggaaagtgg ataacgctct gcagtcaggc   2040

aatagccagg aatccgtgac tgagcaggat tctaaggaca gtacctattc actgtcaagc   2100

acactgactc tgagcaaagc agactacgaa aagcataaag tgtatgcctg cgaagtcacc   2160

caccaggggc tgaggtctcc agtcactaag tctttcaaca gaggggaatg ctgataactc   2220

gag                                                                 2223


<210> SEQ ID NO 66
<211> LENGTH: 733
<212> TYPE: PRT
<213> ORGANISM: Artificial Sequence
<220> FEATURE:
<223> OTHER INFORMATION: CHIKV-snapi amino acid sequence

<400> SEQUENCE: 66

Met Asp Trp Thr Trp Ile Leu Phe Leu Val Ala Ala Ala Thr Arg Val
1               5                   10                  15

His Ser Gln Val Gln Leu Gln Gln Pro Gly Ala Ala Leu Val Lys Pro
            20                  25                  30

Gly Ala Ser Ala Met Met Ser Cys Lys Ala Ser Gly Tyr Thr Phe Thr
        35                  40                  45

Ser Tyr Trp Ile Thr Trp Val Lys Gln Arg Pro Gly Gln Gly Leu Glu
    50                  55                  60

Trp Ile Gly Asp Ile Tyr Pro Gly Thr Gly Arg Thr Ile Tyr Lys Glu
65                  70                  75                  80

Lys Phe Lys Thr Lys Ala Thr Leu Thr Val Asp Thr Ser Ser Ser Thr
                85                  90                  95

Ala Phe Met Gln Leu Asn Ser Leu Thr Ser Glu Asp Ser Ala Val Tyr
            100                 105                 110

Tyr Cys Ala Arg Gly Tyr Gly Ser Pro Tyr Tyr Ala Leu Asp Tyr Trp
        115                 120                 125

Gly Gln Gly Thr Ser Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

-continued

```
His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys Arg Gly Arg Lys Arg Arg Ser Gly Ser Gly Ala Thr
465                 470                 475                 480

Asn Phe Ser Leu Leu Lys Gln Ala Gly Asp Val Glu Glu Asn Pro Gly
                485                 490                 495

Pro Met Asp Trp Thr Trp Ile Leu Phe Leu Val Ala Ala Ala Thr Arg
            500                 505                 510

Val His Ser Asp Ile Val Leu Thr Gln Ser Pro Ala Ser Leu Ala Val
        515                 520                 525

Ser Gln Gly Gln Arg Ala Thr Ile Ser Cys Lys Ala Ser Gln Ser Val
    530                 535                 540

Asp Tyr Asp Gly Asp Ser Tyr Val Asn Trp Tyr Gln Gln Lys Pro Gly
545                 550                 555                 560

Gln Ser Pro Lys Leu Leu Ile Tyr Asp Ala Ser Asn Leu Glu Ser Gly
                565                 570                 575

Ile Pro Ala Arg Phe Ser Gly Ser Gly Ser Gly Thr Asp Phe Thr Leu
            580                 585                 590

Asn Ile His Pro Val Glu Glu Glu Asp Val Ala Thr Tyr Tyr Cys Gln
        595                 600                 605

Glu Ser Asn Glu Asp Pro Arg Thr Phe Gly Gly Gly Thr Lys Leu Glu
    610                 615                 620

Ile Lys Arg Thr Val Ala Ala Pro Ser Val Phe Ile Phe Pro Pro Ser
625                 630                 635                 640

Asp Glu Gln Leu Lys Ser Gly Thr Ala Ser Val Val Cys Leu Leu Asn
                645                 650                 655

Asn Phe Tyr Pro Arg Glu Ala Lys Val Gln Trp Lys Val Asp Asn Ala
            660                 665                 670

Leu Gln Ser Gly Asn Ser Gln Glu Ser Val Thr Glu Gln Asp Ser Lys
        675                 680                 685

Asp Ser Thr Tyr Ser Leu Ser Ser Thr Leu Thr Leu Ser Lys Ala Asp
    690                 695                 700

Tyr Glu Lys His Lys Val Tyr Ala Cys Glu Val Thr His Gln Gly Leu
```

705 710 715 720

Arg Ser Pro Val Thr Lys Ser Phe Asn Arg Gly Glu Cys
725 730

<210> SEQ ID NO 67
<211> LENGTH: 2241
<212> TYPE: DNA
<213> ORGANISM: Artificial Sequence
<220> FEATURE:
<223> OTHER INFORMATION: DVSF-1 WT nucleic acid sequence

<400> SEQUENCE: 67
ggatccgcca ccatggactg gacttggagg attctgtttc tggtcgccgc cgctactggg 60
actcacgctc aggcacatct ggtcgaatct ggaggaggag tggtccagcc tggccgatcc 120
ctgcgactgt cttgcgcagc tagcgccttc aacttcagca caaacgcaat gcactgggtg 180
cgacaggcac caggcaaggg actggagtgg gtcgctgtga tctcatacga cggaagccat 240
aagtactatg cagattctgt gaaaggccgg ttcaccattt ccagggacaa ttctaagaac 300
accctgtatc tgcagatgaa tagcctgcgc gcagccgata ccgcagtgta ctattgcgca 360
actgtcggcg tgctgacctg gccagtgaac gccgaatact ttcaccattg gggacagggc 420
agtctggtct cagtgagctc cgcaagtact aagggaccat cagtgttccc actggcaccc 480
tctagtaaat ctactagtgg cgggaccgct gcactgggat gtctggtgaa ggactatttc 540
cccgagcctg tcaccgtgag ctggaattcc ggagccctga caagcggcgt ccacactttt 600
cccgctgtgc tgcagtcaag cggactgtac tccctgtcct ctgtggtcac tgtgcctagt 660
tcaagcctgg gcactcagac ctatatctgc aatgtgaacc acaagccctc taacaccaaa 720
gtcgacaaga aagtggaacc taagagctgt gataaaacac atacttgccc accttgtcca 780
gcaccagagc tgctgggagg accaagcgtg ttcctgtttc cacccaagcc taaagacaca 840
ctgatgatta gccggacacc tgaagtcact tgcgtggtcg tggacgtgtc ccacgaggac 900
cccgaagtca agtttaattg gtacgtggat ggcgtcgagg tgcataacgc caagaccaaa 960
ccccgggagg aacagtacaa tagcacatat agagtcgtgt ccgtcctgac tgtgctgcat 1020
caggattggc tgaatgggaa ggagtataag tgcaaagtgt ctaacaaggc tctgcctgca 1080
ccaatcgaga aaaccattag caaggctaaa ggccagccta gggaaccaca ggtgtacaca 1140
ctgcctccaa gtcgcgacga gctgaccaag aatcaggtct ccctgacatg tctggtgaaa 1200
ggcttctatc catcagatat cgccgtggag tgggaaagca acgggcagcc cgaaaacaat 1260
tacaagacca caccccctgt gctggactct gatggcagtt tctttctgta ttctaagctg 1320
accgtggaca aaagtagatg gcagcagggg aatgtctttt catgtagcgt gatgcacgag 1380
gccctgcaca accattacac acagaagtcc ctgtctctga gtcccggaaa gaggggccgc 1440
aaacggagat cagggagcgg agctactaat ttcagcctgc tgaaacaggc aggggatgtg 1500
gaggaaaacc ccggacctat ggcttggacc ccactgttcc tgtttctgct gacatgctgt 1560
cccgggggca gcaattctca gagtgtcctg acacagccac catcagtgag cggagcacca 1620
ggacagaggg tgaccatctc ctgcacaggc agcagcagca acattggcgc cgggtacgac 1680
gtgcattggt atcagcagct gcccggcacc gctcctaagc tgctgatctg tggcaacaat 1740
aaccgcccat ctggggtgcc cgatcgattc tccggctcta aaagtgggac ttcagccagc 1800
ctggctatta ccggcctgca ggccgaggac gaagctgatt actattgcca gagctacgac 1860
tcaagcctga ccggagtcgt gttcggagga ggaaccaagc tgacagtcct gggacagcct 1920

```
aaagccgctc caagcgtgac actgtttcct ccatcctctg aggaactgca ggcaaacaag   1980

gccaccctgg tgtgcctgat ttccgacttc taccccgggg cagtcactgt ggcttggaag   2040

gcagatagtt cacctgtcaa agccggagtg gagactacca caccatcaaa gcagagcaat   2100

aacaaatacg cagccagctc ctatctgtcc ctgacccctg agcagtggaa gtctcacaaa   2160

tcctattctt gccaggtcac tcacgaagga agcactgtgg agaaaactgt cgcaccaacc   2220

gaatgtagtt gataactcga g                                             2241


<210> SEQ ID NO 68
<211> LENGTH: 739
<212> TYPE: PRT
<213> ORGANISM: Artificial Sequence
<220> FEATURE:
<223> OTHER INFORMATION: DVSF-1 WT amino acid sequence

<400> SEQUENCE: 68

Met Asp Trp Thr Trp Arg Ile Leu Phe Leu Val Ala Ala Ala Thr Gly
1               5                   10                  15

Thr His Ala Gln Ala His Leu Val Glu Ser Gly Gly Gly Val Val Gln
            20                  25                  30

Pro Gly Arg Ser Leu Arg Leu Ser Cys Ala Ala Ser Ala Phe Asn Phe
        35                  40                  45

Ser Thr Asn Ala Met His Trp Val Arg Gln Ala Pro Gly Lys Gly Leu
    50                  55                  60

Glu Trp Val Ala Val Ile Ser Tyr Asp Gly Ser His Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Ala Asp Thr Ala Val
            100                 105                 110

Tyr Tyr Cys Ala Thr Val Gly Val Leu Thr Trp Pro Val Asn Ala Glu
        115                 120                 125

Tyr Phe His His Trp Gly Gln Gly Ser Leu Val Ser Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300
```

-continued

```
Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Ala Trp Thr Pro Leu Phe Leu Phe Leu
            500                 505                 510

Leu Thr Cys Cys Pro Gly Gly Ser Asn Ser Gln Ser Val Leu Thr Gln
        515                 520                 525

Pro Pro Ser Val Ser Gly Ala Pro Gly Gln Arg Val Thr Ile Ser Cys
    530                 535                 540

Thr Gly Ser Ser Ser Asn Ile Gly Ala Gly Tyr Asp Val His Trp Tyr
545                 550                 555                 560

Gln Gln Leu Pro Gly Thr Ala Pro Lys Leu Leu Ile Cys Gly Asn Asn
                565                 570                 575

Asn Arg Pro Ser Gly Val Pro Asp Arg Phe Ser Gly Ser Lys Ser Gly
            580                 585                 590

Thr Ser Ala Ser Leu Ala Ile Thr Gly Leu Gln Ala Glu Asp Glu Ala
        595                 600                 605

Asp Tyr Tyr Cys Gln Ser Tyr Asp Ser Ser Leu Thr Gly Val Val Phe
    610                 615                 620

Gly Gly Gly Thr Lys Leu Thr Val Leu Gly Gln Pro Lys Ala Ala Pro
625                 630                 635                 640

Ser Val Thr Leu Phe Pro Pro Ser Ser Glu Glu Leu Gln Ala Asn Lys
                645                 650                 655

Ala Thr Leu Val Cys Leu Ile Ser Asp Phe Tyr Pro Gly Ala Val Thr
            660                 665                 670

Val Ala Trp Lys Ala Asp Ser Ser Pro Val Lys Ala Gly Val Glu Thr
        675                 680                 685

Thr Thr Pro Ser Lys Gln Ser Asn Asn Lys Tyr Ala Ala Ser Ser Tyr
    690                 695                 700

Leu Ser Leu Thr Pro Glu Gln Trp Lys Ser His Lys Ser Tyr Ser Cys
705                 710                 715                 720

Gln Val Thr His Glu Gly Ser Thr Val Glu Lys Thr Val Ala Pro Thr
```

725 730 735

Glu Cys Ser

<210> SEQ ID NO 69
<211> LENGTH: 2241
<212> TYPE: DNA
<213> ORGANISM: Artificial Sequence
<220> FEATURE:
<223> OTHER INFORMATION: DVSF-1 LALA nucleic acid sequence

<400> SEQUENCE: 69
ggatccgcca ccatggactg gacttggagg attctgtttc tggtcgccgc cgctactggg 60
actcacgctc aggcacatct ggtcgaatct ggaggaggag tggtccagcc tggccgatcc 120
ctgcgactgt cttgcgcagc tagcgccttc aacttcagca caaacgcaat gcactgggtg 180
cgacaggcac caggcaaggg actggagtgg gtcgctgtga tctcatacga cggaagccat 240
aagtactatg cagattctgt gaaaggccgg ttcaccattt ccagggacaa ttctaagaac 300
accctgtatc tgcagatgaa tagcctgcgc gcagccgata ccgcagtgta ctattgcgca 360
actgtcggcg tgctgacctg gccagtgaac gccgaatact ttcaccattg gggacagggc 420
agtctggtct cagtgagctc cgcaagtact aagggaccat cagtgttccc actggcaccc 480
tctagtaaat ctactagtgg cgggaccgct gcactgggat gtctggtgaa ggactatttc 540
cccgagcctg tcaccgtgag ctggaattcc ggagccctga caagcggcgt ccacactttt 600
cccgctgtgc tgcagtcaag cggactgtac tccctgtcct ctgtggtcac tgtgcctagt 660
tcaagcctgg gcactcagac ctatatctgc aatgtgaacc acaagccctc taacaccaaa 720
gtcgacaaga aagtggaacc taagagctgt gataaaacac atacttgccc accttgtcca 780
gcaccagagg cagctggagg accaagcgtg ttcctgtttc cacccaagcc taaagacaca 840
ctgatgatta gccggacacc tgaagtcact tgcgtggtcg tggacgtgtc ccacgaggac 900
cccgaagtca agtttaattg gtacgtggat ggcgtcgagg tgcataacgc caagaccaaa 960
ccccgggagg aacagtacaa tagcacatat agagtcgtgt ccgtcctgac tgtgctgcat 1020
caggattggc tgaatgggaa ggagtataag tgcaaagtgt ctaacaaggc tctgcctgca 1080
ccaatcgaga aaaccattag caaggctaaa ggccagccta gggaaccaca ggtgtacaca 1140
ctgcctccaa gtcgcgacga gctgaccaag aatcaggtct ccctgacatg tctggtgaaa 1200
ggcttctatc catcagatat cgccgtggag tgggaaagca acgggcagcc cgaaaacaat 1260
tacaagacca cacccccctgt gctggactct gatggcagtt tctttctgta ttctaagctg 1320
accgtggaca aaagtagatg gcagcagggg aatgtctttt catgtagcgt gatgcacgag 1380
gccctgcaca accattacac acagaagtcc ctgtctctga gtcccggaaa gaggggccgc 1440
aaacggagat cagggagcgg agctactaat ttcagcctgc tgaaacaggc aggggatgtg 1500
gaggaaaacc ccggacctat ggcttggacc ccactgttcc tgtttctgct gacatgctgt 1560
cccgggggca gcaattctca gagtgtcctg acacagccac catcagtgag cggagcacca 1620
ggacagaggg tgaccatctc ctgcacaggc agcagcagca acattggcgc cgggtacgac 1680
gtgcattggt atcagcagct gcccggcacc gctcctaagc tgctgatctg tggcaacaat 1740
aaccgcccat ctggggtgcc cgatcgattc tccggctcta aaagtgggac ttcagccagc 1800
ctggctatta ccggcctgca ggccgaggac gaagctgatt actattgcca gagctacgac 1860
tcaagcctga ccggagtcgt gttcggagga ggaaccaagc tgacagtcct gggacagcct 1920
aaagccgctc caagcgtgac actgtttcct ccatcctctg aggaactgca ggcaaacaag 1980
gccaccctgg tgtgcctgat ttccgacttc taccccgggg cagtcactgt ggcttggaag 2040
gcagatagtt cacctgtcaa agccggagtg gagactacca caccatcaaa gcagagcaat 2100
aacaaatacg cagccagctc ctatctgtcc ctgacccctg agcagtggaa gtctcacaaa 2160
tcctattctt gccaggtcac tcacgaagga agcactgtgg agaaaactgt cgcaccaacc 2220
gaatgtagtt gataactcga g 2241

<210> SEQ ID NO 70
<211> LENGTH: 739
<212> TYPE: PRT
<213> ORGANISM: Artificial Sequence
<220> FEATURE:
<223> OTHER INFORMATION: DVSF-1 LALA amino acid sequence

<400> SEQUENCE: 70

Met Asp Trp Thr Trp Arg Ile Leu Phe Leu Val Ala Ala Ala Thr Gly
1 5 10 15

Thr His Ala Gln Ala His Leu Val Glu Ser Gly Gly Gly Val Val Gln
20 25 30

Pro Gly Arg Ser Leu Arg Leu Ser Cys Ala Ala Ser Ala Phe Asn Phe
35 40 45

Ser Thr Asn Ala Met His Trp Val Arg Gln Ala Pro Gly Lys Gly Leu
50 55 60

Glu Trp Val Ala Val Ile Ser Tyr Asp Gly Ser His Lys Tyr Tyr Ala
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Ala Asp Thr Ala Val
100 105 110

Tyr Tyr Cys Ala Thr Val Gly Val Leu Thr Trp Pro Val Asn Ala Glu
115 120 125

Tyr Phe His His Trp Gly Gln Gly Ser Leu Val Ser Val Ser Ser Ala
130 135 140

Ser Thr Lys Gly Pro Ser Val Phe Pro Leu Ala Pro Ser Ser Lys Ser
145 150 155 160

Thr Ser Gly Gly Thr Ala Ala Leu Gly Cys Leu Val Lys Asp Tyr Phe
165 170 175

Pro Glu Pro Val Thr Val Ser Trp Asn Ser Gly Ala Leu Thr Ser Gly
180 185 190

Val His Thr Phe Pro Ala Val Leu Gln Ser Ser Gly Leu Tyr Ser Leu
195 200 205

Ser Ser Val Val Thr Val Pro Ser Ser Ser Leu Gly Thr Gln Thr Tyr
210 215 220

Ile Cys Asn Val Asn His Lys Pro Ser Asn Thr Lys Val Asp Lys Lys
225 230 235 240

Val Glu Pro Lys Ser Cys Asp Lys Thr His Thr Cys Pro Pro Cys Pro
245 250 255

Ala Pro Glu Ala Ala Gly Gly Pro Ser Val Phe Leu Phe Pro Pro Lys
260 265 270

Pro Lys Asp Thr Leu Met Ile Ser Arg Thr Pro Glu Val Thr Cys Val
275 280 285

Val Val Asp Val Ser His Glu Asp Pro Glu Val Lys Phe Asn Trp Tyr
290 295 300

Val Asp Gly Val Glu Val His Asn Ala Lys Thr Lys Pro Arg Glu Glu

-continued

```
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Ala Trp Thr Pro Leu Phe Leu Phe Leu
            500                 505                 510

Leu Thr Cys Cys Pro Gly Gly Ser Asn Ser Gln Ser Val Leu Thr Gln
        515                 520                 525

Pro Pro Ser Val Ser Gly Ala Pro Gly Gln Arg Val Thr Ile Ser Cys
    530                 535                 540

Thr Gly Ser Ser Ser Asn Ile Gly Ala Gly Tyr Asp Val His Trp Tyr
545                 550                 555                 560

Gln Gln Leu Pro Gly Thr Ala Pro Lys Leu Leu Ile Cys Gly Asn Asn
                565                 570                 575

Asn Arg Pro Ser Gly Val Pro Asp Arg Phe Ser Gly Ser Lys Ser Gly
            580                 585                 590

Thr Ser Ala Ser Leu Ala Ile Thr Gly Leu Gln Ala Glu Asp Glu Ala
        595                 600                 605

Asp Tyr Tyr Cys Gln Ser Tyr Asp Ser Ser Leu Thr Gly Val Val Phe
    610                 615                 620

Gly Gly Gly Thr Lys Leu Thr Val Leu Gly Gln Pro Lys Ala Ala Pro
625                 630                 635                 640

Ser Val Thr Leu Phe Pro Pro Ser Ser Glu Glu Leu Gln Ala Asn Lys
                645                 650                 655

Ala Thr Leu Val Cys Leu Ile Ser Asp Phe Tyr Pro Gly Ala Val Thr
            660                 665                 670

Val Ala Trp Lys Ala Asp Ser Ser Pro Val Lys Ala Gly Val Glu Thr
        675                 680                 685

Thr Thr Pro Ser Lys Gln Ser Asn Asn Lys Tyr Ala Ala Ser Ser Tyr
    690                 695                 700

Leu Ser Leu Thr Pro Glu Gln Trp Lys Ser His Lys Ser Tyr Ser Cys
705                 710                 715                 720

Gln Val Thr His Glu Gly Ser Thr Val Glu Lys Thr Val Ala Pro Thr
                725                 730                 735
```

Glu Cys Ser

<210> SEQ ID NO 71
<211> LENGTH: 2241
<212> TYPE: DNA
<213> ORGANISM: Artificial Sequence
<220> FEATURE:
<223> OTHER INFORMATION: DVSF-2 WT nucleic acid sequence

<400> SEQUENCE: 71
ggatccgcca ccatggactg gacatggaga atcctgttcc tggtcgccgc cgcaaccggg 60
acacacgccg aagtgcagct ggtggaatct ggagggggat gggtgcagcc aggagggtcc 120
ctgcgactgt cttgcgccgc tagtggcttc acttttccca gatacgacat gcactgggtc 180
aggcaggtga ccggaaaggg cctggaatgg gtgagcgcaa tcaccacagc cggagacaca 240
tactatcccg attctgtgaa gggccggttc accattagtc gggagaacgc caaaagctcc 300
ctgtatctgc agatgaacaa tctgagagct ggcgacaccg cactgtacta ttgcgctagg 360
ggccccccta cagattgctc tagtggacga tgtctgggag tcggagtggg actggaccca 420
tgggggcagg gaacactggt cactgtgtca agcgcctcca caaagggacc ctctgtgttc 480
cctctggctc catcctctaa aagtacttca ggaggaaccg cagcactggg atgtctggtg 540
aaggattact tcccagagcc cgtcaccgtg agctggaact ccggagctct gactagcggc 600
gtccatacct ttcctgcagt gctgcagagt tcaggcctgt acagcctgag ctccgtggtc 660
accgtgccat ctagttcact ggggacccag acatatatct gcaacgtgaa tcacaagcca 720
tctaatacaa aagtcgacaa gaaagtggaa cccaagagtt gtgataaaac tcatacctgc 780
ccaccatgtc ctgcaccaga gctgctggga ggaccatccg tgttcctgtt tcctccaaag 840
cccaaagaca cactgatgat tagcaggaca cccgaagtca cttgcgtggt cgtggacgtg 900
agccacgagg accccgaagt caagtttaac tggtacgtgg atggcgtcga ggtgcataat 960
gccaagacca aaccccggga ggaacagtac aacagtacct atagagtcgt gtcagtcctg 1020
acagtgctgc accaggactg gctgaacggg aaagagtata agtgcaaagt gtccaataag 1080
gcactgcccg cccctatcga gaaaaccatt tctaaggcca aaggacagcc ccgagaacct 1140
caggtgtaca cactgccccc tagccgcgac gagctgacaa agaaccaggt ctccctgact 1200
tgtctggtga aagggttcta tccttcagat atcgccgtgg agtgggaaag caatggacag 1260
ccagaaaaca attacaagac taccccaccc gtgctggact ctgatggcag tttctttctg 1320
tatagcaagc tgaccgtgga caaatcccgc tggcagcagg ggaacgtctt tagctgctcc 1380
gtgatgcatg aggccctgca caatcattac actcagaagt ctctgagtct gtcacctgga 1440
aagaggggac gaaaacgaag aagcggctcc ggagcaacca acttcagcct gctgaaacag 1500
gccggggatg tggaggaaaa tccaggaccc atggcatgga ctcctctgtt cctgtttctg 1560
ctgacctgct gtccaggcgg gagcaacagc tcctacgagg tgacccagcc tccatctgtc 1620
agtgtgtcac ccggccagac cgcttcaatc acatgtagcg ggacaagct gggaaagaaa 1680 tacacaagtt ggtatcagca gaaaccagga cagtcacccc tgctggtcat ctaccaggat 1740
actaagcgcc ctagcggcat tccagaacgg ttcagcggct ccaactctgg gaatacagct 1800
actctgacca tctccggcac ccaggccatg gacgaggctg attactattg ccaggcatgg 1860
gattctacaa ctcacgtcat tttcggaggc gggaccaagc tgacagtgct ggggcagccc 1920
aaagctgcac ctagcgtcac cctgtttccc ccttctagtg aggaactgca ggctaataag 1980
gcaacactgg tgtgtctgat ttccgacttc tacccaggag cagtcactgt ggcatggaag 2040
gctgattcaa gccccgtcaa agccggagtg gaaaccacaa ctccttcaaa gcagagcaac 2100
aacaagtacg ccgcttcctc ttatctgtcc ctgactcccg agcagtggaa gtctcacaaa 2160
agttattcat gccaggtgac ccatgagggc tccactgtcg aaaagaccgt ggcccctaca 2220
gagtgttctt gataactcga g 2241

<210> SEQ ID NO 72
<211> LENGTH: 739
<212> TYPE: PRT
<213> ORGANISM: Artificial Sequence
<220> FEATURE:
<223> OTHER INFORMATION: DVSF-2 WT amino acid sequence

<400> SEQUENCE: 72

Met Asp Trp Thr Trp Arg Ile Leu Phe Leu Val Ala Ala Ala Thr Gly
1 5 10 15

Thr His Ala Glu Val Gln Leu Val Glu Ser Gly Gly Gly Trp Val Gln
20 25 30

Pro Gly Gly Ser Leu Arg Leu Ser Cys Ala Ala Ser Gly Phe Thr Phe
35 40 45

Ser Arg Tyr Asp Met His Trp Val Arg Gln Val Thr Gly Lys Gly Leu
50 55 60

Glu Trp Val Ser Ala Ile Thr Thr Ala Gly Asp Thr Tyr Tyr Pro Asp
65 70 75 80

Ser Val Lys Gly Arg Phe Thr Ile Ser Arg Glu Asn Ala Lys Ser Ser
85 90 95

Leu Tyr Leu Gln Met Asn Asn Leu Arg Ala Gly Asp Thr Ala Leu Tyr
100 105 110

Tyr Cys Ala Arg Gly Pro Pro Thr Asp Cys Ser Ser Gly Arg Cys Leu
115 120 125

Gly Val Gly Val Gly Leu Asp Pro Trp Gly Gln Gly Thr Leu Val Thr
130 135 140

Val Ser Ser Ala Ser Thr Lys Gly Pro Ser Val Phe Pro Leu Ala Pro
145 150 155 160

Ser Ser Lys Ser Thr Ser Gly Gly Thr Ala Ala Leu Gly Cys Leu Val
165 170 175

Lys Asp Tyr Phe Pro Glu Pro Val Thr Val Ser Trp Asn Ser Gly Ala
180 185 190

Leu Thr Ser Gly Val His Thr Phe Pro Ala Val Leu Gln Ser Ser Gly
195 200 205

Leu Tyr Ser Leu Ser Ser Val Val Thr Val Pro Ser Ser Ser Leu Gly
210 215 220

Thr Gln Thr Tyr Ile Cys Asn Val Asn His Lys Pro Ser Asn Thr Lys
225 230 235 240

Val Asp Lys Lys Val Glu Pro Lys Ser Cys Asp Lys Thr His Thr Cys
245 250 255

Pro Pro Cys Pro Ala Pro Glu Leu Leu Gly Gly Pro Ser Val Phe Leu
260 265 270

Phe Pro Pro Lys Pro Lys Asp Thr Leu Met Ile Ser Arg Thr Pro Glu
275 280 285

Val Thr Cys Val Val Val Asp Val Ser His Glu Asp Pro Glu Val Lys
290 295 300

Phe Asn Trp Tyr Val Asp Gly Val Glu Val His Asn Ala Lys Thr Lys
305 310 315 320

-continued

```
Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Arg Gly Arg
465                 470                 475                 480

Lys Arg Arg Ser Gly Ser Gly Ala Thr Asn Phe Ser Leu Leu Lys Gln
                485                 490                 495

Ala Gly Asp Val Glu Glu Asn Pro Gly Pro Met Ala Trp Thr Pro Leu
            500                 505                 510

Phe Leu Phe Leu Leu Thr Cys Cys Pro Gly Gly Ser Asn Ser Ser Tyr
        515                 520                 525

Glu Val Thr Gln Pro Pro Ser Val Ser Val Ser Pro Gly Gln Thr Ala
    530                 535                 540

Ser Ile Thr Cys Ser Gly Asp Lys Leu Gly Lys Lys Tyr Thr Ser Trp
545                 550                 555                 560

Tyr Gln Gln Lys Pro Gly Gln Ser Pro Leu Leu Val Ile Tyr Gln Asp
                565                 570                 575

Thr Lys Arg Pro Ser Gly Ile Pro Glu Arg Phe Ser Gly Ser Asn Ser
            580                 585                 590

Gly Asn Thr Ala Thr Leu Thr Ile Ser Gly Thr Gln Ala Met Asp Glu
        595                 600                 605

Ala Asp Tyr Tyr Cys Gln Ala Trp Asp Ser Thr Thr His Val Ile Phe
    610                 615                 620

Gly Gly Gly Thr Lys Leu Thr Val Leu Gly Gln Pro Lys Ala Ala Pro
625                 630                 635                 640

Ser Val Thr Leu Phe Pro Pro Ser Ser Glu Glu Leu Gln Ala Asn Lys
                645                 650                 655

Ala Thr Leu Val Cys Leu Ile Ser Asp Phe Tyr Pro Gly Ala Val Thr
            660                 665                 670

Val Ala Trp Lys Ala Asp Ser Ser Pro Val Lys Ala Gly Val Glu Thr
        675                 680                 685

Thr Thr Pro Ser Lys Gln Ser Asn Asn Lys Tyr Ala Ala Ser Ser Tyr
    690                 695                 700

Leu Ser Leu Thr Pro Glu Gln Trp Lys Ser His Lys Ser Tyr Ser Cys
705                 710                 715                 720

Gln Val Thr His Glu Gly Ser Thr Val Glu Lys Thr Val Ala Pro Thr
                725                 730                 735
```

Glu Cys Ser

<210> SEQ ID NO 73
<211> LENGTH: 2241
<212> TYPE: DNA
<213> ORGANISM: Artificial Sequence
<220> FEATURE:
<223> OTHER INFORMATION: DVSF-2 LALA nucleic acid sequence

<400> SEQUENCE: 73
ggatccgcca ccatggactg gacatggaga atcctgttcc tggtcgccgc cgctactggg 60
actcacgccg aagtgcagct ggtcgagagt ggagggggat gggtgcagcc cggcggcagc 120
ctgaggctgt cttgcgccgc tagtggcttc actttttcta gatacgacat gcactgggtc 180
cggcaggtga ccgggaaggg actggaatgg gtgagcgcca tcaccacagc aggggacaca 240
tactatcccg attctgtgaa gggcaggttc accattagta gggagaacgc aaaaagctcc 300
ctgtatctgc agatgaacaa tctgagagcc ggcgacaccg ctctgtacta ttgcgccagg 360
ggccctccca cagattgctc tagtggacgc tgtctgggag tcggagtggg actggaccca 420
tggggacagg ggacactggt caccgtgagc agcgcctcca ctaagggacc aagcgtgttc 480
cctctggcac catcctctaa aagtacttca gggggcaccg cagccctggg atgtctggtg 540
aaggattact tcccagagcc cgtcacagtg agctggaact ccggggccct gacttccgga 600
gtccacacct ttcctgctgt gctgcagagt tcaggcctgt actctctgag ctccgtggtc 660
acagtgccat ctagttcact gggaacccag acatatatct gcaacgtgaa tcacaagcca 720
agtaatacta aagtcgacaa gaaagtggaa cccaagtctt gtgataaaac tcatacctgc 780
ccaccctgtc ctgcaccaga ggctgcagga gggccatccg tgttcctgtt tcctccaaag 840
cccaaagaca ccctgatgat tagccggaca cccgaagtca cttgcgtggt cgtggacgtg 900
tcccacgagg accccgaagt caagtttaac tggtacgtgg atggcgtcga ggtgcataat 960
gccaagacaa aacccaggga ggaacagtac aacagtacct atagagtcgt gtcagtcctg 1020
acagtgctgc accaggactg gctgaacgga aaggagtata agtgcaaagt gtctaataag 1080
gctctgcccg cacctatcga gaaaaccatt agcaaggcca aagggcagcc ccgagaacct 1140
caggtgtaca cactgccccc ttcccgcgac gagctgacaa agaaccaggt ctctctgact 1200
tgtctggtga aaggattcta tccttcagat atcgccgtgg agtgggaaag caatgggcag 1260
ccagaaaaca attacaagac taccccaccc gtgctggact ctgatggcag tttctttctg 1320
tatagcaagc tgaccgtgga caaatcccgc tggcagcagg gaaacgtctt tagctgctcc 1380
gtgatgcatg aggccctgca caatcattac acccagaagt ctctgagtct gtcacctggg 1440
aagcgaggac gaaaaaggag aagcggctcc ggagctacaa acttctccct gctgaaacag 1500
gcaggagatg tggaggaaaa tccagggccc atggcctgga ctcctctgtt cctgtttctg 1560
ctgacctgct gtccaggcgg aagcaacagc tcctacgagg tgacccagcc tccaagcgtg 1620
agcgtgagcc caggccagac cgcttcaatc acatgtagcg gagacaagct ggggaagaaa 1680
tacactagtt ggtatcagca gaaaccaggg cagtcacccc tgctggtcat ctaccaggat 1740
accaagcgcc ctagcggcat tccagaacga ttcagcggct ccaactctgg aaatacagcc 1800
actctgacca tcagcggcac ccaggcaatg gacgaggccg attactattg ccaggcttgg 1860
gattccacaa ctcacgtcat tttcgggggc ggaaccaagc tgacagtgct gggacagccc 1920
aaagccgctc cttccgtcac cctgtttccc ccttctagtg aggaactgca ggccaataag 1980
gccaccctgg tgtgcctgat tagcgacttc taccccggag ctgtcactgt ggcatggaag 2040

```
gccgattcaa gccccgtcaa agcaggggtg gaaaccacaa ctccttcaaa gcagagcaac   2100

aacaagtacg cagcctcctc ttatctgtcc ctgacccctg agcagtggaa gtctcataaa   2160

agttattcat gtcaggtcac ccatgagggc agcacagtgg aaaaaaccgt ggcaccaaca   2220

gaatgtagct gataactcga g                                              2241


<210> SEQ ID NO 74
<211> LENGTH: 739
<212> TYPE: PRT
<213> ORGANISM: Artificial Sequence
<220> FEATURE:
<223> OTHER INFORMATION: DVSF-2 LALA amino acid sequence

<400> SEQUENCE: 74

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Trp Val Gln
            20                  25                  30

Pro Gly Gly Ser Leu Arg Leu Ser Cys Ala Ala Ser Gly Phe Thr Phe
        35                  40                  45

Ser Arg Tyr Asp Met His Trp Val Arg Gln Val Thr Gly Lys Gly Leu
    50                  55                  60

Glu Trp Val Ser Ala Ile Thr Thr Ala Gly Asp Thr Tyr Tyr Pro Asp
65                  70                  75                  80

Ser Val Lys Gly Arg Phe Thr Ile Ser Arg Glu Asn Ala Lys Ser Ser
                85                  90                  95

Leu Tyr Leu Gln Met Asn Asn Leu Arg Ala Gly Asp Thr Ala Leu Tyr
            100                 105                 110

Tyr Cys Ala Arg Gly Pro Pro Thr Asp Cys Ser Ser Gly Arg Cys Leu
        115                 120                 125

Gly Val Gly Val Gly Leu Asp Pro Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Asp Lys Thr His Thr Cys
                245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320
```

-continued

```
Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Arg Gly Arg
465                 470                 475                 480

Lys Arg Arg Ser Gly Ser Gly Ala Thr Asn Phe Ser Leu Leu Lys Gln
                485                 490                 495

Ala Gly Asp Val Glu Glu Asn Pro Gly Pro Met Ala Trp Thr Pro Leu
            500                 505                 510

Phe Leu Phe Leu Leu Thr Cys Cys Pro Gly Gly Ser Asn Ser Ser Tyr
        515                 520                 525

Glu Val Thr Gln Pro Pro Ser Val Ser Val Ser Pro Gly Gln Thr Ala
    530                 535                 540

Ser Ile Thr Cys Ser Gly Asp Lys Leu Gly Lys Lys Tyr Thr Ser Trp
545                 550                 555                 560

Tyr Gln Gln Lys Pro Gly Gln Ser Pro Leu Leu Val Ile Tyr Gln Asp
                565                 570                 575

Thr Lys Arg Pro Ser Gly Ile Pro Glu Arg Phe Ser Gly Ser Asn Ser
            580                 585                 590

Gly Asn Thr Ala Thr Leu Thr Ile Ser Gly Thr Gln Ala Met Asp Glu
        595                 600                 605

Ala Asp Tyr Tyr Cys Gln Ala Trp Asp Ser Thr Thr His Val Ile Phe
    610                 615                 620

Gly Gly Gly Thr Lys Leu Thr Val Leu Gly Gln Pro Lys Ala Ala Pro
625                 630                 635                 640

Ser Val Thr Leu Phe Pro Pro Ser Ser Glu Glu Leu Gln Ala Asn Lys
                645                 650                 655

Ala Thr Leu Val Cys Leu Ile Ser Asp Phe Tyr Pro Gly Ala Val Thr
            660                 665                 670

Val Ala Trp Lys Ala Asp Ser Ser Pro Val Lys Ala Gly Val Glu Thr
        675                 680                 685

Thr Thr Pro Ser Lys Gln Ser Asn Asn Lys Tyr Ala Ala Ser Ser Tyr
    690                 695                 700

Leu Ser Leu Thr Pro Glu Gln Trp Lys Ser His Lys Ser Tyr Ser Cys
705                 710                 715                 720

Gln Val Thr His Glu Gly Ser Thr Val Glu Lys Thr Val Ala Pro Thr
                725                 730                 735

Glu Cys Ser
```

<210> SEQ ID NO 75
<211> LENGTH: 2229
<212> TYPE: DNA
<213> ORGANISM: Artificial Sequence
<220> FEATURE:
<223> OTHER INFORMATION: DVSF-3 WT nucleic acid sequence

<400> SEQUENCE: 75
ggatccgcca ccatggactg gacatggaga atcctgttcc tggtcgccgc cgcaaccggg 60
acacacgccg aagtgcagct ggtggaatca gggggagggc tggtgcagcc tggaagaagt 120
ctgaggctgt catgcgccgc tagcggcttc acctttgacg attacgccat gttctgggtg 180
aggcaggctc caggcaaggg actggaatgg atcagcggca tttcctggaa ctctgcaact 240
atcgggtatg ccgactccgt gaaaggacgg tttaccattt caagagacaa cgccaagaaa 300
agcctggatc tgcagatgaa ttccctgcgg cccgacgata ccgctctgta ctattgcgca 360
aagggaggac ctagaggcct gcagctgctg agctcctggg tggactactg gggacagggc 420
actctggtca ccgtgtctag tgcttccaca aagggacctt ctgtgttccc actggcaccc 480
tcaagcaaat caacaagcgg aggaactgca gcactgggat gtctggtgaa ggattatttc 540
cccgagcctg tcaccgtgag ttggaactca ggagcactga cttccggagt ccacaccttt 600
ccagcagtgc tgcagtcctc tggactgtac agcctgagtt cagtggtcac agtgcctagc 660
tcctctctgg gcacacagac ttatatctgc aacgtgaatc acaagcctag caatactaaa 720
gtcgacaaga aagtggaacc aaagtcctgt gataaaaccc atacatgccc accttgtcca 780
gcaccagagc tgctgggggg accaagcgtg ttcctgtttc cacccaagcc caaagacaca 840
ctgatgattt ctcggacccc tgaagtcaca tgtgtggtcg tggacgtgag ccacgaggac 900
cccgaagtca agttcaactg gtacgtggat ggcgtcgagg tgcataatgc taagaccaaa 960
ccccgagagg aacagtacaa cagcacttat cgggtcgtgt ccgtcctgac cgtgctgcac 1020
caggactggc tgaacgggaa ggagtataag tgcaaagtgt ccaataaggc cctgcctgct 1080
ccaatcgaga aaacaatttc taaggcaaaa ggacagcctc gcgaaccaca ggtgtacact 1140
ctgcctccat cccgagacga gctgaccaag aaccaggtct ctctgacatg tctggtgaaa 1200
ggcttctatc caagtgatat cgctgtggag tgggaaagca atgggcagcc cgaaaacaat 1260
tacaagacca cacccctgt gctggacagc gatggctcct tctttctgta ttctaagctg 1320
accgtggata aaagtagatg gcagcagggg aacgtctttt cctgctctgt gatgcatgag 1380
gccctgcaca atcattacac acagaagagt ctgtcactga gcccagggaa gcgaggacgg 1440
aaacggagat ccgggtctgg agcaaccaac ttctccctgc tgaaacaggc aggcgacgtg 1500
gaggaaaatc caggacctat ggtcctgcag acccaggtgt ttatctctct gctgctgtgg 1560
attagtggcg cctacgggga tatccagatg acacagtccc ccagttcact gagtgcctca 1620
gtcggcgaca gggtgactat cacctgtcgc gctagccagg atattaggcg ctacctgaac 1680
tggtatcagc agcgaccagg acgagtgcct cagctgctga tctacactac ctccaccctg 1740
cagtctggag tcccaagtag gttcagcggc tccgggtctg tgacagactt tacactgact 1800
attagctccc tgcagcccga agatttcggc acttactatt gccagcagag ttattcacca 1860
ccccacacat ttggacaggg cactaagctg gaaatcaaaa ctgtcgctgc accctcagtg 1920
ttcatttttc ctccatctga cgagcagctg aagtcaggca ccgccagcgt cgtgtgtctg 1980
ctgaacaatt tctaccctcg cgaggctaag gtccagtgga aagtggataa cgcactgcag 2040

```
tctgggaata gtcaggagtc agtgacagaa caggacagca aggattccac ttattctctg   2100

tctagtaccc tgacactgag caaagccgac tacgagaagc acaaagtcta tgcttgcgaa   2160

gtgacccatc aggggctgag aagtcccgtg acaaagagct tcaacagggg agagtgttga   2220

taactcgag                                                           2229
```

<210> SEQ ID NO 76
<211> LENGTH: 735
<212> TYPE: PRT
<213> ORGANISM: Artificial Sequence
<220> FEATURE:
<223> OTHER INFORMATION: DVSF-3 WT amino acid sequence

<400> SEQUENCE: 76

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met Phe Trp Val Arg Gln Ala Pro Gly Lys Gly Leu
    50                  55                  60

Glu Trp Ile Ser Gly Ile Ser Trp Asn Ser Ala Thr Ile Gly Tyr Ala
65                  70                  75                  80

Asp Ser Val Lys Gly Arg Phe Thr Ile Ser Arg Asp Asn Ala Lys Lys
                85                  90                  95

Ser Leu Asp Leu Gln Met Asn Ser Leu Arg Pro Asp Asp Thr Ala Leu
            100                 105                 110

Tyr Tyr Cys Ala Lys Gly Gly Pro Arg Gly Leu Gln Leu Leu Ser Ser
        115                 120                 125

Trp Val Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
```

-continued

```
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Val Leu Gln Thr Gln Val Phe Ile Ser
            500                 505                 510

Leu Leu Leu Trp Ile Ser Gly Ala Tyr Gly Asp Ile Gln Met Thr Gln
        515                 520                 525

Ser Pro Ser Ser Leu Ser Ala Ser Val Gly Asp Arg Val Thr Ile Thr
    530                 535                 540

Cys Arg Ala Ser Gln Asp Ile Arg Arg Tyr Leu Asn Trp Tyr Gln Gln
545                 550                 555                 560

Arg Pro Gly Arg Val Pro Gln Leu Leu Ile Tyr Thr Thr Ser Thr Leu
                565                 570                 575

Gln Ser Gly Val Pro Ser Arg Phe Ser Gly Ser Gly Ser Val Thr Asp
            580                 585                 590

Phe Thr Leu Thr Ile Ser Ser Leu Gln Pro Glu Asp Phe Gly Thr Tyr
        595                 600                 605

Tyr Cys Gln Gln Ser Tyr Ser Pro Pro His Thr Phe Gly Gln Gly Thr
    610                 615                 620

Lys Leu Glu Ile Lys Thr Val Ala Ala Pro Ser Val Phe Ile Phe Pro
625                 630                 635                 640

Pro Ser Asp Glu Gln Leu Lys Ser Gly Thr Ala Ser Val Val Cys Leu
                645                 650                 655

Leu Asn Asn Phe Tyr Pro Arg Glu Ala Lys Val Gln Trp Lys Val Asp
            660                 665                 670

Asn Ala Leu Gln Ser Gly Asn Ser Gln Glu Ser Val Thr Glu Gln Asp
        675                 680                 685

Ser Lys Asp Ser Thr Tyr Ser Leu Ser Ser Thr Leu Thr Leu Ser Lys
    690                 695                 700

Ala Asp Tyr Glu Lys His Lys Val Tyr Ala Cys Glu Val Thr His Gln
705                 710                 715                 720

Gly Leu Arg Ser Pro Val Thr Lys Ser Phe Asn Arg Gly Glu Cys
                725                 730                 735
```

<210> SEQ ID NO 77

<211> LENGTH: 2229
<212> TYPE: DNA
<213> ORGANISM: Artificial Sequence
<220> FEATURE:
<223> OTHER INFORMATION: DVSF-3 LALA nucleic acid sequence

<400> SEQUENCE: 77
ggatccgcca ccatggactg gacttggaga atcctgtttc tggtcgccgc cgcaactgga 60
acccacgccg aggtgcagct ggtcgaatca gggggaggcc tggtgcagcc tgggagaagt 120
ctgcggctgt catgcgccgc tagcggcttc acctttgacg attacgcaat gttctgggtg 180
aggcaggcac caggcaaggg actggaatgg atcagcggca tttcctggaa ctctgctacc 240
atcggatatg cagacagcgt gaaagggagg tttacaattt ctagagacaa cgccaagaaa 300
agtctggatc tgcagatgaa ttcactgcgc cccgacgata ccgccctgta ctattgcgct 360
aagggcggac ccaggggcct gcagctgctg agctcctggg tggactactg gggcagggc 420 actctggtca ccgtgtctag tgcctccaca aagggcccta gcgtgttccc actggctccc 480
tcaagcaaat caacaagcgg gggcactgca gccctgggat gtctggtgaa ggattatttc 540
cccgagcctg tcaccgtgag ttggaactca ggggctctga ctagcggcgt ccacaccttt 600
cccgcagtgc tgcagtcctc tggcctgtac agcctgagtt cagtggtcac tgtccctagc 660
tcctctctgg gaacacagac ttatatctgc aacgtgaatc acaagccttc caataccaaa 720
gtcgacaaga aagtggaacc aaagtcttgt gataaaaccc atacatgccc tccctgtcca 780
gcaccagagg ctgcaggagg gccaagcgtg ttcctgtttc cacccaagcc caaagacaca 840
ctgatgatta gccggacccc tgaagtcaca tgcgtggtcg tggacgtgag ccacgaggac 900
cccgaagtca agtttaactg gtacgtggat ggcgtcgagg tgcataatgc taagaccaaa 960
ccccgagagg aacagtacaa cagtacttat agggtcgtgt cagtcctgac cgtgctgcac 1020
caggactggc tgaacgggaa ggagtataag tgcaaagtgt ccaataaggc actgcctgcc 1080
ccaatcgaga aaactatttc taaggctaaa ggccagccta gagaaccaca ggtgtacacc 1140
ctgcctccaa gccgggacga gctgaccaag aaccaggtca gcctgacatg tctggtgaaa 1200
ggattctatc catccgatat cgcagtggag tgggaatcta atgggcagcc cgaaaacaat 1260
tacaagacca cacccctgt gctggacagc gatggcagct tcttcctgta tagcaagctg 1320
accgtggata aatcccgctg gcagcagggg aacgtctttt cctgctctgt gatgcatgag 1380
gccctgcaca atcattacac acagaagagt ctgtcactga gcccaggaaa gcgagggagg 1440
aaaaggagat ccggatctgg ggctactaac ttctccctgc tgaagcaggc aggcgacgtg 1500
gaggaaaatc ccggacctat ggtcctgcag acacaggtgt ttatcagcct gctgctgtgg 1560
atttccggcg cttacggaga tatccagatg actcagtccc ccagttcact gagtgcatca 1620
gtcggcgacc gggtgactat cacctgtcgc gcctctcagg atattcggcg ctacctgaat 1680
tggtatcagc agcgaccagg acgagtgcct cagctgctga tctacactac ctccacactg 1740
cagtctggcg tcccaagtag gttcagcggc tccggatctg tgactgactt tacactgact 1800
attagctccc tgcagcccga ggatttcggc acctactatt gccagcagag ttattcacca 1860
ccccacacat ttgggcaggg cactaagctg gaaatcaaaa ccgtcgccgc tcccagcgtg 1920
ttcatctttc ctccaagtga cgagcagctg aagtcaggaa cagccagcgt ggtgtgcctg 1980
ctgaacaatt tctaccctag agaagccaag gtccagtgga aagtggataa cgctctgcag 2040
tctgggaata gtcaggagtc agtgacagaa caggacagca aggattccac ttattctctg 2100
tctagtaccc tgacactgag caaagcagac tacgagaagc ataaagtgta tgcctgcgaa 2160

```
gtcacccacc aggggctgcg gtcaccagtc acaaaatcct ttaacagagg cgaatgctga   2220

taactcgag                                                           2229


<210> SEQ ID NO 78
<211> LENGTH: 735
<212> TYPE: PRT
<213> ORGANISM: Artificial Sequence
<220> FEATURE:
<223> OTHER INFORMATION: DSVF-3 LALA amino acid sequence

<400> SEQUENCE: 78

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met Phe Trp Val Arg Gln Ala Pro Gly Lys Gly Leu
    50                  55                  60

Glu Trp Ile Ser Gly Ile Ser Trp Asn Ser Ala Thr Ile Gly Tyr Ala
65                  70                  75                  80

Asp Ser Val Lys Gly Arg Phe Thr Ile Ser Arg Asp Asn Ala Lys Lys
                85                  90                  95

Ser Leu Asp Leu Gln Met Asn Ser Leu Arg Pro Asp Asp Thr Ala Leu
            100                 105                 110

Tyr Tyr Cys Ala Lys Gly Gly Pro Arg Gly Leu Gln Leu Leu Ser Ser
        115                 120                 125

Trp Val Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
```

-continued

```
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys Arg Gly Arg Lys Arg Arg Ser
465                 470                 475                 480

Gly Ser Gly Ala Thr Asn Phe Ser Leu Leu Lys Gln Ala Gly Asp Val
                485                 490                 495

Glu Glu Asn Pro Gly Pro Met Val Leu Gln Thr Gln Val Phe Ile Ser
            500                 505                 510

Leu Leu Leu Trp Ile Ser Gly Ala Tyr Gly Asp Ile Gln Met Thr Gln
        515                 520                 525

Ser Pro Ser Ser Leu Ser Ala Ser Val Gly Asp Arg Val Thr Ile Thr
    530                 535                 540

Cys Arg Ala Ser Gln Asp Ile Arg Arg Tyr Leu Asn Trp Tyr Gln Gln
545                 550                 555                 560

Arg Pro Gly Arg Val Pro Gln Leu Leu Ile Tyr Thr Thr Ser Thr Leu
                565                 570                 575

Gln Ser Gly Val Pro Ser Arg Phe Ser Gly Ser Gly Ser Val Thr Asp
            580                 585                 590

Phe Thr Leu Thr Ile Ser Ser Leu Gln Pro Glu Asp Phe Gly Thr Tyr
        595                 600                 605

Tyr Cys Gln Gln Ser Tyr Ser Pro Pro His Thr Phe Gly Gln Gly Thr
    610                 615                 620

Lys Leu Glu Ile Lys Thr Val Ala Ala Pro Ser Val Phe Ile Phe Pro
625                 630                 635                 640

Pro Ser Asp Glu Gln Leu Lys Ser Gly Thr Ala Ser Val Val Cys Leu
                645                 650                 655

Leu Asn Asn Phe Tyr Pro Arg Glu Ala Lys Val Gln Trp Lys Val Asp
            660                 665                 670

Asn Ala Leu Gln Ser Gly Asn Ser Gln Glu Ser Val Thr Glu Gln Asp
        675                 680                 685

Ser Lys Asp Ser Thr Tyr Ser Leu Ser Ser Thr Leu Thr Leu Ser Lys
    690                 695                 700

Ala Asp Tyr Glu Lys His Lys Val Tyr Ala Cys Glu Val Thr His Gln
705                 710                 715                 720

Gly Leu Arg Ser Pro Val Thr Lys Ser Phe Asn Arg Gly Glu Cys
                725                 730                 735
```